US 11,905,306 B2

(12) United States Patent
Ahmed et al.

(10) Patent No.: US 11,905,306 B2
(45) Date of Patent: Feb. 20, 2024

(54) SUBSTITUTED PHENYL ETHYNYL PYRIDINE CARBOXAMIDES AS POTENT INHIBITORS OF SARS VIRUS

(71) Applicants: Southern Research Institute, Birmingham, AL (US); The University of North Carolina at Chapel Hill, Chapel Hill, NC (US); Vanderbilt University, Nashville, TN (US)

(72) Inventors: Syed Kaleem Ahmed, Hoover, AL (US); Shilpa Dutta, Birmingham, AL (US); John Phillip Tillotson, Birmingham, AL (US); Corinne E. Augelli-Szafran, Homewood, AL (US); Ashish Kumar Pathak, Hoover, AL (US); Omar Moukha-Chafiq, Hoover, AL (US); Timothy Patrick Sheahan, Chapel Hill, NC (US); Ralph S. Baric, Haw River, NC (US); Amy Catherine Sims, Richland, WA (US); Mark R. Denison, Nashville, TN (US)

(73) Assignees: Southern Research Institute, Birmingham, AL (US); Vanderbilt University, Nashville, TN (US); University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 18/086,445

(22) Filed: Dec. 21, 2022

(65) Prior Publication Data
US 2023/0192733 A1 Jun. 22, 2023

Related U.S. Application Data

(60) Provisional application No. 63/292,407, filed on Dec. 21, 2021.

(51) Int. Cl.
C07F 9/58 (2006.01)
C07D 213/56 (2006.01)
C07D 401/12 (2006.01)
C07D 413/12 (2006.01)
C07D 417/12 (2006.01)

(52) U.S. Cl.
CPC .............. C07F 9/58 (2013.01); C07D 213/56 (2013.01); C07D 401/12 (2013.01); C07D 413/12 (2013.01); C07D 417/12 (2013.01)

(58) Field of Classification Search
CPC ....... C07F 9/58; C07D 213/56; C07D 401/12; C07D 413/12; C07D 417/12
See application file for complete search history.

(56) References Cited

U.S. PATENT DOCUMENTS 8,937,055 B2 * 1/2015 Ujikawa .................. A61P 1/00
546/268.1
10,618,900 B2 4/2020 Liu et al.
2018/0194767 A1 7/2018 Liu et al.

FOREIGN PATENT DOCUMENTS

| CN | 104250253 | 4/2017 |
| CN | 106699729 | 5/2017 |
| CN | 107226809 | 10/2017 |
| WO | WO 1999/002497 | 1/1999 |
| WO | WO 2000/041531 | 7/2000 |
| WO | WO 2013/081783 | 6/2013 |
| WO | WO 2015/038503 | 3/2015 |
| WO | WO 2016/144351 | 9/2016 |

OTHER PUBLICATIONS

PubChem-SID-372264414, Modify Date May 25, 2018.
PubChem-SID-293677308, Modify Date: Jan. 20, 2016.
PubChem-SID-133076981, Modify Date: May 31, 2019.
Alexander et al., (Acyloxy)alkyl carbamates as novel bioreversible prodrugs for amines: increased permeation through biological membranes, J. Med. Chem. 1988, 31, 318.
Almarasson, O., et. al., Crystal engineering of the composition of pharmaceutical phases. Do pharmaceutical co-crystals represent a new path to improved medicines?, The Royal Society of Chemistry, 1889-1896, 2004.
Young et al., Structure-activity relationships of substituted 1-pyridyl-2-phenyl-1,2-ethanediones: potent, selective carboxylesterase inhibitors, (2010) J Med Chem 53(24): 8709-8715.
Desai et al., Rapid discovery of a novel series of Abl kinase inhibitors by application of an integrated microfluidic synthesis and screening platform, (2013) J Med Chem 56(7): 3033-3047.
Kaitsiotou et al., Inhibitors to Overcome Secondary Mutations in the Stem Cell Factor Receptor KIT (2017) J Med Chem 60(21): 8801-8815.
U.S. Appl. No. 63/292,407, filed Dec. 21, 2021, Syed Kaleem Ahmed.
WO, PCT/US2022/053714, Dec. 21, 2022, Syed Kaleem Ahmed.

* cited by examiner

*Primary Examiner* — Sikarl A Witherspoon
(74) *Attorney, Agent, or Firm* — Ballard Spahr LLP

(57) ABSTRACT

The present disclosure is concerned with substituted phenyl ethynyl pyridine carboxamide compounds, pharmaceutical compositions comprising the compounds, and methods of treating viral infections due to a Coronavirus such as, for example, Middle East respiratory syndrome coronavirus (MERS-CoV), severe acute respiratory syndrome coronavirus (SARS-CoV), and severe acute respiratory syndrome coronavirus disease 2019 (SARS-CoV-2), using the compounds. This abstract is intended as a scanning tool for purposes of searching in the particular art and is not intended to be limiting of the present invention.

20 Claims, No Drawings

SUBSTITUTED PHENYL ETHYNYL PYRIDINE CARBOXAMIDES AS POTENT INHIBITORS OF SARS VIRUS

CROSS-REFERENCE TO RELATED APPLICATIONS

This application claims the benefit of U.S. Application No. 63/292,407, filed on Dec. 21, 2021, the contents of which are incorporated herein by reference in their entirety.

STATEMENT REGARDING FEDERALLY SPONSORED RESEARCH

This invention was made with government support under grant number 1U19AI0109680-01 and 1U19AI142759-01, awarded by the National Institute of Allergy and Infectious Diseases (NIAID) and the National Institutes of Health (NIH). The government has certain rights in the invention.

BACKGROUND

Coronaviruses are single-stranded, RNA viruses with a large genome in which mutations are very common. There are seven known human types of coronavirus: 229E, OC43, NL63, HKU1, which are often associated with mild upper respiratory tract infections, as well as the virus causing severe acute respiratory syndrome (SARS-CoV), Middle East respiratory syndrome (MERS-CoV), and severe acute respiratory syndrome coronavirus 2 (SARS-CoV-2), each of which are zoonotic but have also caused human disease. Interspecies transmission and the resulting emergent coronaviruses have been important factors in emerging respiratory disease as coronaviruses are known to infect feline, swine, canine, and bat species. Indeed, MERS-CoV, SARS-CoV, and SARS-CoV-2 emerged from animal reservoirs and are now increasingly important respiratory virus threats. To date, over 239 million cases of SARS-CoV-2 have been confirmed in humans, resulting in over 4,500,000 deaths. Thus, there remains a need for potent therapies that can ameliorate coronavirus infection. These needs and others are met by the present invention.

SUMMARY

In accordance with the purpose(s) of the invention, as embodied and broadly described herein, the invention, in one aspect, relates to substituted phenyl ethynyl pyridine carboxamide compounds, pharmaceutical compositions containing the compounds, and methods of using the compounds in, for example, the prevention and treatment of viral infections due to a Coronavirus such as, for example, 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

Thus, in one aspect, disclosed are compounds having a structure represented by a formula:

wherein A is selected from —$NR^{10}C(O)$— and —$C(O)NR^{11}$; wherein each of $R^{10}$, when present, and $R^{11}$, when present, is selected from hydrogen and C1-C4 alkyl; wherein each of $Z^1$ and $Z^2$ is independently selected from —N= and —$C(R^{13})$=; wherein each occurrence of $R^{13}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —$NR^{14}C(O)R^{15}$, —$C(O)NR^{16a}R^{16b}$, —$OSO_2NR^{16a}R^{16b}$, —$NR^{17}SO_2R^{18}$, —$P(O)(OR^{19})_2$, —$CO_2$(C1-C4 alkyl), —$CO_2Cy^1$, —$CO_2$(C1-C4 alkyl)$Cy^1$, $Cy^1$, and —$CH_2Cy^5$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —$OR^{20}$, —$NR^{21a}R^{21b}$, $CH_2NR^{21a}R^{21b}$, and $Cy^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $R^{19}$, when present, is independently selected from hydrogen and C1-C4 alkyl; wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then $R^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and $R^3$ is —NR$^{14}$C(O)R$^{15}$, then $R^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

Also disclosed are compounds having a structure represented by a formula:

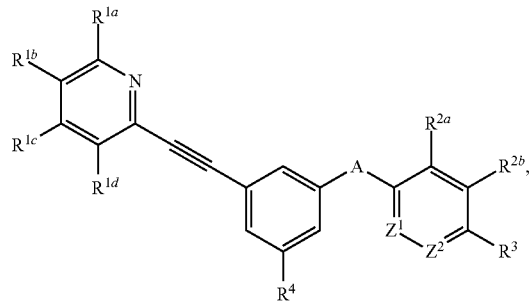

wherein A is selected from —NR$^{10}$C(O)— and —C(O)NR$^{11}$; wherein each of $R^{10}$, when present, and $R^{11}$, when present, is selected from hydrogen and C1-C4 alkyl; wherein each of $Z^1$ and $Z^2$ is independently selected from —N= and —C(R$^{13}$)=; wherein each occurrence of $R^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$; and Cy$^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then $R^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and $R^3$ is —NR$^{14}$C(O)R$^{15}$, then $R^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

Also disclosed are compounds selected from:

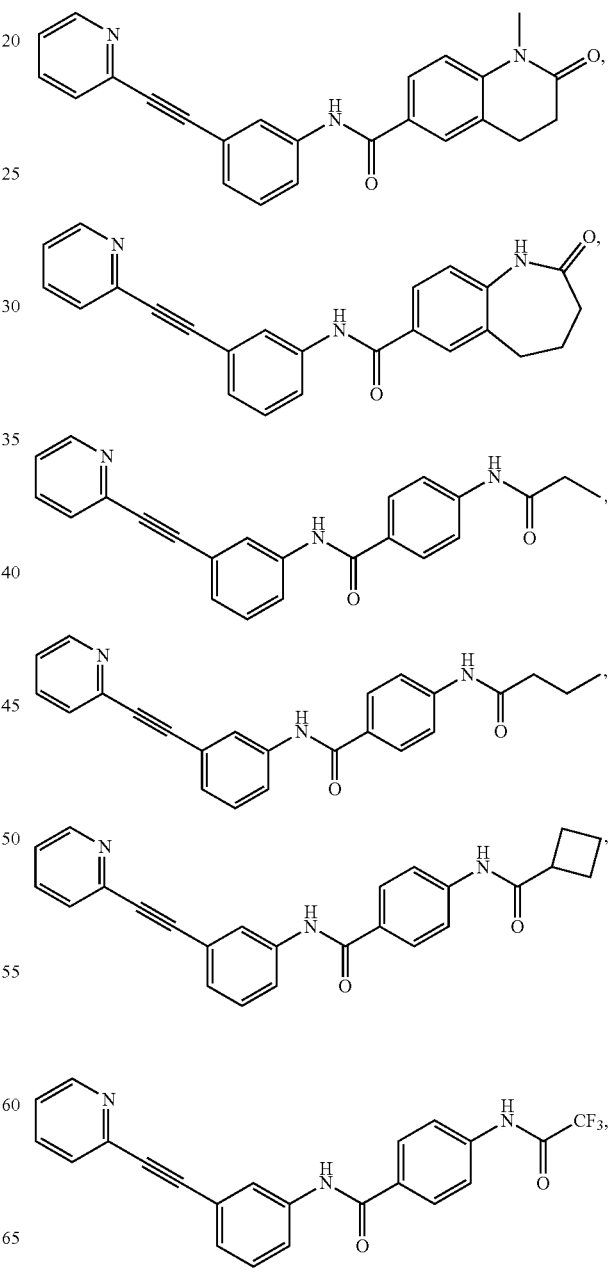

-continued
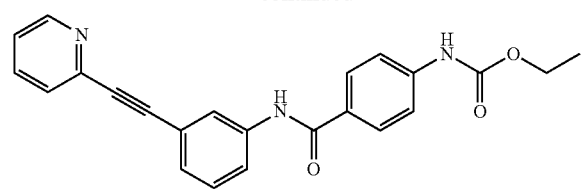
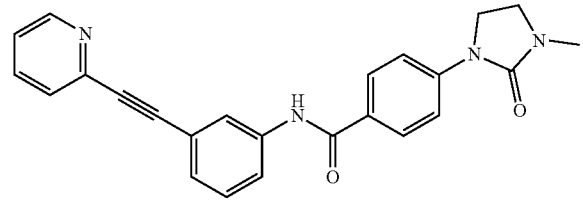
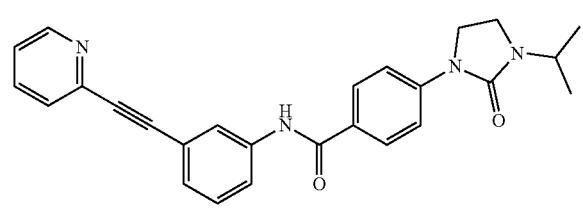
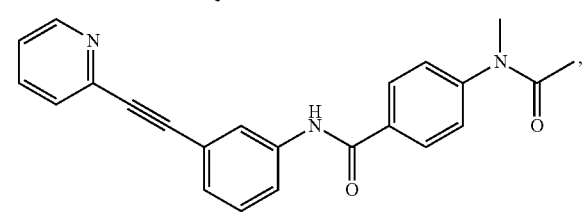
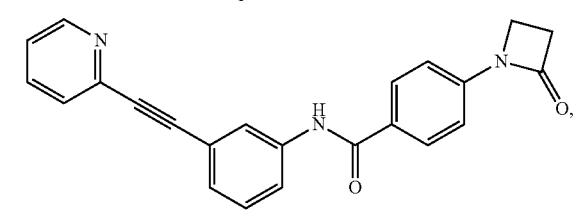
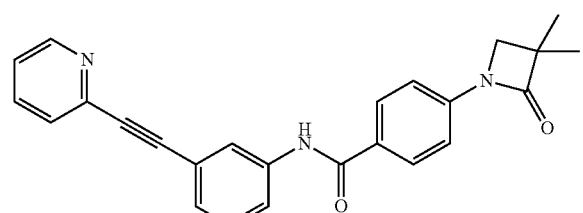
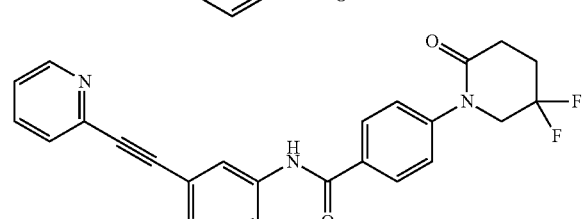
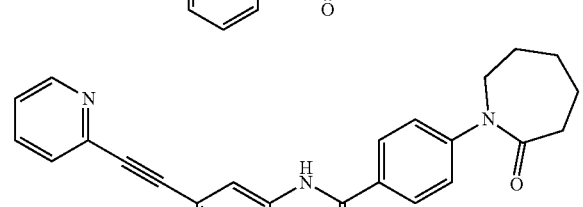
-continued
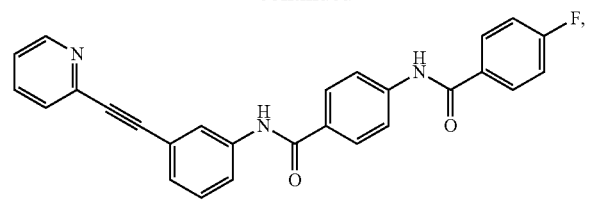
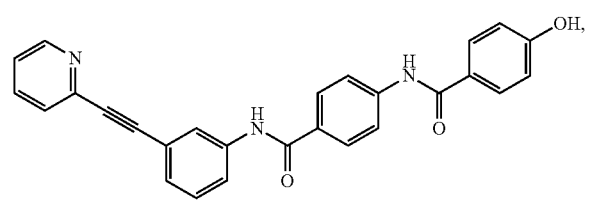
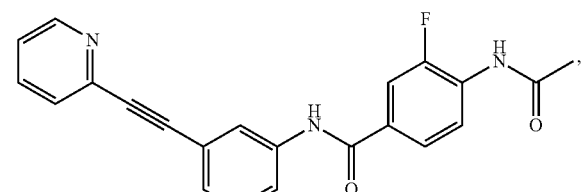
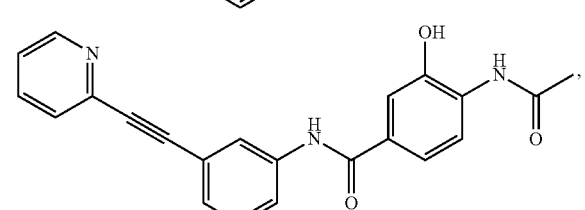
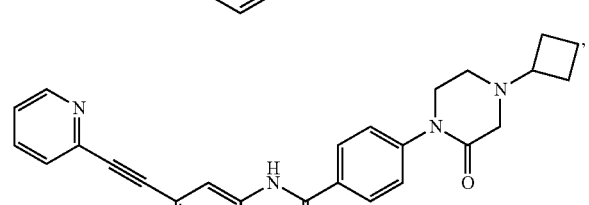
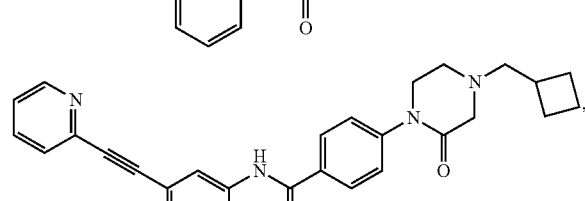
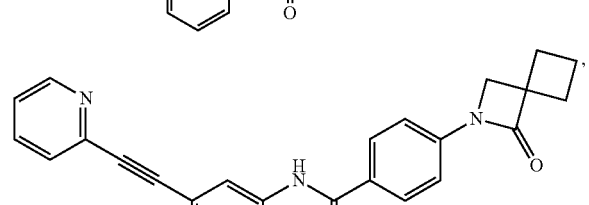
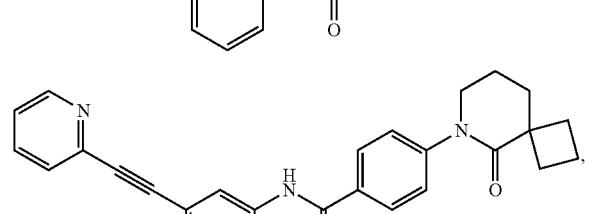

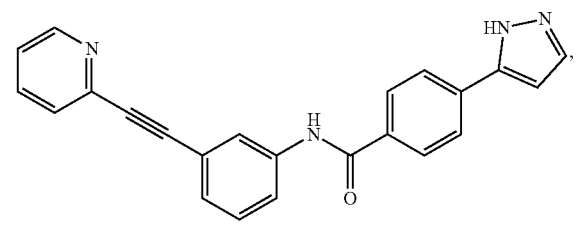
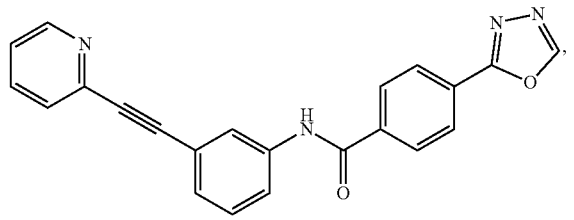
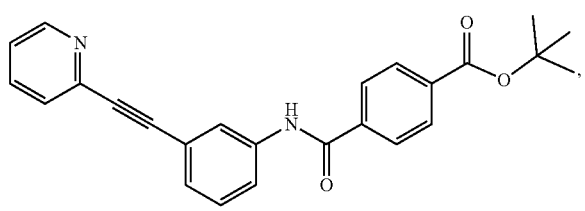
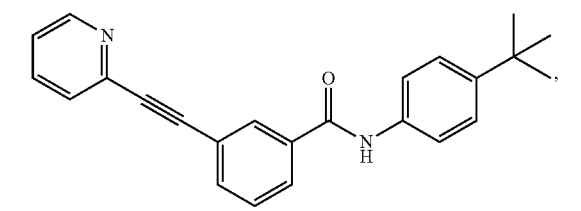
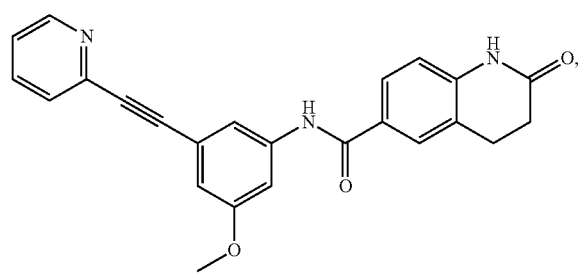
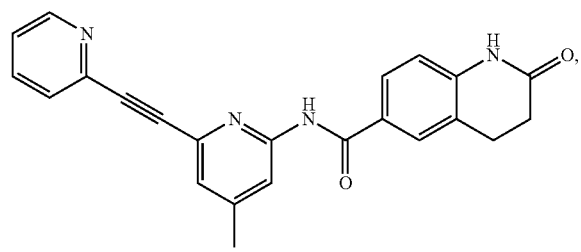
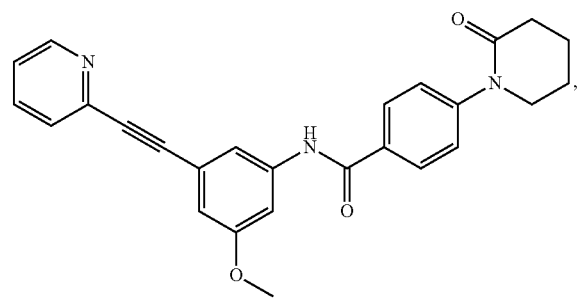
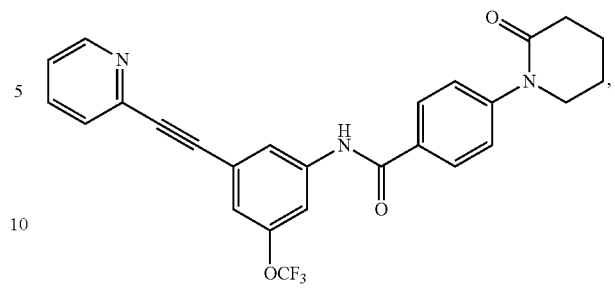
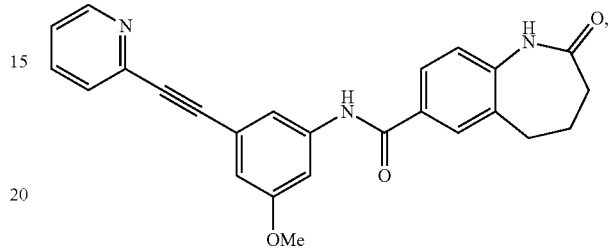
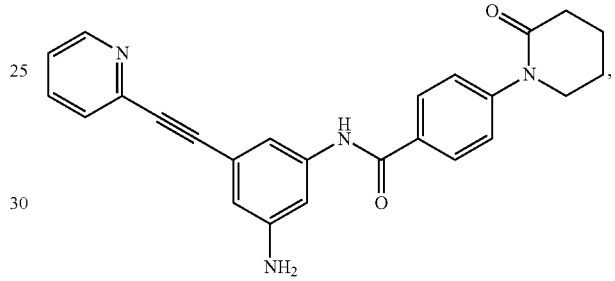
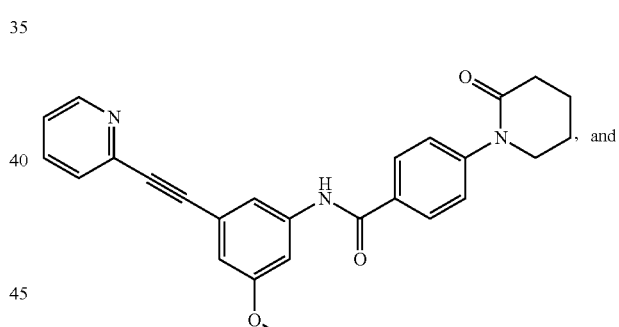
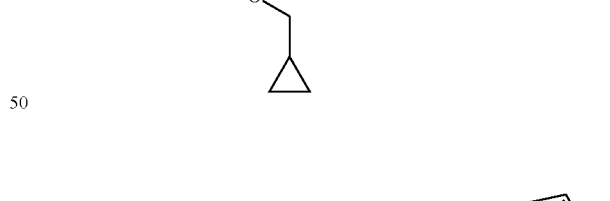
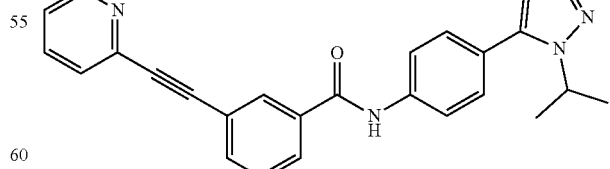
or a pharmaceutically acceptable salt thereof.
Also disclosed are pharmaceutical compositions comprising a therapeutically effective amount of a compound having a structure represented by a formula:

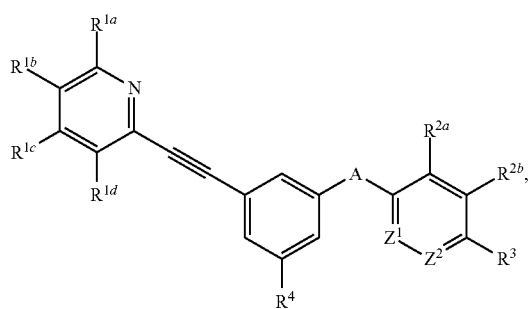

wherein A is selected from —NR¹⁰C(O)— and —C(O)NR¹¹; wherein each of R¹⁰, when present, and R^H, when present, is selected from hydrogen and C1-C4 alkyl; wherein each of $Z^1$ and $Z^2$ is independently selected from —N= and —C($R^{13}$)=; wherein each occurrence of $R^{13}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR¹⁴C(O)R¹⁵, —C(O)NR^{16a}R^{16b}, —OSO₂NR^{16a}R^{16b}, —NR¹⁷SO₂R¹⁸, —P(O)(OR¹⁹)₂, —CO₂(C1-C4 alkyl), —CO₂Cy¹, —CO₂(C1-C4 alkyl)Cy¹, Cy¹, and —CH₂Cy⁵; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR^{21a}R^{21b}, CH₂NR^{21a}R^{21b}, and Cy²; wherein R²⁰, when present, is selected from hydrogen and C1-C4 alkyl; wherein each of R^{21a} and R^{21b}, when present, is independently selected from hydrogen and C1-C4 alkyl; or wherein R^{21a} and R^{21b}, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and R²ᵇ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R^{16a} and R^{16b}, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy⁵, when present, is a C3-C6 heterocycloalkyl substituted with at least one =O group, and substituted with 0, 1, or 2 additional groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R²ᵃ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R²ᵇ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

Also disclosed are pharmaceutical compositions comprising a therapeutically effective amount of a compound having a structure represented by a formula:

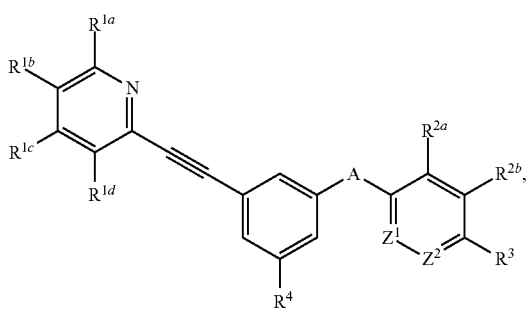

wherein A is selected from —NR¹⁰C(O)— and —C(O)NR¹¹; wherein each of R¹⁰, when present, and R¹¹, when present, is selected from hydrogen and C1-C4 alkyl; wherein each of Z¹ and Z² is independently selected from —N= and —C(R¹³)=; wherein each occurrence of R¹³, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹ᵃ, R¹ᵇ, R¹ᶜ, and R¹ᵈ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R²ᵃ and R²ᵇ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R³ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, —CH₂NR²¹ᵃR²¹ᵇ, and Cy²; wherein R²⁰, when present, is selected from hydrogen and C1-C4 alkyl; wherein each of R²¹ᵃ and R²¹ᵇ, when present, is independently selected from hydrogen and C1-C4 alkyl; or wherein R²¹ᵃ and R²¹ᵇ, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and R²ᵇ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹⁶ᵃ and R¹⁶ᵇ, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; and wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R²ᵃ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R²ᵇ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

Also disclosed are methods for treating a viral infection in a subject in need thereof, the method comprising administering to the subject a compound having a structure represented by a formula:

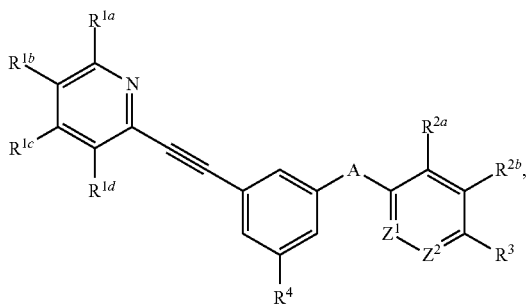

wherein A is selected from —NR¹⁰C(O)— and —C(O)NR¹¹; wherein each of R¹⁰, when present, and R¹¹, when present, is selected from hydrogen and C1-C4 alkyl; wherein each of $Z^1$ and $Z^2$ is independently selected from —N= and —C(R¹³)=; wherein each occurrence of R¹³, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —OSO₂NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, Cy¹, and —CH₂Cy⁵; wherein R¹⁴, when present, is selected from hydrogen and C1-C4 alkyl; —wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, CH₂NR²¹ᵃR²¹ᵇ, and Cy²; wherein R²⁰, when present, is selected from hydrogen and C1-C4 alkyl; wherein each of R²¹ᵃ and R²¹ᵇ, when present, is independently selected from hydrogen and C1-C4 alkyl; or wherein R²¹ᵃ and R²¹ᵇ, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹⁶ᵃ and R¹⁶ᵇ, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy⁵, when present, is a C3-C6 heterocycloalkyl substituted with at least one =O group, and substituted with 0, 1, or 2 additional groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R²ᵃ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl, and wherein R²ᵇ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

Also disclosed are methods for treating a viral infection in a subject in need thereof, the method comprising administering to the subject an effective amount of a compound having a structure represented by a formula:

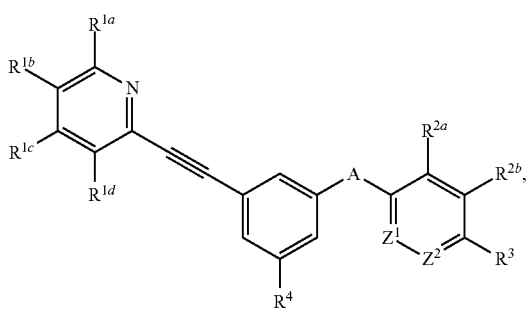

wherein A is selected from —NR¹⁰C(O)— and —C(O)NR¹¹—; wherein each of $R^{10}$, when present, and $R^{11}$, when present, is selected from hydrogen and C1-C4 alkyl; wherein each of $Z^1$ and $Z^2$ is independently selected from —N═ and —C($R^{13}$)═; wherein each occurrence of $R^{13}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, —CH₂NR²¹ᵃR²¹ᵇ, and Cy²; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; and wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein Ra is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

Also disclosed are kits comprising a compound having a structure represented by a formula:

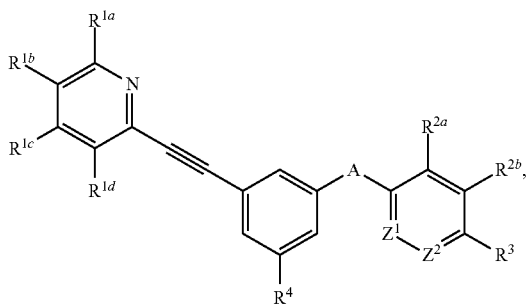

wherein A is selected from —NR¹⁰C(O)— and —C(O)NR¹¹; wherein each of R¹⁰, when present, and R¹¹, when present, is selected from hydrogen and C1-C4 alkyl; wherein each of $Z^1$ and $Z^2$ is independently selected from —N= and —C(R¹³)=; wherein each occurrence of R¹³, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —OSO₂NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, aCy¹, and —CH₂Cy⁵; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, CH₂NR²¹ᵃR²¹ᵇ, and Cy²; wherein R²⁰, when present, is selected from hydrogen and C1-C4 alkyl; wherein each of R²¹ᵃ and R²¹ᵇ, when present, is independently selected from hydrogen and C1-C4 alkyl; or wherein R²¹ᵃ and R²¹ᵇ, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and R²ᵇ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹⁶ᵃ and R¹⁶ᵇ, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy⁵, when present, is a C3-C6 heterocycloalkyl substituted with at least one =O group, and substituted with 0, 1, or 2 additional groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R²ᵃ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R²ᵇ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more selected from: (a) at least one antiviral agent; (b) at least one immunity booster; (c) instructions for administering the compound in connection with treating a viral infection; (d) instructions for administering the compound in connection with reducing the risk of viral infection; and (e) instructions for treating a viral infection, wherein the viral infection is due to a Coronavirus.

Also disclosed are kits comprising a compound having a structure represented by a formula:

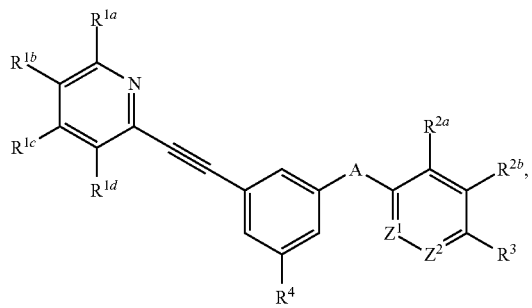

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more selected from: (a) at least one antiviral agent; (b) at least one immunity booster; (c) instructions for administering the compound in connection with treating a viral infection; (d) instructions for administering the compound in connection with reducing the risk of viral infection; and (e) instructions for treating a viral infection, wherein the viral infection is due to a Coronavirus.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$CC_{50}$" is intended to refer to the concentration of a substance (e.g., a compound or a drug) that is required for 50% reduction of cell viability. In one aspect, a $CC_{50}$ can refer to the concentration of a substance that is required for 50% reduction of cell viability in vivo, as further defined elsewhere herein. In a further aspect, $CC_{50}$ can refer to the concentration of a substance that is required for 50% reduction of cell viability in vitro, as further defined elsewhere herein.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and cosolvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful in treating disorders associated with a viral infection due to a Coronavirus (e.g., Middle East Respiratory Syndromes coronavirus (MERS-CoV), Severe Acute Respiratory Syndrome coronavirus (SARS-CoV), and SARS-CoV-2).

In one aspect, the disclosed compounds exhibit antiviral activity.

In one aspect, the compounds of the invention are useful in inhibiting viral activity in a mammal. In a further aspect, the compounds of the invention are useful in inhibiting viral activity in at least one cell.

In one aspect, the compounds of the invention are useful in the treatment of viral infections, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

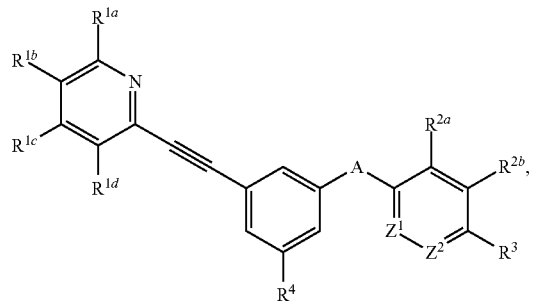

wherein A is selected from —NR$^{10}$C(O)— and —C(O)NR$^{11}$; wherein each of R$^{10}$, when present, and R$^H$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and R²ᵇ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹⁶ᵃ and R¹⁶ᵇ, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise a 5- to 7-membered heterocycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of R¹⁹, when present, is independently selected from hydrogen and C1-C4 alkyl; wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy⁵, when present, is a C3-C6 heterocycloalkyl substituted with at least one =O group, and substituted with 0, 1, or 2 additional groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R²ᵃ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R²ᵇ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR¹⁰C(O)—, then R³ is —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹, and provided that when A is —NR¹⁰C(O)— and R³ is —NR¹⁴C(O)R¹⁵, then R¹⁵ is selected from C1-C4 alkyl, C1-C4 haloalkyl, C1-C4 alkoxy, C1-C4 haloalkoxy, C1-C4 aminoalkyl, —NR²¹ᵃR²¹ᵇ, and —CH₂NR²¹ᵃR²¹ᵇ, or a pharmaceutically acceptable salt thereof.

In one aspect, disclosed are compounds having a structure represented by a formula:

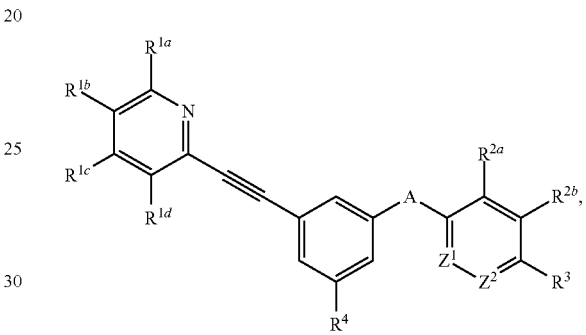

wherein A is selected from —NR¹⁰C(O)— and —C(O)NR¹¹; wherein each of R¹⁰, when present, and R¹¹, when present, is selected from hydrogen and C1-C4 alkyl; wherein each of Z¹ and Z² is independently selected from —N= and —C(R¹³)=; wherein each occurrence of R¹³, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R¹ᵃ, R¹ᵇ, R¹ᶜ, and R¹ᵈ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R³ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, —CH₂NR²¹ᵃR²¹ᵇ; and Cy²; wherein R²⁰, when present, is selected from hydrogen and C1-C4 alkyl; wherein each of R²¹ᵃ and R²¹ᵇ, when present, is independently selected from hydrogen and C1-C4 alkyl; or wherein R²¹ᵃ and R²¹ᵇ, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then R$^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and R$^3$ is —NR$^{14}$C(O)R$^{15}$, then R$^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

In one aspect, disclosed are compounds selected from:

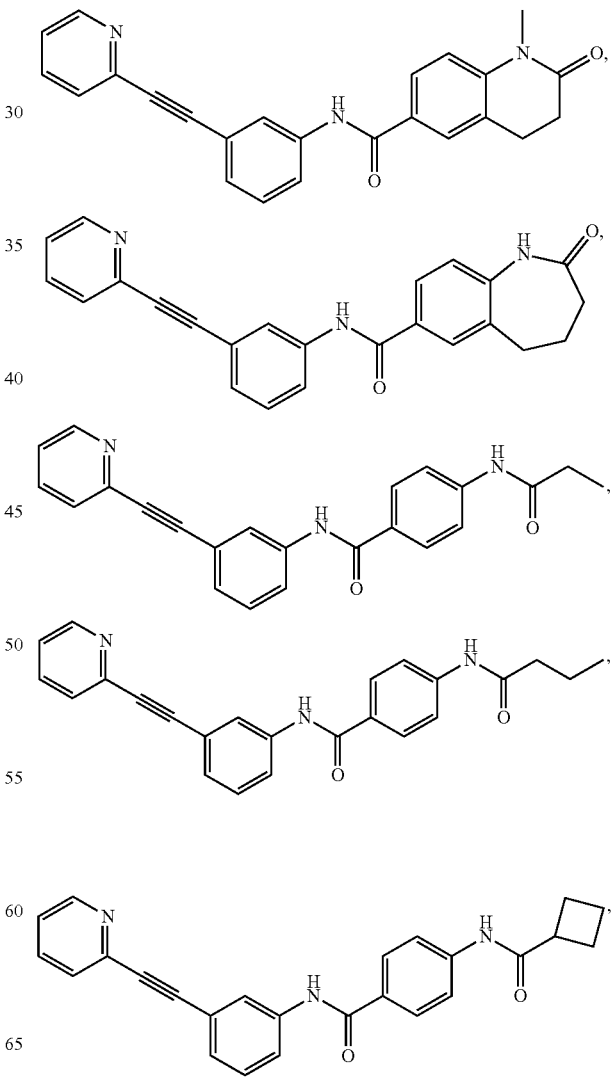

37
-continued
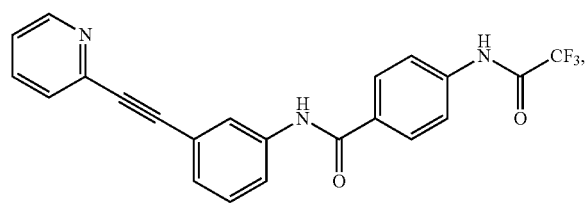
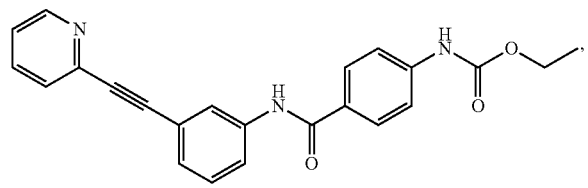
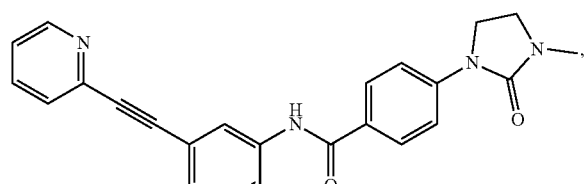
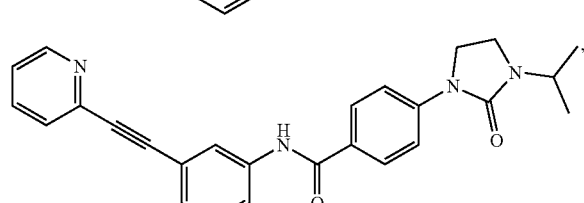
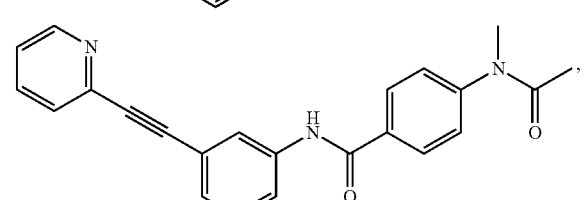
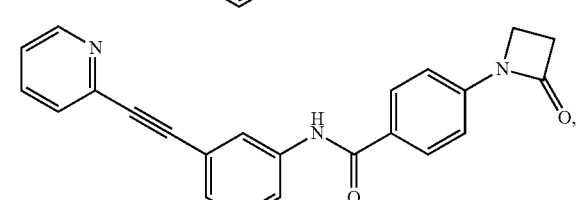
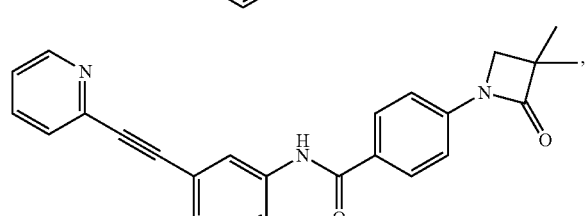
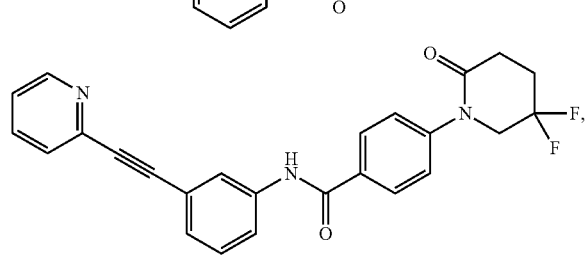
38
-continued
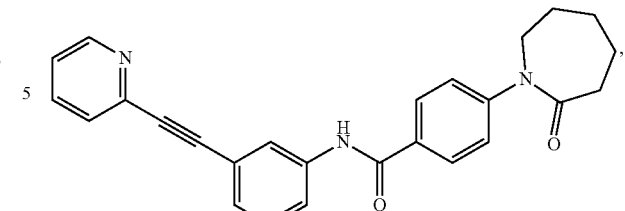
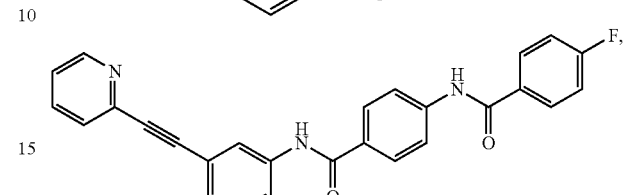
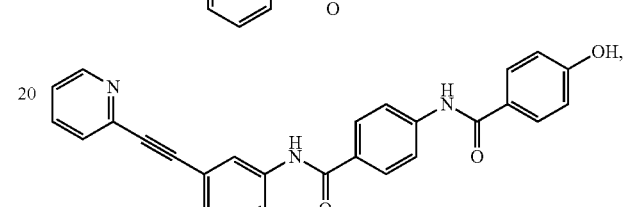
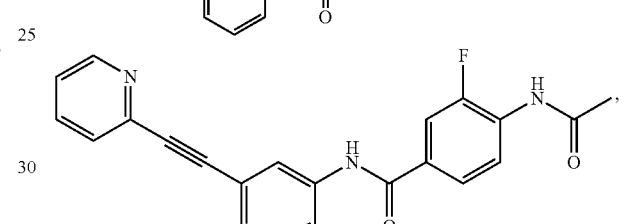
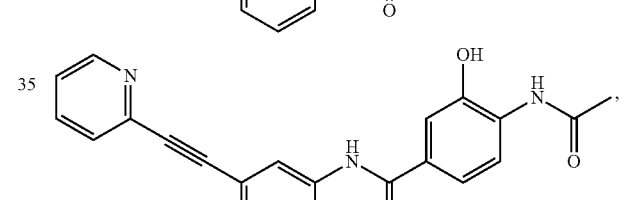
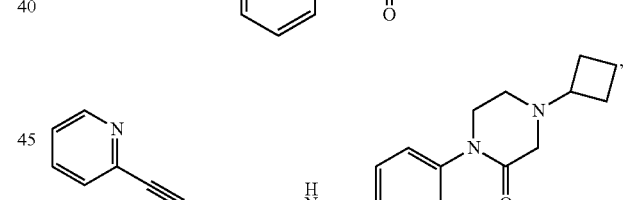
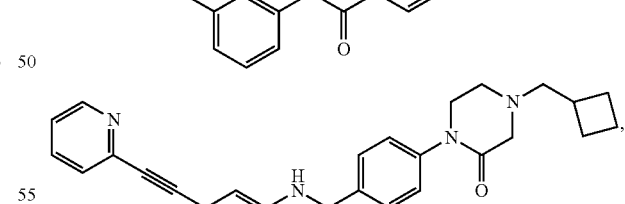
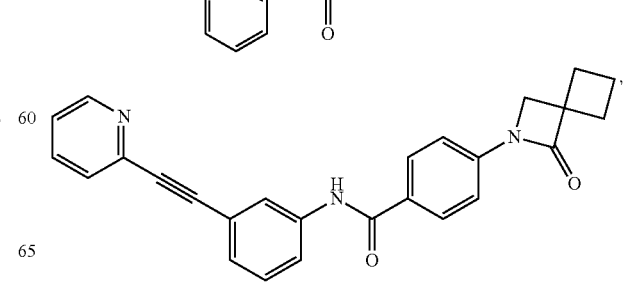

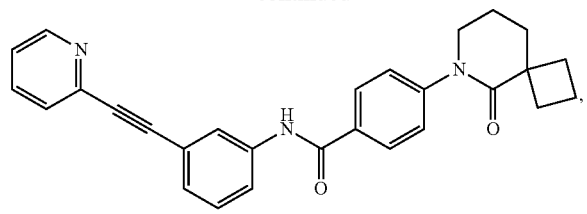
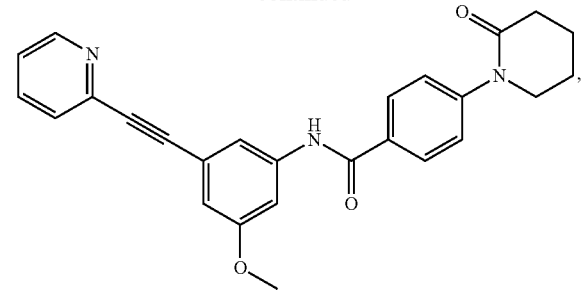
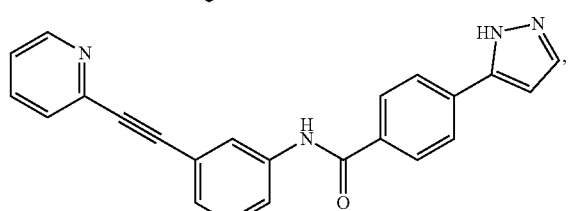
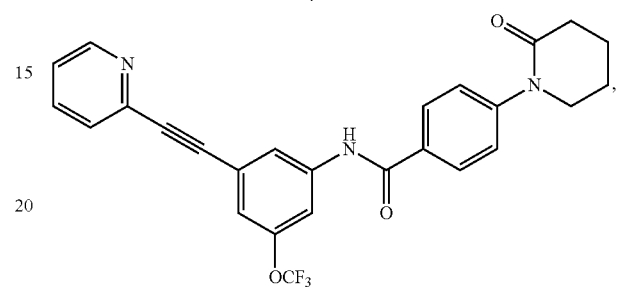
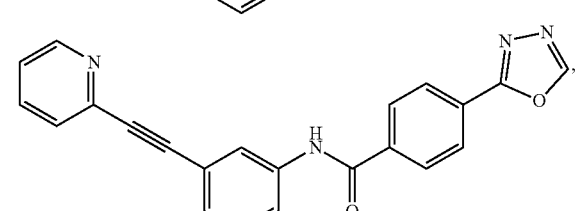
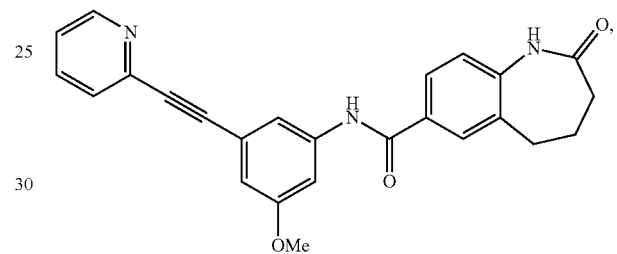
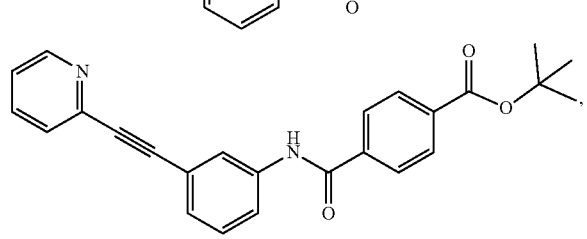
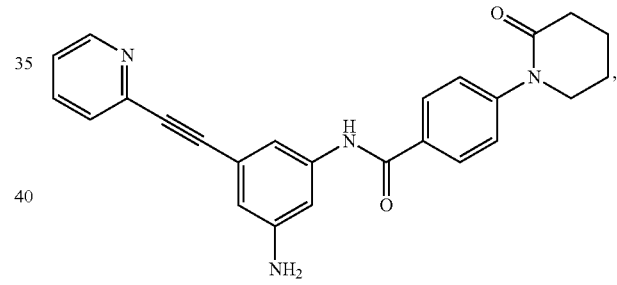
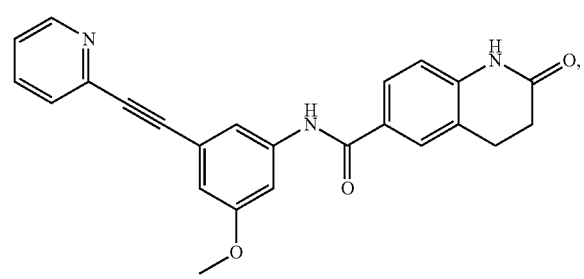
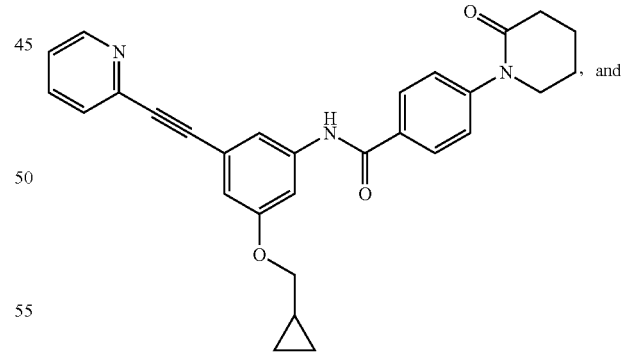
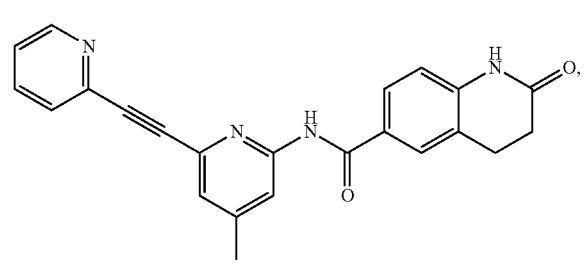
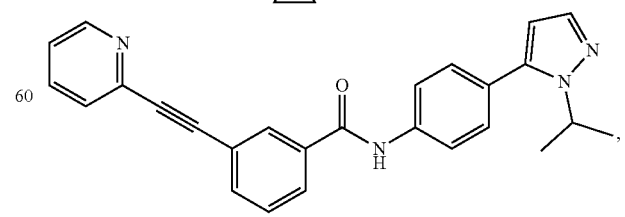
or a pharmaceutically acceptable salt thereof.

In various aspects, the compound has a structure represented by a formula:

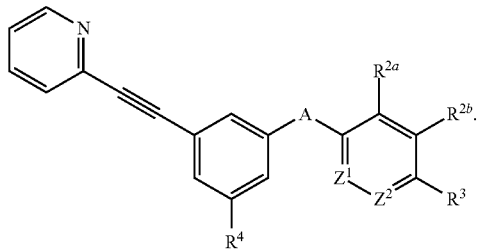

In various aspects, the compound has a structure represented by a formula:

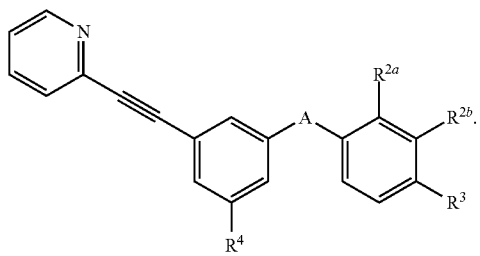

In various aspects, the compound has a structure represented by a formula:

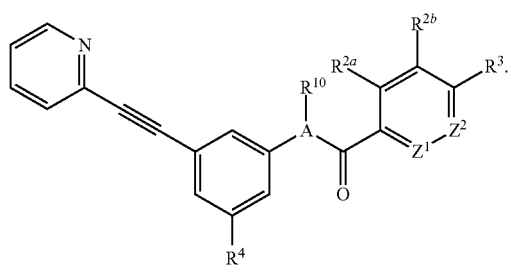

In various aspects, the compound has a structure represented by a formula:

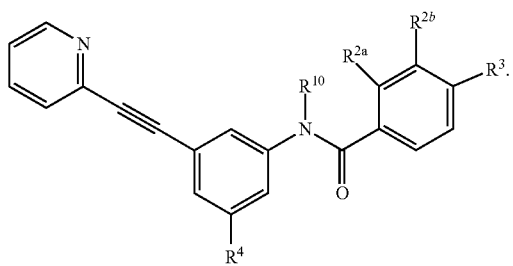

In various aspects, the compound has a structure represented by a formula:

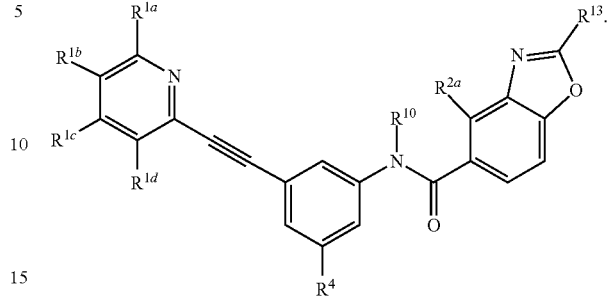

In various aspects, the compound has a structure represented by a formula:

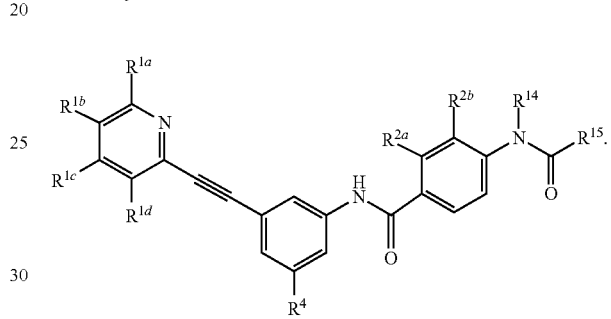

In various aspects, the compound has a structure represented by a formula:

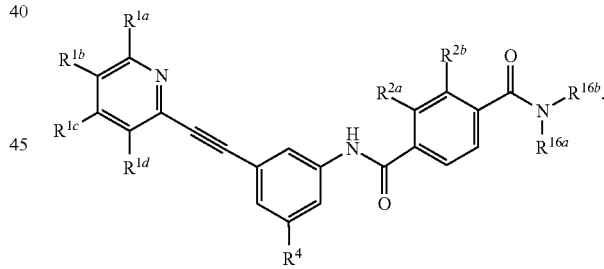

In various aspects, the compound has a structure represented by a formula:

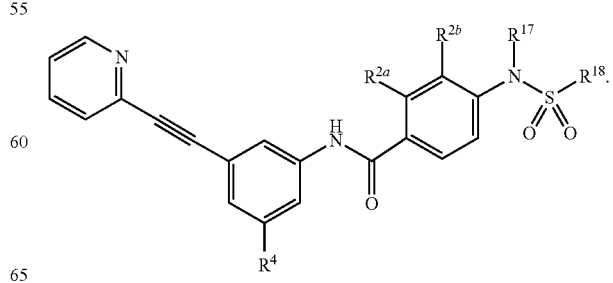

In various aspects, the compound has a structure represented by a formula:

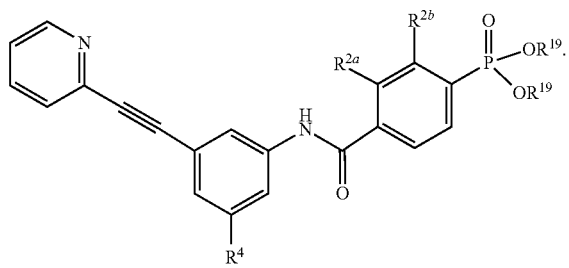

In various aspects, the compound has a structure represented by a formula:

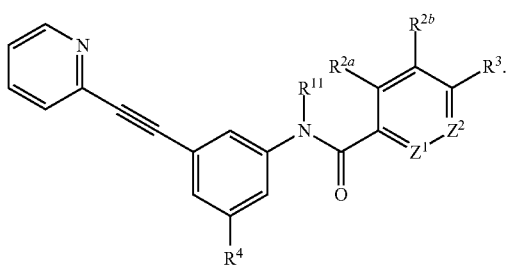

In various aspects, the compound has a structure represented by a formula:

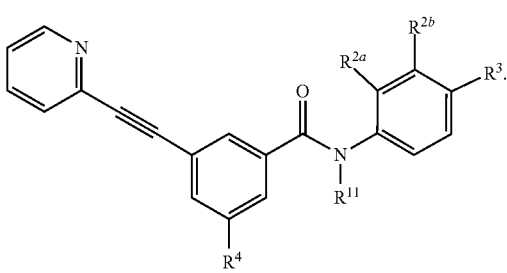

In various aspects, the compound has a structure represented by a formula:

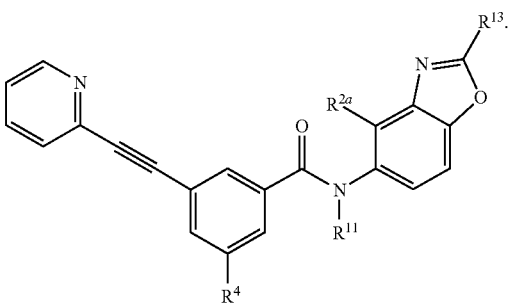

In various aspects, the compound has a structure represented by a formula:

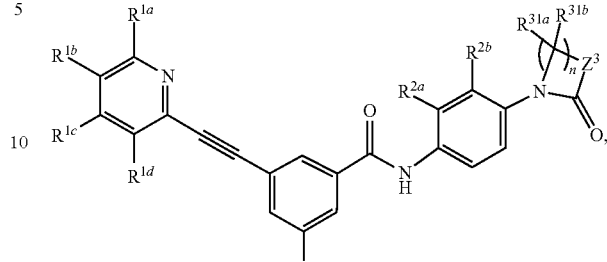

wherein n is selected from 1, 2, 3, 4, 5, and 6; wherein $Z^3$ is selected from —O—, —$NR^{40}$—, and —$CR^{41a}R^{41b}$—; wherein $R^{40}$, when present, is selected from hydrogen and C1-C4 alkyl; wherein each of $R^{41a}$ and $R^{41b}$, when present, is independently selected from hydrogen and C1-C4 alkyl; and wherein each occurrence of $R^{31a}$ and $R^{31b}$, when present, is independently selected from hydrogen, halogen, and C1-C4 alkyl.

In various aspects, the compound has a structure represented by a formula:

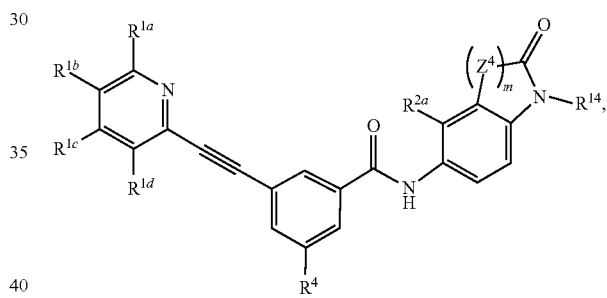

wherein m is selected from 1, 2, and 3; wherein each occurrence of $Z^4$ is independently selected from —O—, —$NR^{42}$—, and —$CR^{43a}R^{43b}$—; wherein each occurrence of $R^{42}$, when present, is independently selected from hydrogen and C1-C4 alkyl; and wherein each occurrence of $R^{43a}$ and $R^{43b}$, when present, is independently selected from hydrogen and C1-C4 alkyl, provided that no more than one occurrence of $Z^4$ is —O— or —$NR^{42}$—.

In various aspects, the compound has a structure represented by a formula:

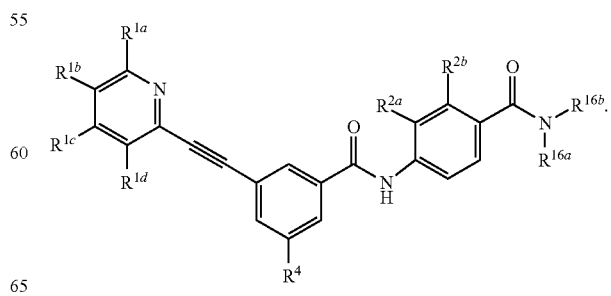

In various aspects, the compound has a structure represented by a formula:

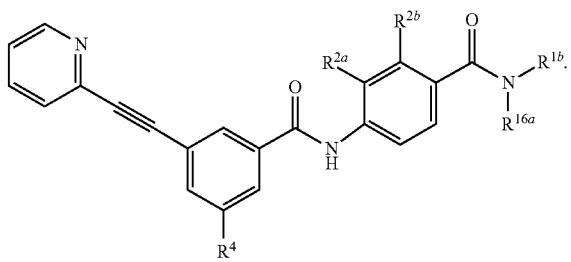

In various aspects, the compound has a structure represented by a formula:

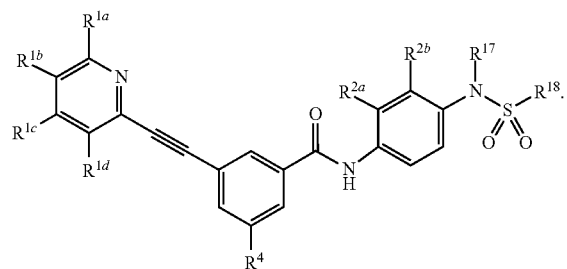

In various aspects, the compound has a structure represented by a formula:

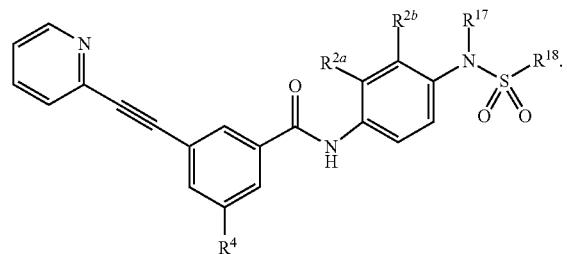

In various aspects, the compound has a structure represented by a formula:

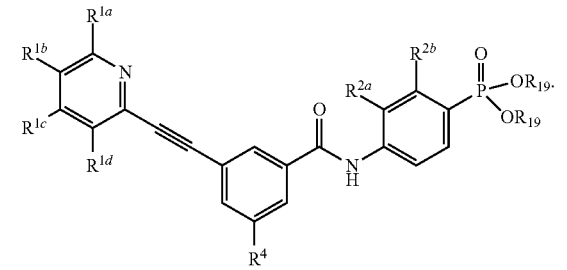

In various aspects, the compound has a structure represented by a formula:

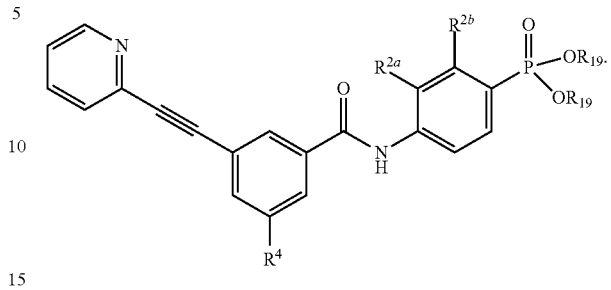

In various aspects, the compound is selected from:

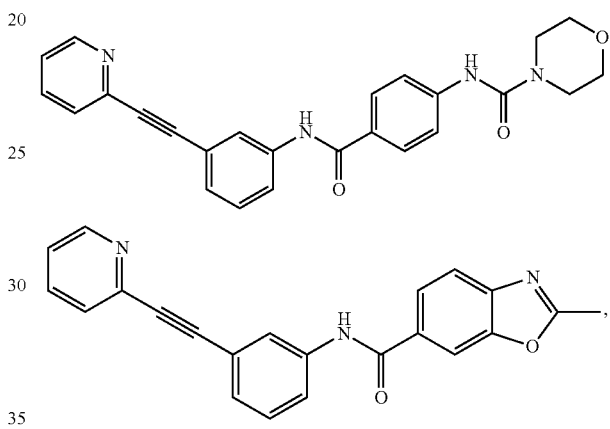

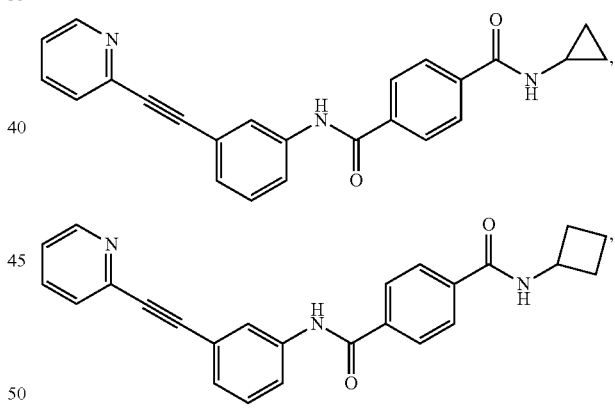

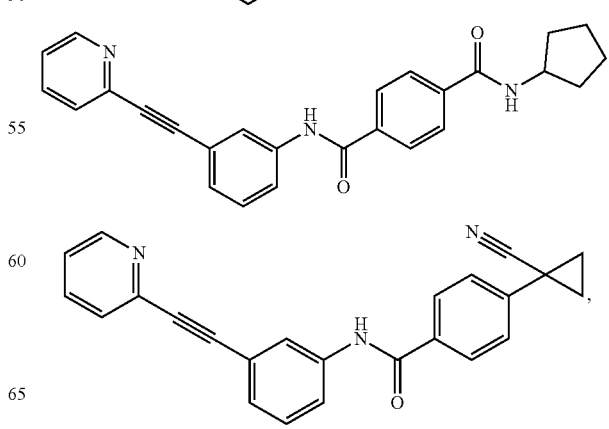

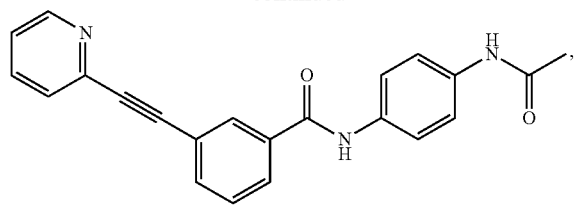
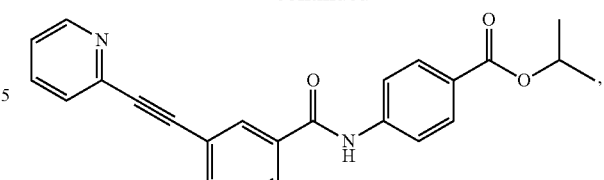
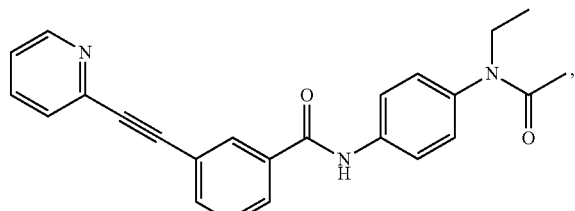
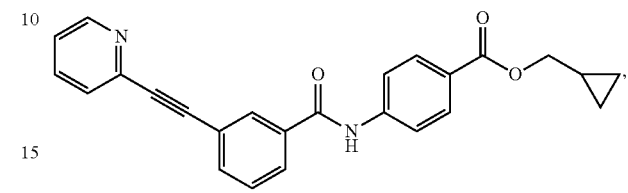
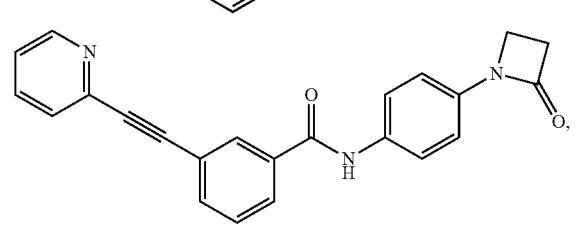
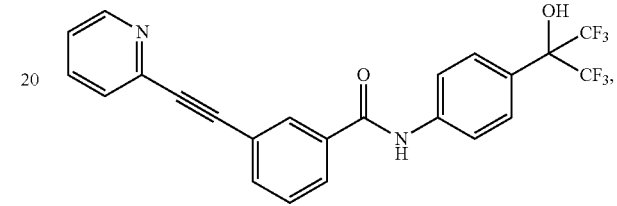
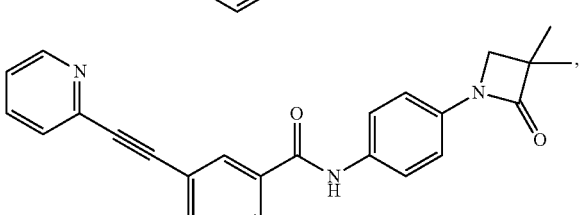
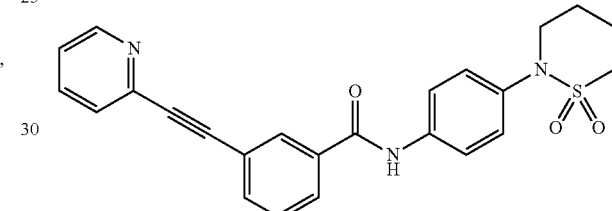
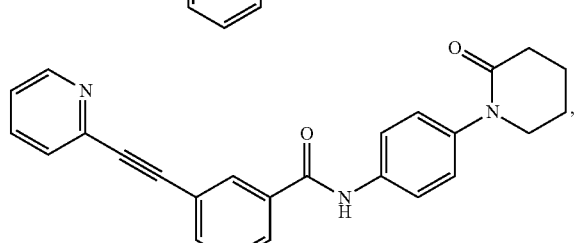
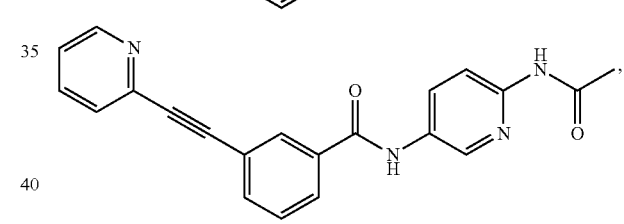
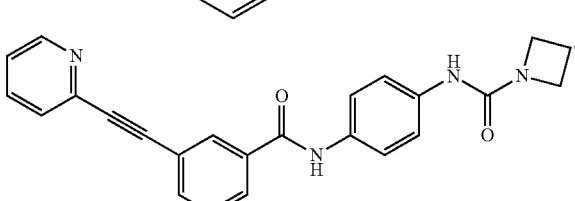
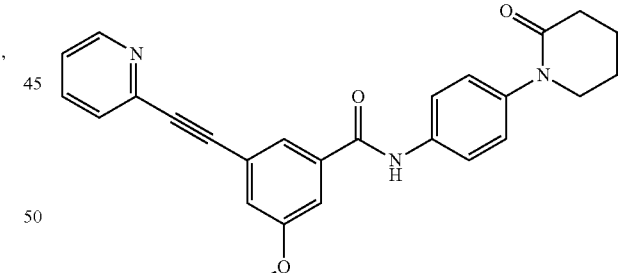
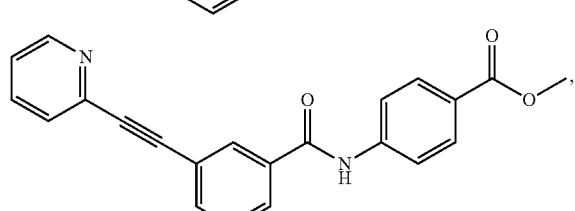
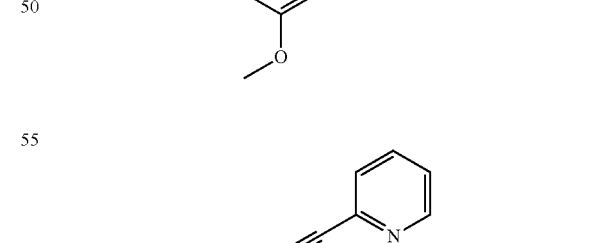
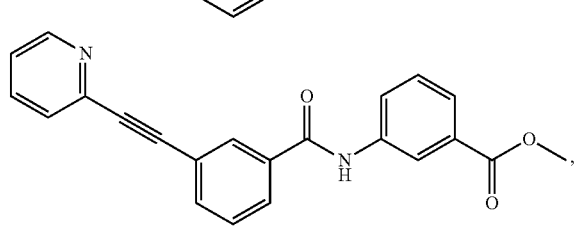
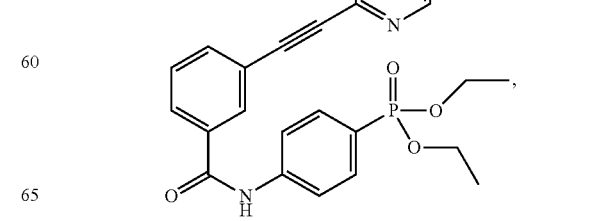

-continued
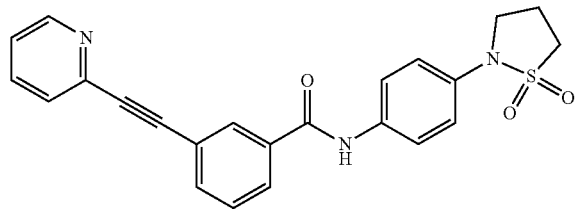
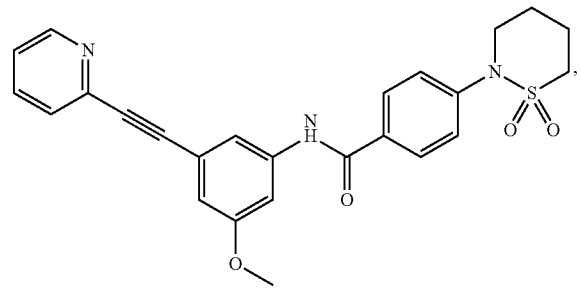
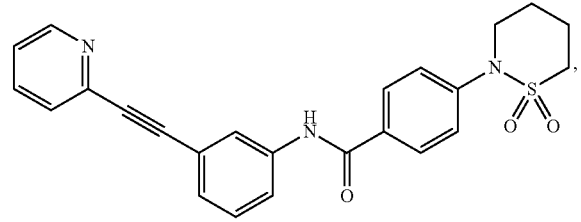
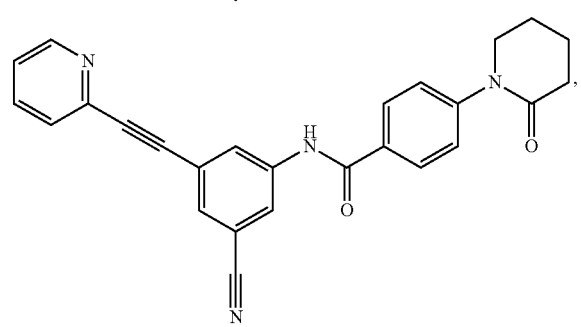
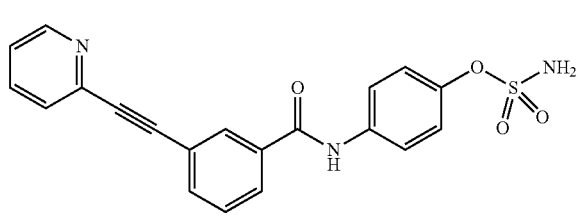
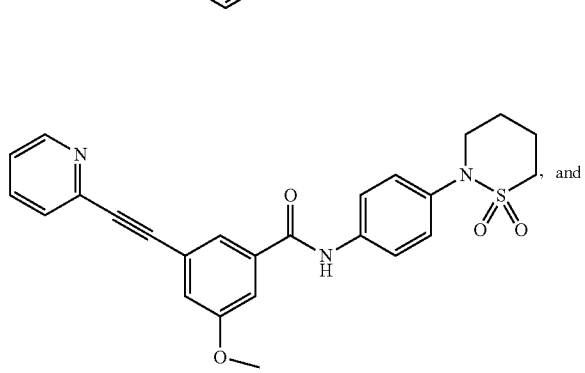
-continued
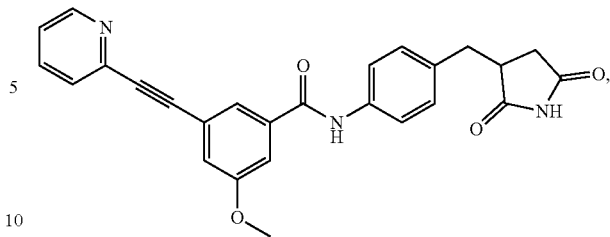
or a pharmaceutically acceptable salt thereof.
In various aspects, the compound is selected from:
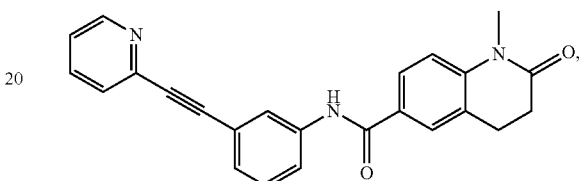
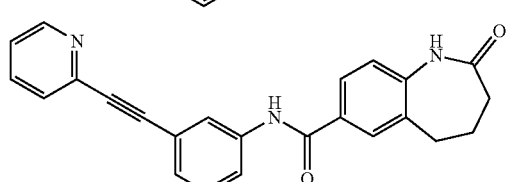
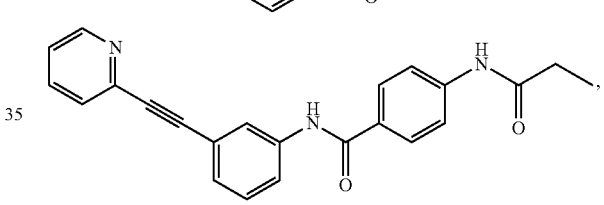
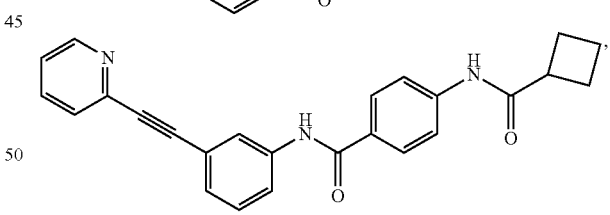
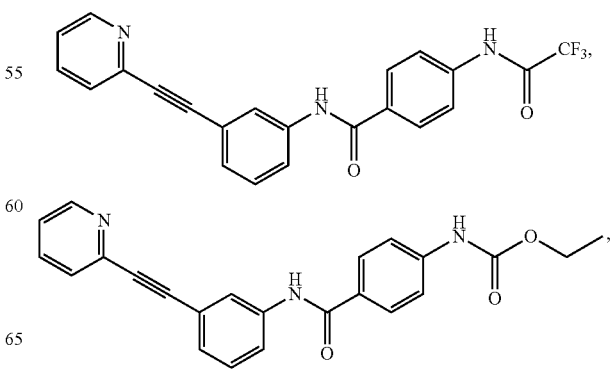

51
-continued
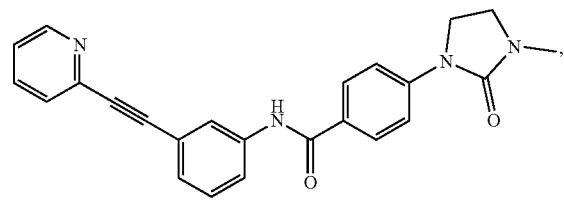
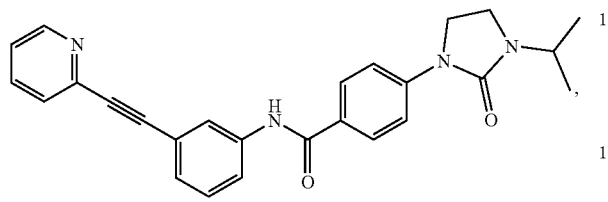
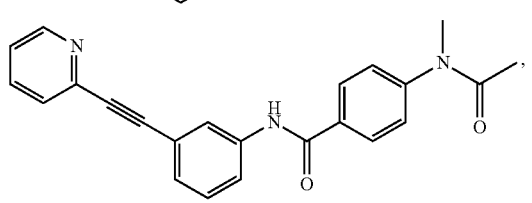
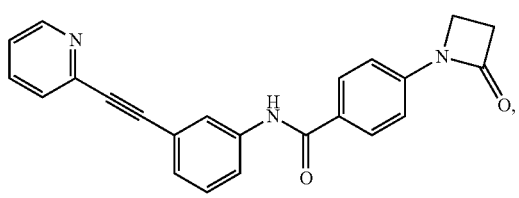
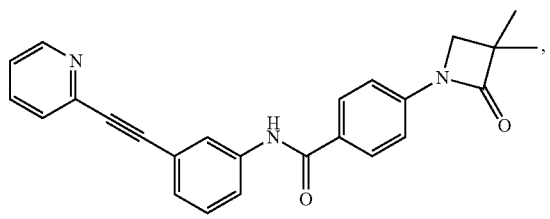
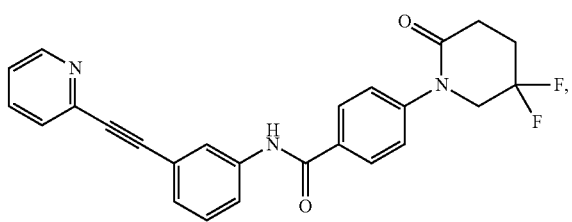
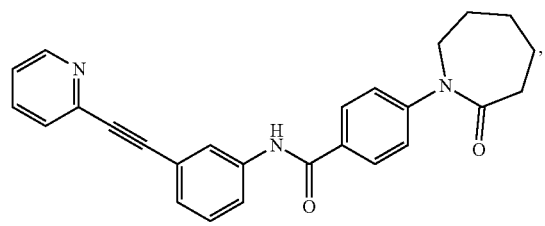
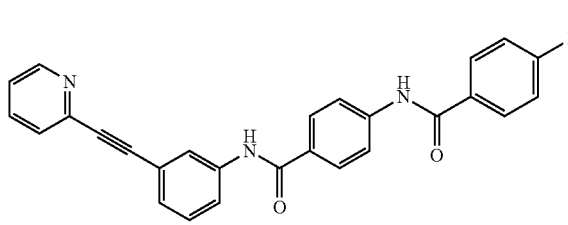
52
-continued
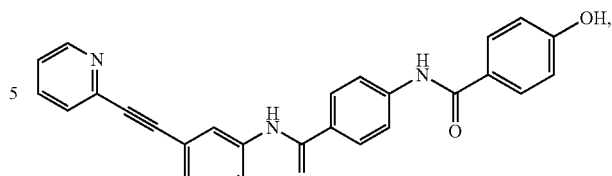
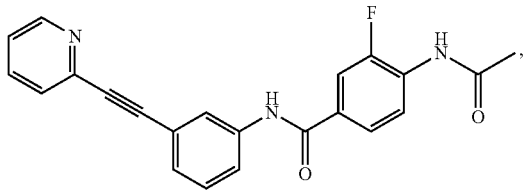
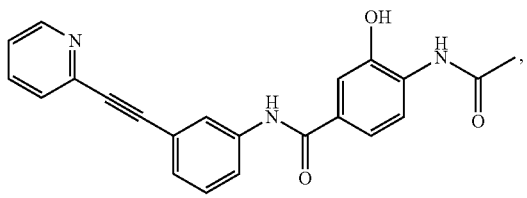
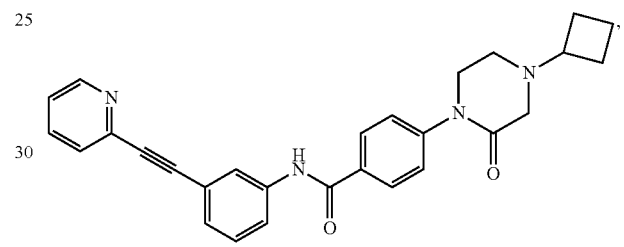
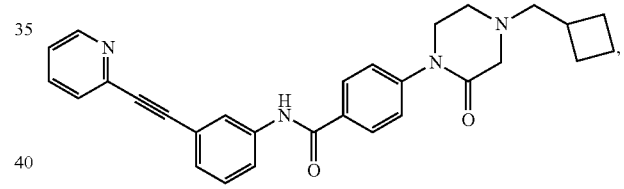
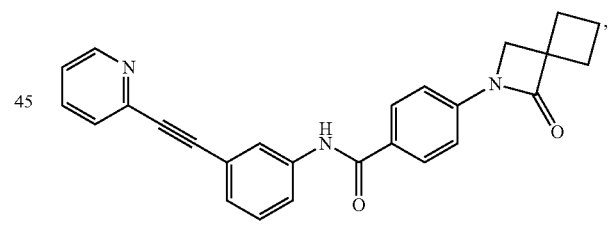
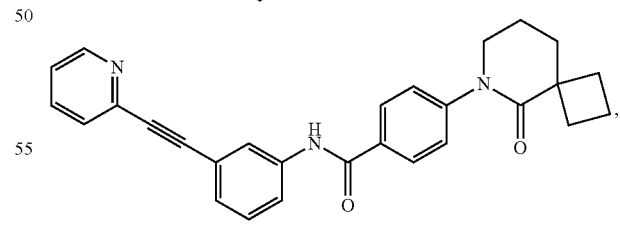
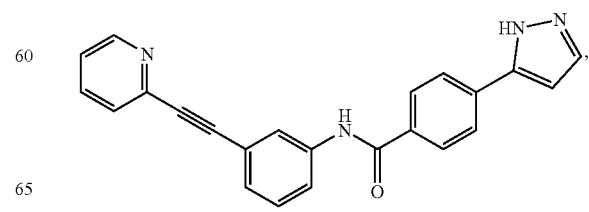

53
-continued

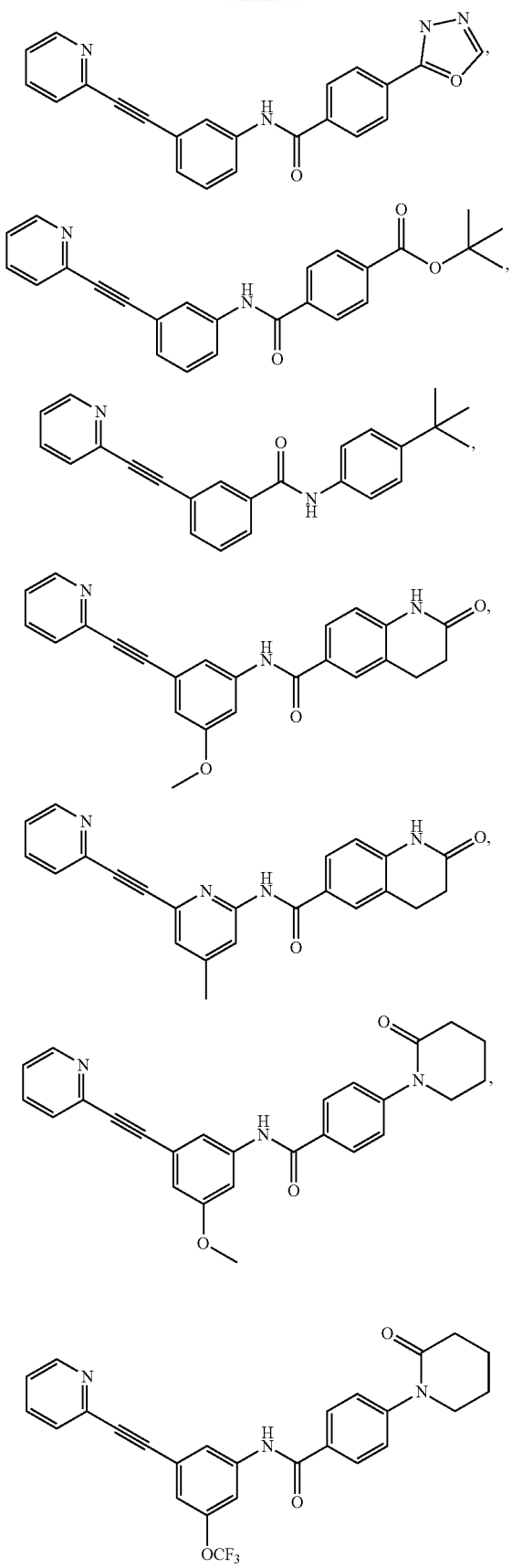

54
-continued

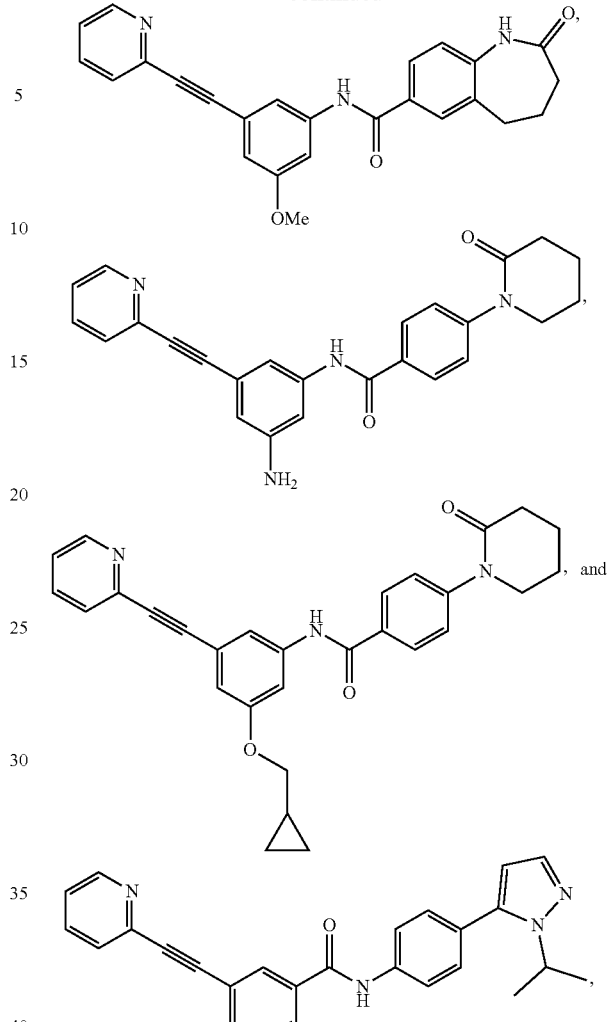

or a pharmaceutically acceptable salt thereof.

In various aspects, the compound has a structure represented by a formula:

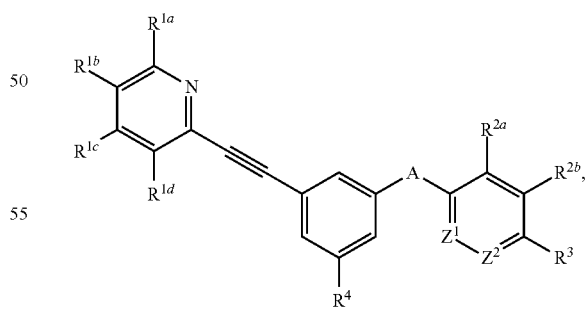

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N═ and —C(R$^{13}$)═; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

In various aspects, the compound has a structure represented by a formula:

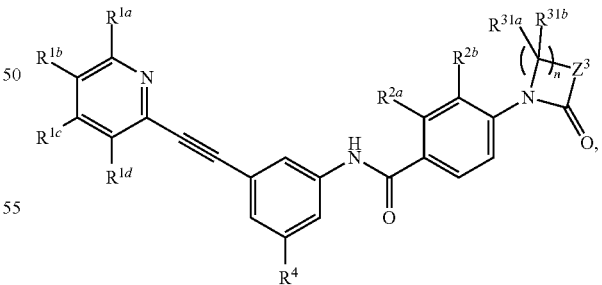

wherein n is selected from 1, 2, 3, 4, 5, and 6; wherein $Z^3$ is selected from —O—, —NR$^{40}$—, and —CR$^{41a}$R$^{41b}$, wherein $R^{40}$, when present, is selected from hydrogen and C1-C4 alkyl; wherein each of $R^{41a}$ and $R^{41b}$, when present, is independently selected from hydrogen and C1-C4 alkyl; and wherein each occurrence of $R^{31a}$ and $R^{31b}$, when present, is independently selected from hydrogen, halogen, and C1-C4 alkyl.

In various aspects, the compound has a structure represented by a formula:

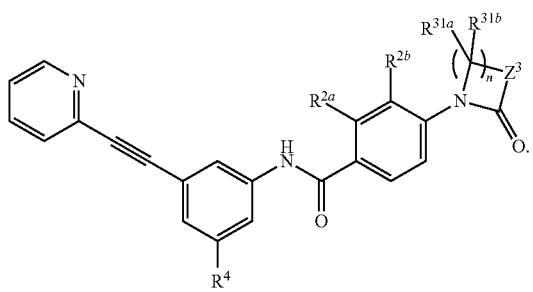

In various aspects, the compound has a structure represented by a formula:

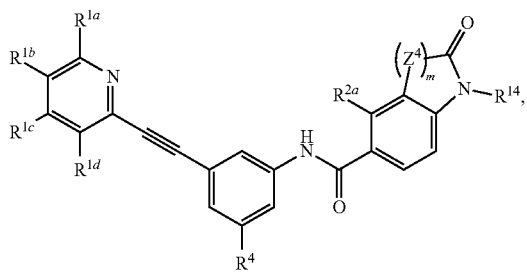

wherein m is selected from 1, 2, and 3; wherein each occurrence of $Z^4$ is independently selected from —O—, —NR$^{42}$—, and —CR$^{43a}$R$^{43b}$; wherein each occurrence of R$^{42}$, when present, is independently selected from hydrogen and C1-C4 alkyl; and wherein each occurrence of R$^{43a}$ and R$^{43b}$, when present, is independently selected from hydrogen and C1-C4 alkyl, provided that no more than one occurrence of $Z^4$ is —O— or —NR$^{42}$—.

In various aspects, the compound has a structure represented by a formula:

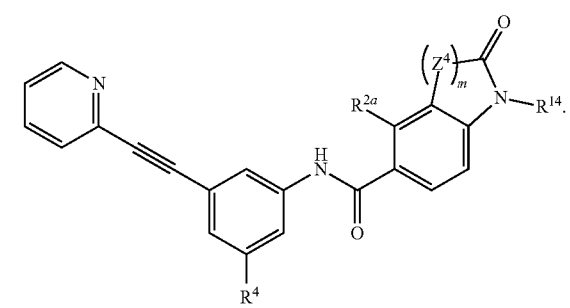

In various aspects, the compound is:

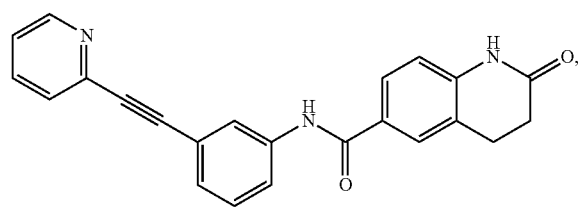

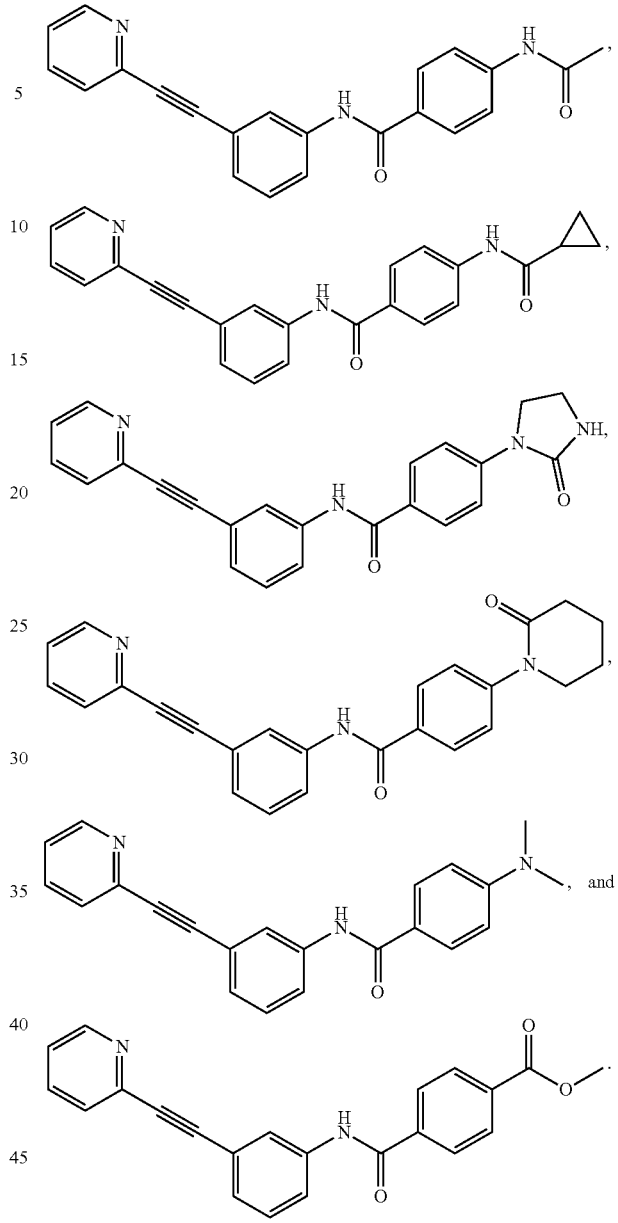

In various aspects, n is selected from 1, 2, 3, 4, 5, and 6. In a further aspect, n is selected from 1, 2, 3, 4, and 5. In a still further aspect, n is selected from 1, 2, 3, and 4. In yet a further aspect, n is selected from 1, 2, and 3. In an even further aspect, n is selected from 1 and 2. In a still further aspect, n is 3. In yet a further aspect, n is 2. In an even further aspect, n is 1.

In various aspects, m is selected from 1, 2, and 3. In a further aspect, m is selected from 1 and 2. In a still further aspect, m is 3. In yet a further aspect, m is 2. In an even further aspect, m is 1.

a. A Groups

In one aspect, A is selected from —NR$^{10}$C(O)— and —C(O)NR$^{11}$—.

In a further aspect, A is —NR$^{10}$C(O)—. In a still further aspect, A is —N(C1-C4 alkyl)C(O)—. In yet a further aspect, A is —NHC(O)—.

In a further aspect, A is —C(O)NR$^{11}$—. In a still further aspect, A is —C(O)N(C1-C4 alkyl)-. In yet a further aspect, A is —C(O)NH—.

b. $Z^1$ and $Z^2$ Groups

In one aspect, each of $Z^1$ and $Z^2$ is independently selected from —N= and —C(R$^{13}$)=. In a further aspect, each of $Z^1$ and $Z^2$ is —N=. In a still further aspect, each of $Z^1$ and $Z^2$ is —C(R$^{13}$)=. In yet a further aspect, each of $Z^1$ and $Z^2$ is —C(R$^{13}$)=, wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, each of $Z^1$ and $Z^2$ is —CH=.

In a further aspect, one of $Z^1$ and $Z^2$ is —N=. In a still further aspect, each of $Z^1$ and $Z^2$ is —N=.

In a further aspect, one of $Z^1$ and $Z^2$ is —C(R$^{13}$)=. In a still further aspect, each of $Z^1$ and $Z^2$ is —C(R$^{13}$)=. In yet a further aspect, each occurrence of R$^{13}$ is hydrogen.

In a further aspect, $Z^1$ is —N= and $Z^2$ is —C(R$^{13}$)=. In a still further aspect, $Z^1$ is —N= and $Z^2$ is —C(R$^{13}$)=, wherein R$^{13}$ is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Z^1$ is —N= and $Z^2$ is —CH=.

In a further aspect, $Z^2$ is —N= and $Z^1$ is —C(R$^{13}$)=. In a still further aspect, $Z^2$ is —N= and $Z^1$ is —C(R$^{13}$)=, wherein R$^{13}$ is selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Z^2$ is —N= and $Z^1$ is —CH=.

c. $Z^3$ Groups

In one aspect, $Z^3$ is selected from —O—, —NR$^{40}$—, and —CR$^{41a}$R$^{41b}$—. In a further aspect, $Z^3$ is selected from —O— and —NR$^{40}$—. In a still further aspect, $Z^3$ is —O—. In yet a further aspect, $Z^3$ is —NR$^{40}$—. In an even further aspect, $Z^3$ is —CR$^{41a}$R$^{41b}$—.

In various aspects, $Z^3$ is selected from —O—, —NH—, and —CH$_2$—. In a further aspect, $Z^3$ is selected from —O— and —NH—. In a still further aspect, $Z^3$ is —NH—. In an even further aspect, $Z^3$ is —CH$_2$—.

d. $Z^4$ Groups

In one aspect, each occurrence of $Z^4$ is independently selected from —O—, —NR$^{42}$—, and —CR$^{43a}$R$^{43b}$—, provided that no more than one occurrence of $Z^4$ is —O— or —NR$^{42}$—. In a further aspect, each occurrence of $Z^4$ is independently selected from —O— and —CR$^{43a}$R$^{43b}$—. In a still further aspect, each occurrence of $Z^4$ is independently selected from —NR$^{42}$— and —CR$^{43a}$R$^{43b}$—. In an even further aspect, each occurrence of $Z^4$ is —CR$^{43a}$R$^{43b}$—.

In various aspects, each occurrence of $Z^4$ is independently selected from —O—, —NR$^{42}$—, and —CH$_2$—. In a further aspect, each occurrence of $Z^4$ is independently selected from —O— and —CH$_2$—. In a still further aspect, each occurrence of $Z^4$ is independently selected from —NR$^{42}$— and —CH$_2$—. In an even further aspect, each occurrence of $Z^4$ is —CH$_2$—.

e. $R^{1a}$, $R^{1b}$, $R^{1c}$, and $R^{1d}$ Groups

In one aspect, each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{1a}$, $R^{1b}$, $R^{1c}$, and $R^{1d}$ is independently selected from hydrogen, —F, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of $R^{1a}$, $R^{1b}$, $R^{1c}$, and $R^{1d}$ is independently selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of $R^{1a}$, $R^{1b}$, $R^{1c}$, and $R^{1d}$ is independently selected from hydrogen, —F, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, and —CH$_2$NH$_2$.

In various aspects, each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, and C2-C4 alkenyl. Thus, in various further aspects, each of $R^{1a}$, $R^{1b}$, $R^{1c}$, and $R^{1d}$ is independently selected from hydrogen, —F, —Cl, —NH$_2$, —CN, —OH, —NO$_2$, methyl, ethyl, n-propyl, i-propyl, ethenyl, propenyl, and isopropenyl. In a further aspect, each of $R^{1a}$, $R^{1b}$, $R^{1c}$, and $R^{1d}$ is independently selected from hydrogen, —F, —Cl, —NH$_2$, —CN, —OH, —NO$_2$, methyl, ethyl, and ethenyl. In a still further aspect, each of $R^{1a}$, $R^{1b}$, $R^{1c}$, and $R^{1d}$ is independently selected from hydrogen, —F, —Cl, —NH$_2$, —CN, —OH, —NO$_2$, and methyl.

In various aspects, each of $R^{1a}$, $R^{1b}$, $R^{1c}$, and $R^{1d}$ is independently selected from hydrogen, C1-C4 alkyl, and C2-C4 alkenyl. Thus, in various further aspects, each of $R^{1a}$, $R^{1b}$, $R^{1c}$, and $R^{1d}$ is independently selected from hydrogen, methyl, ethyl, n-propyl, propyl, ethenyl, propenyl, and isopropenyl. In a further aspect, each of $R^{1a}$, $R^{1b}$, $R^{1c}$, and $R^{1d}$ is independently selected from hydrogen, methyl, ethyl, and ethenyl. In a still further aspect, each of $R^{1a}$, $R^{1b}$, $R^{1c}$, and $R^{1d}$ is independently selected from hydrogen and methyl.

In various aspects, each of $R^{1a}$, $R^{1b}$, $R^{1c}$, and $R^{1d}$ is independently selected from hydrogen, halogen, —CN, —NH$_2$, —OH, —NO$_2$, C1-C4 haloalkyl, and C1-C4 haloalkoxy. Thus, in various further aspects, each of $R^{1a}$, $R^{1b}$, $R^{1c}$, and $R^{1d}$ is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of $R^{1a}$, $R^{1b}$, $R^{1c}$, and $R^{1d}$ is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, each of $R^{1a}$, $R^{1b}$, $R^{1c}$, and $R^{1d}$ is independently selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, each of R$^{1a}$, R$^{1b}$, R$^{1c}$, and R$^{1d}$ is independently selected from hydrogen, halogen, C1-C4 haloalkyl, and C1-C4 haloalkoxy. Thus, in various further aspects, each of R$^{1a}$, R$^{1b}$, R$^{1c}$, and R$^{1d}$ is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of R$^{1a}$, R$^{1b}$, R$^{1c}$, and R$^{1d}$ is independently selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, each of R$^{1a}$, R$^{1b}$, R$^{1c}$, and R$^{1d}$ is independently selected from hydrogen, —F, —Cl, —CH$_2$F, —CH$_2$Cl, —OCF$_3$, and —OCH$_2$CF$_3$.

In various aspects, each of R$^{1a}$, R$^{1b}$, R$^{1c}$, and R$^{1d}$ is independently selected from hydrogen, halogen, —CN, —NH$_2$, —OH, —NO$_2$, and C1-C4 cyanoalkyl. Thus, in various further aspects, each of R$^{1a}$, R$^{1b}$, R$^{1c}$, and R$^{1d}$ is independently selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, each of R$^{1a}$, R$^{1b}$, R$^{1c}$, and R$^{1d}$ is independently selected from hydrogen, —F, —Cl, —NH$_2$, —CN, —OH, —NO$_2$, —CH$_2$CN, and —CH$_2$CH$_2$CN. In a still further aspect, each of R$^{1a}$, R$^{1b}$, R$^{1c}$, and R$^{1d}$ is independently selected from hydrogen, —F, —Cl, —NH$_2$, —CN, —OH, —NO$_2$, and —CH$_2$CN.

In various aspects, each of R$^{1a}$, R$^{1b}$, R$^{1c}$, and R$^{1d}$ is independently selected from hydrogen and C1-C4 cyanoalkyl. Thus, in various further aspects, each of R$^{1a}$, R$^{1b}$, R$^{1c}$, and R$^{1d}$ is independently selected from hydrogen, —CH$_2$CN, —CH$_2$CH$_2$CN, —CH$_2$CH$_2$CH$_2$CN, and —CH(CH$_3$)CH$_2$CN. In a further aspect, each of R$^{1a}$, R$^{1b}$, R$^{1c}$, and R$^{1d}$ is independently selected from hydrogen, —CH$_2$CN, and —CH$_2$CH$_2$CN. In a still further aspect, each of R$^{1a}$, R$^{1b}$, R$^{1c}$, and R$^{1d}$ is independently selected from hydrogen and —CH$_2$CN.

In various aspects, each of R$^{1a}$, R$^{1b}$, R$^{1c}$, and R$^{1d}$ is independently selected from hydrogen, halogen, —CN, —NH$_2$, —OH, —NO$_2$, C1-C4 hydroxyalkyl, and C1-C4 alkoxy. Thus, in various further aspects, each of R$^{1a}$, R$^{1b}$, R$^{1c}$, and R$^{1d}$ is independently selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of R$^{1a}$, R$^{1b}$, R$^{1c}$, and R$^{1d}$ is independently selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, each of R$^{1a}$, R$^{1b}$, R$^{1c}$, and R$^{1d}$ is independently selected from hydrogen, —F, —Cl, —NH$_2$, —CN, —OH, —NO$_2$, —CH$_2$OH, and —OCH$_3$.

In various aspects, each of R$^{1a}$, R$^{1b}$, R$^{1c}$, and R$^{1d}$ is independently selected from hydrogen, C1-C4 hydroxyalkyl, and C1-C4 alkoxy. Thus, in various further aspects, each of R$^{1a}$, R$^{1b}$, R$^{1c}$, and R$^{1d}$ is independently selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of R$^{1a}$, R$^{1b}$, R$^{1c}$, and R$^{1d}$ is independently selected from hydrogen, —CH$_2$OH, —CH$_2$CH$_2$OH, —OCH$_3$, and —OCH$_2$CH$_3$. In a still further aspect, each of R$^{1a}$, R$^{1b}$, R$^{1c}$, and R$^{1d}$ is independently selected from hydrogen, —CH$_2$OH, and —OCH$_3$.

In various aspects, each of R$^{1a}$, R$^{1b}$, R$^{1c}$, and R$^{1d}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, each of R$^{1a}$, R$^{1b}$, R$^{1c}$, and R$^{1d}$ is independently selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of R$^{1a}$, R$^{1b}$, R$^{1c}$, and R$^{1d}$ is independently selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of R$^{1a}$, R$^{1b}$, R$^{1c}$, and R$^{1d}$ is independently selected from hydrogen, —F, —Cl, —NH$_2$, —CN, —OH, —NO$_2$, —NHCH$_3$, —N(CH$_3$)$_2$, and —CH$_2$NH$_2$.

In various aspects, each of R$^{1a}$, R$^{1b}$, R$^{1c}$, and R$^{1d}$ is independently selected from hydrogen, C1-C4 alkylamino, (C1-C4)(C1-C4) dialkylamino, and C1-C4 aminoalkyl. Thus, in various further aspects, each of R$^{1a}$, R$^{1b}$, R$^{1c}$, and R$^{1d}$ is independently selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of R$^{1a}$, R$^{1b}$, R$^{1c}$, and R$^{1d}$ is independently selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of R$^{1a}$, R$^{1b}$, R$^{1c}$, and R$^{1d}$ is independently selected from hydrogen, —NHCH$_3$, —N(CH$_3$)$_2$, and —CH$_2$NH$_2$.

In various aspects, each of R$^{1a}$, R$^{1b}$, R$^{1c}$, and R$^{1d}$ is hydrogen.

f. R$^{2a}$, R$^{2b}$, and R$^3$ Groups

In one aspect, each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$, or R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In one aspect, each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and R$^3$ is selected from C1-C4 alkyl, C1-C4 haloalkyl, C1-C4 haloalkoxy, C1-C4 hydroxyhaloalkyl, —NR$^{10}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, or R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$.

In various aspects, each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R$^{2a}$ and R$^{2b}$ is independently selected from hydrogen, —F, —Cl, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of R$^{2a}$ and R$^{2b}$ is independently selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of R$^{2a}$ and R$^{2b}$ is independently selected from hydrogen, —F, —Cl, —NH$_2$, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, and —CH$_2$NH$_2$.

In various aspects, each of R$^{2a}$ and R$^{2b}$ is independently selected from hydrogen, halogen, —CN, —NH$_2$, —OH, —NO$_2$, C1-C4 alkyl, and C2-C4 alkenyl. Thus, in various further aspects, each of R$^{2a}$ and R$^{2b}$ is independently selected from hydrogen, —F, —Cl, —NH$_2$, —CN, —OH, —NO$_2$, methyl, ethyl, n-propyl, i-propyl, ethenyl, propenyl, and isopropenyl. In a further aspect, each of R$^{2a}$ and R$^{2b}$ is independently selected from hydrogen, —F, —Cl, —NH$_2$, —CN, —OH, —NO$_2$, methyl, ethyl, and ethenyl. In a still further aspect, each of R$^{2a}$ and R$^{2b}$ is independently selected from hydrogen, —F, —Cl, —NH$_2$, —CN, —OH, —NO$_2$, and methyl.

In various aspects, each of R$^{2a}$ and R$^{2b}$ is independently selected from hydrogen, C1-C4 alkyl, and C2-C4 alkenyl. Thus, in various further aspects, each of R$^{2a}$ and R$^{2b}$ is independently selected from hydrogen, methyl, ethyl, n-propyl, i-propyl, ethenyl, propenyl, and isopropenyl. In a further aspect, each of R$^{2a}$ and R$^{2b}$ is independently selected from hydrogen, methyl, ethyl, and ethenyl. In a still further aspect, each of R$^{2a}$ and R$^{2b}$ is independently selected from hydrogen and methyl.

In various aspects, each of R$^{2a}$ and R$^{2b}$ is independently selected from hydrogen, halogen, —CN, —NH$_2$, —OH, —NO$_2$, C1-C4 haloalkyl, and C1-C4 haloalkoxy. Thus, in various further aspects, each of R$^{2a}$ and R$^{2b}$ is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of R$^{2a}$ and R$^{2b}$ is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, each of R$^{2a}$ and R$^{2b}$ is independently selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, each of R$^{2a}$ and R$^{2b}$ is independently selected from hydrogen, halogen, C1-C4 haloalkyl, and C1-C4 haloalkoxy. Thus, in various further aspects, each of R$^{2a}$ and R$^{2b}$ is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each of R$^{2a}$ and R$^{2b}$ is independently selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, each of R$^{2a}$ and R$^{2b}$ is independently selected from hydrogen, —F, —Cl, —CH$_2$F, —CH$_2$Cl, —OCF$_3$, and —OCH$_2$CF$_3$.

In various aspects, each of R$^{2a}$ and R$^{2b}$ is independently selected from hydrogen, halogen, —CN, —NH$_2$, —OH, —NO$_2$, and C1-C4 cyanoalkyl. Thus, in various further aspects, each of R$^{2a}$ and R$^{2b}$ is independently selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, each of R$^{2a}$ and R$^{2b}$ is independently selected from hydrogen, —F, —Cl, —NH$_2$, —CN, —OH, —NO$_2$, —CH$_2$CN, and —CH$_2$CH$_2$CN. In a still further aspect, each of R$^{2a}$ and R$^{2b}$ is independently selected from hydrogen, —F, —Cl, —NH$_2$, —CN, —OH, —NO$_2$, and —CH$_2$CN.

In various aspects, each of R$^{2a}$ and R$^{2b}$ is independently selected from hydrogen and C1-C4 cyanoalkyl. Thus, in various further aspects, each of R$^{2a}$ and R$^{2b}$ is independently selected from hydrogen, —CH$_2$CN, —CH$_2$CH$_2$CN, —CH$_2$CH$_2$CH$_2$CN, and —CH(CH$_3$)CH$_2$CN. In a further aspect, each of R$^{2a}$ and R$^{2b}$ is independently selected from hydrogen, —CH$_2$CN, and —CH$_2$CH$_2$CN. In a still further aspect, each of R$^{2a}$ and R$^{2b}$ is independently selected from hydrogen and —CH$_2$CN.

In various aspects, each of R$^{2a}$ and R$^{2b}$ is independently selected from hydrogen, halogen, —CN, —NH$_2$, —OH, —NO$_2$, C1-C4 hydroxyalkyl, and C1-C4 alkoxy. Thus, in various further aspects, each of R$^{2a}$ and R$^{2b}$ is independently selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of R$^{ea}$ and R$^{2b}$ is independently selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, each of R$^{2a}$ and R$^{2b}$ is independently selected from hydrogen, —F, —Cl, —NH$_2$, —CN, —OH, —NO$_2$, —CH$_2$OH, and —OCH$_3$.

In various aspects, each of R$^{2a}$ and R$^{2b}$ is independently selected from hydrogen, C1-C4 hydroxyalkyl, and C1-C4 alkoxy. Thus, in various further aspects, each of R$^{2a}$ and R$^{2b}$ is independently selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each of R$^{2a}$ and R$^{2b}$ is independently selected from hydrogen, —CH$_2$OH, —CH$_2$CH$_2$OH, —OCH$_3$, and —OCH$_2$CH$_3$. In a still further aspect, each of R$^{2a}$ and R$^{2b}$ is independently selected from hydrogen, —CH$_2$OH, and —OCH$_3$.

In various aspects, each of R$^{2a}$ and R$^{2b}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, each of R$^{2a}$ and R$^{2b}$ is independently selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of R$^{2a}$ and R$^{2b}$ is independently selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$.

In a still further aspect, each of R$^{2a}$ and R$^{2b}$ is independently selected from hydrogen, —F, —Cl, —NH$_2$, —CN, —OH, —NO$_2$, —NHCH$_3$, —N(CH$_3$)$_2$, and —CH$_2$NH$_2$.

In various aspects, each of R$^{2a}$ and R$^{2b}$ is independently selected from hydrogen, C1-C4 alkylamino, (C1-C4)(C1-C4) dialkylamino, and C1-C4 aminoalkyl. Thus, in various further aspects, each of R$^{2a}$ and R$^{2b}$ is independently selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each of R$^{2a}$ and R$^{2b}$ is independently selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each of R$^{2a}$ and R$^{2b}$ is independently selected from hydrogen, —NHCH$_3$, —N(CH$_3$)$_2$, and —CH$_2$NH$_2$.

In various aspects, each of R$^{2a}$ and R$^{2b}$ is hydrogen.

In various aspects, R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$. In a further aspect, R$^3$ is selected from methyl, ethyl, n-propyl, isopropyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$F, —OCH$_2$Cl, —OCH$_2$CH$_2$F, —OCH$_2$CH$_2$Cl, —OCH$_2$CH$_2$CH$_2$F, —OCH$_2$CH$_2$CH$_2$Cl, —OCH(CH$_3$)CH$_2$F, —OCH(CH$_3$)CH$_2$Cl, —CH(OH)F, —CH(OH)CF$_3$, —C(OH)(CF$_3$)$_2$, —CH$_2$CH(OH)CH$_2$F, —CH$_2$CH(OH)CHF$_2$, —C(CH$_3$)(OH)CF$_3$, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$Cy$^1$, —CO$_2$CH$_2$Cy$^1$, —CO$_2$CH$_2$CH$_2$Cy$^1$, —CO$_2$CH$_2$CH$_2$CH$_2$Cy$^1$, —CO$_2$CH(CH$_3$)CH$_2$Cy$^1$, Cy$^1$, and —CH$_2$Cy$^5$. In a still further aspect, R$^3$ is selected from methyl, ethyl, —CH$_2$F, —CH$_2$Cl, —CH$_2$CH$_2$F, —CH$_2$CH$_2$Cl, —OCH$_2$F, —OCH$_2$Cl, —OCH$_2$CH$_2$F, —OCH$_2$CH$_2$Cl, —CH(OH)F, —CH(OH)CF$_3$, —C(OH)(CF$_3$)$_2$, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$CH$_2$CH$_3$, —CO$_2$Cy$^1$, —CO$_2$CH$_2$Cy$^1$, —CO$_2$CH$_2$CH$_2$Cy$^1$, Cy$^1$, and —CH$_2$Cy$^5$. In yet a further aspect, R$^3$ is selected from methyl, —CH$_2$F, —CH$_2$Cl, —OCH$_2$F, —OCH$_2$Cl, —CH(OH)F, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$Cy$^1$, —CO$_2$CH$_2$Cy$^1$, Cy$^1$, and —CH$_2$Cy$^5$.

In various aspects, R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$. In a further aspect, R$^3$ is selected from methyl, ethyl, n-propyl, isopropyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$F, —OCH$_2$Cl, —OCH$_2$CH$_2$F, —OCH$_2$CH$_2$Cl, —OCH$_2$CH$_2$CH$_2$F, —OCH$_2$CH$_2$CH$_2$Cl, —OCH(CH$_3$)CH$_2$F, —OCH(CH$_3$)CH$_2$Cl, —CH(OH)F, —CH(OH)CF$_3$, —C(OH)(CF$_3$)$_2$, —CH$_2$CH(OH)CH$_2$F, —CH$_2$CH(OH)CHF$_2$, —C(CH$_3$)(OH)CF$_3$, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$Cy$^1$, —CO$_2$CH$_2$Cy$^1$, —CO$_2$CH$_2$CH$_2$Cy$^1$, —CO$_2$CH$_2$CH$_2$CH$_2$Cy$^1$, —CO$_2$CH(CH$_3$)CH$_2$Cy$^1$, and Cy$^1$. In a still further aspect, R$^3$ is selected from methyl, ethyl, —CH$_2$F, —CH$_2$Cl, —CH$_2$CH$_2$F, —CH$_2$CH$_2$Cl, —OCH$_2$F, —OCH$_2$Cl, —OCH$_2$CH$_2$F, —OCH$_2$CH$_2$Cl, —CH(OH)F, —CH(OH)CF$_3$, —C(OH)(CF$_3$)$_2$, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$CH$_2$CH$_3$, —CO$_2$Cy$^1$, —CO$_2$CH$_2$Cy$^1$, —CO$_2$CH$_2$CH$_2$Cy$^1$, and Cy$^1$. In yet a further aspect, R$^3$ is selected from methyl, —CH$_2$F, —CH$_2$Cl, —OCH$_2$F, —OCH$_2$Cl, —CH(OH)F, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$CH$_3$, —CO$_2$Cy$^1$, —CO$_2$CH$_2$Cy$^1$, and Cy$^1$.

In various aspects, R$^3$ is selected from C1-C4 alkyl, —CO$_2$(C1-C4 alkyl), —CO$_2$Cy$^1$, —CO$_2$(C1-C4 alkyl)Cy$^1$, and Cy$^1$. In a further aspect, R$^3$ is selected from methyl, ethyl, n-propyl, isopropyl, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$Cy$^1$, —CO$_2$CH$_2$Cy$^1$, —CO$_2$CH$_2$CH$_2$Cy$^1$, —CO$_2$CH$_2$CH$_2$CH$_2$Cy$^1$, —CO$_2$CH(CH$_3$)CH$_2$Cy$^1$, and Cy$^1$. In a still further aspect, R$^3$ is selected from methyl, ethyl, —CO$_2$CH$_3$, —CO$_2$CH$_2$CH$_3$, —CO$_2$Cy$^1$, —CO$_2$CH$_2$Cy$^1$, —CO$_2$CH$_2$CH$_2$Cy$^1$, and Cy$^1$. In yet a further aspect, R$^3$ is selected from methyl, —CO$_2$CH$_3$, —CO$_2$Cy$^1$, —CO$_2$CH$_2$Cy$^1$, and Cy$^1$.

In various aspects, R$^3$ is C1-C4 alkyl. In a further aspect, R$^3$ is selected from methyl, ethyl, n-propyl, and isopropyl. In a still further aspect, R$^3$ is selected from methyl and ethyl. In yet a further aspect, R$^3$ is methyl.

In various aspects, R$^3$ is selected from —CO$_2$(C1-C4 alkyl), —CO$_2$Cy$^1$, and —CO$_2$(C1-C4 alkyl)Cy$^1$. In a further aspect, $R^3$ is selected from —CO$_2$CH$_3$, —CO$_2$CH$_2$CH$_3$, —CO$_2$CH$_2$CH$_2$CH$_3$, —CO$_2$CH(CH$_3$)$_2$, —CO$_2$Cy$^1$, —CO$_2$CH$_2$Cy$^1$, —CO$_2$CH$_2$CH$_2$Cy$^1$, —CO$_2$CH$_2$CH$_2$CH$_2$Cy$^1$, and —CO$_2$CH(CH$_3$)CH$_2$Cy$^1$. In a still further aspect, $R^3$ is selected from —CO$_2$CH$_3$, —CO$_2$CH$_2$CH$_3$, —CO$_2$Cy$^1$, —CO$_2$CH$_2$Cy$^1$, and —CO$_2$CH$_2$CH$_2$Cy$^1$. In yet a further aspect, $R^3$ is selected from —CO$_2$CH$_3$, —CO$_2$Cy$^1$, and —CO$_2$CH$_2$Cy$^1$.

In various aspects, $R^3$ is Cy$^1$.

In various aspects, $R^3$ is selected from C1-C4 haloalkyl, C1-C4 haloalkoxy, and C1-C4 hydroxyhaloalkyl. In a further aspect, $R^3$ is selected from —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$F, —OCH$_2$Cl, —OCH$_2$CH$_2$F, —OCH$_2$CH$_2$Cl, —OCH$_2$CH$_2$CH$_2$F, —OCH$_2$CH$_2$CH$_2$Cl, —OCH(CH$_3$)CH$_2$F, —OCH(CH$_3$)CH$_2$Cl, —CH(OH)F, —CH(OH)CF$_3$, —C(OH)(CF$_3$)$_2$, —CH$_2$CH(OH)CH$_2$F, —CH$_2$CH(OH)CHF$_2$, and —C(CH$_3$)(OH)CF$_3$. In a still further aspect, $R^3$ is selected from —CH$_2$F, —CH$_2$Cl, —CH$_2$CH$_2$F, —CH$_2$CH$_2$Cl, —OCH$_2$F, —OCH$_2$Cl, —OCH$_2$CH$_2$F, —OCH$_2$CH$_2$Cl, —CH(OH)F, —CH(OH)CF$_3$, and —C(OH)(CF$_3$)$_2$. In yet a further aspect, $R^3$ is selected from —CH$_2$F, —CH$_2$Cl, —OCH$_2$F, —OCH$_2$Cl, and —CH(OH)F.

In various aspects, $R^3$ is selected from —NR$^{14}$C(O)R$^{15}$, —C(O)NR$^{16a}$R$^{16b}$, —NR$^{17}$SO$_2$R$^{18}$, and —P(O)(OR$^{19}$)$_2$. In a further aspect, $R^3$ is selected from —NR$^{14}$C(O)R$^{15}$, —C(O)NR$^{16a}$R$^{16b}$, and —NR$^{17}$SO$_2$R$^{18}$. In a still further aspect, $R^3$ is selected from —NR$^{14}$C(O)R$^{15}$ and —C(O)NR$^{16a}$R$^{16b}$. In yet a further aspect, $R^3$ is selected from —NR$^{17}$SO$_2$R$^{18}$ and —P(O)(OR$^{19}$)$_2$. In an even further aspect, $R^3$ is —NR$^{14}$C(O)R$^{15}$. In a still further aspect, $R^3$ is —C(O)NR$^{16a}$R$^{16b}$. In yet a further aspect, $R^3$ is —NR$^{17}$SO$_2$R$^{18}$. In an even further aspect, $R^3$ is —P(O)(OR$^{19}$)$_2$.

In various aspects, $R^3$ is selected from C1-C4 alkyl, C1-C4 haloalkyl, C1-C4 haloalkoxy, C1-C4 hydroxyhaloalkyl, —CO$_2$(C1-C4 alkyl), —CO$_2$Cy$^1$, —CO$_2$(C1-C4 alkyl)Cy$^1$, and Cy$^1$. In a further aspect, $R^3$ is selected from methyl, ethyl, n-propyl, isopropyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$F, —OCH$_2$Cl, —OCH$_2$CH$_2$F, —OCH$_2$CH$_2$Cl, —OCH$_2$CH$_2$CH$_2$F, —OCH$_2$CH$_2$CH$_2$Cl, —OCH(CH$_3$)CH$_2$F, —OCH(CH$_3$)CH$_2$Cl, —CH(OH)F, —CH(OH)CF$_3$, —C(OH)(CF$_3$)$_2$, —CH$_2$CH(OH)CH$_2$F, —CH$_2$CH(OH)CHF$_2$, —C(CH$_3$)(OH)CF$_3$, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$Cy$^1$, —CO$_2$CH$_2$Cy$^1$, —CO$_2$CH$_2$CH$_2$Cy$^1$, —CO$_2$CH$_2$CH$_2$CH$_2$Cy$^1$, —CO$_2$CH(CH$_3$)CH$_2$Cy$^1$, and Cy$^1$. In a still further aspect, $R^3$ is selected from methyl, ethyl, —CH$_2$F, —CH$_2$Cl, —CH$_2$CH$_2$F, —CH$_2$CH$_2$Cl, —OCH$_2$F, —OCH$_2$Cl, —OCH$_2$CH$_2$F, —OCH$_2$CH$_2$Cl, —CH(OH)F, —CH(OH)CF$_3$, —C(OH)(CF$_3$)$_2$, —CO$_2$CH$_3$, —CO$_2$CH$_2$CH$_3$, —CO$_2$Cy$^1$, —CO$_2$CH$_2$Cy$^1$, —CO$_2$CH$_2$CH$_2$Cy$^1$, and Cy$^1$. In yet a further aspect, $R^3$ is selected from methyl, —CH$_2$F, —CH$_2$Cl, —OCH$_2$F, —OCH$_2$Cl, —CH(OH)F, —CO$_2$CH$_3$, —CO$_2$Cy$^1$, —CO$_2$CH$_2$Cy$^1$, and Cy$^1$.

In various aspects, $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2a}$ is selected from hydrogen, —F, —Cl, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, $R^{2a}$ is selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, $R^{2a}$ is selected from hydrogen, —F, —Cl, —NH$_2$, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, and —CH$_2$NH$_2$.

In various aspects, $R^{2a}$ is selected from hydrogen, halogen, —CN, —NH$_2$, —OH, —NO$_2$, C1-C4 alkyl, and C2-C4 alkenyl. Thus, in various further aspects, $R^{2a}$ is selected from hydrogen, —F, —Cl, —NH$_2$, —CN, —OH, —NO$_2$, methyl, ethyl, n-propyl, i-propyl, ethenyl, propenyl, and isopropenyl. In a further aspect, $R^{2a}$ is selected from hydrogen, —F, —Cl, —NH$_2$, —CN, —OH, —NO$_2$, methyl, ethyl, and ethenyl. In a still further aspect, $R^{2a}$ is selected from hydrogen, —F, —Cl, —NH$_2$, —CN, —OH, —NO$_2$, and methyl.

In various aspects, $R^{2a}$ is selected from hydrogen, C1-C4 alkyl, and C2-C4 alkenyl. Thus, in various further aspects, $R^{2a}$ is selected from hydrogen, methyl, ethyl, n-propyl, i-propyl, ethenyl, propenyl, and isopropenyl. In a further aspect, $R^{2a}$ is selected from hydrogen, methyl, ethyl, and ethenyl. In a still further aspect, $R^{2a}$ is selected from hydrogen and methyl.

In various aspects, $R^{2a}$ is selected from hydrogen, halogen, —CN, —NH$_2$, —OH, —NO$_2$, C1-C4 haloalkyl, and C1-C4 haloalkoxy. Thus, in various further aspects, $R^{2a}$ is selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, $R^{2a}$ is selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, $R^{2a}$ is selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, $R^{2a}$ is selected from hydrogen, halogen, C1-C4 haloalkyl, and C1-C4 haloalkoxy. Thus, in various further aspects, $R^{2a}$ is selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, $R^{2a}$ is selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, $R^{2a}$ is selected from hydrogen, —F, —Cl, —CH$_2$F, —CH$_2$Cl, —OCF$_3$, and —OCH$_2$CF$_3$.

In various aspects, $R^{2a}$ is selected from hydrogen, halogen, —CN, —NH$_2$, —OH, —NO$_2$, and C1-C4 cyanoalkyl. Thus, in various further aspects, $R^{2a}$ is selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, $R^{2a}$ is selected from hydrogen, —F, —Cl, —NH$_2$, —CN, —OH, —NO$_2$, —CH$_2$CN, and —CH$_2$CH$_2$CN. In a still further aspect, $R^{2a}$ is selected from hydrogen, —F, —Cl, —NH$_2$, —CN, —OH, —NO$_2$, and —CH$_2$CN.

In various aspects, $R^{2a}$ is selected from hydrogen and C1-C4 cyanoalkyl. Thus, in various further aspects, $R^{2a}$ is selected from hydrogen, —CH$_2$CN, —CH$_2$CH$_2$CN, —CH$_2$CH$_2$CH$_2$CN, and —CH(CH$_3$)CH$_2$CN. In a further aspect, $R^{2a}$ is selected from hydrogen, —CH$_2$CN, and —CH$_2$CH$_2$CN. In a still further aspect, $R^{2a}$ is selected from hydrogen and —CH$_2$CN.

In various aspects, $R^{2a}$ is selected from hydrogen, halogen, —CN, —NH$_2$, —OH, —NO$_2$, C1-C4 hydroxyalkyl, and C1-C4 alkoxy. Thus, in various further aspects, $R^{2a}$ is selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, $R^{2a}$ is selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, $R^{2a}$ is selected from hydrogen, —F, —Cl, —NH$_2$, —CN, —OH, —NO$_2$, —CH$_2$OH, and —OCH$_3$.

In various aspects, $R^{2a}$ is selected from hydrogen, C1-C4 hydroxyalkyl, and C1-C4 alkoxy. Thus, in various further aspects, $R^{2a}$ is selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, $R^{2a}$ is selected from hydrogen, —CH$_2$OH, —CH$_2$CH$_2$OH, —OCH$_3$, and —OCH$_2$CH$_3$. In a still further aspect, $R^{2a}$ is selected from hydrogen, —CH$_2$OH, and —OCH$_3$.

In various aspects, $R^{2a}$ is selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, $R^{2a}$ is selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, $R^{2a}$ is selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, $R^{2a}$ is selected from hydrogen, —F, —Cl, —NH$_2$, —CN, —OH, —NO$_2$, —NHCH$_3$, —N(CH$_3$)$_2$, and —CH$_2$NH$_2$.

In various aspects, $R^{2a}$ is selected from hydrogen, C1-C4 alkylamino, (C1-C4)(C1-C4) dialkylamino, and C1-C4 aminoalkyl. Thus, in various further aspects, $R^{2a}$ is selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, $R^{2a}$ is selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, $R^{2a}$ is selected from hydrogen, —NHCH$_3$, —N(CH$_3$)$_2$, and —CH$_2$NH$_2$.

In a further aspect, $R^{2a}$ is hydrogen.

In various aspects, $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of 5- and 6-membered heteroaryls include, but are not limited to, furan, pyrrole, thiophene, oxazole, isothiazole, pyridine, and triazine. In a further aspect, $R^{2b}$ and $R^3$ are covalently bonded, and, together with the intermediate atoms, comprise a 5- or 6-membered heteroaryl, and are substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2b}$ and $R^3$ are covalently bonded, and, together with the intermediate atoms, comprise a 5- or 6-membered heteroaryl, and are substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2b}$ and $R^3$ are covalently bonded, and, together with the intermediate atoms, comprise a 5- or 6-membered heteroaryl, and are monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2b}$ and $R^3$ are covalently bonded, and, together with the intermediate atoms, comprise an unsubstituted 5- or 6-membered heteroaryl.

In various aspects, $R^{2b}$ and $R^3$ are covalently bonded, and, together with the intermediate atoms, comprise a 5-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2b}$ and $R^3$ are covalently bonded, and, together with the intermediate atoms, comprise a 5-membered heteroaryl, and are substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2b}$ and $R^3$ are covalently bonded, and, together with the intermediate atoms, comprise a 5-membered heteroaryl, and are substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2b}$ and $R^3$ are covalently bonded, and, together with the intermediate atoms, comprise a 5-membered heteroaryl, and are monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2b}$ and $R^3$ are covalently bonded, and, together with the intermediate atoms, comprise an unsubstituted 5-membered heteroaryl.

In various aspects, $R^{2b}$ and $R^3$ are covalently bonded, and, together with the intermediate atoms, comprise a heteroaryl having a structure represented by a formula:

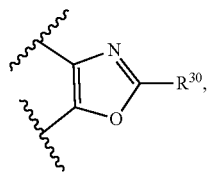

wherein $R^{30}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, $R^{2b}$ and $R^3$ are covalently bonded, and, together with the intermediate atoms, comprise a heteroaryl having a structure represented by a formula:

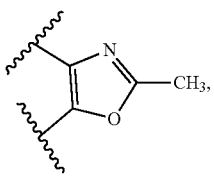 [SMILES: *c1nc(C)oc1*]

In various aspects, $R^{2b}$ and $R^3$ are covalently bonded, and, together with the intermediate atoms, comprise a 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{2b}$ and $R^3$ are covalently bonded, and, together with the intermediate atoms, comprise a 6-membered heteroaryl, and are substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{2b}$ and $R^3$ are covalently bonded, and, together with the intermediate atoms, comprise a 6-membered heteroaryl, and are substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{2b}$ and $R^3$ are covalently bonded, and, together with the intermediate atoms, comprise a 6-membered heteroaryl, and are monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{2b}$ and $R^3$ are covalently bonded, and, together with the intermediate atoms, comprise an unsubstituted 6-membered heteroaryl.

g. $R^4$ Groups

In one aspect, $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$. In a further aspect, $R^4$ is selected from hydrogen, —F, —Cl, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, $R^4$ is selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, $R^4$ is selected from hydrogen, —F, —Cl, —NH$_2$, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, and —CH$_2$NH$_2$.

In various aspects, $R^4$ is selected from hydrogen, halogen, —CN, —NH$_2$, —OH, —NO$_2$, C1-C4 alkyl, and C2-C4 alkenyl. Thus, in various further aspects, $R^4$ is selected from hydrogen, —F, —Cl, —NH$_2$, —CN, —OH, —NO$_2$, methyl, ethyl, n-propyl, i-propyl, ethenyl, propenyl, and isopropenyl. In a further aspect, $R^4$ is selected from hydrogen, —F, —Cl, —NH$_2$, —CN, —OH, —NO$_2$, methyl, ethyl, and ethenyl. In a still further aspect, $R^4$ is selected from hydrogen, —F, —Cl, —NH$_2$, —CN, —OH, —NO$_2$, and methyl.

In various aspects, $R^4$ is selected from hydrogen, C1-C4 alkyl, and C2-C4 alkenyl. Thus, in various further aspects, $R^4$ is selected from hydrogen, methyl, ethyl, n-propyl, i-propyl, ethenyl, propenyl, and isopropenyl. In a further aspect, $R^4$ is selected from hydrogen, methyl, ethyl, and ethenyl. In a still further aspect, $R^4$ is selected from hydrogen and methyl.

In various aspects, $R^4$ is selected from hydrogen, halogen, —CN, —NH$_2$, —OH, —NO$_2$, C1-C4 haloalkyl, and C1-C4 haloalkoxy. Thus, in various further aspects, $R^4$ is selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, R$^4$ is selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, R$^4$ is selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, R$^4$ is selected from hydrogen, halogen, C1-C4 haloalkyl, and C1-C4 haloalkoxy. Thus, in various further aspects, R$^4$ is selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, R$^4$ is selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, R$^4$ is selected from hydrogen, —F, —Cl, —CH$_2$F, —CH$_2$Cl, —OCF$_3$, and —OCH$_2$CF$_3$.

In various aspects, R$^4$ is selected from hydrogen, halogen, —CN, —NH$_2$, —OH, —NO$_2$, and C1-C4 cyanoalkyl. Thus, in various further aspects, R$^4$ is selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, R$^4$ is selected from hydrogen, —F, —NH$_2$, —CN, —OH, —NO$_2$, —CH$_2$CN, and —CH$_2$CH$_2$CN. In a still further aspect, R$^4$ is selected from hydrogen, —F, —Cl, —NH$_2$, —CN, —OH, —NO$_2$, and —CH$_2$CN.

In various aspects, R$^4$ is selected from hydrogen and C1-C4 cyanoalkyl. Thus, in various further aspects, R$^4$ is selected from hydrogen, —CH$_2$CN, —CH$_2$CH$_2$CN, —CH$_2$CH$_2$CH$_2$CN, and —CH(CH$_3$)CH$_2$CN. In a further aspect, R$^4$ is selected from hydrogen, —CH$_2$CN, and —CH$_2$CH$_2$CN. In a still further aspect, R$^4$ is selected from hydrogen and —CH$_2$CN.

In various aspects, R$^4$ is selected from hydrogen, halogen, —CN, —NH$_2$, —OH, —NO$_2$, C1-C4 hydroxyalkyl, and C1-C4 alkoxy. Thus, in various further aspects, R$^4$ is selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, R$^4$ is selected from hydrogen, —F, —NH$_2$, —CN, —OH, —NO$_2$, —CH$_2$OH, —CH$_2$CH$_2$OH, —OCH$_3$, and —OCH$_2$CH$_3$. In a still further aspect, R$^4$ is selected from hydrogen, —F, —Cl, —NH$_2$, —CN, —OH, —NO$_2$, —CH$_2$OH, and —OCH$_3$.

In various aspects, R$^4$ is selected from hydrogen, C1-C4 hydroxyalkyl, and C1-C4 alkoxy. Thus, in various further aspects, R$^4$ is selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, R$^4$ is selected from hydrogen, —CH$_2$OH, —CH$_2$CH$_2$OH, —OCH$_3$, and —OCH$_2$CH$_3$. In a still further aspect, R$^4$ is selected from hydrogen, —CH$_2$OH, and —OCH$_3$.

In various aspects, R$^4$ is selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, R$^4$ is selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, R$^4$ is selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, R$^4$ is selected from hydrogen, —F, —Cl, —NH$_2$, —CN, —OH, —NO$_2$, —NHCH$_3$, —N(CH$_3$)$_2$, and —CH$_2$NH$_2$.

In various aspects, R$^4$ is selected from hydrogen, C1-C4 alkylamino, (C1-C4)(C1-C4) dialkylamino, and C1-C4 aminoalkyl. Thus, in various further aspects, R$^4$ is selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, R$^4$ is selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, R$^4$ is selected from hydrogen, —NHCH$_3$, —N(CH$_3$)$_2$, and —CH$_2$NH$_2$.

In various aspects, R$^4$ is hydrogen.

h. R$^{10}$ and R$^{11}$ Groups

In one aspect, each of R$^{10}$, when present, and R$^{11}$, when present, is selected from hydrogen and C1-C4 alkyl. In a further aspect, each of R$^{10}$, when present, and R$^{11}$, when present, is hydrogen.

In various aspects, each of R$^{10}$, when present, and R$^{11}$, when present, is selected from hydrogen, methyl, ethyl, n-propyl, and isopropyl. In a further aspect, each of R$^{10}$, when present, and R$^{11}$, when present, is selected from hydrogen, methyl, and ethyl. In a still further aspect, each of R$^{10}$, when present, and R$^{11}$, when present, is selected from hydrogen and ethyl. In yet a further aspect, each of R$^{10}$, when present, and R$^{11}$, when present, is selected from hydrogen and methyl.

In various aspects, each of R$^{10}$, when present, and R$^{11}$, when present, is C1-C4 alkyl. In a further aspect, each of R$^{10}$, when present, and R$^{11}$, when present, is selected from methyl, ethyl, n-propyl, and isopropyl. In a still further aspect, each of R$^{10}$, when present, and R$^{11}$, when present, is selected from methyl and ethyl. In yet a further aspect, each of R$^{10}$, when present, and R$^{11}$, when present, is ethyl. In an even further aspect, each of R$^{10}$, when present, and R$^{11}$, when present, is methyl.

i. R$^{13}$ Groups

In one aspect, each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each occurrence of R$^{13}$, when present, is independently selected from hydrogen, —F, —Cl, —NH$_2$, —CN, —OH, —NO$_2$, methyl, ethyl, n-propyl, i-propyl, ethenyl, propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each occurrence of R$^{13}$, when present, is independently selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each occurrence of R$^{13}$, when present, is independently selected from hydrogen, —F, —Cl, —NH$_2$, —CN, —OH, —NO$_2$, methyl, —CH$_2$F, —CH$_2$Cl, —CH$_2$CN, —CH$_2$OH, —OCF$_3$, —OCH$_2$CF$_3$, —OCH$_3$, —NHCH$_3$, —N(CH$_3$)$_2$, and —CH$_2$NH$_2$.

In various aspects, each occurrence of R$^{13}$, when present, is independently selected from hydrogen, halogen, —CN, —NH$_2$, —OH, —NO$_2$, C1-C4 alkyl, and C2-C4 alkenyl. Thus, in various further aspects, each occurrence of R$^{13}$, when present, is independently selected from hydrogen, —F, —Cl, —NH$_2$, —CN, —OH, —NO$_2$, methyl, ethyl, n-propyl, i-propyl, ethenyl, propenyl, and isopropenyl. In a further aspect, each occurrence of R$^{13}$, when present, is independently selected from hydrogen, —F, —Cl, —NH$_2$, —CN, —OH, —NO$_2$, methyl, ethyl, and ethenyl. In a still further aspect, each occurrence of R$^{13}$, when present, is independently selected from hydrogen, —F, —Cl, —NH$_2$, —CN, —OH, —NO$_2$, and methyl.

In various aspects, each occurrence of R$^{13}$, when present, is independently selected from hydrogen, C1-C4 alkyl, and C2-C4 alkenyl. Thus, in various further aspects, each occurrence of R$^{13}$, when present, is independently selected from hydrogen, methyl, ethyl, n-propyl, i-propyl, ethenyl, propenyl, and isopropenyl. In a further aspect, each occurrence of R$^{13}$, when present, is independently selected from hydrogen, methyl, ethyl, and ethenyl. In a still further aspect, each occurrence of R$^{13}$, when present, is independently selected from hydrogen and methyl.

In various aspects, each occurrence of R$^{13}$, when present, is independently selected from hydrogen, halogen, —CN, —NH$_2$, —OH, —NO$_2$, C1-C4 haloalkyl, and C1-C4 haloalkoxy. Thus, in various further aspects, each occurrence of R$^{13}$, when present, is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each occurrence of R$^{13}$, when present, is independently selected from hydrogen, —F, —Cl, —NH$_2$, —CN, —OH, —NO$_2$, —CH$_2$F, —CH$_2$Cl, —CH$_2$CH$_2$F, —CH$_2$CH$_2$Cl, —OCF$_3$, and —OCH$_2$CF$_3$. In a still further aspect, each occurrence of R$^{13}$, when present, is independently selected from hydrogen, —F, —Cl, —NH$_2$, —CN, —OH, —NO$_2$, —CH$_2$F, —CH$_2$Cl, —OCF$_3$, and —OCH$_2$CF$_3$.

In various aspects, each occurrence of R$^{13}$, when present, is independently selected from hydrogen, halogen, C1-C4 haloalkyl, and C1-C4 haloalkoxy. Thus, in various further aspects, each occurrence of R$^{13}$, when present, is independently selected from hydrogen, —F, —Cl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCF$_3$, —OCH$_2$CF$_3$, —OCH$_2$CH$_2$CF$_3$, and —OCH(CH$_3$)CF$_3$. In a further aspect, each occurrence of R$^{13}$, when present, is independently selected from hydrogen, —F, —Cl, —CH$_2$F, —CH$_2$Cl, —CH$_2$CH$_2$F, —CH$_2$CH$_2$Cl, —OCF$_3$, and —OCH$_2$CF$_3$. In a still further aspect, each occurrence of R$^{13}$, when present, is independently selected from hydrogen, —F, —Cl, —CH$_2$F, —CH$_2$Cl, —OCF$_3$, and —OCH$_2$CF$_3$.

In various aspects, each occurrence of R$^{13}$, when present, is independently selected from hydrogen, halogen, —CN, —NH$_2$, —OH, —NO$_2$, and C1-C4 cyanoalkyl. Thus, in various further aspects, each occurrence of R$^{13}$, when present, is independently selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, each occurrence of R$^{13}$, when present, is independently selected from hydrogen, —F, —Cl, —NH$_2$, —CN, —OH, —NO$_2$, —CH$_2$CN, and —CH$_2$CH$_2$CN. In a still further aspect, each occurrence of R$^{13}$, when present, is independently selected from hydrogen, —F, —Cl, —NH$_2$, —CN, —OH, —NO$_2$, and —CH$_2$CN.

In various aspects, each occurrence of R$^{13}$, when present, is independently selected from hydrogen and C1-C4 cyanoalkyl. Thus, in various further aspects, each occurrence of R$^{13}$, when present, is independently selected from hydrogen, —CH$_2$CN, —CH$_2$CH$_2$CN, —CH$_2$CH$_2$CH$_2$CN, and —CH(CH$_3$)CH$_2$CN. In a further aspect, each occurrence of R$^{13}$, when present, is independently selected from hydrogen, —CH$_2$CN, and —CH$_2$CH$_2$CN. In a still further aspect, each occurrence of R$^{13}$, when present, is independently selected from hydrogen and —CH$_2$CN.

In various aspects, each occurrence of R$^{13}$, when present, is independently selected from hydrogen, halogen, —CN, —NH$_2$, —OH, —NO$_2$, C1-C4 hydroxyalkyl, and C1-C4 alkoxy. Thus, in various further aspects, each occurrence of R$^{13}$, when present, is independently selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each occurrence of R$^{13}$, when present, is independently selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, each occurrence of R$^{13}$, when present, is independently selected from hydrogen, —F, —Cl, —NH$_2$, —CN, —OH, —NO$_2$, —CH$_2$OH, and —OCH$_3$.

In various aspects, each occurrence of R$^{13}$, when present, is independently selected from hydrogen, C1-C4 hydroxyalkyl, and C1-C4 alkoxy. Thus, in various further aspects, each occurrence of R$^{13}$, when present, is independently selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, each occurrence of R$^{13}$, when present, is independently selected from hydrogen, —CH$_2$OH, —CH$_2$CH$_2$OH, —OCH$_3$, and —OCH$_2$CH$_3$. In a still further aspect, each occurrence of R$^{13}$, when present, is independently selected from hydrogen, —CH$_2$OH, and —OCH$_3$.

In various aspects, each occurrence of R$^{13}$, when present, is independently selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, each occurrence of R$^{13}$, when present, is independently selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each occurrence of R$^{13}$, when present, is independently selected from hydrogen, —F, —Cl, —NH$_2$, —CN, —OH, —NO$_2$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each occurrence of R$^{13}$, when present, is independently selected from hydrogen, —F, —Cl, —NH$_2$, —CN, —OH, —NO$_2$, —NHCH$_3$, —N(CH$_3$)$_2$, and —CH$_2$NH$_2$.

In various aspects, each occurrence of R$^{13}$, when present, is independently selected from hydrogen, C1-C4 alkylamino, (C1-C4)(C1-C4) dialkylamino, and C1-C4 aminoalkyl. Thus, in various further aspects, each occurrence of R$^{13}$, when present, is independently selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, each occurrence of R$^{13}$, when present, is independently selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, each occurrence of R$^{13}$, when present, is independently selected from hydrogen, —NHCH$_3$, —N(CH$_3$)$_2$, and —CH$_2$NH$_2$.

In various aspects, each occurrence of R$^{13}$, when present, is hydrogen.

j. R$^{14}$ and R$^{15}$ Groups

In one aspect, R$^{14}$, when present, is selected from hydrogen and C1-C4 alkyl, and R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; or R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, R$^{14}$, when present, is selected from hydrogen and C1-C4 alkyl. In a further aspect, R$^{14}$, when present, is selected from hydrogen, methyl, ethyl, n-propyl, and isopropyl. In a still further aspect, R$^{14}$, when present, is selected from hydrogen, methyl, and ethyl. In yet a further aspect, R$^{14}$, when present, is selected from hydrogen and ethyl. In an even further aspect, R$^{14}$, when present, is selected from hydrogen and methyl.

In various aspects, R$^{14}$, when present, is C1-C4 alkyl. In a further aspect, R$^{14}$, when present, is selected from methyl, ethyl, n-propyl, and isopropyl. In a still further aspect, R$^{14}$, when present, is selected from methyl and ethyl. In yet a further aspect, R$^{14}$, when present, is ethyl. In an even further aspect, R$^{14}$, when present, is methyl.

In various aspects, R$^{14}$, when present, is hydrogen.

In various aspects, R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$.

In a further aspect, R$^{15}$, when present, is selected from methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_3$, —OCH$_2$CH$_3$, —OCH$_2$CH$_2$CH$_3$, —OCH(CH$_3$)CH$_3$, —OCF$_3$, —OCH$_2$CF$_3$, —OCH$_2$CH$_2$CF$_3$, —OCH(CH$_3$)CF$_3$, —CH$_2$NH$_2$, —CH$_2$CH$_2$NH$_2$, —CH$_2$CH$_2$CH$_2$NH$_2$, —CH(CH$_3$)CH$_2$NH$_2$, —OR$^{20}$, —NR$^{21a}$R$^{21b}$, —CH$_2$NR$^{21a}$R$^{21b}$, and Cy$^2$. In a still further aspect, R$^{15}$, when present, is selected from methyl, ethyl, —CH$_2$F, —CH$_2$Cl, —CH$_2$CH$_2$F, —CH$_2$CH$_2$Cl, —OCH$_3$, —OCH$_2$CH$_3$, —OCF$_3$, —OCH$_2$CF$_3$, —CH$_2$NH$_2$, —CH$_2$CH$_2$NH$_2$, —OR$^{20}$, —NR$^{21a}$R$^{21b}$, —CH$_2$NR$^{21a}$R$^{21b}$, and Cy$^2$. In yet a further aspect, R$^{15}$, when present, is selected from methyl, —CH$_2$F, —CH$_2$Cl, —OCH$_3$, —OCF$_3$, —CH$_2$NH$_2$, —OR$^{20}$, —NR$^{21a}$R$^{21b}$, —CH$_2$NR$^{21a}$R$^{21b}$, and Cy$^2$.

In various aspects, R$^{15}$, when present, is selected from C1-C4 alkyl, C1-C4 alkoxy, —OR$^{20}$, and Cy$^2$. In a further aspect, R$^{15}$, when present, is selected from methyl, ethyl, n-propyl, i-propyl, —OCH$_3$, —OCH$_2$CH$_3$, —OCH$_2$CH$_2$CH$_3$, —OCH(CH$_3$)CH$_3$, —OR$^{20}$, and Cy$^2$. In a still further aspect, R$^{15}$, when present, is selected from methyl, ethyl, —OCH$_3$, —OCH$_2$CH$_3$, —OR$^{20}$, and Cy$^2$. In yet a further aspect, R$^{15}$, when present, is selected from methyl, —OCH$_3$, —OR$^{20}$, and Cy$^2$.

In various aspects, R$^{15}$, when present, is selected from C1-C4 haloalkyl and C1-C4 haloalkoxy. In a further aspect, R$^{15}$, when present, is selected from methyl, ethyl, n-propyl, i-propyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, and —CH(CH$_3$)CH$_2$Cl. In a still further aspect, R$^{15}$, when present, is selected from methyl, ethyl, —CH$_2$F, —CH$_2$Cl, —CH$_2$CH$_2$F, and —CH$_2$CH$_2$Cl. In yet a further aspect, R$^{15}$, when present, is selected from methyl, —CH$_2$F, and —CH$_2$Cl.

In various aspects, R$^{15}$, when present, is selected from C1-C4 aminoalkyl, —NR$^{21a}$R$^{21b}$, and —CH$_2$NR$^{21a}$R$^{21b}$. In a further aspect, R$^{15}$, when present, is selected from —CH$_2$NH$_2$, —CH$_2$CH$_2$NH$_2$, —CH$_2$CH$_2$CH$_2$NH$_2$, —CH(CH$_3$)CH$_2$NH$_2$, —NR$^{21a}$R$^{21b}$, and —CH$_2$NR$^{21a}$R$^{21b}$. In a still further aspect, R$^{15}$, when present, is selected from —CH$_2$NH$_2$, —CH$_2$CH$_2$NH$_2$, —NR$^{21a}$R$^{21b}$, and —CH$_2$NR$^{21a}$R$^{21b}$. In yet a further aspect, R$^{15}$, when present, is selected from —CH$_2$NH$_2$, —NR$^{21a}$R$^{21b}$, and —CH$_2$NR$^{21a}$R$^{21b}$.

In various aspects, R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{14}$ and R$^{15}$, when present, are covalently bonded, and, together with the intermediate atoms, comprise a 4- to 9-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{14}$ and R$^{15}$, when present, are covalently bonded, and, together with the intermediate atoms, comprise a 4- to 9-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{14}$ and R$^{15}$, when present, are covalently bonded, and, together with the intermediate atoms, comprise a 4- to 9-membered heterocycloalkyl ring monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{14}$ and $R^{15}$, when present, are covalently bonded, and, together with the intermediate atoms, comprise an unsubstituted 4- to 9-membered heterocycloalkyl ring.

In various aspects, $R^{14}$ and $R^{15}$, when present, are covalently bonded, and, together with the intermediate atoms, comprise a 4- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{14}$ and $R^{15}$, when present, are covalently bonded, and, together with the intermediate atoms, comprise a 4- to 7-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{14}$ and $R^{15}$, when present, are covalently bonded, and, together with the intermediate atoms, comprise a 4- to 7-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{14}$ and $R^{15}$, when present, are covalently bonded, and, together with the intermediate atoms, comprise a 4- to 7-membered heterocycloalkyl ring monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{14}$ and $R^{15}$, when present, are covalently bonded, and, together with the intermediate atoms, comprise an unsubstituted 4- to 7-membered heterocycloalkyl ring.

In various aspects, $R^{14}$ and $R^{15}$, when present, are covalently bonded, and, together with the intermediate atoms, comprise a 5- to 6-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{14}$ and $R^{15}$, when present, are covalently bonded, and, together with the intermediate atoms, comprise a 5- to 6-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{14}$ and $R^{15}$, when present, are covalently bonded, and, together with the intermediate atoms, comprise a 5- to 6-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{14}$ and $R^{15}$, when present, are covalently bonded, and, together with the intermediate atoms, comprise a 5- to 6-membered heterocycloalkyl ring monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{14}$ and $R^{15}$, when present, are covalently bonded, and, together with the intermediate atoms, comprise an unsubstituted 5- to 6-membered heterocycloalkyl ring.

In various aspects, $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{15}$, when present, and $R^{2b}$ are covalently bonded, and, together with the intermediate atoms, comprise a 5- to 7-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{15}$, when present, and $R^{2b}$ are covalently bonded, and, together with the intermediate atoms, comprise a 5- to 7-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{15}$, when present, and $R^{2b}$ are covalently bonded, and, together with the intermediate atoms, comprise an unsubstituted 5- to 7-membered heterocycloalkyl ring.

In various aspects, $R^{14}$ and $R^{15}$, when present, are covalently bonded, and, together with the intermediate atoms, comprise a 5- to 6-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{14}$ and $R^{15}$, when present, are covalently bonded, and, together with the intermediate atoms, comprise a 5- to 6-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{14}$ and $R^{15}$, when present, are covalently bonded, and, together with the intermediate atoms, comprise a 5- to 6-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{14}$ and $R^{15}$, when present, are covalently bonded, and, together with the intermediate atoms, comprise a 5- to 6-membered heterocycloalkyl ring monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{14}$ and $R^{15}$, when present, are covalently bonded, and, together with the intermediate atoms, comprise an unsubstituted 5- to 6-membered heterocycloalkyl ring.

In various aspects, $R^{15}$, when present, and $R^{2b}$ are covalently bonded, and, together with the intermediate atoms, comprise a 5- to 6-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{15}$, when present, and $R^{2b}$ are covalently bonded, and, together with the intermediate atoms, comprise a 5- to 6-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{15}$, when present, and $R^{2b}$ are covalently bonded, and, together with the intermediate atoms, comprise a 5- to 6-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{15}$, when present, and $R^{2b}$ are covalently bonded, and, together with the intermediate atoms, comprise an unsubstituted 5- to 6-membered heterocycloalkyl ring.

In various aspects, $R^{14}$ and $R^{15}$, when present, are covalently bonded, and, together with the intermediate atoms, comprise a 5- to 6-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{14}$ and $R^{15}$, when present, are covalently bonded, and, together with the intermediate atoms, comprise a 5- to 6-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{14}$ and $R^{15}$, when present, are covalently bonded, and, together with the intermediate atoms, comprise a 5- to 6-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{14}$ and $R^{15}$, when present, are covalently bonded, and, together with the intermediate atoms, comprise a 5- to 6-membered heterocycloalkyl ring monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{14}$ and $R^{15}$, when present, are covalently bonded, and, together with the intermediate atoms, comprise an unsubstituted 5- to 6-membered heterocycloalkyl ring.

In various aspects, $R^{15}$, when present, and $R^{2b}$ are covalently bonded, and, together with the intermediate atoms, comprise a 5-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{15}$, when present, and $R^{2b}$ are covalently bonded, and, together with the intermediate atoms, comprise a 5-membered heterocycloalkyl ring substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{15}$, when present, and $R^{2b}$ are covalently bonded, and, together with the intermediate atoms, comprise a 5-membered heterocycloalkyl ring substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{15}$, when present, and $R^{2b}$ are covalently bonded, and, together with the intermediate atoms, comprise an unsubstituted 5-membered heterocycloalkyl ring.

k. $R^{16a}$ and $R^{16b}$ Groups

In one aspect, each of $R^{16a}$ and $R^{16b}$, when present, is independently selected from hydrogen, C1-C4 alkyl, and $Cy^3$. In a further aspect, each of $R^{16a}$ and $R^{16b}$, when present, is independently selected from hydrogen, methyl, ethyl, n-propyl, isopropyl, and $Cy^3$. In a still further aspect, each of $R^{16a}$ and $R^{16b}$, when present, is independently selected from hydrogen, methyl, ethyl, and $Cy^3$. In yet a further aspect, each of $R^{16a}$ and $R^{16b}$, when present, is independently selected from hydrogen, methyl, and $Cy^3$.

In various aspects, each of $R^{16a}$ and $R^{16b}$, when present, is independently selected from hydrogen and C1-C4 alkyl. In a further aspect, each of $R^{16a}$ and $R^{16b}$, when present, is independently selected from hydrogen, methyl, ethyl, n-propyl, and isopropyl. In a still further aspect, each of $R^{16a}$ and $R^{16b}$, when present, is independently selected from hydrogen, methyl, and ethyl. In yet a further aspect, each of $R^{16a}$ and $R^{16b}$, when present, is independently selected from hydrogen and methyl.

In various aspects, each of $R^{16a}$ and $R^{16b}$, when present, is independently C1-C4 alkyl. In a further aspect, each of $R^{16a}$ and $R^{16b}$, when present, is independently selected from methyl, ethyl, n-propyl, and isopropyl. In a still further aspect, each of $R^{16a}$ and $R^{16b}$, when present, is independently selected from methyl and ethyl. In yet a further aspect, each of $R^{16a}$ and $R^{16b}$, when present, is methyl.

In various aspects, each of $R^{16a}$ and $R^{16b}$, when present, is independently selected from hydrogen and $Cy^3$. In a further aspect, each of $R^{16a}$ and $R^{16b}$, when present, is $Cy^3$.

In various aspects, each of $R^{16a}$ and $R^{16b}$, when present, is hydrogen.

l. $R^{17}$ and $R^{18}$ Groups

In one aspect, $R^{17}$, when present, is selected from hydrogen and C1-C4 alkyl, and $R^{18}$, when present is a C1-C4 alkyl, or $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, R$^{17}$, when present, is selected from hydrogen and C1-C4 alkyl, and R$^{18}$, when present is a C1-C4 alkyl.

In a further aspect, R$^{17}$, when present, is selected from hydrogen, methyl, ethyl, n-propyl, and isopropyl. In a still further aspect, R$^{17}$, when present, is selected from hydrogen, methyl, and ethyl. In yet a further aspect, R$^{17}$, when present, is selected from hydrogen and ethyl. In an even further aspect, R$^{17}$, when present, is selected from hydrogen and methyl.

In various aspects, R$^{17}$, when present, is C1-C4 alkyl. In a further aspect, R$^{17}$, when present, is selected from methyl, ethyl, n-propyl, and isopropyl. In a still further aspect, R$^{17}$, when present, is selected from methyl and ethyl. In yet a further aspect, R$^{17}$, when present, is ethyl. In an even further aspect, R$^{17}$, when present, is methyl.

In various aspects, R$^{17}$, when present, is hydrogen.

In various aspects, R$^{18}$, when present is a C1-C4 alkyl. In a further aspect, R$^{18}$, when present is selected from methyl, ethyl, n-propyl, and isopropyl. In a still further aspect, R$^{18}$, when present is selected from methyl and ethyl. In yet a further aspect, R$^{18}$, when present is methyl.

In various aspects, R$^{17}$ and R$^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{17}$ and R$^{18}$, when present, are covalently bonded, and together with the intermediate atoms, comprise a 5- to 7-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{17}$ and R$^{18}$, when present, are covalently bonded, and together with the intermediate atoms, comprise a 5- to 7-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{17}$ and R$^{18}$, when present, are covalently bonded, and together with the intermediate atoms, comprise a 5- to 7-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{17}$ and R$^{18}$, when present, are covalently bonded, and together with the intermediate atoms, comprise an unsubstituted 5- to 7-membered heterocycloalkyl.

In various aspects, R$^{17}$ and R$^{18}$, when present, are covalently bonded, and together with the intermediate atoms, comprise a 5- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{17}$ and R$^{18}$, when present, are covalently bonded, and together with the intermediate atoms, comprise a 5- to 6-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{17}$ and R$^{18}$, when present, are covalently bonded, and together with the intermediate atoms, comprise a 5- to 6-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{17}$ and R$^{18}$, when present, are covalently bonded, and together with the intermediate atoms, comprise a 5- to 6-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{17}$ and R$^{18}$, when present, are covalently bonded, and together with the intermediate atoms, comprise an unsubstituted 5- to 6-membered heterocycloalkyl.

In various aspects, R$^{17}$ and R$^{18}$, when present, are covalently bonded, and together with the intermediate atoms, comprise a 5-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, R$^{17}$ and R$^{18}$, when present, are covalently bonded, and together with the intermediate atoms, comprise a 5-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, R$^{17}$ and R$^{18}$, when present, are covalently bonded, and together with the intermediate atoms, comprise a 5-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, R$^{17}$ and R$^{18}$, when present, are covalently bonded, and together with the intermediate atoms, comprise a 5-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, R$^{17}$ and R$^{18}$, when present, are covalently bonded, and together with the intermediate atoms, comprise an unsubstituted 5-membered heterocycloalkyl.

m. R$^{19}$ Groups

In one aspect, each occurrence of R$^{19}$, when present, is independently selected from hydrogen and C1-C4 alkyl. In a further aspect, each occurrence of $R^{19}$, when present, is independently selected from hydrogen, methyl, ethyl, n-propyl, and isopropyl. In yet a further aspect, each occurrence of $R^{19}$, when present, is independently selected from hydrogen, methyl, and ethyl. In an even further aspect, each occurrence of $R^{19}$, when present, is independently selected from hydrogen and methyl.

In various aspects, each occurrence of $R^{19}$, when present, is independently C1-C4 alkyl. In a further aspect, each occurrence of $R^{19}$, when present, is independently selected from methyl, ethyl, n-propyl, and isopropyl. In yet a further aspect, each occurrence of $R^{19}$, when present, is independently selected from methyl and ethyl. In an even further aspect, each occurrence of $R^{19}$, when present, is methyl.

In various aspects, each occurrence of $R^{19}$, when present, is hydrogen.

n. $R^{20}$ Groups

In one aspect, $R^{20}$, when present, is selected from hydrogen and C1-C4 alkyl. In a further aspect, $R^{20}$, when present, is selected from hydrogen, methyl, ethyl, n-propyl, and isopropyl. In a still further aspect, $R^{20}$, when present, is selected from hydrogen, methyl, and ethyl. In yet a further aspect, $R^{20}$, when present, is selected from hydrogen and ethyl. In an even further aspect, $R^{20}$, when present, is selected from hydrogen and methyl.

In various aspects, $R^{20}$, when present, is C1-C4 alkyl. In a further aspect, $R^{20}$, when present, is selected from methyl, ethyl, n-propyl, and isopropyl. In a still further aspect, $R^{20}$, when present, is selected from methyl and ethyl. In yet a further aspect, $R^{20}$, when present, is ethyl. In an even further aspect, $R^{20}$, when present, is methyl.

In various aspects, $R^{20}$, when present, is hydrogen.

o. $R^{21a}$ and $R^{21b}$ Groups

In one aspect, each of $R^{21a}$ and $R^{21b}$, when present, is independently selected from hydrogen and C1-C4 alkyl, or $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In various aspects, each of $R^{21a}$ and $R^{21b}$, when present, is independently selected from hydrogen and C1-C4 alkyl. In a further aspect, each of $R^{21a}$ and $R^{21b}$, when present, is independently selected from hydrogen, methyl, ethyl, n-propyl, and isopropyl. In a still further aspect, each of $R^{21a}$ and $R^{21b}$, when present, is independently selected from hydrogen, methyl, and ethyl. In yet a further aspect, each of $R^{21a}$ and $R^{21b}$, when present, is independently selected from hydrogen and ethyl. In an even further aspect, each of $R^{21a}$ and $R^{21b}$, when present, is independently selected from hydrogen and methyl.

In various aspects, each of $R^{21a}$ and $R^{21b}$, when present, is independently C1-C4 alkyl. In a further aspect, each of $R^{21a}$ and $R^{21b}$, when present, is independently selected from methyl, ethyl, n-propyl, and isopropyl. In a still further aspect, each of $R^{21a}$ and $R^{21b}$, when present, is independently selected from methyl and ethyl. In yet a further aspect, each of $R^{21a}$ and $R^{21b}$, when present, is ethyl. In an even further aspect, each of $R^{21a}$ and $R^{21b}$, when present, is methyl.

In various aspects, each of $R^{21a}$ and $R^{21b}$, when present, is hydrogen.

In various aspects, $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$, when present, are covalently bonded, and, together with the intermediate atoms, comprise a 4- to 6-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, are covalently bonded, and, together with the intermediate atoms, comprise a 4- to 6-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, are covalently bonded, and, together with the intermediate atoms, comprise a 4- to 6-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, are covalently bonded, and, together with the intermediate atoms, comprise a 4- to 6-membered unsubstituted heterocycloalkyl.

In various aspects, $R^{21a}$ and $R^{21b}$, when present, are covalently bonded, and, together with the intermediate atoms, comprise a 4-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$, when present, are covalently bonded, and, together with the intermediate atoms, comprise a 4-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, are covalently bonded, and, together with the intermediate atoms, comprise a 4-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, are covalently bonded, and, together with the intermediate atoms, comprise a 4-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, are covalently bonded, and, together with the intermediate atoms, comprise a 4-membered unsubstituted heterocycloalkyl.

In various aspects, $R^{21a}$ and $R^{21b}$, when present, are covalently bonded, and, together with the intermediate atoms, comprise a 5-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$, when present, are covalently bonded, and, together with the intermediate atoms, comprise a 5-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, are covalently bonded, and, together with the intermediate atoms, comprise a 5-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, are covalently bonded, and, together with the intermediate atoms, comprise a 5-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, are covalently bonded, and, together with the intermediate atoms, comprise a 5-membered unsubstituted heterocycloalkyl.

In various aspects, $R^{21a}$ and $R^{21b}$, when present, are covalently bonded, and, together with the intermediate atoms, comprise a 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{21a}$ and $R^{21b}$, when present, are covalently bonded, and, together with the intermediate atoms, comprise a 6-membered heterocycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $R^{21a}$ and $R^{21b}$, when present, are covalently bonded, and, together with the intermediate atoms, comprise a 6-membered heterocycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $R^{21a}$ and $R^{21b}$, when present, are covalently bonded, and, together with the intermediate atoms, comprise a 6-membered heterocycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $R^{21a}$ and $R^{21b}$, when present, are covalently bonded, and, together with the intermediate atoms, comprise a 6-membered unsubstituted heterocycloalkyl.

p. $R^{30}$ Groups

In one aspect, $R^{30}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $R^{30}$ is selected from hydrogen, —F, —Cl, —NH$_2$, —CN, —OH, —NO$_2$, methyl, ethyl, n-propyl, i-propyl, ethenyl, propenyl, isopropenyl, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, $R^{30}$ is selected from hydrogen, —F, —Cl, —NH$_2$, —CN, —OH, —NO$_2$, methyl, ethyl, ethenyl, —CH$_2$F, —CH$_2$Cl, —CH$_2$CH$_2$F, —CH$_2$CH$_2$Cl, —CH$_2$CN, —CH$_2$CH$_2$CN, —CH$_2$OH, —CH$_2$CH$_2$OH, —OCF$_3$, —OCH$_2$CF$_3$, —OCH$_3$, —OCH$_2$CH$_3$, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, $R^{30}$ is selected from hydrogen, —F, —Cl, —NH$_2$, —CN, —OH, —NO$_2$, methyl, —CH$_2$F, —CH$_2$Cl, —CH$_2$CN, —CH$_2$OH, —OCH$_2$CF$_3$, —OCH$_3$, —NHCH$_3$, —N(CH$_3$)$_2$, and —CH$_2$NH$_2$.

In various aspects, $R^{30}$ is selected from hydrogen, halogen, —CN, —NH$_2$, —OH, —NO$_2$, C1-C4 alkyl, and C2-C4 alkenyl. Thus, in various further aspects, $R^{30}$ is selected from hydrogen, —F, —Cl, —NH$_2$, —CN, —OH, —NO$_2$, methyl, ethyl, n-propyl, i-propyl, ethenyl, propenyl, and isopropenyl. In a further aspect, $R^{30}$ is selected from hydrogen, —F, —Cl, —NH$_2$, —CN, —OH, —NO$_2$, methyl, ethyl, and ethenyl. In a still further aspect, $R^{30}$ is selected from hydrogen, —F, —Cl, —NH$_2$, —CN, —OH, —NO$_2$, and methyl.

In various aspects, $R^{30}$ is selected from hydrogen, C1-C4 alkyl, and C2-C4 alkenyl. Thus, in various further aspects, $R^{30}$ is selected from hydrogen, methyl, ethyl, n-propyl, i-propyl, ethenyl, propenyl, and isopropenyl. In a further aspect, $R^{30}$ is independently selected from hydrogen, methyl, ethyl, and ethenyl. In a still further aspect, $R^{30}$ is selected from hydrogen and methyl.

In various aspects, $R^{30}$ is selected from hydrogen, halogen, —CN, —NH$_2$, —OH, —NO$_2$, C1-C4 haloalkyl, and C1-C4 haloalkoxy. Thus, in various further aspects, $R^{30}$ is selected from hydrogen, —F, —Cl, —NH$_2$, —CN, —OH, —NO$_2$, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$CF$_3$, —OCH$_2$CH$_2$CF$_3$, and —OCH(CH$_3$)CF$_3$. In a further aspect, $R^{30}$ is selected from hydrogen, —F, —Cl, —NH$_2$, —CN, —OH, —NO$_2$, —CH$_2$Cl, —CH$_2$CH$_2$F, —CH$_2$CH$_2$Cl, —OCF$_3$, and —OCH$_2$CF$_3$. In a still further aspect, $R^{30}$ is selected from hydrogen, —F, —Cl, —NH$_2$, —CN, —OH, —NO$_2$, —CH$_2$Cl, —OCF$_3$, and —OCH$_2$CF$_3$.

In various aspects, R$^{30}$ is selected from hydrogen, halogen, C1-C4 haloalkyl, and C1-C4 haloalkoxy. Thus, in various further aspects, R$^{30}$ is selected from hydrogen, —F, —Cl, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —OCH$_2$CF$_3$, —OCH$_2$CH$_2$CF$_3$, and —OCH(CH$_3$)CF$_3$.

In a further aspect, R$^{30}$ is selected from hydrogen, —F, —Cl, —CH$_2$Cl, —CH$_2$CH$_2$F, —CH$_2$CH$_2$Cl, —OCF$_3$, and —OCH$_2$CF$_3$. In a still further aspect, R$^{30}$ is selected from hydrogen, —F, —Cl, —CH$_2$Cl, —OCF$_3$, and —OCH$_2$CF$_3$.

In various aspects, R$^{30}$ is selected from hydrogen, halogen, —CN, —NH$_2$, —OH, —NO$_2$, and C1-C4 cyanoalkyl. Thus, in various further aspects, R$^{30}$ is selected from hydrogen, —F, —Cl, —NH$_2$, —CN, —OH, —NO$_2$, —CH$_2$CN, —CH$_2$CH$_2$CN, —CH$_2$CH$_2$CH$_2$CN, and —CH(CH$_3$)CH$_2$CN. In a further aspect, R$^{30}$ is selected from hydrogen, —F, —Cl, —NH$_2$, —CN, —OH, —NO$_2$, —CH$_2$CN, and —CH$_2$CH$_2$CN. In a still further aspect, R$^{30}$ is selected from hydrogen, —F, —Cl, —NH$_2$, —CN, —OH, —NO$_2$, and —CH$_2$CN.

In various aspects, R$^{30}$ is selected from hydrogen and C1-C4 cyanoalkyl. Thus, in various further aspects, R$^{30}$ is selected from hydrogen, —CH$_2$CN, —CH$_2$CH$_2$CN, —CH$_2$CH$_2$CH$_2$CN, and —CH(CH$_3$)CH$_2$CN. In a further aspect, R$^{30}$ is selected from hydrogen, —CH$_2$CN, and —CH$_2$CH$_2$CN. In a still further aspect, R$^{30}$ is selected from hydrogen and —CH$_2$CN.

In various aspects, R$^{30}$ is selected from hydrogen, halogen, —CN, —NH$_2$, —OH, —NO$_2$, C1-C4 hydroxyalkyl, and C1-C4 alkoxy. Thus, in various further aspects, R$^{30}$ is selected from hydrogen, —F, —Cl, —NH$_2$, —CN, —OH, —NO$_2$, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, R$^{30}$ is selected from hydrogen, —F, —Cl, —NH$_2$, —CN, —OH, —NO$_2$, —CH$_2$OH, —CH$_2$CH$_2$OH, —OCH$_3$, and —OCH$_2$CH$_3$. In a still further aspect, R$^{30}$ is selected from hydrogen, —F, —Cl, —NH$_2$, —CN, —OH, —NO$_2$, —CH$_2$OH, and —OCH$_3$.

In various aspects, R$^{30}$ is selected from hydrogen, C1-C4 hydroxyalkyl, and C1-C4 alkoxy. Thus, in various further aspects, R$^{30}$ is selected from hydrogen, —CH$_2$OH, —CH$_2$CH$_2$OH, —CH$_2$CH$_2$CH$_2$OH, —CH(CH$_3$)CH$_2$OH, —OCH$_3$, —OCH$_2$CH$_3$, —OCH$_2$CH$_2$CH$_3$, and —OCH(CH$_3$)CH$_3$. In a further aspect, R$^{30}$ is selected from hydrogen, —CH$_2$OH, —CH$_2$CH$_2$OH, —OCH$_3$, and —OCH$_2$CH$_3$. In a still further aspect, R$^{30}$ is selected from hydrogen, —CH$_2$OH, and —OCH$_3$.

In various aspects, R$^{30}$ is selected from hydrogen, halogen, —CN, —NH$_2$, —OH, —NO$_2$, C1-C4 alkylamino, (C1-C4)(C1-C4) dialkylamino, and C1-C4 aminoalkyl. Thus, in various further aspects, R$^{30}$ is selected from hydrogen, —F, —Cl, —NH$_2$, —CN, —OH, —NO$_2$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, R$^{30}$ is selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, R$^{30}$ is selected from hydrogen, —F, —Cl, —NH$_2$, —CN, —OH, —NO$_2$, —NHCH$_3$, —N(CH$_3$)$_2$, and —CH$_2$NH$_2$.

In various aspects, R$^{30}$ is selected from hydrogen, C1-C4 alkylamino, (C1-C4)(C1-C4) dialkylamino, and C1-C4 aminoalkyl. Thus, in various further aspects, R$^{30}$ is selected from hydrogen, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$. In a further aspect, R$^{30}$ is selected from hydrogen, —NHCH$_3$, —NHCH$_2$CH$_3$, —N(CH$_3$)$_2$, —N(CH$_2$CH$_3$)$_2$, —N(CH$_3$)(CH$_2$CH$_3$), —CH$_2$NH$_2$, and —CH$_2$CH$_2$NH$_2$. In a still further aspect, R$^{30}$ is selected from hydrogen, —NHCH$_3$, —N(CH$_3$)$_2$, and —CH$_2$NH$_2$.

In various aspects, R$^{30}$ is C1-C4 alkyl. In a further aspect, R$^{30}$ is selected from methyl, ethyl, n-propyl, and isopropyl. In a still further aspect, R$^{30}$ is selected from methyl and ethyl. In yet a further aspect, R$^{30}$ is methyl.

In various aspects, R$^{30}$ is hydrogen.

q. R$^{31a}$ and R$^{31b}$ Groups

In one aspect, each occurrence of R$^{31a}$ and R$^{31b}$, when present, is independently selected from hydrogen, halogen, and C1-C4 alkyl. In a further aspect, each occurrence of R$^{31a}$ and R$^{31b}$, when present, is independently selected from hydrogen, —F, —Cl, —Br, methyl, ethyl, n-propyl, and isopropyl. In a still further aspect, each occurrence of R$^{31a}$ and R$^{31b}$, when present, is independently selected from hydrogen, —F, —Cl, methyl, and ethyl. In yet a further aspect, each occurrence of R$^{31a}$ and R$^{31b}$, when present, is independently selected from hydrogen, —F, —Cl, and methyl.

In various aspects, each occurrence of R$^{31a}$ and R$^{31b}$, when present, is independently selected from hydrogen and halogen. In a further aspect, each occurrence of R$^{31a}$ and R$^{31b}$, when present, is independently selected from hydrogen, —F, —Cl, and —Br. In a still further aspect, each occurrence of R$^{31a}$ and R$^{31b}$, when present, is independently selected from hydrogen, —F, and —Cl. In yet a further aspect, each occurrence of R$^{31a}$ and R$^{31b}$, when present, is independently selected from hydrogen and —Cl. In an even further aspect, each occurrence of R$^{31a}$ and R$^{31b}$, when present, is independently selected from hydrogen and —F.

In various aspects, each occurrence of R$^{31a}$ and R$^{31b}$, when present, is independently halogen. In a further aspect, each occurrence of R$^{31a}$ and R$^{31b}$, when present, is independently selected from —F, —Cl, and —Br. In a still further aspect, each occurrence of R$^{31a}$ and R$^{31b}$, when present, is independently selected from —F and —Cl. In yet a further aspect, each occurrence of R$^{31a}$ and R$^{31b}$, when present, is —Cl. In an even further aspect, each occurrence of R$^{31a}$ and R$^{31b}$, when present, is —F.

In various aspects, each occurrence of R$^{31a}$ and R$^{31b}$, when present, is independently selected from hydrogen and C1-C4 alkyl. In a further aspect, each occurrence of R$^{31a}$ and R$^{31b}$, when present, is independently selected from hydrogen, methyl, ethyl, n-propyl, and isopropyl. In a still further aspect, each occurrence of R$^{31a}$ and R$^{31b}$, when present, is independently selected from hydrogen, methyl, and ethyl. In yet a further aspect, each occurrence of R$^{31a}$ and R$^{31b}$, when present, is independently selected from hydrogen and methyl.

In various aspects, each occurrence of R$^{31a}$ and R$^{31b}$, when present, is independently C1-C4 alkyl. In a further aspect, each occurrence of R$^{31a}$ and R$^{31b}$, when present, is independently selected from methyl, ethyl, n-propyl, and isopropyl. In a still further aspect, each occurrence of R$^{31a}$ and R$^{31b}$, when present, is independently selected from methyl and ethyl. In yet a further aspect, each occurrence of $R^{31a}$ and $R^{31b}$, when present, is methyl.

In various aspects, each occurrence of $R^{31a}$ and $R^{31b}$, when present, is hydrogen.

r. $R^{40}$ Groups

In one aspect, $R^{40}$, when present, is selected from hydrogen and C1-C4 alkyl. In a further aspect, $R^{40}$, when present, is selected from hydrogen, methyl, ethyl, n-propyl, and isopropyl. In a still further aspect, $R^{40}$, when present, is selected from hydrogen, methyl, and ethyl. In yet a further aspect, $R^{40}$, when present, is selected from hydrogen and ethyl. In an even further aspect, $R^{40}$, when present, is selected from hydrogen and methyl.

In various aspects, $R^{40}$, when present, is C1-C4 alkyl. In a further aspect, $R^{40}$, when present, is selected from methyl, ethyl, n-propyl, and isopropyl. In a still further aspect, $R^{40}$, when present, is selected from methyl and ethyl. In yet a further aspect, $R^{40}$, when present, is ethyl. In an even further aspect, $R^{40}$, when present, is methyl.

In various aspects, $R^{40}$, when present, is hydrogen.

s. $R^{41a}$ and $R^{41b}$ Groups

In one aspect, each of $R^{41a}$ and $R^{41b}$, when present, is independently selected from hydrogen and C1-C4 alkyl. In a further aspect, each of $R^{41a}$ and $R^{41b}$, when present, is independently selected from hydrogen, methyl, ethyl, n-propyl, and isopropyl. In a still further aspect, each of $R^{41a}$ and $R^{41b}$, when present, is independently selected from hydrogen, methyl, and ethyl. In yet a further aspect, each of $R^{41a}$ and $R^{41b}$, when present, is independently selected from hydrogen and ethyl. In an even further aspect, each of $R^{41a}$ and $R^{41b}$, when present, is independently selected from hydrogen and methyl.

In various aspects, each of $R^{41a}$ and $R^{41b}$, when present, is independently C1-C4 alkyl. In a further aspect, each of $R^{41a}$ and $R^{41b}$, when present, is independently selected from methyl, ethyl, n-propyl, and isopropyl. In a still further aspect, each of $R^{41a}$ and $R^{41b}$, when present, is independently selected from methyl and ethyl. In yet a further aspect, each of $R^{41a}$ and $R^{41b}$, when present, is ethyl. In an even further aspect, each of $R^{41a}$ and $R^{41b}$, when present, is methyl.

In various aspects, each of $R^{41a}$ and $R^{41b}$, when present, is hydrogen.

t. $R^{42}$ Groups

In one aspect, each occurrence of $R^{42}$, when present, is independently selected from hydrogen and C1-C4 alkyl. In a further aspect, each occurrence of $R^{42}$, when present, is independently selected from hydrogen, methyl, ethyl, n-propyl, and isopropyl. In a still further aspect, each occurrence of $R^{42}$, when present, is independently selected from hydrogen, methyl, and ethyl. In yet a further aspect, each occurrence of $R^{42}$, when present, is independently selected from hydrogen and ethyl. In an even further aspect, each occurrence of $R^{42}$, when present, is independently selected from hydrogen and methyl.

In various aspects, each occurrence of $R^{42}$, when present, is independently C1-C4 alkyl. In a further aspect, each occurrence of $R^{42}$, when present, is independently selected from methyl, ethyl, n-propyl, and isopropyl. In a still further aspect, each occurrence of $R^{42}$, when present, is independently selected from methyl and ethyl. In yet a further aspect, each occurrence of $R^{42}$, when present, is ethyl. In an even further aspect, each occurrence of $R^{42}$, when present, is methyl.

In various aspects, each occurrence of $R^{42}$, when present, is hydrogen.

u. $R^{43a}$ and $R^{43b}$ Groups

In one aspect, each occurrence of $R^{43a}$ and $R^{43b}$, when present, is independently selected from hydrogen and C1-C4 alkyl. In a further aspect, each occurrence of $R^{43a}$ and $R^{43b}$, when present, is independently selected from hydrogen, methyl, ethyl, n-propyl, and isopropyl. In a still further aspect, each occurrence of $R^{43a}$ and $R^{43b}$, when present, is independently selected from hydrogen, methyl, and ethyl. In yet a further aspect, each occurrence of $R^{43a}$ and $R^{43b}$, when present, is independently selected from hydrogen and ethyl. In an even further aspect, each occurrence of $R^{43a}$ and $R^{43b}$, when present, is independently selected from hydrogen and methyl.

In various aspects, each occurrence of $R^{43a}$ and $R^{43b}$, when present, is independently C1-C4 alkyl. In a further aspect, each occurrence of $R^{43a}$ and $R^{43b}$, when present, is independently selected from methyl, ethyl, n-propyl, and isopropyl. In a still further aspect, each occurrence of $R^{43a}$ and $R^{43b}$, when present, is independently selected from methyl and ethyl. In yet a further aspect, each occurrence of $R^{43a}$ and $R^{43b}$, when present, is ethyl. In an even further aspect, each occurrence of $R^{43a}$ and $R^{43b}$, when present, is methyl.

In various aspects, each occurrence of $R^{43a}$ and $R^{43b}$, when present, is hydrogen.

v. $Cy^1$ Groups

In one aspect, $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 cycloalkyls include, but are not limited to, cyclopropyl, cyclobutyl, cyclopentyl, cyclohexyl, and spiro[2.2]pentane. In a further aspect, $Cy^1$, when present, is a C3-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is a C3-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^1$, when present, is a C3-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^1$, when present, is an unsubstituted C3-C6 cycloalkyl.

In various aspects, $Cy^1$, when present, is a C4-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^1$, when present, is a C4-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^1$, when present, is a C4-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^1$, when present, is a C4-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy$^1$, when present, is an unsubstituted C4-C6 cycloalkyl.

In various aspects, Cy$^1$, when present, is a C5-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy$^1$, when present, is a C5-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^1$, when present, is a C5-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^1$, when present, is a C5-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy$^1$, when present, is an unsubstituted C5-C6 cycloalkyl.

w. Cy$^2$ Groups

In one aspect, Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy$^2$, when present, is selected from C3-C6 cycloalkyl, C3-C6 heterocycloalkyl, C6-C14 aryl, and C2-C10 heteroaryl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^2$, when present, is selected from C3-C6 cycloalkyl, C3-C6 heterocycloalkyl, C6-C14 aryl, and C2-C10 heteroaryl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^2$, when present, is selected from C3-C6 cycloalkyl, C3-C6 heterocycloalkyl, C6-C14 aryl, and C2-C10 heteroaryl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy$^2$, when present, is selected from C3-C6 cycloalkyl, C3-C6 heterocycloalkyl, C6-C14 aryl, and C2-C10 heteroaryl, and is unsubstituted.

In various aspects, Cy$^2$, when present, is selected from C3-C6 cycloalkyl and C3-C6 heterocycloalkyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy$^2$, when present, is selected from C3-C6 cycloalkyl and C3-C6 heterocycloalkyl, and is substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^2$, when present, is selected from C3-C6 cycloalkyl and C3-C6 heterocycloalkyl, and is substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^2$, when present, is selected from C3-C6 cycloalkyl and C3-C6 heterocycloalkyl, and is monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy$^2$, when present, is selected from C3-C6 cycloalkyl and C3-C6 heterocycloalkyl, and is unsubstituted.

In various aspects, Cy$^2$, when present, is C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 cycloalkyls include, but are not limited to, cyclopropyl, cyclobutyl, cyclopentyl, cyclohexyl, and spiro[2.2]pentane. In a further aspect, Cy$^2$, when present, is C3-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^2$, when present, is C3-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^2$, when present, is C3-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-

C4) dialkylamino, and C1-C4 aminoalkyl. In an even further aspect, Cy², when present, is unsubstituted C3-C6 cycloalkyl.

In various aspects, Cy², when present, is C3-C6 heterocycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C5 heterocycloalkyls include, but are not limited to, thiirane, oxirane, aziridine, thietane, azetidine, oxetane, pyrrolidine, imidazolidine, tetrahydrothiophene, tetrahydrofuran, piperidine, piperazine, thiane, and morpholine. In a further aspect, Cy², when present, is C3-C6 heterocycloalkyl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy², when present, is C3-C6 heterocycloalkyl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy², when present, is C3-C6 heterocycloalkyl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy², when present, is unsubstituted C3-C6 heterocycloalkyl.

In various aspects, Cy², when present, is selected from C6-C14 aryl and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy², when present, is selected from C6-C14 aryl and C2-C10 heteroaryl, and is substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy², when present, is selected from C6-C14 aryl and C2-C10 heteroaryl, and is substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy², when present, is selected from C6-C14 aryl and C2-C10 heteroaryl, and is monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy², when present, is selected from C6-C14 aryl and C2-C10 heteroaryl, and is unsubstituted.

In various aspects, Cy², when present, is C6-C14 aryl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C14 aryls include, but are not limited to, phenyl, naphthyl, phenanthryl, and anthracenyl. In a further aspect, Cy², when present, is C6-C14 aryl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy², when present, is C6-C14 aryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy², when present, is C6-C14 aryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy², when present, is unsubstituted C6-C14 aryl.

In various aspects, Cy², when present, is C2-C10 heteroaryl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C2-C10 heteroaryls include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl. In a further aspect, Cy², when present, is C2-C10 heteroaryl substituted with 0, 1, or 2 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy², when present, is C2-C10 heteroaryl substituted with 0 or 1 group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy², when present, is C2-C10 heteroaryl monosubstituted with a group selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy², when present, is unsubstituted C2-C10 heteroaryl.

x. Cy³ Groups

In one aspect, Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 cycloalkyls include, but are not limited to, cyclopropyl, cyclobutyl, cyclopentyl, cyclohexyl, and spiro[2.2]pentane. In a further aspect, $Cy^3$, when present, is a C3-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is a C3-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is a C3-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is an unsubstituted C3-C6 cycloalkyl.

In various aspects, $Cy^3$, when present, is a C4-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is a C4-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is a C4-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is a C4-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is an unsubstituted C4-C6 cycloalkyl.

In various aspects, $Cy^3$, when present, is a C5-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^3$, when present, is a C5-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^3$, when present, is a C5-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^3$, when present, is a C5-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^3$, when present, is an unsubstituted C5-C6 cycloalkyl.

y. $Cy^4$ Groups

In one aspect, $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 cycloalkyls include, but are not limited to, cyclopropyl, cyclobutyl, cyclopentyl, cyclohexyl, and spiro[2.2]pentane. In a further aspect, $Cy^4$, when present, is a C3-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is a C3-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is a C3-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is an unsubstituted C3-C6 cycloalkyl.

In various aspects, $Cy^4$, when present, is a C4-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, $Cy^4$, when present, is a C4-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, $Cy^4$, when present, is a C4-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, $Cy^4$, when present, is a C4-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, $Cy^4$, when present, is an unsubstituted C4-C6 cycloalkyl.

In various aspects, $Cy^4$, when present, is a C5-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy$^4$, when present, is a C5-C6 cycloalkyl substituted with 0, 1, or 2 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^4$, when present, is a C5-C6 cycloalkyl substituted with 0 or 1 group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^4$, when present, is a C5-C6 cycloalkyl monosubstituted with a group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In an even further aspect, Cy$^4$, when present, is an unsubstituted C5-C6 cycloalkyl.

z. Cy$^5$ Groups

In one aspect, Cy$^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C6 heterocycloalkyls substituted with at least one =O group include, but are not limited to, 2,3-pyrrolidinedione, 2,5-pyrrolidinedione, pyrrolidin-2-one, pyrrolidin-3-one, dihydrofuran-2(3H)-one, dihydrothiophen-2(3H)-one, dihydrothiophene-2,5-dione, dihydrofuran-2,5-dione, tetrahydro-2H-pyran-2-one, dihydro-2H-pyran-2,6(3H)-dione, piperidine-2,6-dione, piperidin-2-one, tetrahydro-2H-thiopyran-2-one, and dihydro-2H-thiopyran-2,6(3H)-dione. In a further aspect, Cy$^5$, when present, is a C3-C6 heterocycloalkyl substituted with at least one =O group, and substituted with 0 or 1 additional group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^5$, when present, is a C3-C6 heterocycloalkyl substituted with at least one =O group, and monosubstituted with an additional group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^5$, when present, is a C3-C6 heterocycloalkyl substituted with at least one =O group, and substituted with 0 additional groups.

In various aspects, Cy$^5$, when present, is a pyrrolidinedione substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, Cy$^5$, when present, is a pyrrolidinedione substituted with 0 or 1 additional group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, Cy$^5$, when present, is a pyrrolidinedione monosubstituted with an additional group selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In yet a further aspect, Cy$^5$, when present, is an unsubstituted pyrrolidinedione.

2. Example Compounds

In one aspect, a compound can be present as one or more of the following structures:

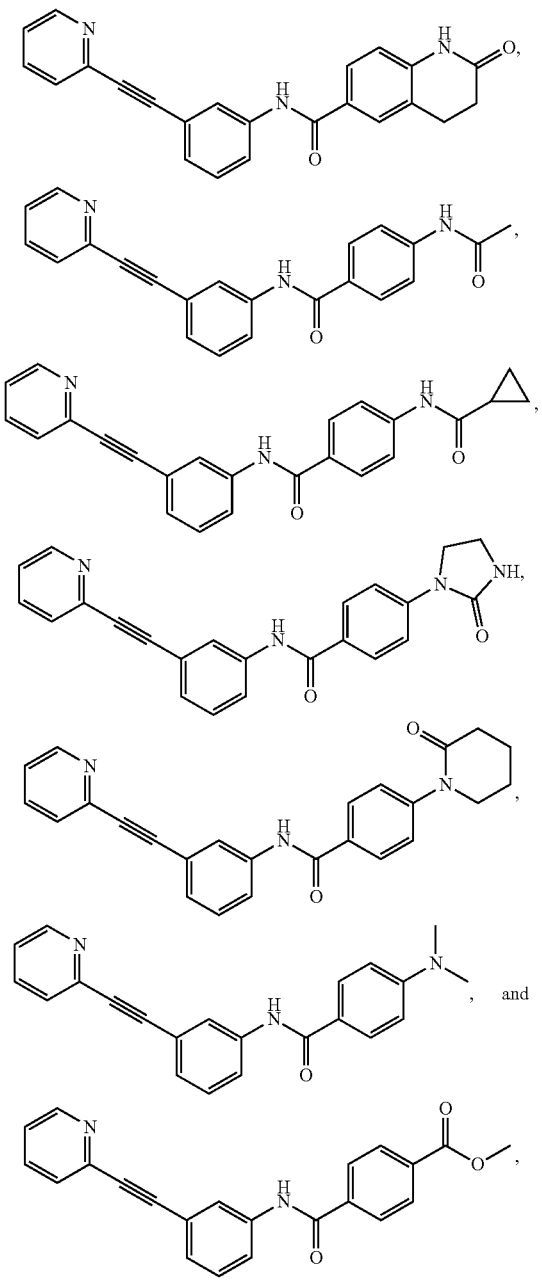

or a pharmaceutically acceptable salt thereof.

In one aspect, a compound can be present as one or more of the following structures:
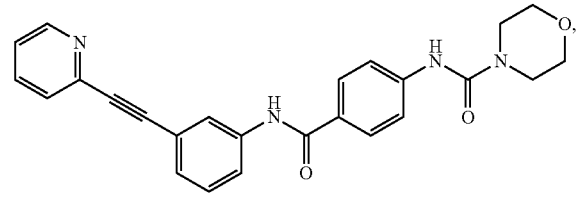
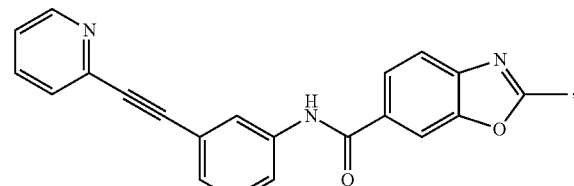
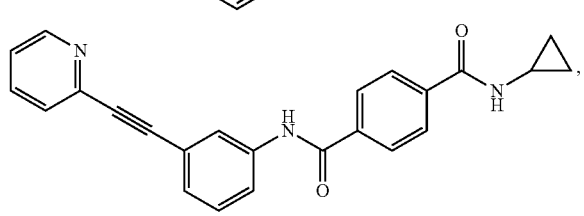
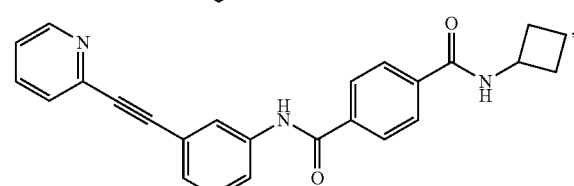
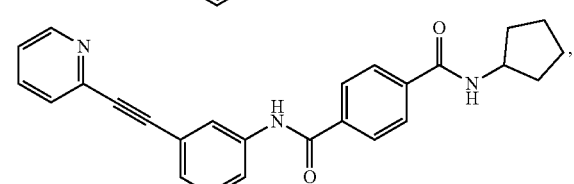
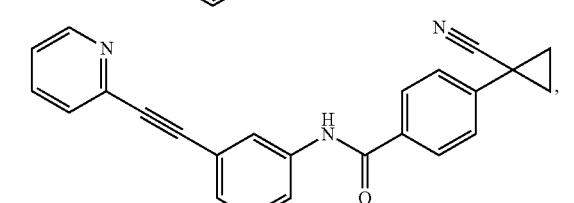
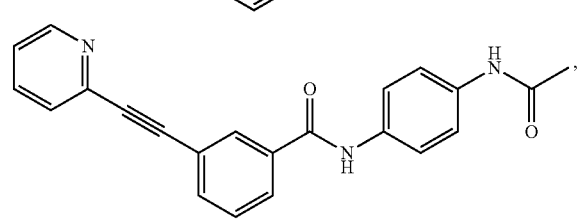
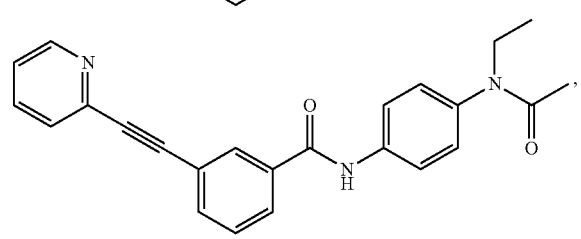
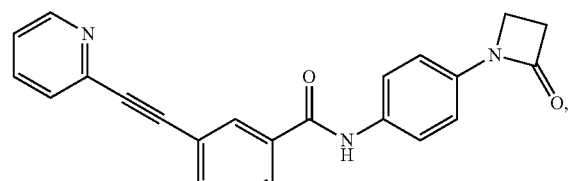
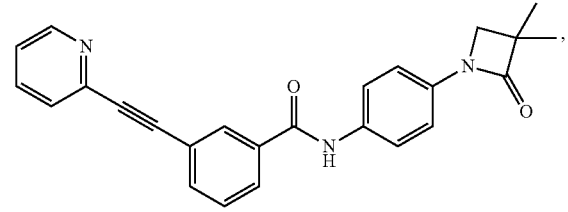
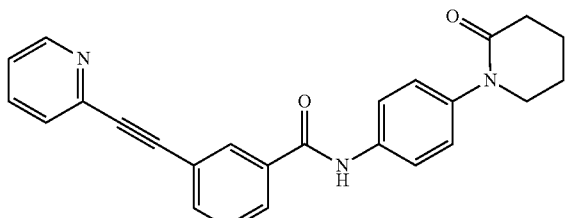
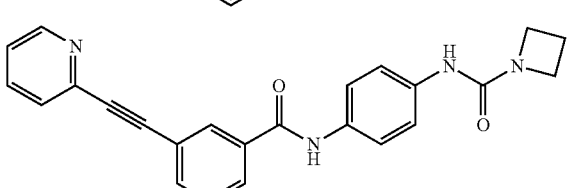
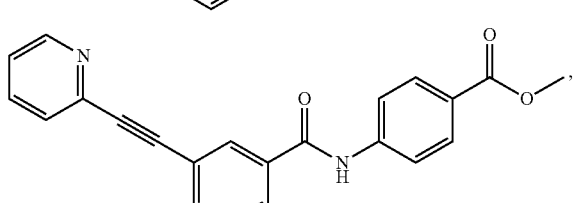
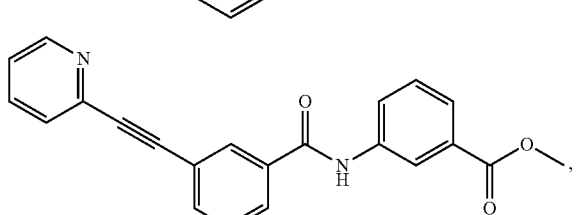
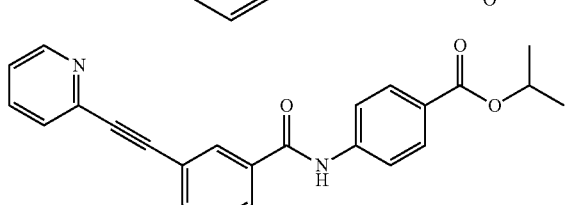
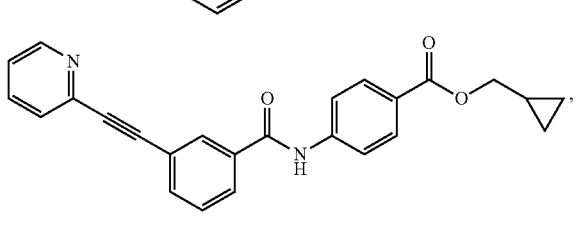

103
-continued
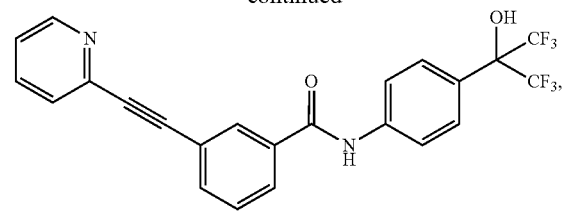
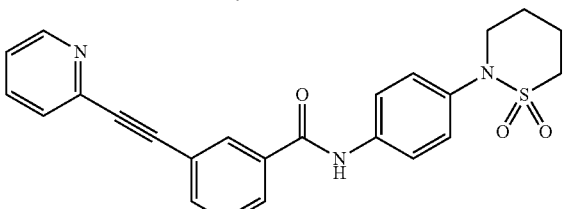
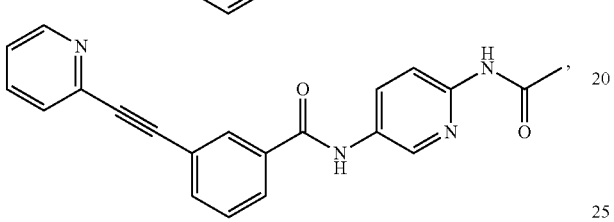
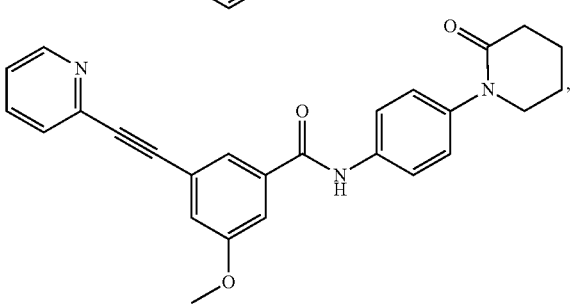
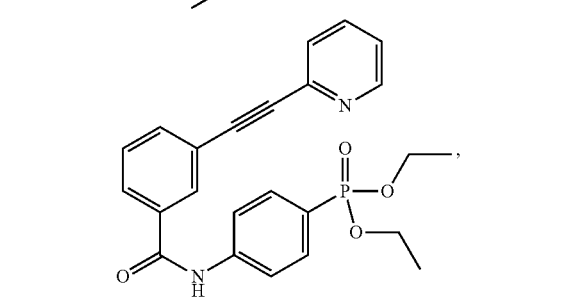
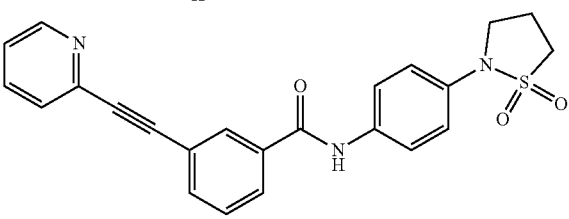
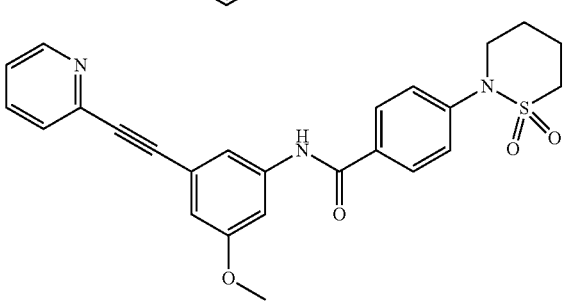
104
-continued
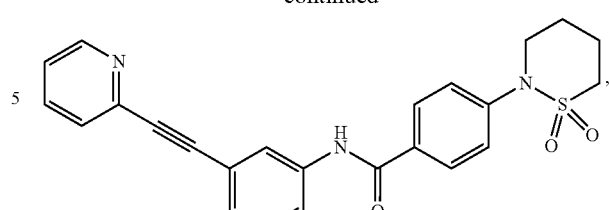
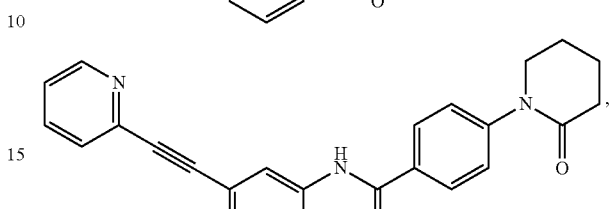
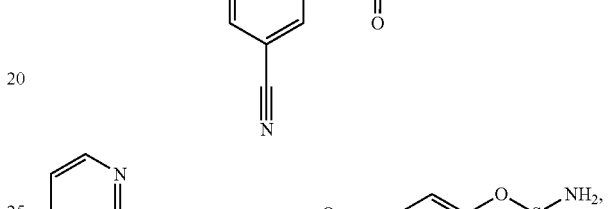
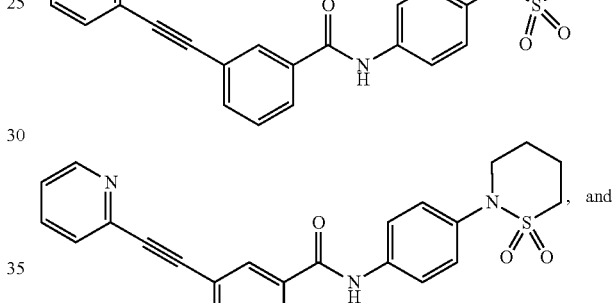
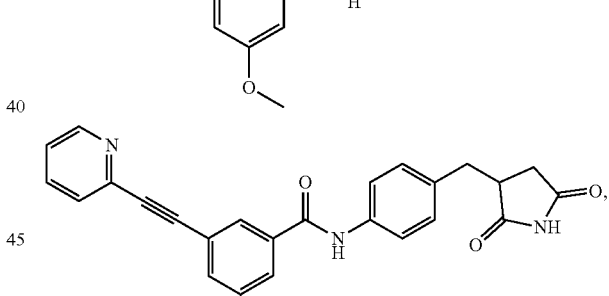
, and
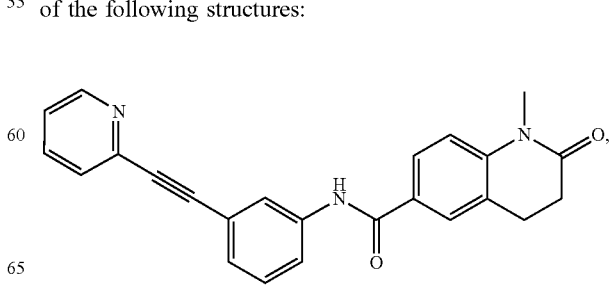
or a pharmaceutically acceptable salt thereof.
In one aspect, a compound can be present as one or more of the following structures:

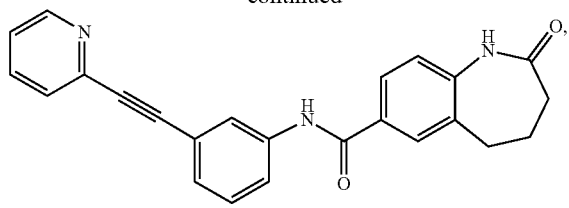
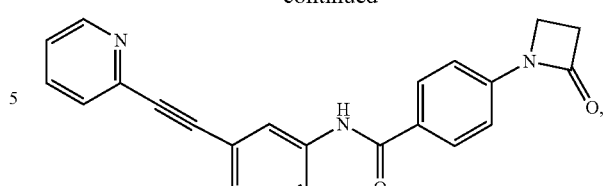
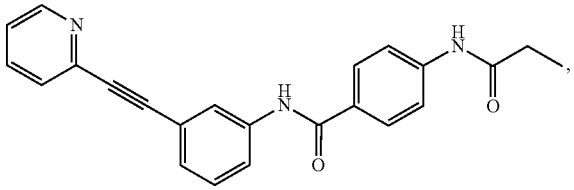
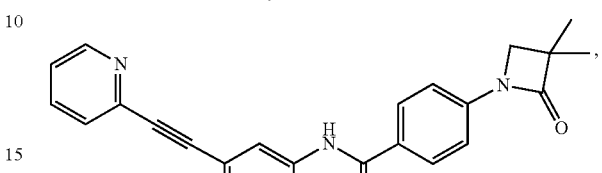
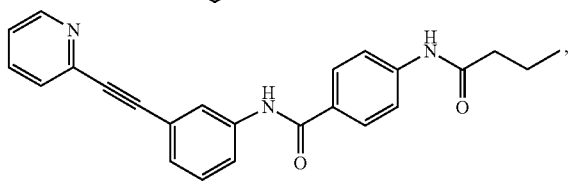
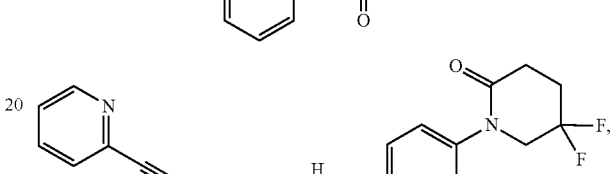
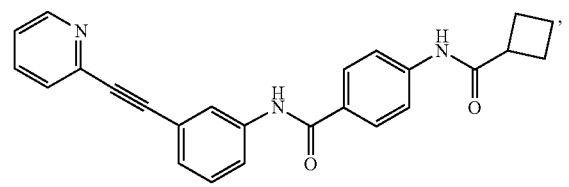
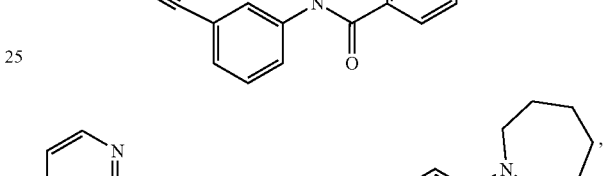
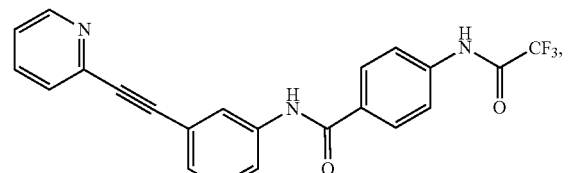
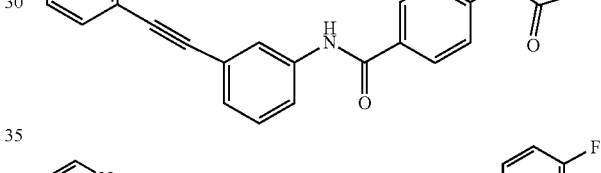
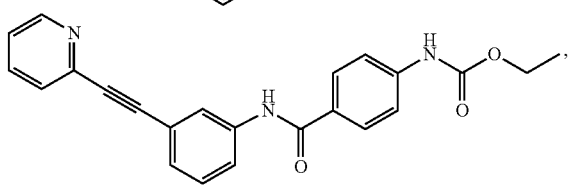
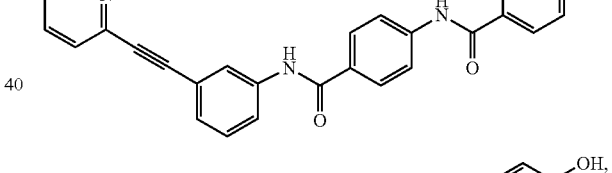
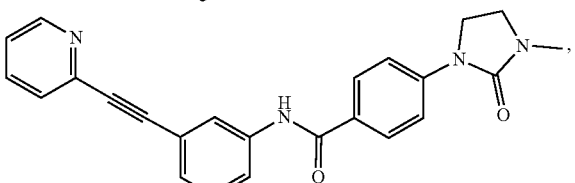
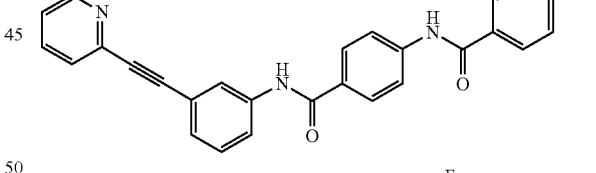
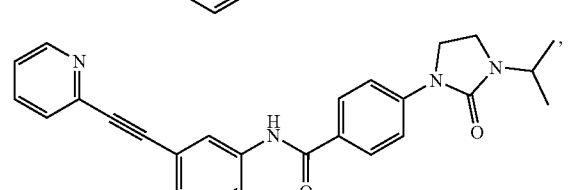
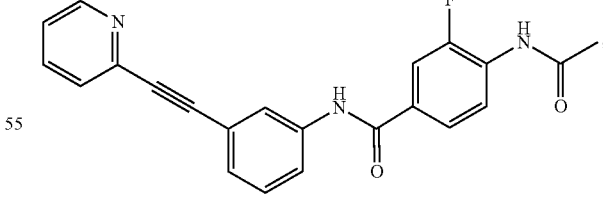
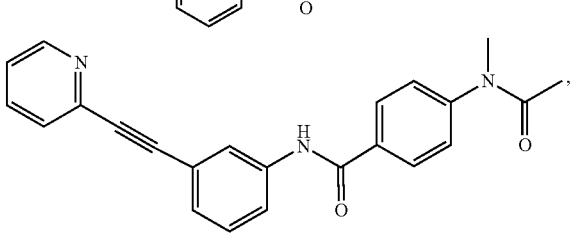
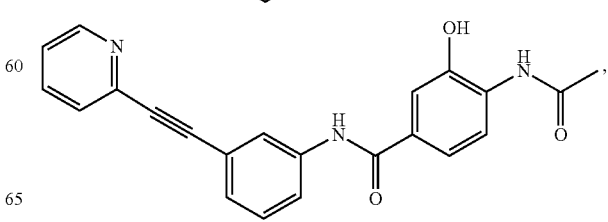

107
-continued
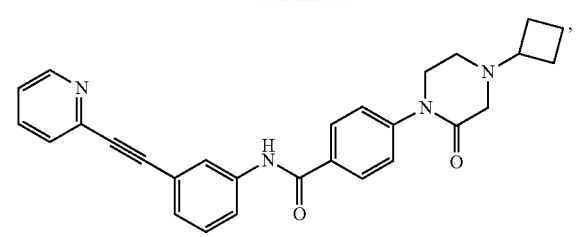
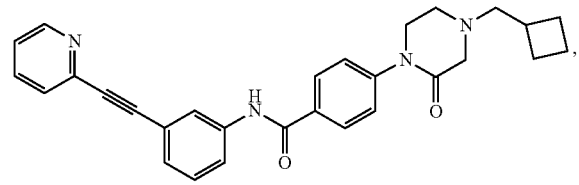
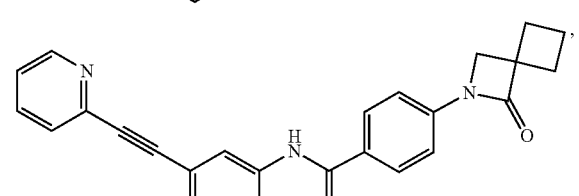
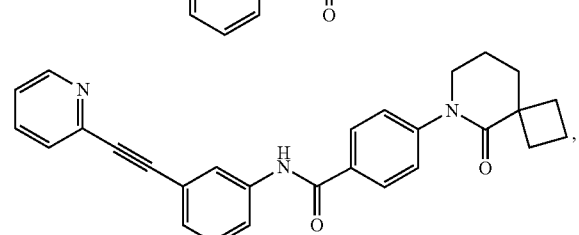
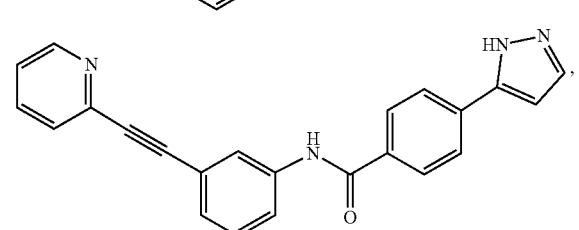
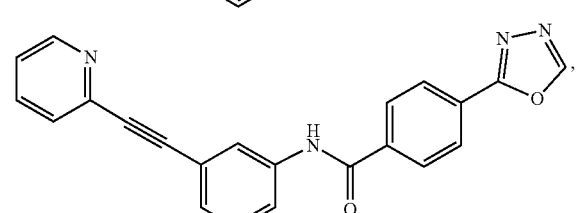
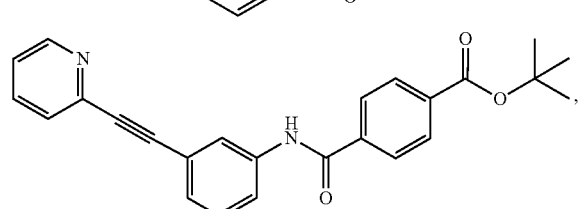
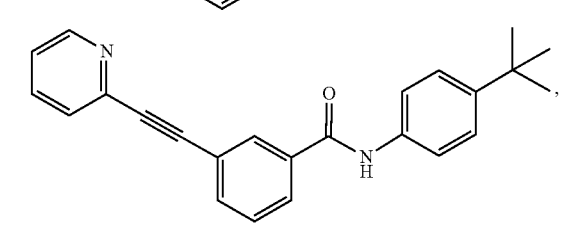
108
-continued
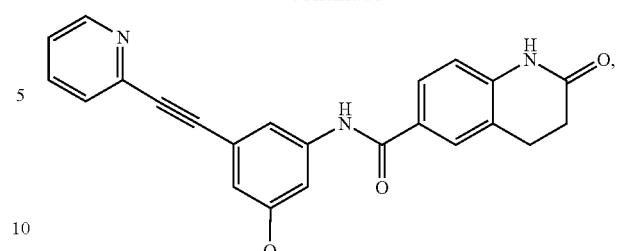
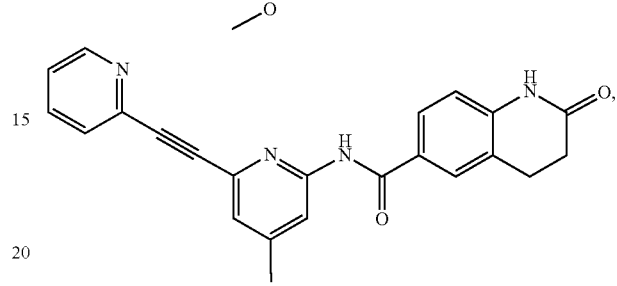
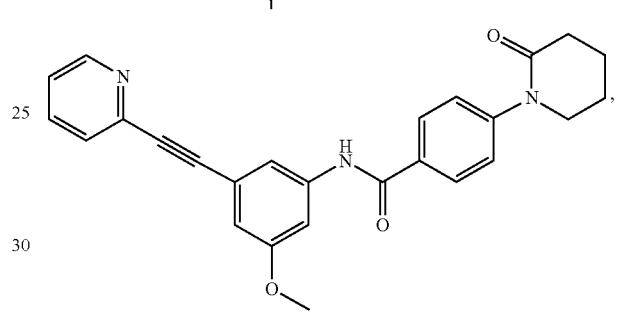
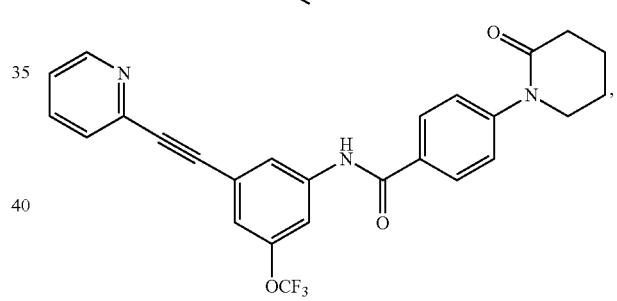
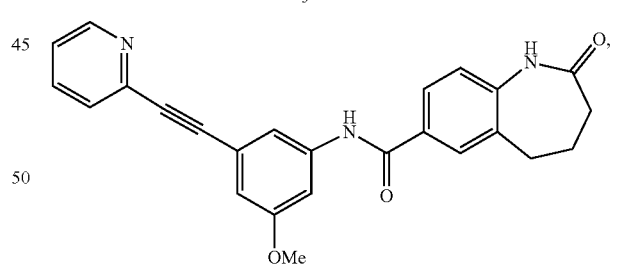
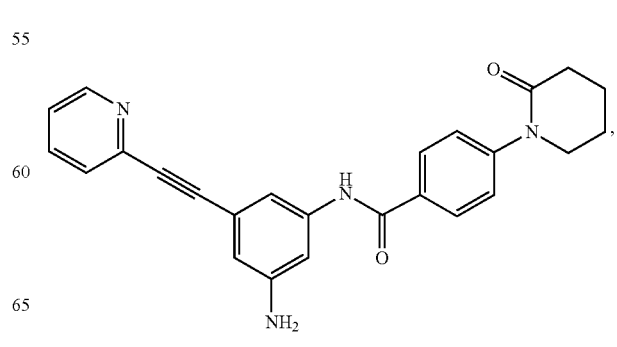

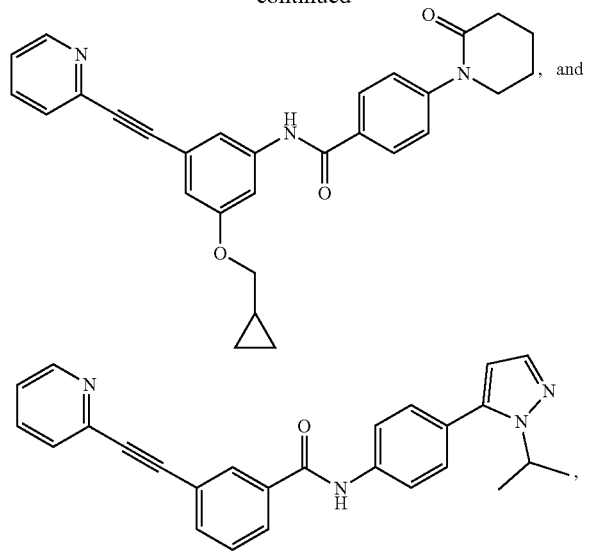

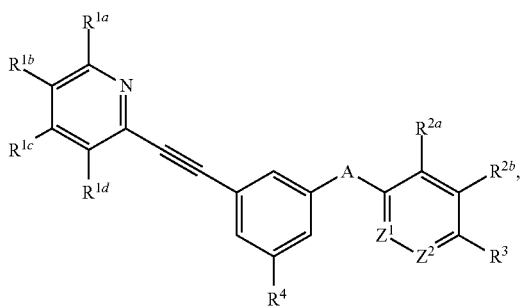

or a pharmaceutically acceptable salt thereof.

C. PHARMACEUTICAL COMPOSITIONS

In one aspect, disclosed are pharmaceutical compositions comprising a therapeutically effective amount of a disclosed compound, or a pharmaceutically acceptable salt thereof, and a pharmaceutically acceptable carrier.

Thus, in one aspect, disclosed are pharmaceutical compositions comprising a therapeutically effective amount of a compound having a structure represented by a formula:

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N═ and —C(R$^{13}$)═; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy$^5$, when present, is a C3-C6 heterocycloalkyl substituted with at least one ═O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

Also disclosed are pharmaceutical compositions comprising a therapeutically effective amount of a compound having a structure represented by a formula:

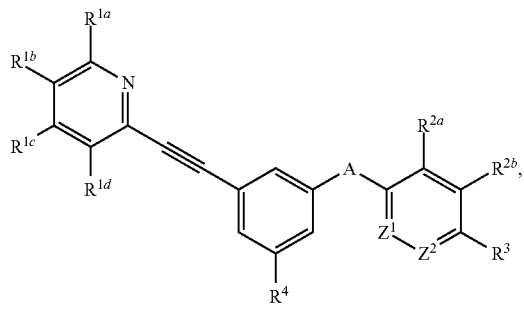

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

In various aspects, disclosed are pharmaceutical compositions comprising a therapeutically effective amount of a compound having a structure represented by a formula:

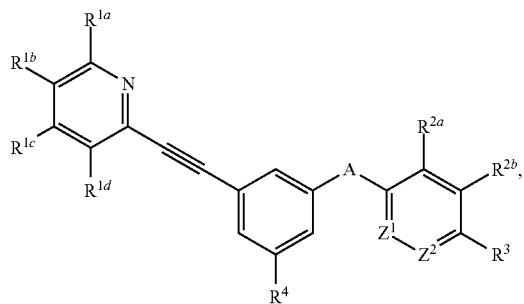

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then R$^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and R$^3$ is —NR$^{14}$C(O)R$^{15}$, then R$^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof, and a pharmaceutically acceptable carrier.

In various aspects, the compound has a structure represented by a formula:

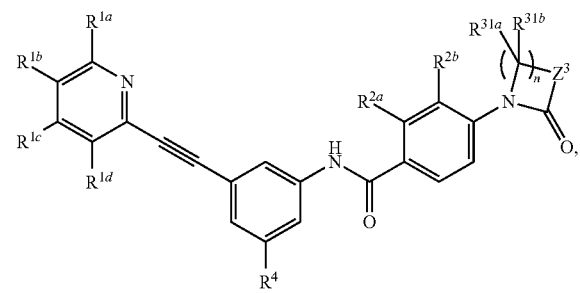

wherein n is selected from 1, 2, 3, 4, 5, and 6; wherein Z$^3$ is selected from —O—, —NR$^{40}$—, and —CR$^{41a}$R$^{41b}$, wherein R$^{40}$, when present, is selected from hydrogen and C1-C4 alkyl; wherein each of R$^{41a}$ and R$^{41b}$, when present, is independently selected from hydrogen and C1-C4 alkyl; and wherein each occurrence of R$^{31a}$ and R$^{31b}$, when present, is independently selected from hydrogen, halogen, and C1-C4 alkyl.

In various aspects, the compound has a structure represented by a formula:

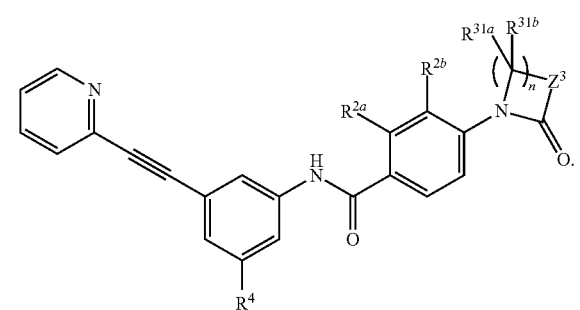

In various aspects, the compound has a structure represented by a formula:

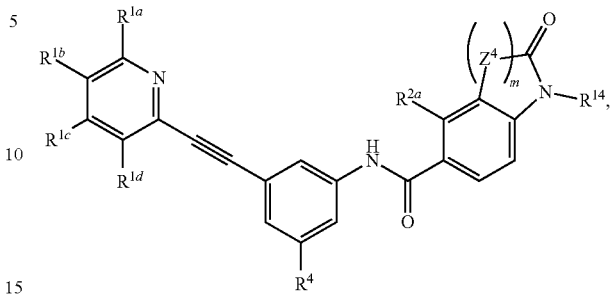

wherein m is selected from 1, 2, and 3; wherein each occurrence of Z$^4$ is independently selected from —O—, —NR$^{42}$—, and —CR$^{43a}$R$^{43b}$; wherein each occurrence of R$^{42}$, when present, is independently selected from hydrogen and C1-C4 alkyl; and wherein each occurrence of R$^{43a}$ and R$^{43b}$, when present, is independently selected from hydrogen and C1-C4 alkyl, provided that no more than one occurrence of Z$^4$ is —O— or —NR$^{42}$—.

In various aspects, the compound has a structure represented by a formula:

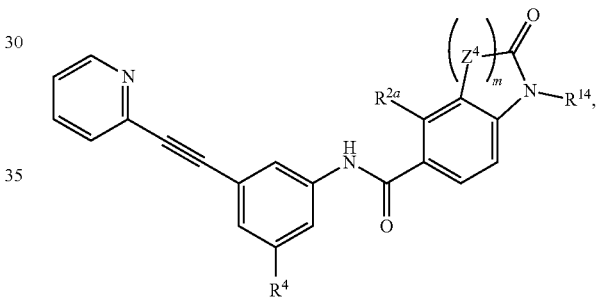

In various aspects, the compound is:

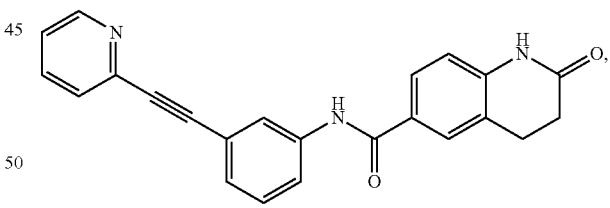

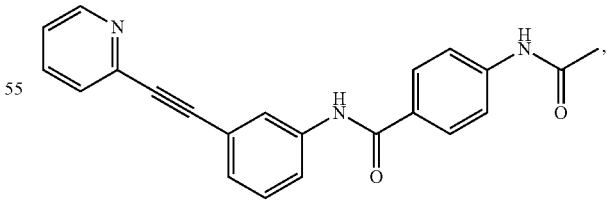

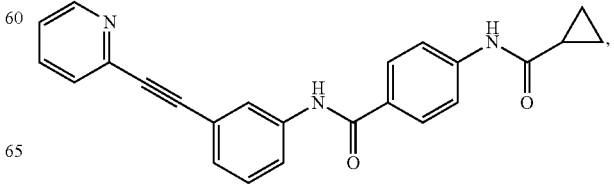

117
-continued
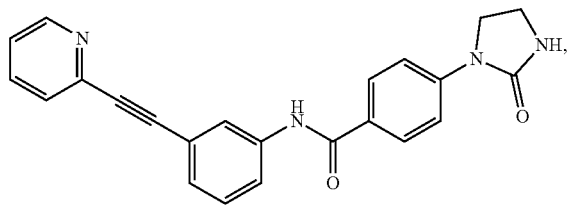
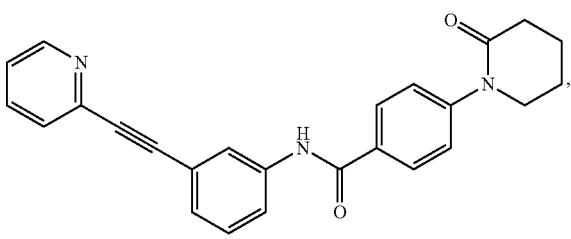
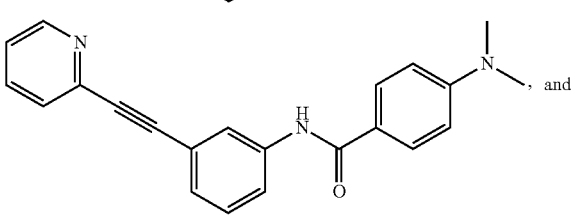
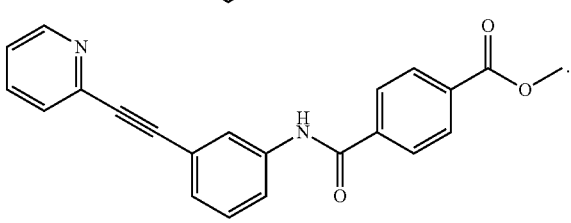
In various aspects, the compound is selected from:
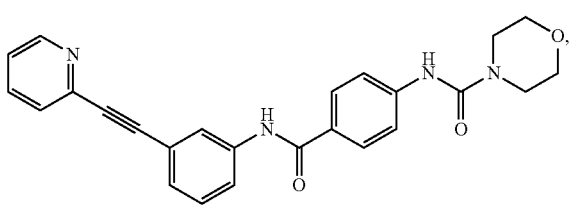
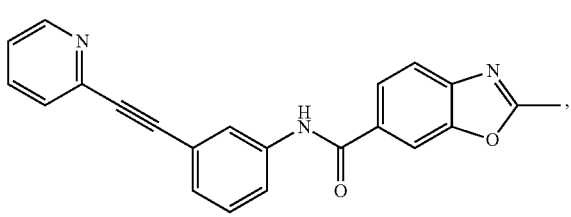
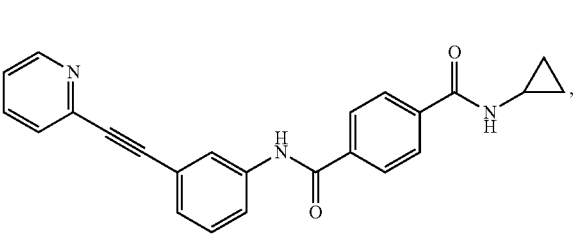
118
-continued
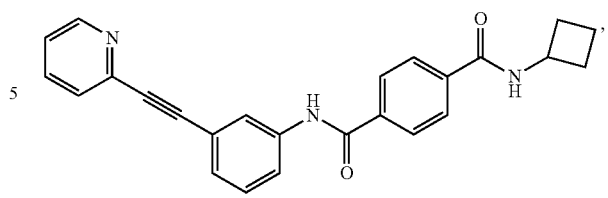
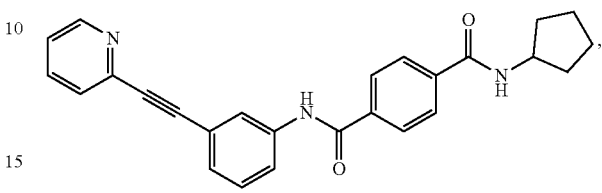
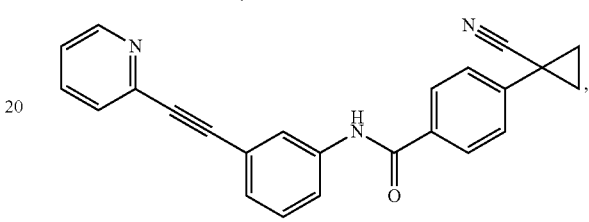
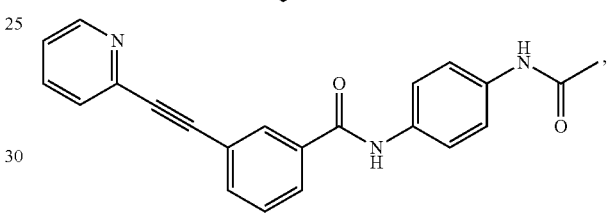
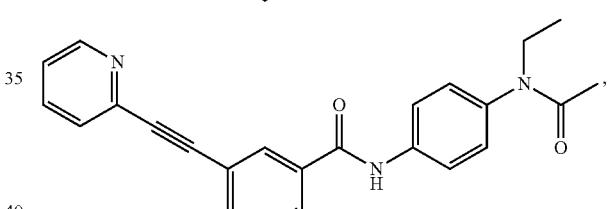
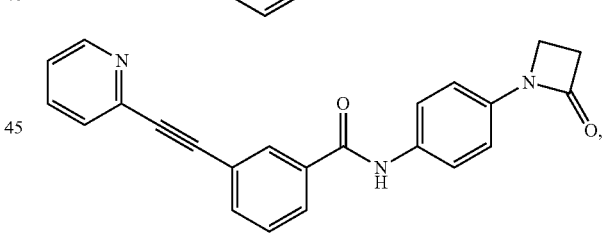
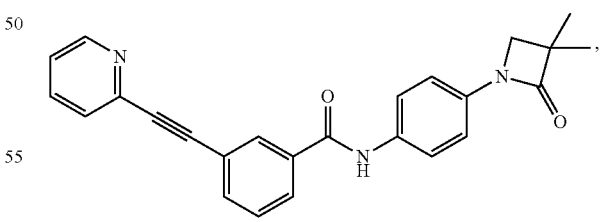
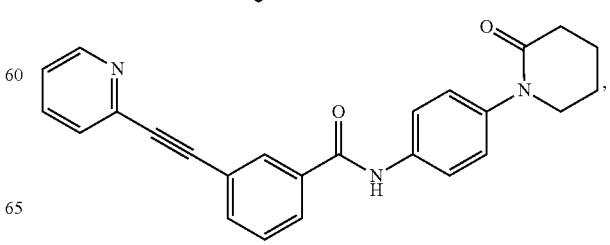

119
-continued
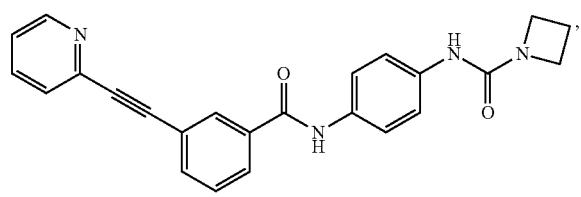
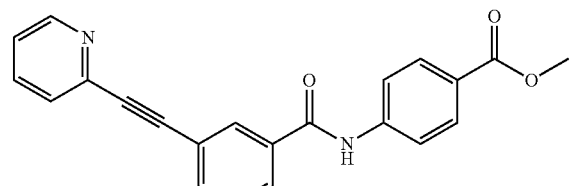 
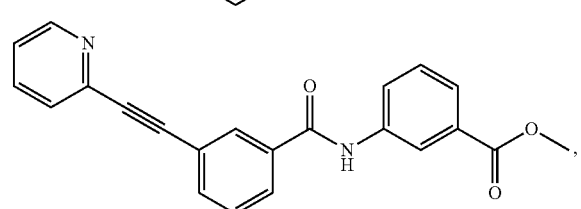 
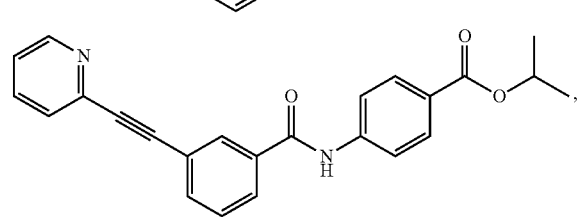 
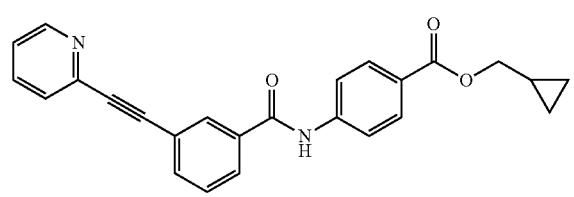 
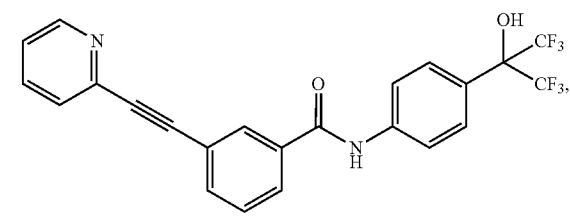 
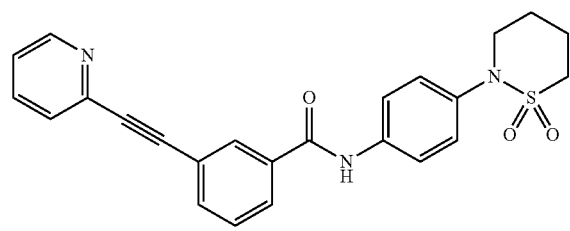 
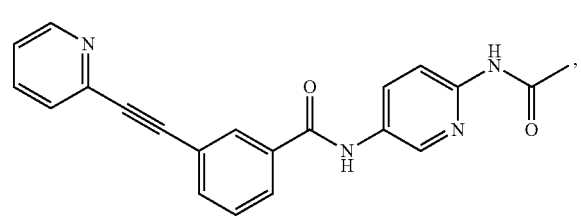 
120
-continued
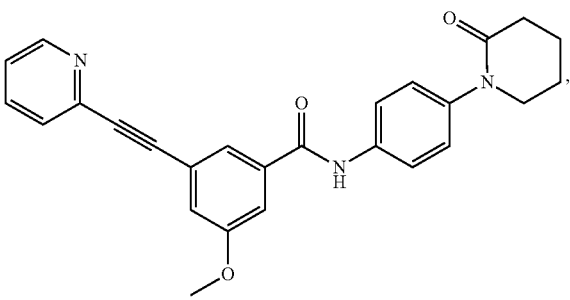
In various aspects, the compound is selected from:

121
-continued
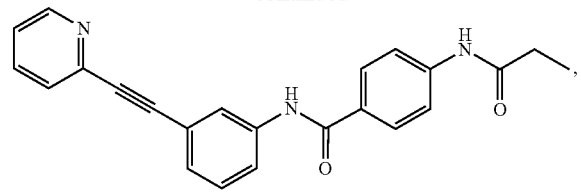
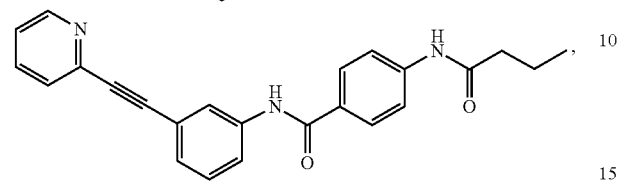
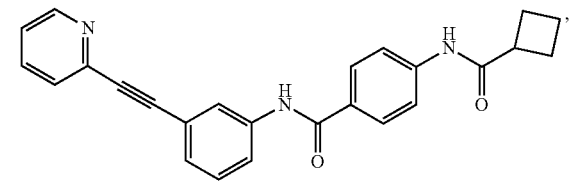
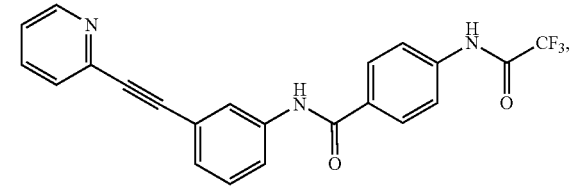
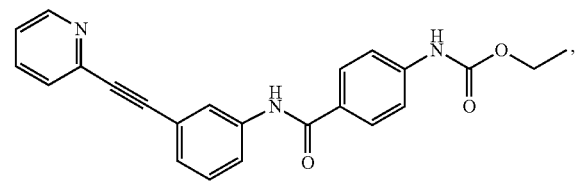
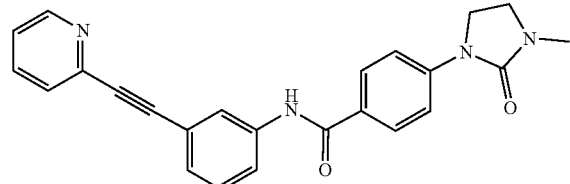
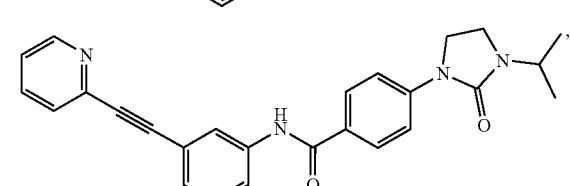
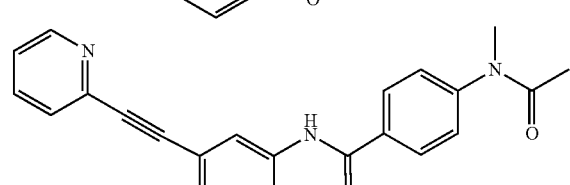
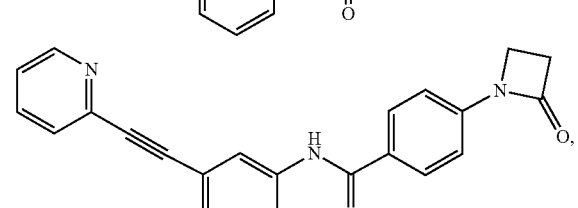
122
-continued
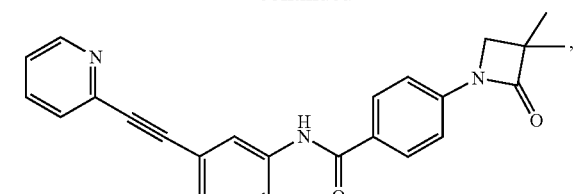
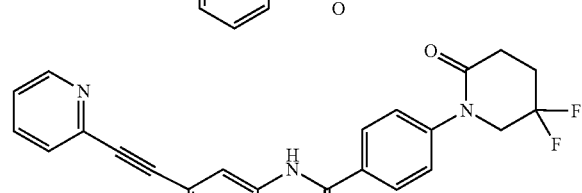
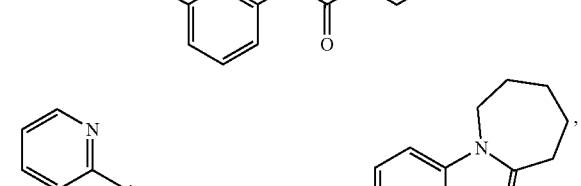
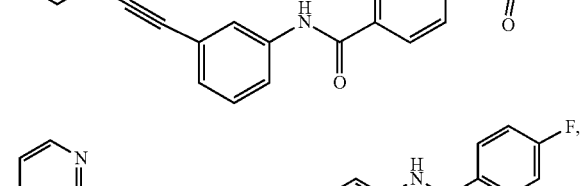
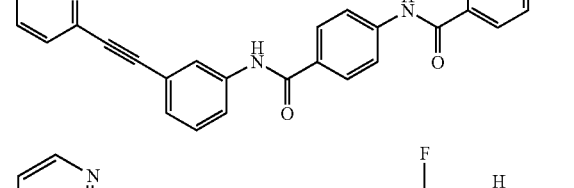
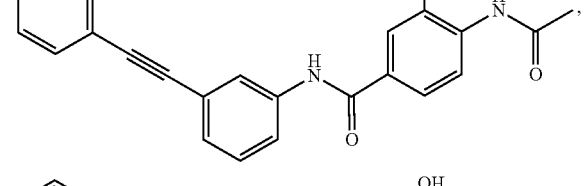
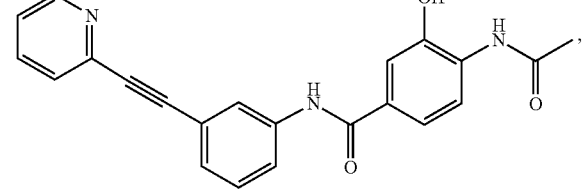
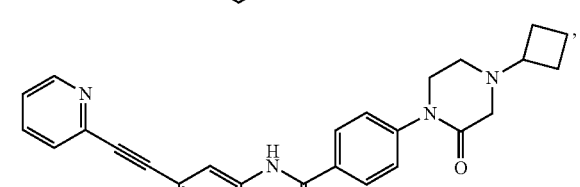

123
-continued
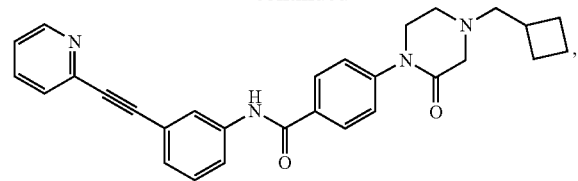
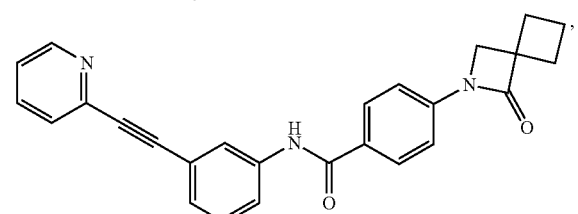
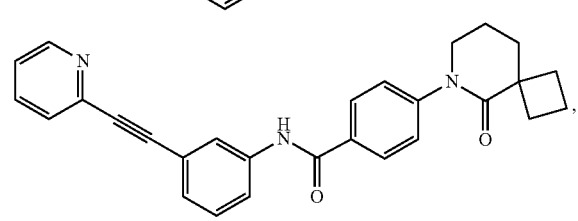
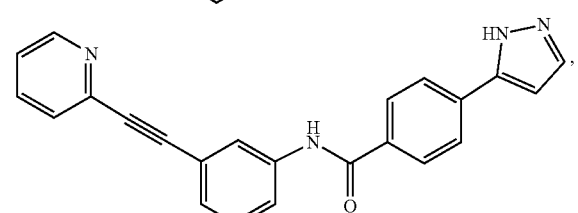
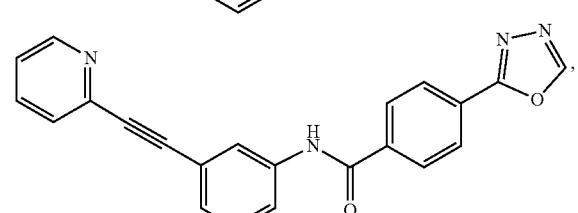
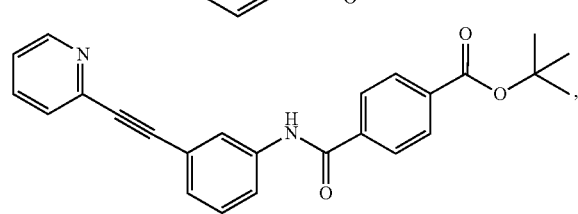
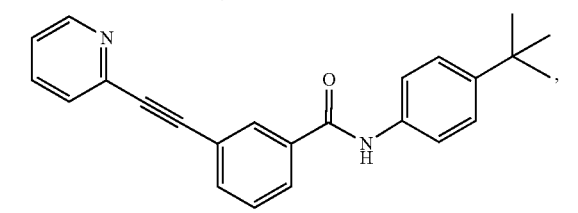
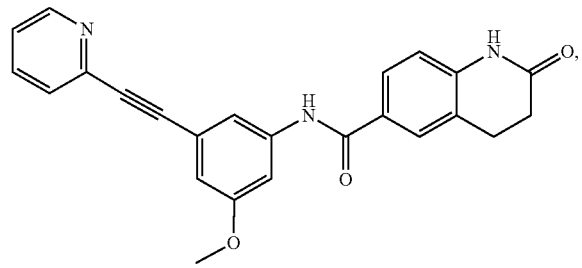
124
-continued
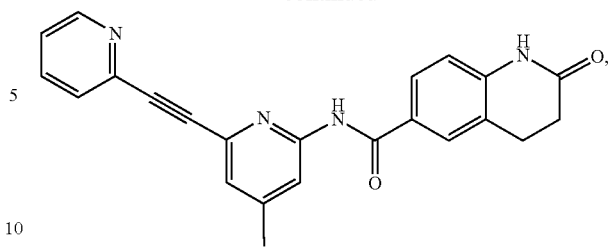
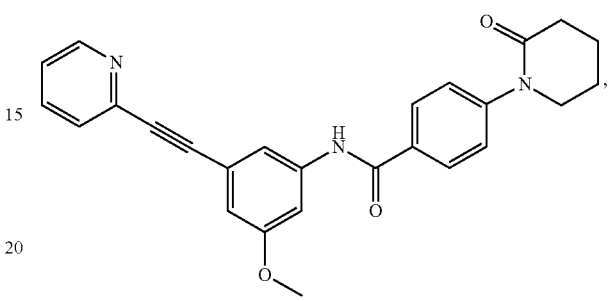
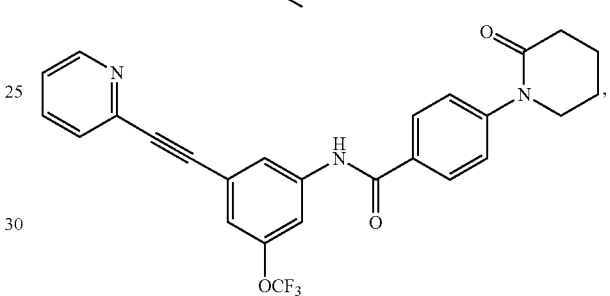
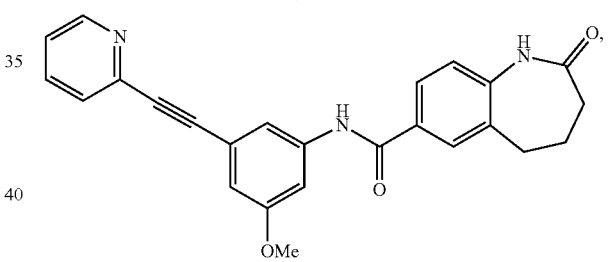
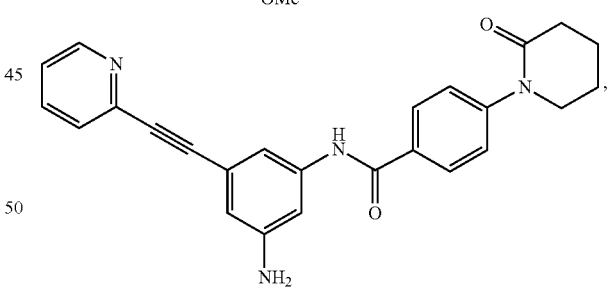
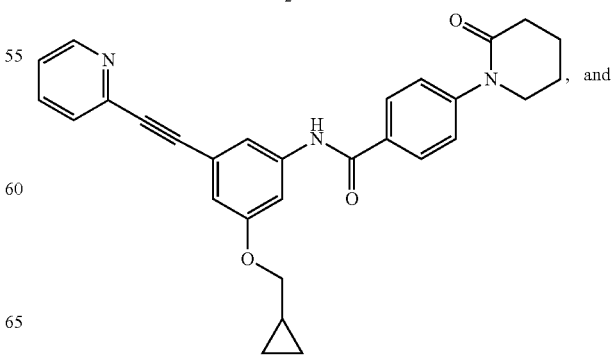

-continued

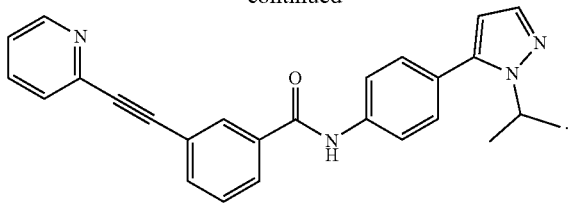

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise a disclosed compound (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, the effective amount is a therapeutically effective amount. In a still further aspect, the effective amount is a prophylactically effective amount.

In a further aspect, the pharmaceutical composition is formulated for nasal administration. For example, in various aspects, the pharmaceutical composition is formulated as a nasal spray. In a further aspect, the nasal spray can be administered as at least one spray per nostril once per day, at least two sprays per nostril once per day, at least one spray per nostril twice per day, or at least two sprays per nostril twice per day. Alternatively, in various aspects, the pharmaceutical composition is formulated for inhalation (e.g., via a nebulizer or metered dose inhaler).

In a further aspect, the pharmaceutical composition is formulated for intravenous administration.

In a further aspect, the pharmaceutical composition is administered to a mammal. In a still further aspect, the mammal is a human. In an even further aspect, the human is a patient.

In a further aspect, the pharmaceutical composition is used to treat a viral infection such as, for example, a coronavirus such as 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

It is understood that the disclosed compositions can be prepared from the disclosed compounds. It is also understood that the disclosed compositions can be employed in the disclosed methods of using.

D. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VI, as described and exemplified below. The following examples are provided so that the invention might be more fully understood, are illustrative only, and should not be construed as limiting.

1. Route I

In one aspect, substituted phenyl ethynyl pyridine carboxamide analogs can be prepared as shown below.

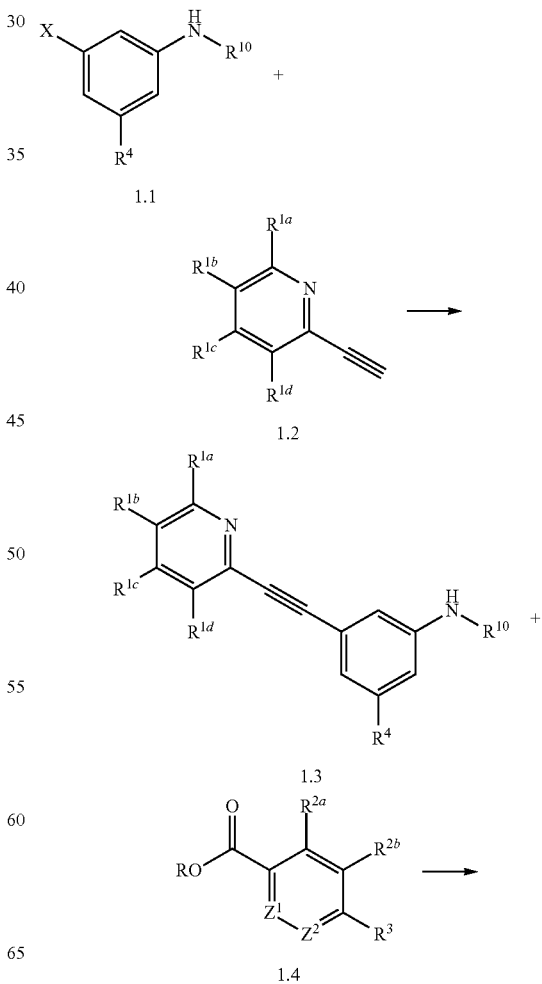

SCHEME 1A.

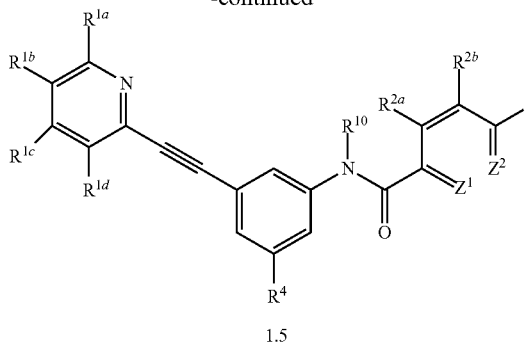

1.5

Compounds are represented in generic form, wherein X is halogen and R is hydrogen or C1-C4 alkyl, and with other substituents as noted in compound descriptions elsewhere herein. A more specific example is set forth below.

SCHEME 1B.

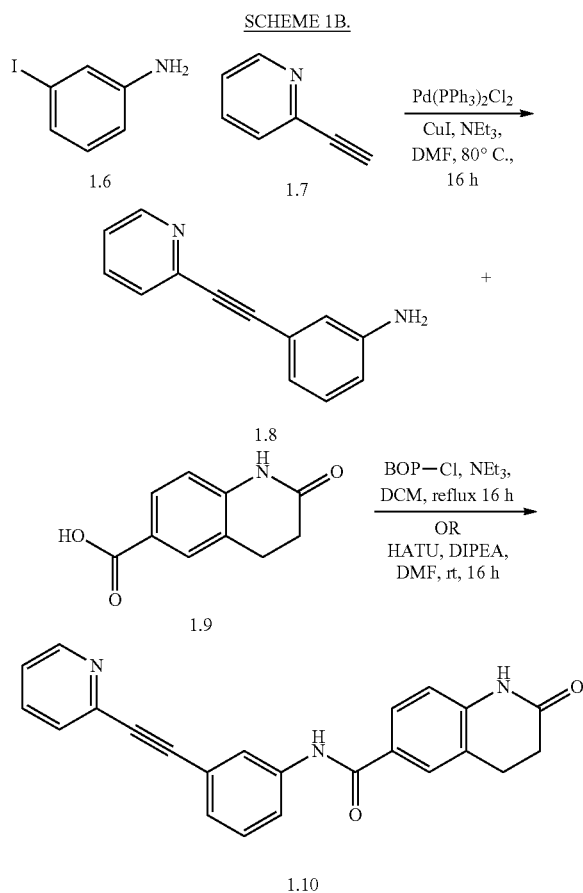

In one aspect, compounds of type 1.10 and similar compounds can be prepared according to reaction Scheme 1B above. Thus, compounds of type 1.8 can be prepared by reacting an appropriate aryl halide, e.g., 1.6 as shown above, with an appropriate alkyne, e.g., 1.7 as shown above. Appropriate aryl halides and appropriate alkynes are commercially available or prepared by methods known to one skilled in the art. The reaction is carried out in the presence of a appropriate catalyst system, e.g., bis(triphenylphosphine)palladium (II) dichloride and copper (I) iodide, and a appropriate base, e.g., triethylamine, in a appropriate solvent, e.g., dimethylformamide, at a appropriate temperature, e.g., 80° C. under conventional heating, for a appropriate period of time, e.g., 16 hours. Compounds of type 1.10 can be prepared by reacting an appropriate amine, e.g., 1.8 as shown above, with an appropriate carboxylic acid, e.g., 1.9 as shown above. Appropriate carboxylic acids are commercially available or prepared by methods known to one skilled in the art. The reaction is carried out in the presence of an appropriate activating agent, e.g., bis(2-oxo-3-oxazolidinyl) phosphinic chloride (BOP-Cl) or 1-[bis(dimethylamino) methylene]-1H-1,2,3-triazolo[4,5-b]pyridinium 3-oxide hexafluorophosphate (HATU), and an appropriate base, e.g., triethylamine (TEA) or diisopropylethylamine (DIPEA), in an appropriate solvent, e.g., dichloromethane (DCM) or dimethylformamide (DMF), for an appropriate period of time, e.g., 16 hours. Alternatively, compounds of type 1.10 can be prepared by reacting an appropriate amine, e.g., 1.8 as shown above, with an appropriate ester. See, e.g., 1.4 as shown above. Appropriate esters are commercially available or prepared by methods known to one skilled in the art. The reaction is carried out in the presence of an appropriate Lewis acid, e.g., trimethylaluminum, in an appropriate solvent, e.g., dichloromethane, at an appropriate temperature, e.g., 0° C. to room temperature. As can be appreciated by one skilled in the art, the above reaction provides an example of a generalized approach wherein compounds similar in structure to the specific reactants above (compounds similar to compounds of type 1.1, 1.2, 1.3, and 1.4) can be substituted in the reaction to provide substituted phenyl ethynyl pyridine carboxamide analogs similar to Formula 1.5.

2. Route II

In one aspect, substituted ester analogs can be prepared as shown below.

SCHEME 2A.

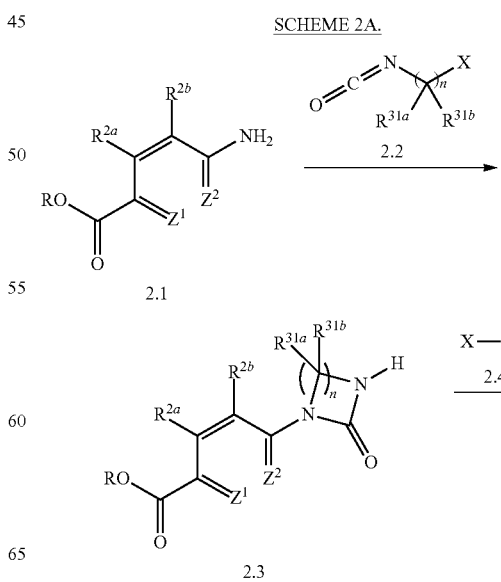

-continued

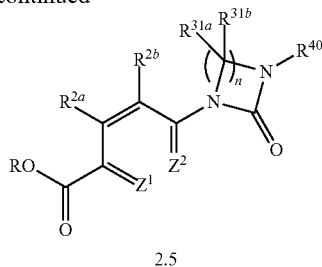

2.5

Compounds are represented in generic form, wherein each X is independently halogen and R is C1-C4 alkyl, and with other substituents as noted in compound descriptions elsewhere herein. A more specific example is set forth below.

SCHEME 2B.

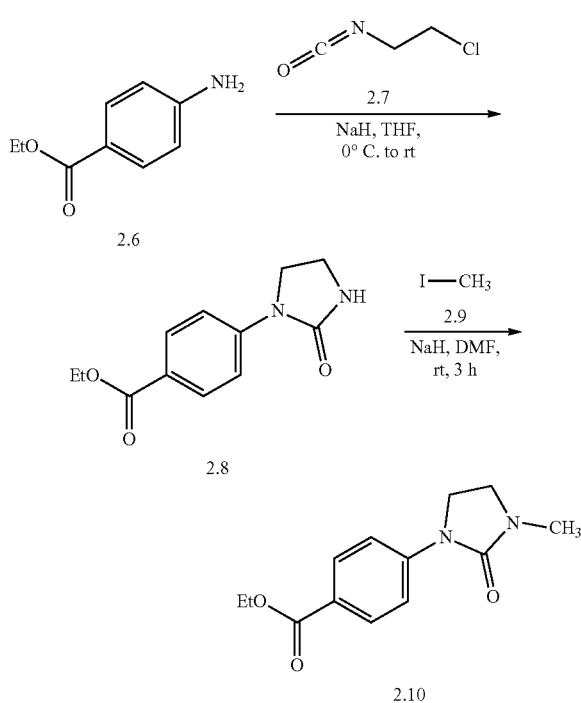

In one aspect, compounds of type 2.10 and similar compounds can be prepared according to reaction Scheme 2B above. Thus, compounds of type 2.8 can be prepared by reacting an appropriate amine, e.g., 2.6 as shown above, with an appropriate haloisocyanate compound, e.g., 2.7 as shown above. Appropriate amines and appropriate haloisocyanate compounds are commercially available or prepared by methods known to one skilled in the art. The reaction is carried out in the presence of an appropriate base, e.g., sodium hydride, in an appropriate solvent, e.g., tetrahydrofuran, at a appropriate temperature, e.g., 0° C. to room temperature. Compounds of type 2.10 can be prepared by reacting an appropriate urea, e.g., 2.8 as shown above, with an appropriate alkyl halide, e.g., 2.9 as shown above. The reaction is carried out in the presence of an appropriate base, e.g., sodium hydride, in an appropriate solvent, e.g., dimethylformamide, for an appropriate period of time, e.g., 3 hours. As can be appreciated by one skilled in the art, the above reaction provides an example of a generalized approach wherein compounds similar in structure to the specific reactants above (compounds similar to compounds of type 2.1, 2.2, 2.3, and 2.4) can be substituted in the reaction to provide substituted ester analogs similar to Formula 2.5.

3. Route III

In one aspect, substituted ester analogs can be prepared as shown below.

SCHEME 3A.

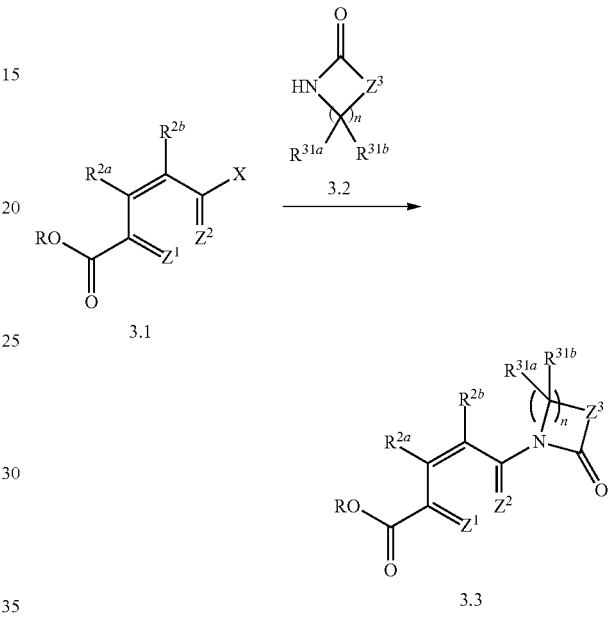

Compounds are represented in generic form, wherein X is halogen and R is C1-C4 alkyl, and with other substituents as noted in compound descriptions elsewhere herein. A more specific example is set forth below.

SCHEME 3B.

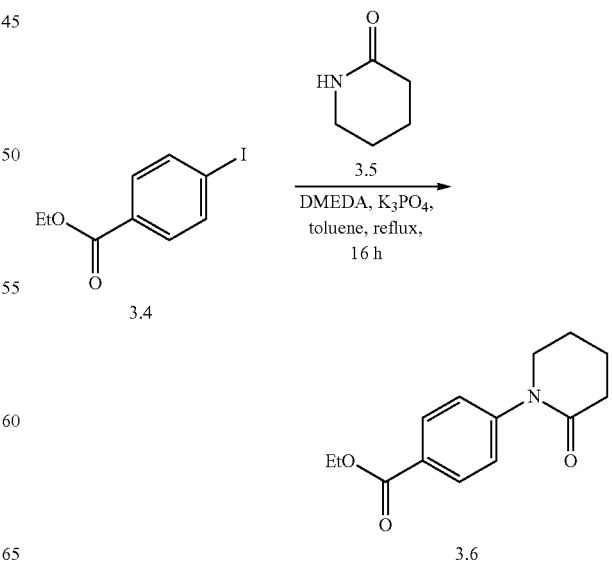

In one aspect, compounds of type 3.6 and similar compounds can be prepared according to reaction Scheme 3B above. Thus, compounds of type 3.6 can be prepared by reacting an appropriate aryl halide, e.g., 3.4 as shown above, with an appropriate amide, e.g., 3.5 as shown above. Appropriate aryl halides and appropriate amides are commercially available or prepared by methods known to one skilled in the art. The reaction is carried out in the presence of an appropriate base, e.g., N,N-dimethylethylenediamine, and an appropriate salt, e.g., potassium phosphate, in a appropriate solvent, e.g., toluene, for an appropriate period of time, e.g., 16 hours, at an appropriate temperature, e.g., reflux. As can be appreciated by one skilled in the art, the above reaction provides an example of a generalized approach wherein compounds similar in structure to the specific reactants above (compounds similar to compounds of type 3.1 and 3.2) can be substituted in the reaction to provide substituted ester analogs similar to Formula 3.3.

4. Route IV

In one aspect, substituted ester analogs can be prepared as shown below.

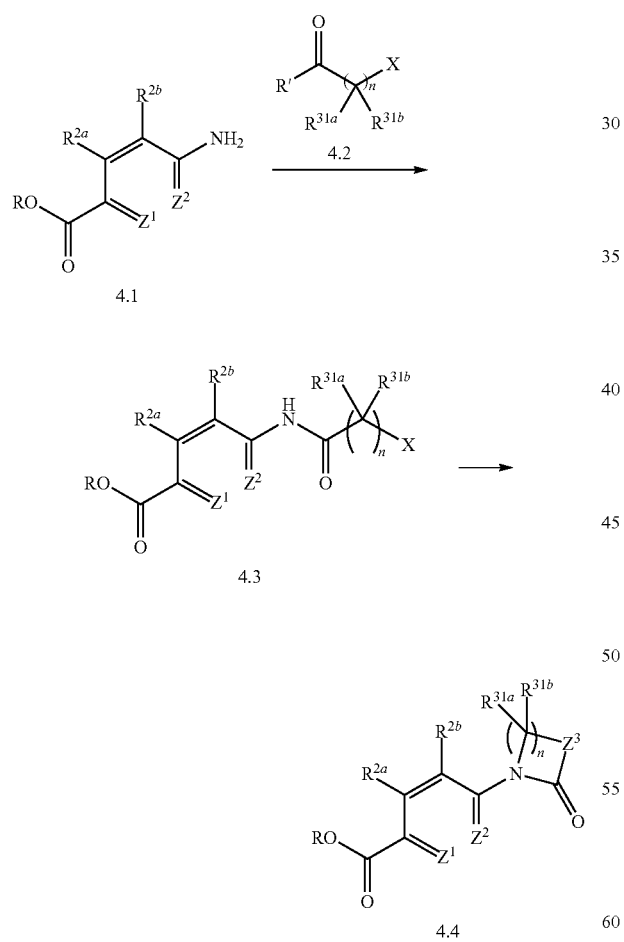

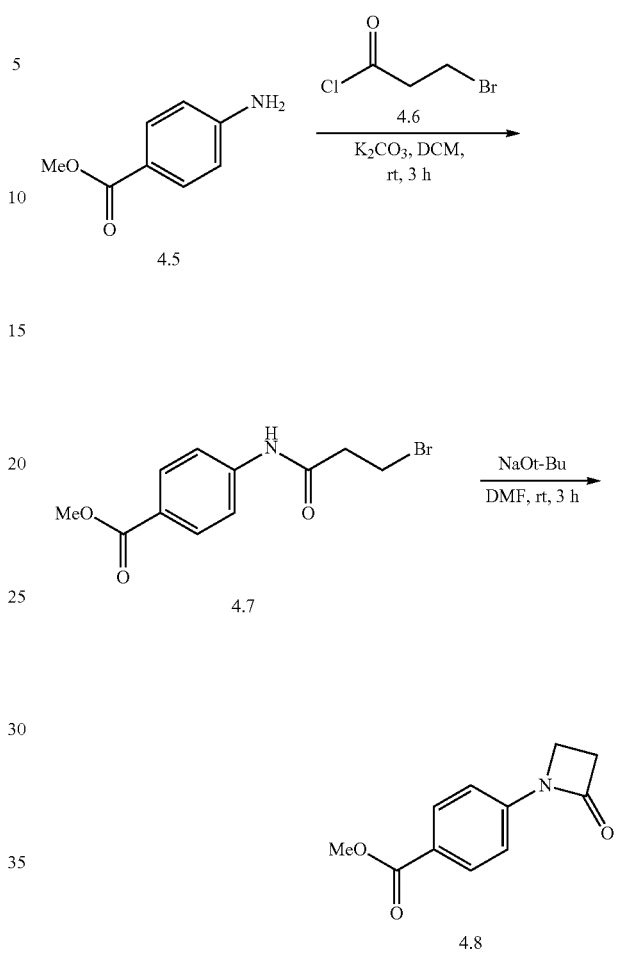

Compounds are represented in generic form, wherein X is halogen, wherein R is C1-C4 alkyl, and wherein R' is halogen or —OH, and with other substituents as noted in compound descriptions elsewhere herein. A more specific example is set forth below.

In one aspect, compounds of type 4.8 and similar compounds can be prepared according to reaction Scheme 4B above. Thus, compounds of type 4.7 can be prepared by reacting an appropriate amine compound, e.g., 4.5 as shown above, with an appropriate carboxylic acid or acyl halide, e.g., 4.6 as shown above. Appropriate amines, appropriate, carboxylic acids, and appropriate acyl halides are commercially available or prepared by methods known to one skilled in the art. The reaction is carried out in the presence of a appropriate base, e.g., potassium carbonate, in a appropriate solvent, e.g., dichloromethane, for an appropriate period of time, e.g., 3 hours. Compounds of type 4.8 can be prepared by cyclizing an appropriate haloamide compound, e.g., 4.7 as shown above. The cyclization is carried out in the presence of an appropriate base, e.g., sodium tert-butoxide, in an appropriate solvent, e.g., dimethylformamide, for an appropriate period of time, e.g., 3 hours. As can be appreciated by one skilled in the art, the above reaction provides an example of a generalized approach wherein compounds similar in structure to the specific reactants above (compounds similar to compounds of type 4.1, 4.2, and 4.3) can be substituted in the reaction to provide substituted ester analogs similar to Formula 4.4.

5. Route V

In one aspect, substituted phenyl ethynyl pyridine carboxamide analogs can be prepared as shown below.

135

SCHEME 5A.

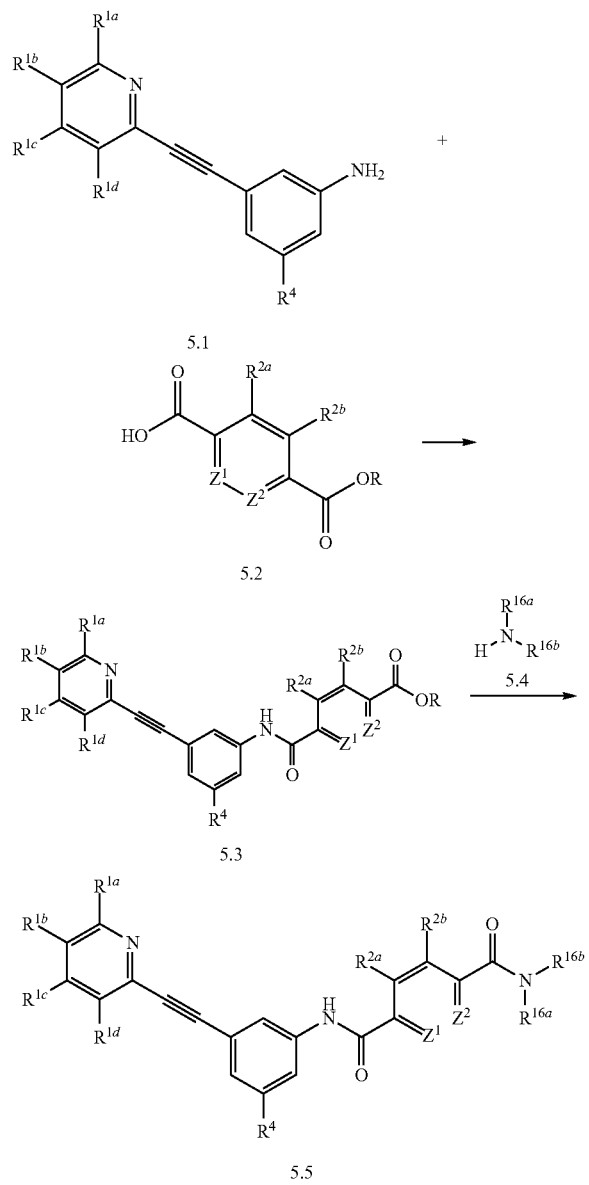

Compounds are represented in generic form, wherein R is C1-C4 alkyl, and with other substituents as noted in compound descriptions elsewhere herein. A more specific example is set forth below.

SCHEME 5B.

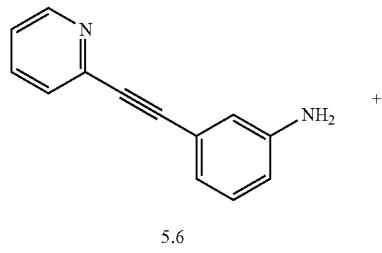

136

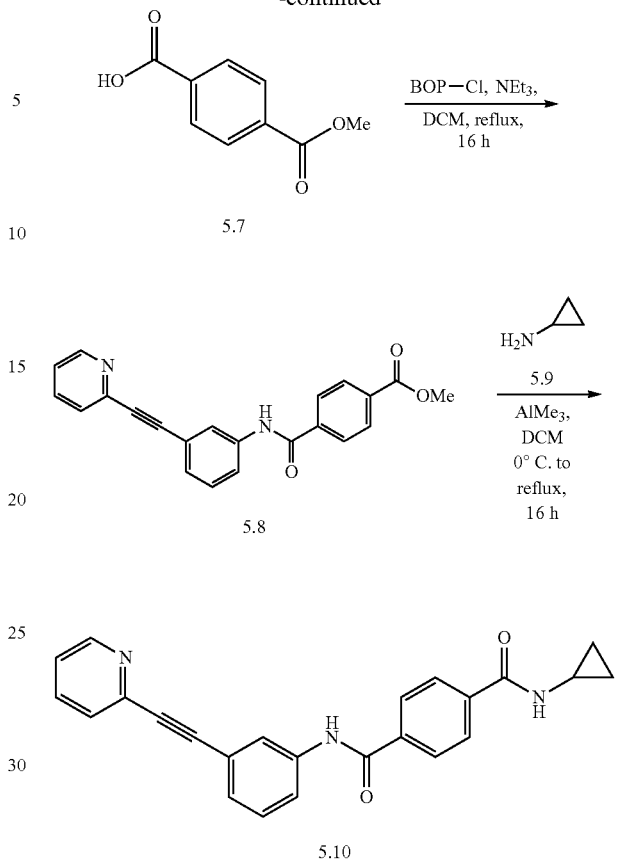

In one aspect, compounds of type 5.10 and similar compounds can be prepared according to reaction Scheme 5B above. Thus, compounds of type 5.8 can be prepared by coupling an appropriate amine, e.g., 5.6 as shown above, with an appropriate carboxylic acid, e.g., 5.7 as shown above. Appropriate amines and appropriate carboxylic acids are commercially available or prepared by methods known to one skilled in the art. The coupling reaction is carried out in the presence of an appropriate coupling agent, e.g., bis(2-oxo-3-oxazolidinyl)phosphinic chloride, and an appropriate base, e.g., triethylamine, in a appropriate solvent, e.g., dichloromethane, for an appropriate period of time, e.g., 3 hours, at an appropriate temperature, e.g., reflux. Compounds of type 5.10 can be prepared by coupling an appropriate ester, e.g., 5.8, and an appropriate amine, e.g., 5.9 as show above. Appropriate amines are commercially available or prepared by methods known to one skilled in the art. The coupling reaction is carried out in the presence of an appropriate Lewis acid, e.g., trimethylaluminum, in an appropriate solvent, e.g., dichloromethane, at an appropriate temperature, e.g., 0° C. to reflux, for an appropriate period of time, e.g., 16 hours. As can be appreciated by one skilled in the art, the above reaction provides an example of a generalized approach wherein compounds similar in structure to the specific reactants above (compounds similar to compounds of type 5.1, 5.2, 5.3, and 5.4) can be substituted in the reaction to provide substituted phenyl ethynyl pyridine carboxamide analogs similar to Formula 5.5.

6. Route VI

In one aspect, substituted ester analogs can be prepared as shown below.

SCHEME 6A.

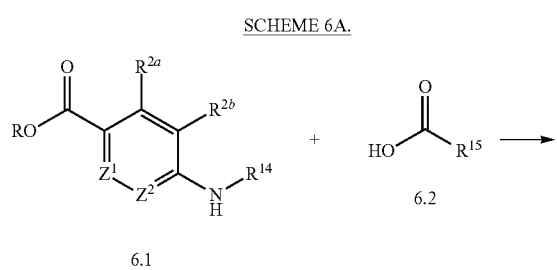

6.1    6.2

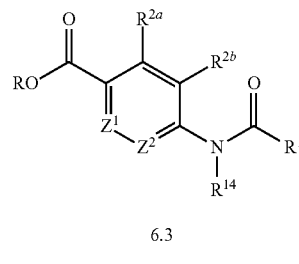

6.3

Compounds are represented in generic form, wherein R is C1-C4 alkyl, and with other substituents as noted in compound descriptions elsewhere herein. A more specific example is set forth below.

SCHEME 6B.

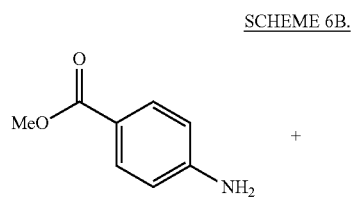

In one aspect, compounds of type 6.6 and similar compounds can be prepared according to reaction Scheme 6B above. Thus, compounds of type 6.6 can be prepared by coupling an appropriate amine, e.g., 6.4 as shown above, with an appropriate carboxylic acid, e.g., 6.5 as shown above. Appropriate amines and appropriate carboxylic acids are commercially available or prepared by methods known to one skilled in the art. The reaction is carried out in the presence of an appropriate coupling agent, e.g., HATU, and an appropriate base, e.g., DIPEA, in a appropriate solvent, e.g., dimethylformamide, at a appropriate temperature, e.g., room temperature. As can be appreciated by one skilled in the art, the above reaction provides an example of a generalized approach wherein compounds similar in structure to the specific reactants above (compounds similar to compounds of type 6.1 and 6.2) can be substituted in the reaction to provide substituted ester analogs similar to Formula 6.3.

7. Route VII

In one aspect, substituted phenyl ethynyl pyridine carboxamide analogs can be prepared as shown below.

SCHEME 7A.

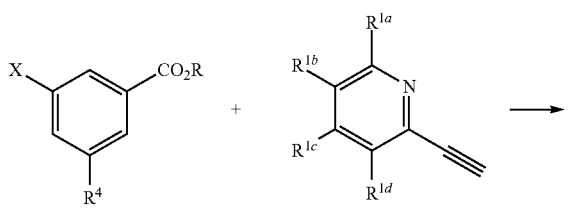

7.1    7.2

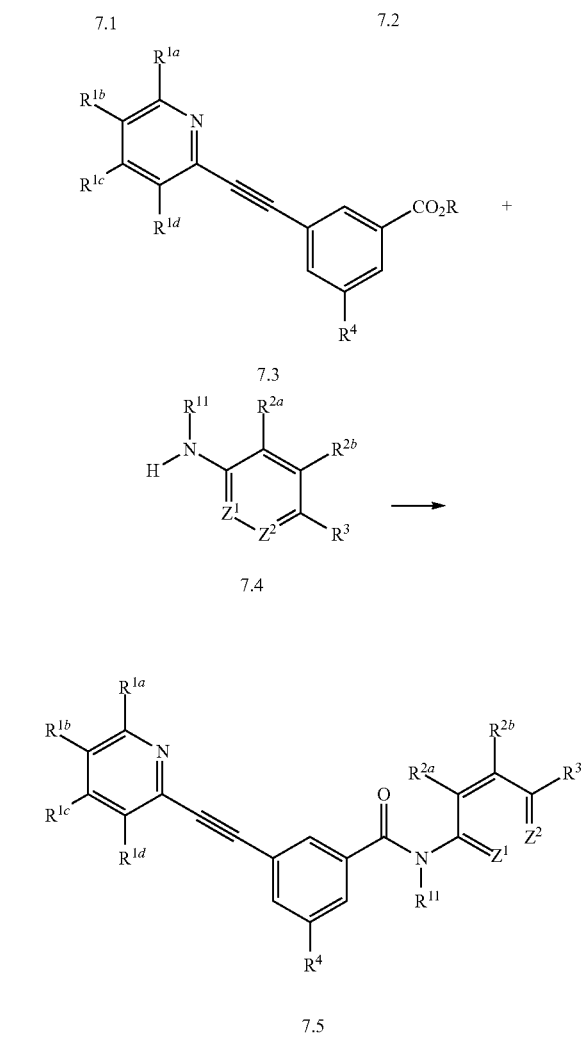

Compounds are represented in generic form, wherein X is halogen and R is C1-C4 alkyl, and with other substituents as noted in compound descriptions elsewhere herein. A more specific example is set forth below.

SCHEME 7B.

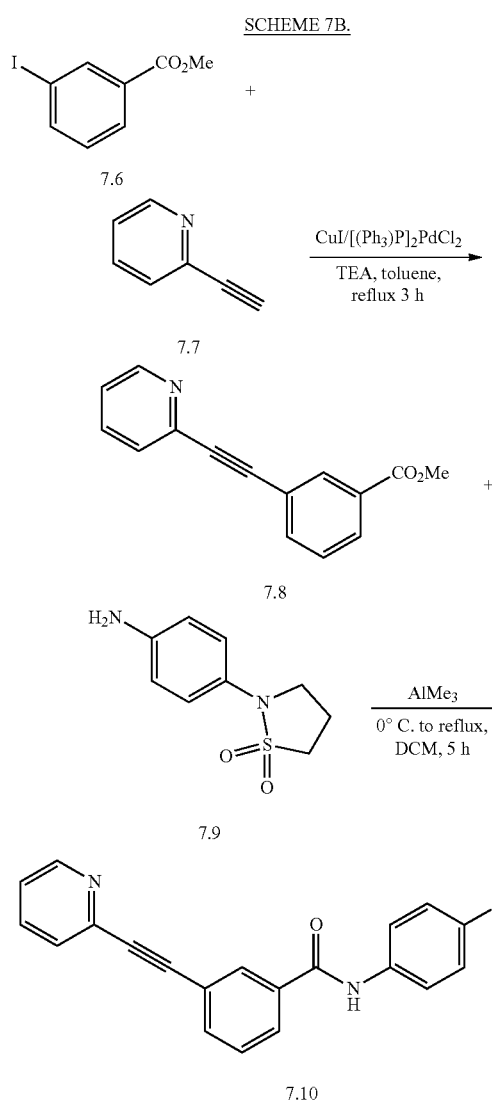

generalized approach wherein compounds similar in structure to the specific reactants above (compounds similar to compounds of type 7.1, 7.2, 7.3, and 7.4) can be substituted in the reaction to provide substituted phenyl ethynyl pyridine carboxamide analogs similar to Formula 7.5.

8. Route VIII

In one aspect, substituted amine analogs can be prepared as shown below.

SCHEME 8A.

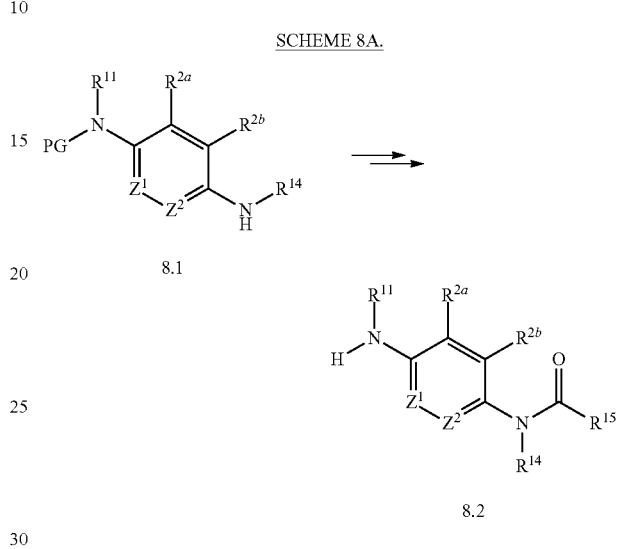

Compounds are represented in generic form, wherein PG is an amine protecting group, and with other substituents as noted in compound descriptions elsewhere herein. A more specific example is set forth below.

SCHEME 8B.

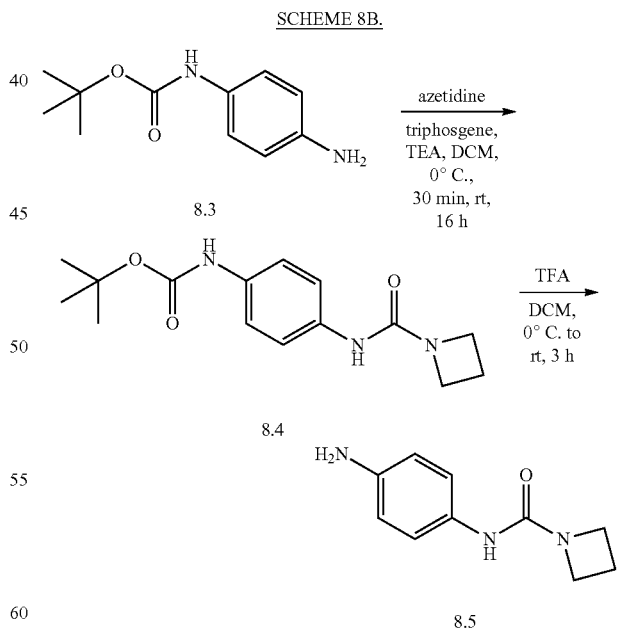

In one aspect, compounds of type 7.10 and similar compounds can be prepared according to reaction Scheme 7B above. Thus, compounds of type 7.8 can be prepared by reacting an appropriate aryl halide, e.g., 7.6 as shown above, with an appropriate nitrile, e.g., 7.7 as shown above. Appropriate aryl halides and appropriate nitriles are commercially available or prepared by methods known to one skilled in the art. The coupling reaction is carried out in the presence of an appropriate catalyst system, e.g., bis(triphenylphosphine) palladium (II) dichloride and copper (I) iodide, and an appropriate base, e.g., triethylamine, in an appropriate solvent, e.g., toluene, at an appropriate temperature, e.g., reflux, for an appropriate period of time, e.g., 3 hours. Compounds of type 7.10 can be prepared by reacting an appropriate ester, e.g., 7.8 as shown above, and an appropriate amine, e.g., 7.9 as shown above. Appropriate amines are commercially available or prepared by methods known to one skilled in the art. The reaction is carried out in the presence of an appropriate Lewis acid, e.g., trimethylaluminum, in an appropriate solvent, e.g., dichloromethane, at an appropriate temperature, e.g., 0° C. to reflux, for an appropriate period of time, e.g., 5 hours. As can be appreciated by one skilled in the art, the above reaction provides an example of a In one aspect, compounds of type 8.5 and similar compounds can be prepared according to reaction Scheme 8B above. Thus, compounds of type 8.4 can be prepared by reacting an appropriate aniline derivative, e.g., 8.3 as shown above, with an appropriate amine, e.g., azeitidine as shown above, in the presence of an appropriate oxidant, e.g., triphosgene. Appropriate aniline derivatives and appropriate amines are commercially available or prepared by methods known to one skilled in the art. The reaction is carried out in the presence of an appropriate base, e.g., triethylamine, in an appropriate solvent, e.g., dichloromethane. Compounds of type 8.5 can be prepared by deprotection of an appropriate urea, e.g., 8.4. The deprotection is carried out in the presence of an appropriate deprotecting agent, e.g., trifluoroacetic acid, in an appropriate solvent, e.g., dichloromethane, at an appropriate temperature, e.g., 0° C. to room temperature, for an appropriate period of time, e.g., 3 hours. As can be appreciated by one skilled in the art, the above reaction provides an example of a generalized approach wherein compounds similar in structure to the specific reactants above (compounds similar to compounds of type 8.1) can be substituted in the reaction to provide substituted amine analogs similar to Formula 8.2.

9. Route IX

In one aspect, substituted amine analogs can be prepared as shown below.

SCHEME 9A.

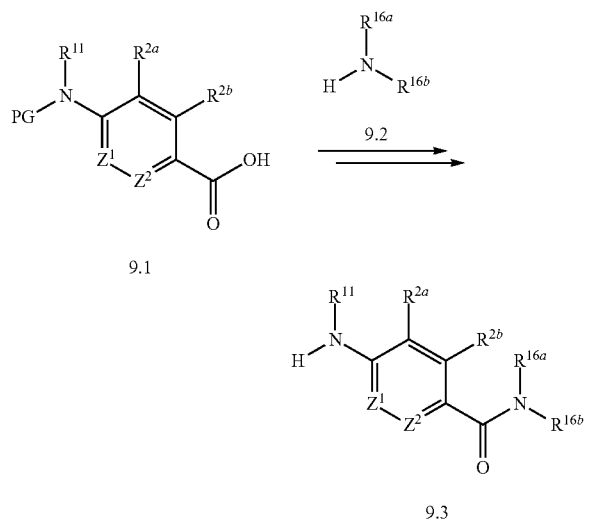

Compounds are represented in generic form, wherein PG is an amine protecting group, and with other substituents as noted in compound descriptions elsewhere herein. A more specific example is set forth below.

SCHEME 9B.

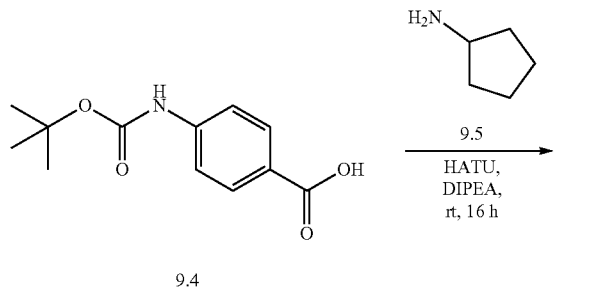

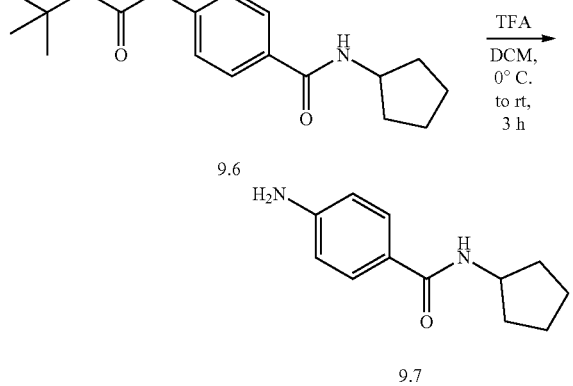

In one aspect, compounds of type 9.7 and similar compounds can be prepared according to reaction Scheme 9B above. Thus, compounds of type 9.6 can be prepared by reacting an appropriate carboxylic acid, e.g., 9.4 as shown above, with an appropriate amine, e.g., 9.5 as shown above. Appropriate carboxylic acids and appropriate amines are commercially available or prepared by methods known to one skilled in the art. The reaction is carried out in the presence of a appropriate base, e.g., DIPEA, and an appropriate coupling agent, e.g., HATU, at a appropriate temperature, e.g., room temperature, for an appropriate period of time, e.g., 16 hours. As can be appreciated by one skilled in the art, the above reaction provides an example of a generalized approach wherein compounds similar in structure to the specific reactants above (compounds similar to compounds of type 9.1 and 9.2) can be substituted in the reaction to provide substituted amine analogs similar to Formula 9.3.

E. METHODS OF TREATING A VIRAL INFECTION

The compounds and pharmaceutical compositions of the invention are useful in treating or controlling disorders associated with a viral infection due to a Coronavirus such as, for example, 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

Thus, in one aspect, disclosed are methods for treating a viral infection in a subject in need thereof, the method comprising administering to the subject a compound having a structure represented by a formula:

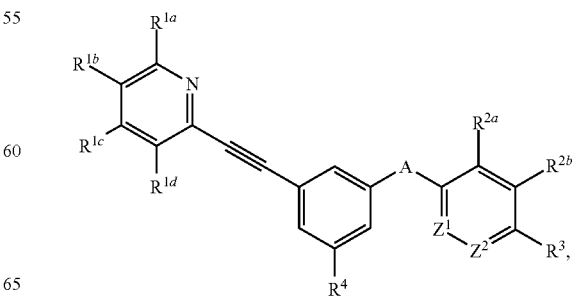

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$; wherein R$^{14}$, when present, is selected from hydrogen and C1-C4 alkyl; —wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy$^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

Also disclosed are methods for treating a viral infection in a subject in need thereof, the method comprising administering to the subject an effective amount of a disclosed compound, or a pharmaceutically acceptable salt thereof, thereby treating the viral infection. In a further aspect, disclosed are methods for treating a viral infection in a subject in need thereof, the method comprising administering to the subject an effective amount of a compound having a structure represented by a formula:

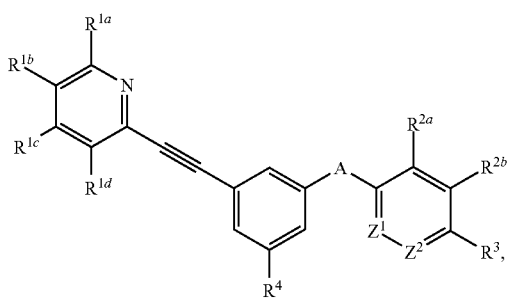

wherein A is selected from —NR¹⁰C(O)— and —C(O)NR¹¹; wherein each of R¹⁰, when present, and R¹¹, when present, is selected from hydrogen and C1-C4 alkyl; wherein each of $Z^1$ and $Z^2$ is independently selected from —N= and —C(R¹³)=; wherein each occurrence of R¹³, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R³ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, —CH₂NR²¹ᵃR²¹ᵇ, and Cy²; wherein R²⁰, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; and wherein Cy¹, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and R³ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

In various aspects, the compound has a structure represented by a formula:

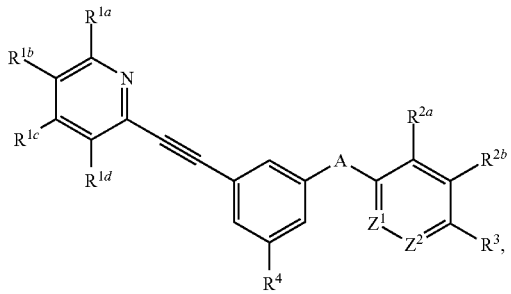

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^{1}$ and Z$^{2}$ is independently selected from —N═ and —C(R$^{13}$)═; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{3}$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^{1}$, —CO$_2$(C1-C4 alkyl)Cy$^{1}$, and Cy$^{1}$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^{2}$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^{2}$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^{3}$; wherein Cy$^{3}$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present, is a C1-C4 alkyl; or wherein R$^{17}$ and R$^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of R$^{19}$, when present, is independently selected from hydrogen and C1-C4 alkyl; and wherein Cy$^{1}$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^{3}$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{4}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^{4}$, and —O(C1-C4 alkyl)Cy$^{4}$; and wherein Cy$^{4}$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then R$^{3}$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^{1}$, —CO$_2$(C1-C4 alkyl)Cy$^{1}$, and Cy$^{1}$, and provided that when A is —NR¹⁰C(O)— and R³ is —NR¹⁴C(O)R¹⁵, then R¹⁵ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

In various aspects, the compound has a structure represented by a formula:

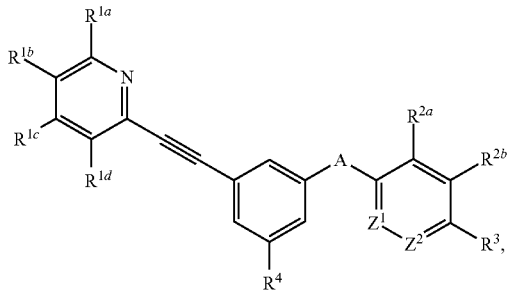

wherein A is selected from —NR¹⁰C(O)— and —C(O)NR¹¹; wherein each of R¹⁰, when present, and R¹¹, when present, is selected from hydrogen and C1-C4 alkyl; wherein each of Z¹ and Z² is independently selected from —N= and —C(R¹³)=; wherein each occurrence of R¹³, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R³ is selected from C1-C4 alkyl, C1-C4 haloalkyl, C1-C4 haloalkoxy, C1-C4 hydroxyhaloalkyl, —NR¹⁴C(O)R¹⁵, —C(O)NR$^{16a}$R$^{16b}$, —NR¹⁷SO$_2$R¹⁸, —P(O)(OR¹⁹)$_2$, —CO$_2$(C1-C4 alkyl), —CO$_2$Cy¹, —CO$_2$(C1-C4 alkyl)Cy¹, and Cy¹; wherein R¹⁴, when present, is selected from hydrogen and C1-C4 alkyl; wherein R¹⁵, when present, is selected from C1-C4 alkyl, C1-C4 haloalkyl, C1-C4 alkoxy, C1-C4 haloalkoxy, C1-C4 aminoalkyl, —OR²⁰, —NR$^{21a}$R$^{21b}$, —CH$_2$NR$^{21a}$R$^{21b}$, and Cy²; wherein R²⁰, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy², when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁴ and R¹⁵, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R¹⁵, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy³; wherein Cy³, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R¹⁷, when present, is selected from hydrogen and C1-C4 alkyl; wherein R¹⁸, when present is a C1-C4 alkyl; or wherein R¹⁷ and R¹⁸, when present, are covalently bonded, and together with the intermediate atoms, comprise an unsubstituted 5- to 7-membered heterocycloalkyl; wherein each occurrence of R¹⁹, when present, is independently selected from hydrogen and C1-C4 alkyl; and wherein Cy¹, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R³ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R⁴ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy⁴, and —O(C1-C4 alkyl)Cy⁴; and wherein Cy⁴, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

151
In various aspects, the compound is:
152
In various aspects, the compound is selected from:
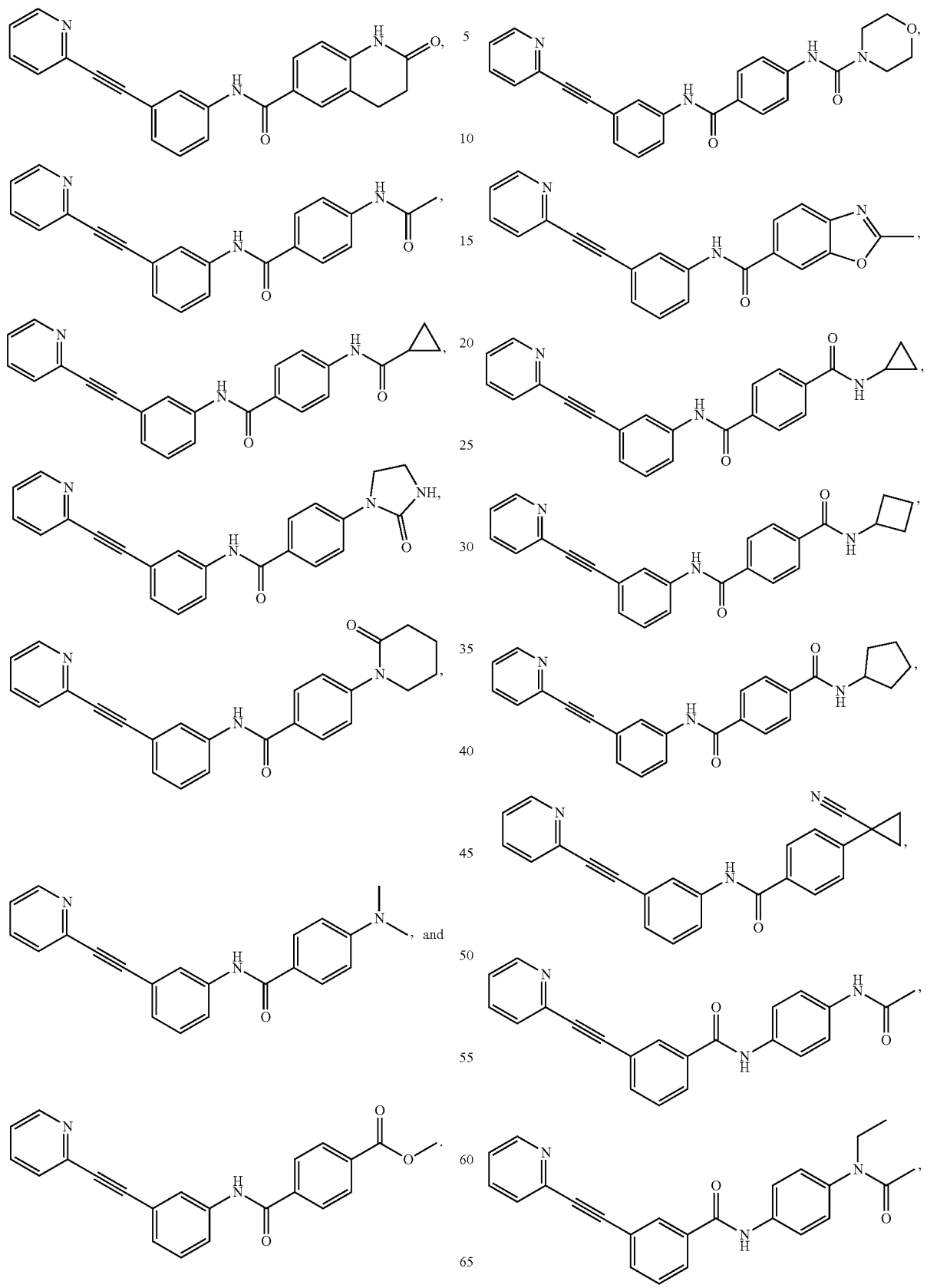

153
-continued
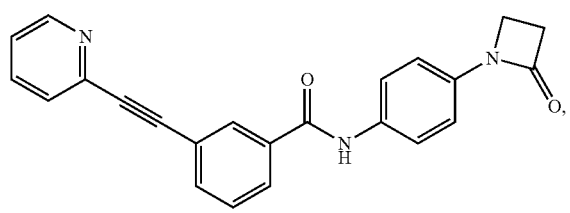
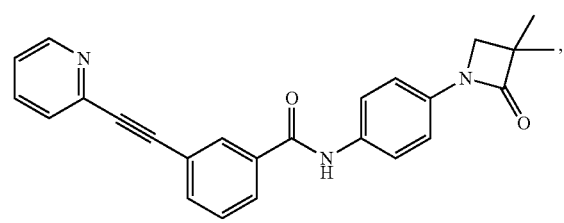
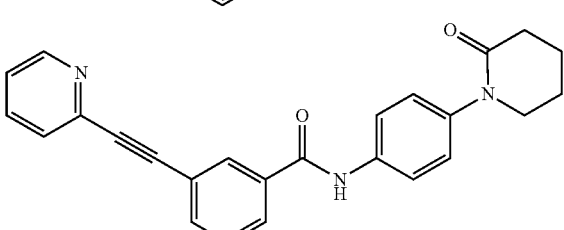
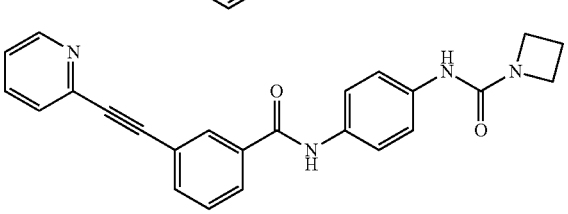
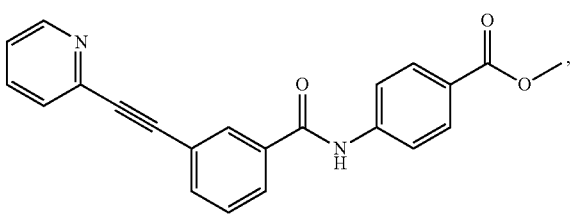
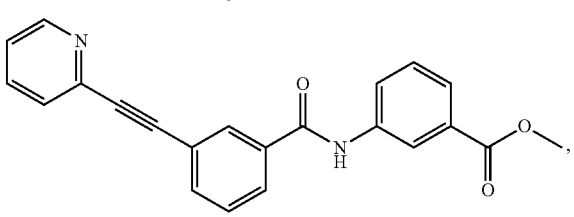
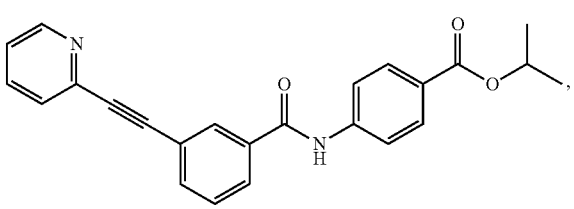
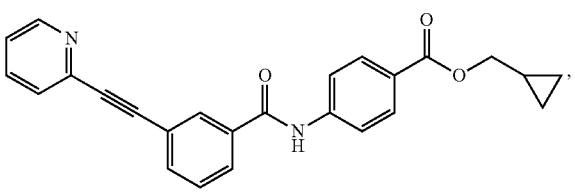
154
-continued
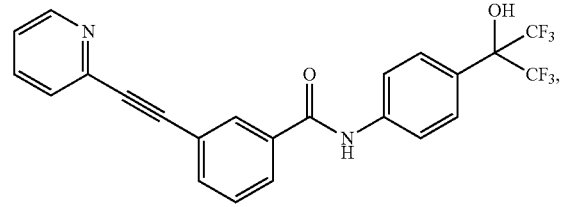
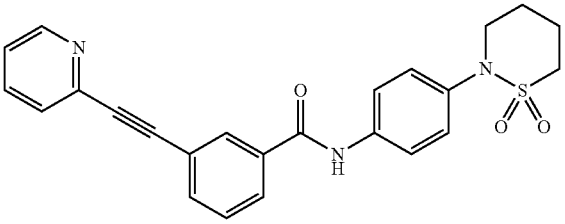
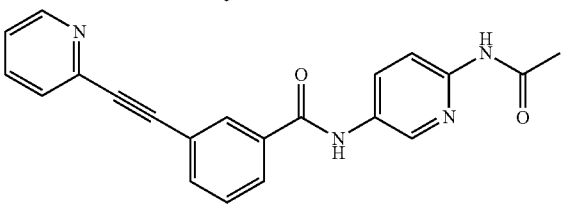
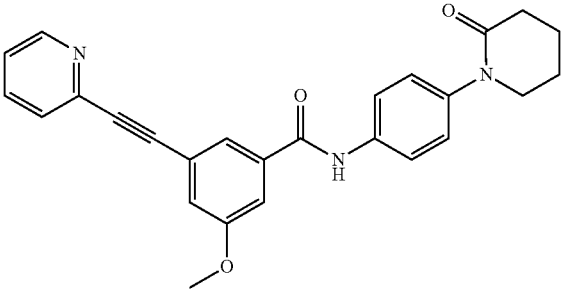
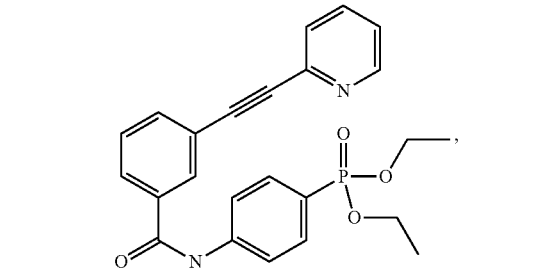
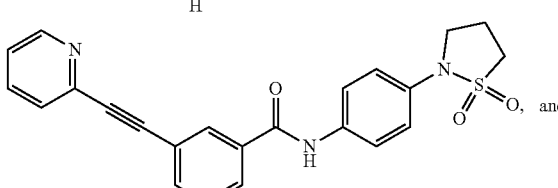, and
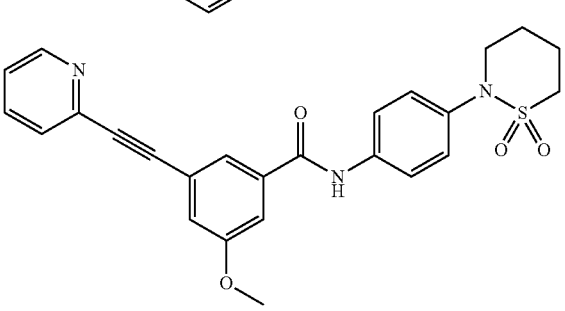

In various aspects, the compound is selected from:
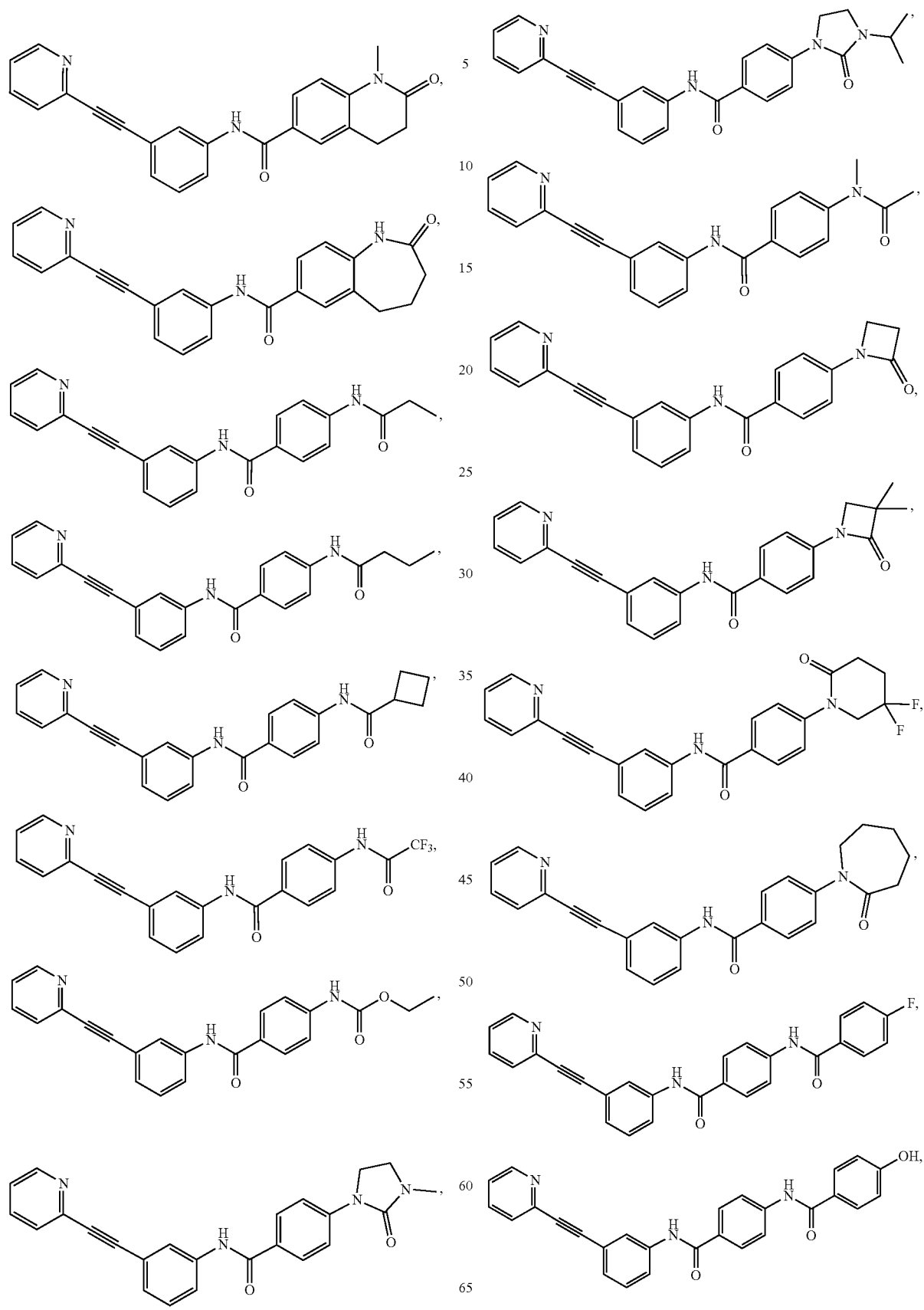

157
-continued
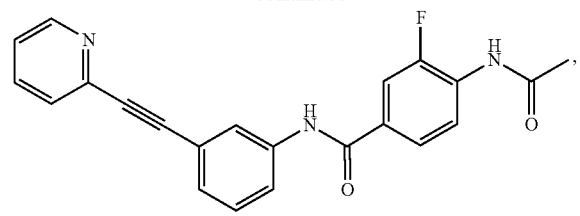
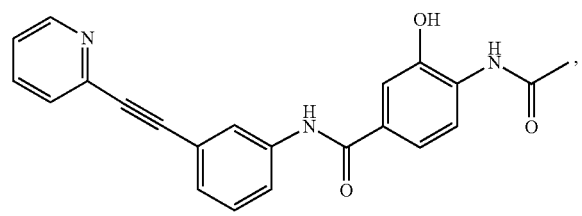
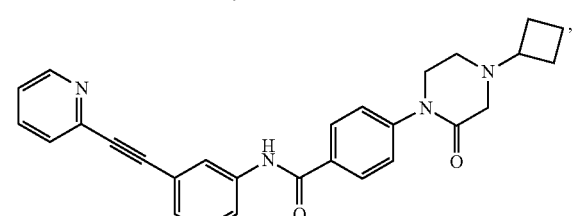
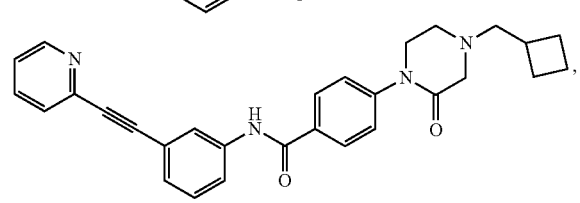
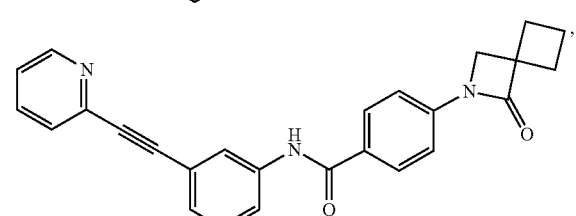
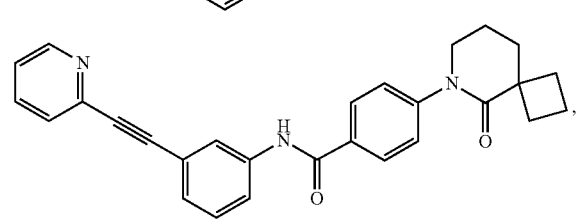
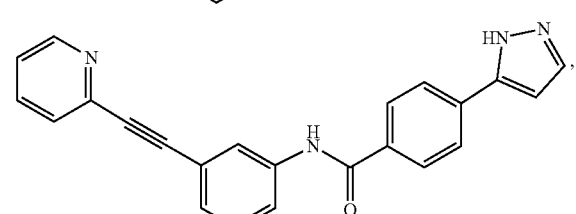
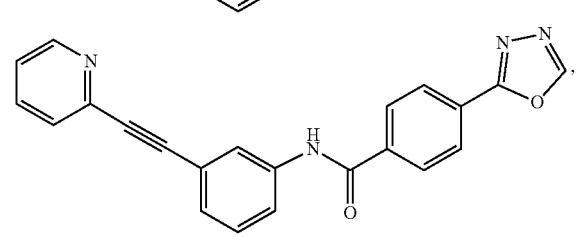
158
-continued
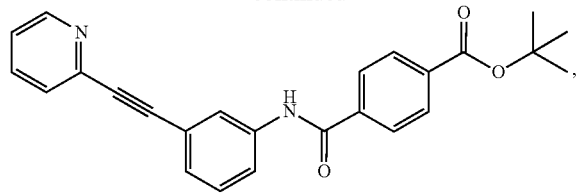
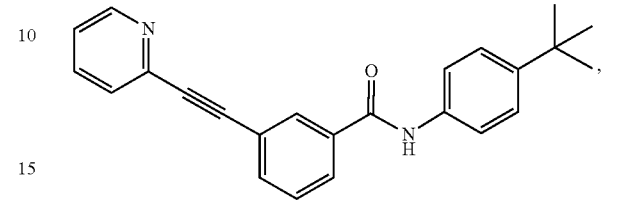
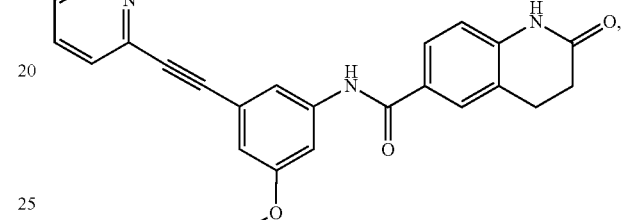
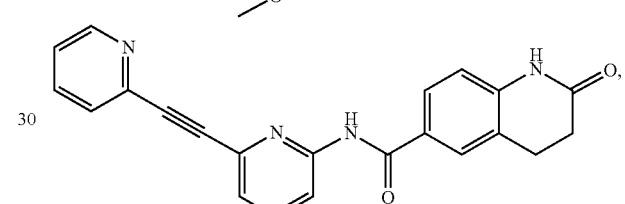
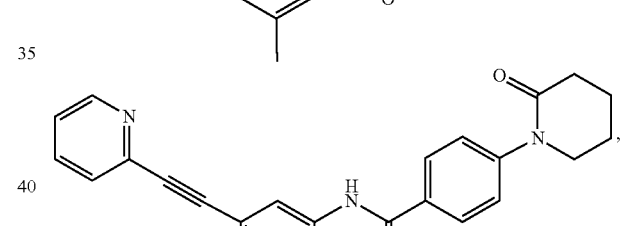
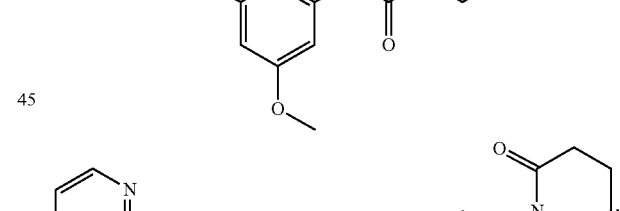
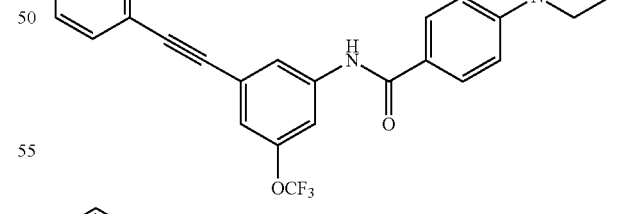
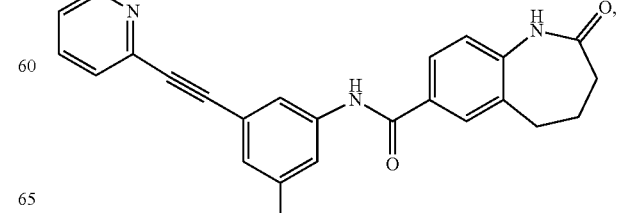

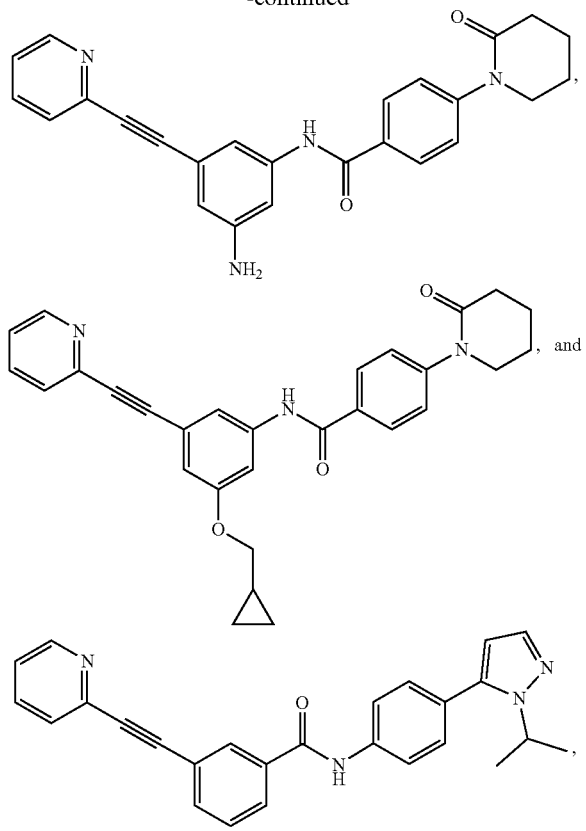

In a further aspect, the viral infection is due to a Coronavirus. In a still further aspect, the Coronavirus is selected from 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2). In yet a further aspect, the Coronavirus is SARS CoV-2.

In one aspect, disclosed are methods for treating SARS-CoV-2 in a subject in need thereof, the method comprising administering to the subject a therapeutically effective amount of a disclosed compound, or a pharmaceutically acceptable salt thereof, thereby treating the SARS-CoV-2.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a viral infection, such as, for example, a coronavirus.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a viral infection, such as, for example, a viral infection due to a Coronavirus.

In a further aspect, the subject has been diagnosed with a need for treatment of the viral infection prior to the administering step.

In a further aspect, the subject is a mammal. In a still further aspect, the mammal is a human.

In a further aspect, the method further comprises the step of identifying a subject in need of treatment of the viral infection.

In a further aspect, the Coronavirus is selected from Middle East Respiratory Syndromes coronavirus (MERS-CoV), Severe Acute Respiratory Syndrome coronavirus (SARS-CoV), and SARS-CoV-2. In a still further aspect, the Coronavirus is SARS-CoV. In yet a further aspect, the Coronavirus is SARS-CoV-2.

In a further aspect, the subject has coronavirus disease 2019 (COVID-19).

The therapeutically effective amount or dosage of each active agent can vary within wide limits. Such a dosage is adjusted to the individual requirements in each particular case including the specific compound(s) being administered, the route of administration, the condition being treated, as well as the patient being treated. In general, in the case of nasal or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

In a further aspect, the effective amount is a therapeutically effective amount. In a still further aspect, the effective amount is a prophylactically effective amount.

In a further aspect, the method further comprises the step of administering an effective amount of at least one antiviral agent. In a still further aspect, the at least one agent is selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxil fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the compound and the agent are administered sequentially. In a still further aspect, the compound and the agent are administered simultaneously.

In a further aspect, the compound and the agent are co-formulated. In a still further aspect, the compound and the agent are co-packaged.

F. METHODS OF INHIBITING A VIRAL INFECTION IN A MAMMAL

The compounds and pharmaceutical compositions of the invention are also useful in inhibiting a viral infection in a mammal. Exemplary viral infections include, but are not limited to, a coronavirus such as 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

Thus, in one aspect, disclosed are methods for inhibiting a viral infection in a mammal, the method comprising administering to the mammal an effective amount of a disclosed compound, or a pharmaceutically acceptable salt thereof, thereby inhibiting the viral infection in the mammal.

In a further aspect, disclosed are methods for inhibiting a viral infection in a mammal, the method comprising administering to the mammal an effective amount of a compound having a structure represented by a formula:

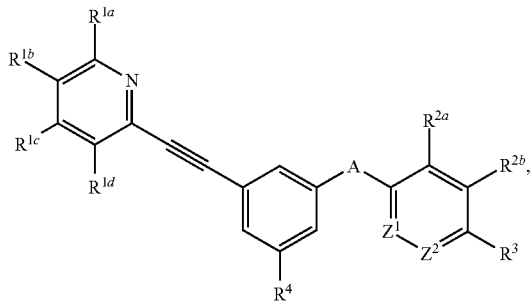

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$; wherein R$^{14}$, when present, is selected from hydrogen and C1-C4 alkyl; —wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy$^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

In a still further aspect, disclosed are methods for inhibiting a viral infection in a mammal, the method comprising administering to the mammal an effective amount of a compound having a structure represented by a formula:

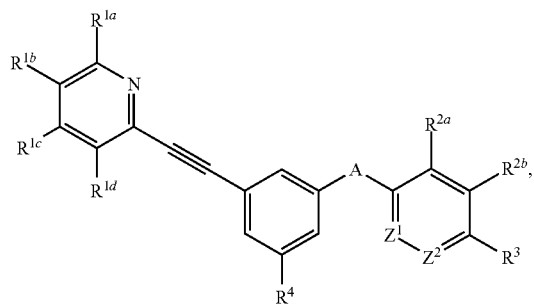

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein Ra is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-

C4)(C1-C4) dialkylamino, and C1-C4 aminoalkyl, and wherein Rb and $R^3$ are covalently bonded, and, together with the intermediate atoms, comprise a 5- or 6-membered heteroaryl, and are substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

In various aspects, the compound has a structure represented by a formula:

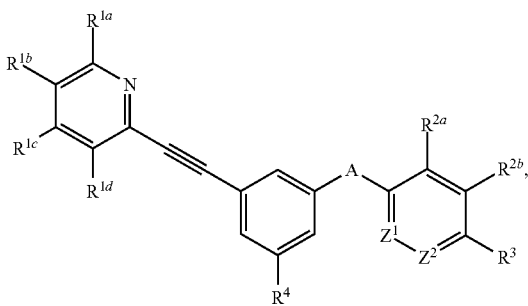

wherein A is selected from —$NR^{10}C(O)$— and —C(O)$NR^{11}$; wherein each of $R^{10}$, when present, and $R^{11}$, when present, is selected from hydrogen and C1-C4 alkyl; wherein each of $Z^1$ and $Z^2$ is independently selected from —N═ and —C($R^{13}$)═; wherein each occurrence of $R^{13}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —$NR^{14}C(O)R^{15}$, —C(O)$NR^{16a}R^{16b}$, —$NR^{17}SO_2R^{18}$, —P(O)$(OR^{19})_2$, —$CO_2$(C1-C4 alkyl), —$CO_2Cy^1$, —$CO_2$(C1-C4 alkyl)$Cy^1$, and $Cy^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —$OR^{20}$, —$NR^{21a}R^{21b}$, —$CH_2NR^{21a}R^{21b}$, and $Cy^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then R$^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and R$^3$ is —NR$^{14}$C(O)R$^{15}$, then R$^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

In various aspects, the compound has a structure represented by a formula:

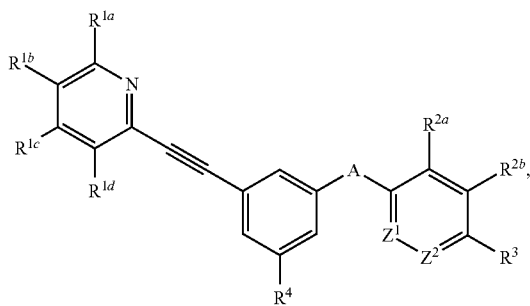

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, the compound exhibits inhibition of a viral infection. In a still further aspect, the compound exhibits a decrease in a viral infection. In yet a further aspect, the viral infection is a coronavirus such as, for example, 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

In a further aspect, the compound exhibits inhibition of viral activity with an $IC_{50}$ of less than about 30 μM. In a still further aspect, the compound exhibits inhibition of viral activity with an $IC_{50}$ of less than about 25 μM. In yet a further aspect, the compound exhibits inhibition of viral activity with an $IC_{50}$ of less than about 20 μM. In an even further aspect, the compound exhibits inhibition of viral activity with an $IC_{50}$ of less than about 15 μM. In a still further aspect, the compound exhibits inhibition of viral activity with an $IC_{50}$ of less than about 10 μM. In yet a further aspect, the compound exhibits inhibition of viral activity with an $IC_{50}$ of less than about 5 μM. In an even further aspect, the compound exhibits inhibition of viral activity with an $IC_{50}$ of less than about 1 μM In a still further aspect, the compound exhibits inhibition of viral activity with an $IC_{50}$ of less than about 0.5 μM.

In a further aspect, the compound exhibits inhibition of viral SARS-CoV-2 activity with an $IC_{50}$ of less than about 30 μM. In a still further aspect, the compound exhibits inhibition of viral SARS-CoV-2 activity with an $IC_{50}$ of less than about 25 μM. In yet a further aspect, the compound exhibits inhibition of viral SARS-CoV-2 activity with an $IC_{50}$ of less than about 20 μM. In an even further aspect, the compound exhibits inhibition of viral SARS-CoV-2 activity with an $IC_{50}$ of less than about 15 μM. In a still further aspect, the compound exhibits inhibition of viral SARS-CoV-2 activity with an $IC_{50}$ of less than about 10 μM. In yet a further aspect, the compound exhibits inhibition of viral SARS-CoV-2 activity with an $IC_{50}$ of less than about 5 μM. In an even further aspect, the compound exhibits inhibition of viral SARS-CoV-2 activity with an $IC_{50}$ of less than about 1 μM. In a still further aspect, the compound exhibits inhibition of viral SARS-CoV-2 activity with an $IC_{50}$ of less than about 0.5 μM.

In a further aspect, the subject is a mammal. In a still further aspect, the subject is a human.

In a further aspect, the subject has been diagnosed with a need for treatment of the viral infection prior to the administering step. In a still further aspect, the method further comprises the step of identifying a subject in need of treatment of the viral infection.

In a further aspect, the subject has coronavirus disease 2019 (COVID-19).

G. METHODS OF INHIBITING A VIRAL INFECTION IN AT LEAST ONE CELL

The compounds and pharmaceutical compositions of the invention are also useful in inhibiting a viral infection in at least one cell. Exemplary viral infections include, but are not limited to, a coronavirus such as 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

Thus, in one aspect, disclosed are methods for inhibiting a viral infection in a cell, the method comprising contacting the cell with an effective amount of a disclosed compound, or a pharmaceutically acceptable salt thereof, thereby inhibiting the viral infection in the cell.

In a further aspect, disclosed are methods for inhibiting a viral infection in a cell, the method comprising contacting the cell with an effective amount of a compound having a structure represented by a formula:

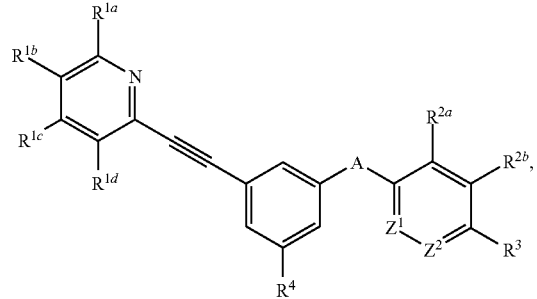

wherein A is selected from —$NR^{10}C(O)$— and —$C(O)NR^{11}$; wherein each of $R^{10}$, when present, and $R^{11}$, when present, is selected from hydrogen and C1-C4 alkyl; wherein each of $Z^1$ and $Z^2$ is independently selected from —N= and —$C(R^{13})$=; wherein each occurrence of $R^{13}$, when present, is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —$NR^{14}C(O)R^{15}$, —$C(O)NR^{16a}R^{16b}$, —$OSO_2NR^{16a}R^{16b}$, —$NR^{17}SO_2R^{18}$, —$P(O)(OR^{19})_2$, —$CO_2$(C1-C4 alkyl), —$CO_2Cy^1$, —$CO_2$(C1-C4 alkyl)$Cy^1$, $Cy^1$, and —$CH_2Cy^5$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —$OR^{20}$, —$NR^{21a}R^{21b}$, $CH_2NR^{21a}R^{21b}$, and $Cy^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

In a still further aspect, disclosed are methods for inhibiting a viral infection in a cell, the method comprising contacting the cell with an effective amount of a compound having a structure represented by a formula:

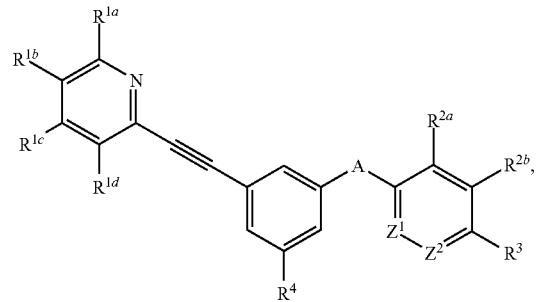

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of $Z^1$ and $Z^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

In various aspects, the compound has a structure represented by a formula:

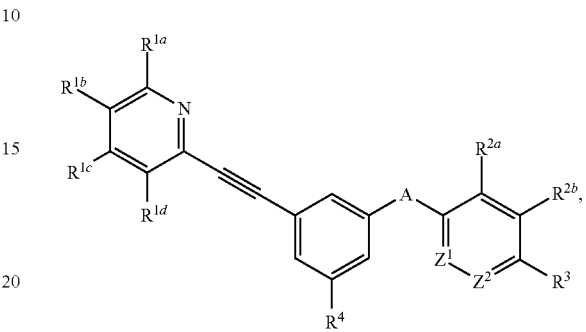

wherein A is selected from —NR$^{10}$C(O)— and —C(O)NR$^{11}$; wherein each of $R^{10}$, when present, and $R^{11}$, when present, is selected from hydrogen and C1-C4 alkyl; wherein each of $Z^1$ and $Z^2$ is independently selected from —N= and —C(R$^{13}$)=; wherein each occurrence of $R^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of Ra and Rb is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR¹⁰C(O)—, then $R^3$ is —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹, and provided that when A is —NR¹⁰C(O)— and $R^3$ is —NR¹⁴C(O)R¹⁵, then $R^{15}$ is selected from C1-C4 alkyl, C1-C4 haloalkyl, C1-C4 alkoxy, C1-C4 haloalkoxy, C1-C4 aminoalkyl, —NR²¹ᵃR²¹ᵇ, and —CH₂NR²¹ᵃR²¹ᵇ, or a pharmaceutically acceptable salt thereof.

In various aspects, the compound has a structure represented by a formula:

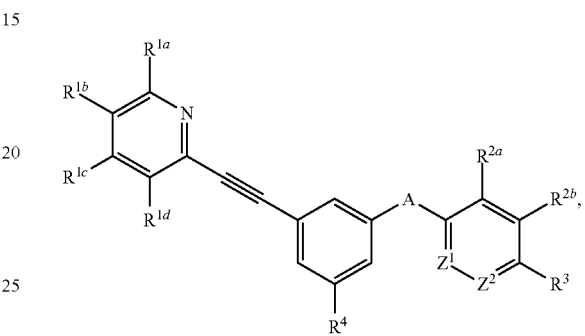

wherein A is selected from —NR¹⁰C(O)— and —C(O)NR¹¹; wherein each of $R^{10}$, when present, and $R^{11}$, when present, is selected from hydrogen and C1-C4 alkyl; wherein each of $Z^1$ and $Z^2$ is independently selected from —N═ and —C(R¹³)═; wherein each occurrence of $R^{13}$, when present, is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR¹⁴C(O)R¹⁵, —C(O)NR¹⁶ᵃR¹⁶ᵇ, —NR¹⁷SO₂R¹⁸, —P(O)(OR¹⁹)₂, —CO₂(C1-C4 alkyl), —CO₂Cy¹, —CO₂(C1-C4 alkyl)Cy¹, and Cy¹; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR²⁰, —NR²¹ᵃR²¹ᵇ, —CH₂NR²¹ᵃR²¹ᵇ, and Cy²; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, the cell is mammalian. In a still further aspect, the cell is human. In yet a further aspect, the cell has been isolated from a mammal prior to the contacting step.

In a further aspect, contacting is via administration to a mammal.

H. USE OF COMPOUNDS

In one aspect, the invention relates to the use of a disclosed compound or a product of a disclosed method. In a further aspect, a use relates to the manufacture of a medicament for the treatment of a viral infection such as, for example, a coronavirus, in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a viral infection in a subject. Also disclosed is the use of a compound for antagonism of a viral infection. In one aspect, the use is characterized in that the subject is a human. In one aspect, the use is characterized in that the disorder is a viral infection.

In a further aspect, the use relates to the manufacture of a medicament for the treatment of a viral infection in a subject.

In a further aspect, the use relates to antagonism of a viral infection in a subject. In a further aspect, the use relates to modulating viral activity in a subject. In a still further aspect, the use relates to modulating viral activity in a cell. In yet a further aspect, the subject is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a viral infection in a mammal. In a further aspect, the viral infection is selected from 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2).

I. MANUFACTURE OF A MEDICAMENT

In one aspect, the invention relates to a method for the manufacture of a medicament for treating a viral infection in a subject having the viral infection, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of a viral infection. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

J. KITS

In one aspect, disclosed are kits comprising an effective amount of a disclosed compound, or a pharmaceutically acceptable salt thereof, and one or more of: (a) at least one antiviral agent; (b) at least one immunity booster; (c) instructions for administering the compound in connection with treating a viral infection; (d) instructions for administering the compound in connection with reducing the risk of a viral infection; and (e) instructions for treating a viral infection.

In one aspect, disclosed are kits comprising a compound having a structure represented by a formula:

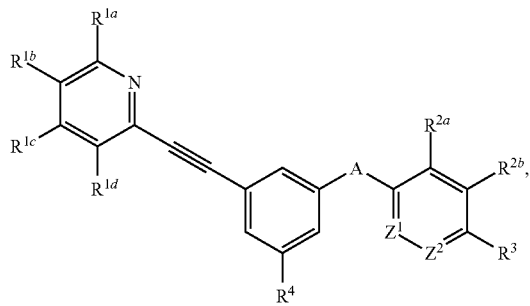

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N= and —C(R$^{13}$)=; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, aCy$^1$, and —CH$_2$Cy$^5$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; wherein $Cy^2$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more selected from: (a) at least one antiviral agent; (b) at least one immunity booster; (c) instructions for administering the compound in connection with treating a viral infection; (d) instructions for administering the compound in connection with reducing the risk of viral infection; and (e) instructions for treating a viral infection, wherein the viral infection is due to a Coronavirus.

In one aspect, disclosed are kits comprising a compound having a structure represented by a formula:

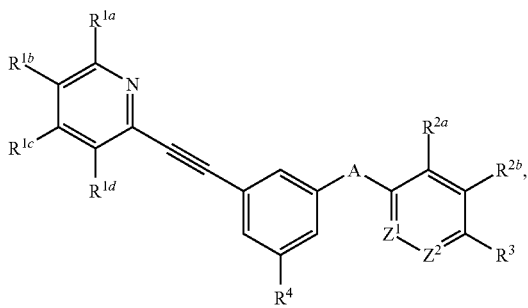

wherein A is selected from —NR$^{10}$C(O)— and —C(O)NR$^{11}$; wherein each of $R^{10}$, when present, and $R^{11}$, when present, is selected from hydrogen and C1-C4 alkyl; wherein each of $Z^1$ and $Z^2$ is independently selected from =N— and —C(R$^{13}$)=; wherein each occurrence of $R^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise an unsubstituted 4- to 6-membered heterocycloalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^{17}$, when present, is selected from hydrogen and C1-C4 alkyl; wherein $R^{18}$, when present is a C1-C4 alkyl; or wherein $R^{17}$ and $R^{18}$, when present, are covalently bonded, and together with the intermediate atoms, comprise an unsubstituted 5- to 7-membered heterocycloalkyl; wherein each occurrence of $R^{19}$, when present, is independently selected from hydrogen and C1-C4 alkyl; and wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more selected from: (a) at least one antiviral agent; (b) at least one immunity booster; (c) instructions for administering the compound in connection with treating a viral infection; (d) instructions for administering the compound in connection with reducing the risk of viral infection; and (e) instructions for treating a viral infection, wherein the viral infection is due to a Coronavirus.

In various aspects, the compound has a structure represented by a formula:

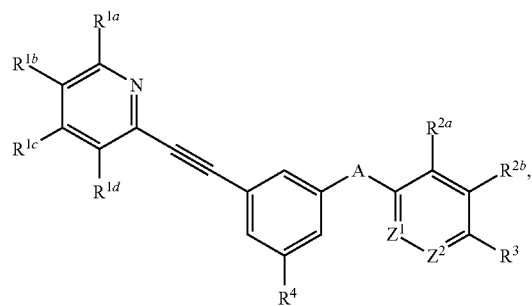

wherein A is selected from —NR$^{10}$C(O)— and —C(O)NR$^{11}$; wherein each of $R^{10}$, when present, and $R^{11}$, when present, is selected from hydrogen and C1-C4 alkyl; wherein each of $Z^1$ and $Z^2$ is independently selected from —N= and —C(R$^{13}$)=; wherein each occurrence of $R^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein $R^{14}$, when present, is selected from hydrogen and C1-C4 alkyl; wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein $R^{20}$, when present, is selected from hydrogen and C1-C4 alkyl; wherein each of $R^{21a}$ and $R^{21b}$, when present, is independently selected from hydrogen and C1-C4 alkyl; or wherein $R^{21a}$ and $R^{21b}$, when present, are covalently bonded, and, together with the intermediate atoms, comprise a 4- to 6-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^{16a}$ and $R^{16b}$, when present, is independently selected from hydrogen, C1-C4 alkyl, and $Cy^3$; wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when A is —NR$^{10}$C(O)—, then R$^3$ is —NR$^{10}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and provided that when A is —NR$^{10}$C(O)— and R$^3$ is —NR$^{14}$C(O)R$^{15}$, then R$^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

In various aspects, the compound has a structure represented by a formula:

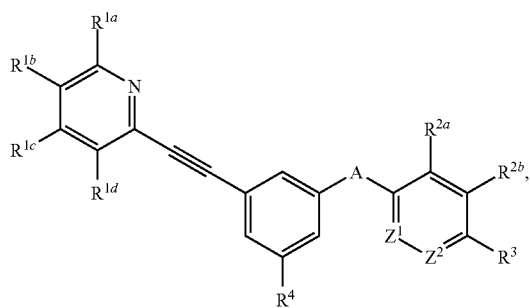

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N═ and —C(R$^{13}$)═; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$; and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein R$^{2b}$ and R$^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In various aspects, the compound has a structure represented by a formula:

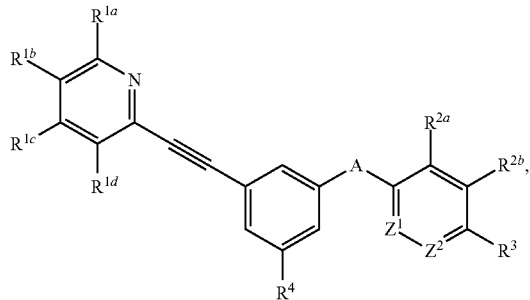

wherein A is selected from —NR$^{10}$C(O)— and —C(O)NR$^{11}$; wherein each of R$^{10}$, when present, and R$^{11}$, when present, is selected from hydrogen and C1-C4 alkyl; wherein each of Z$^1$ and Z$^2$ is independently selected from —N═ and —C(R$^{13}$)═; wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$; wherein R$^{14}$, when present, is selected from hydrogen and C1-C4 alkyl; wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$; wherein R$^{20}$, when present, is selected from hydrogen and C1-C4 alkyl; wherein each of R$^{21a}$ and R$^{21b}$, when present, is independently selected from hydrogen and C1-C4 alkyl; or wherein R$^{21a}$ and R$^{21b}$, when present, are covalently bonded, and, together with the intermediate atoms, comprise an unsubstituted 4- to 6-membered heterocycloalkyl; wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{14}$ and R$^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R$^{15}$, when present, and R$^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R$^{16a}$ and R$^{16b}$, when present, is independently selected from hydrogen, C1-C4 alkyl, and Cy$^3$; wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^{17}$, when present, is selected from hydrogen and C1-C4 alkyl; wherein R$^{18}$, when present is a C1-C4 alkyl; or wherein R$^{17}$ and R$^{18}$, when present, are covalently bonded, and together with the intermediate atoms, comprise an unsubstituted 5- to 7-membered heterocycloalkyl; wherein each occurrence of R$^{19}$, when present, is independently selected from hydrogen and C1-C4 alkyl; and wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In a further aspect, the viral infection is selected from 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2). In a still further aspect, the viral infection is due to a Coronavirus. In yet a further aspect, the Coronavirus is selected from 229E, NL63, OC43, HKU1, Middle East respiratory syndrome coronavirus (MERS-CoV), severe acute respiratory syndrome coronavirus (SARS-CoV), and severe acute respiratory syndrome coronavirus disease 2019 (SARS-CoV-2). In an even further aspect, the Coronavirus is SARS-CoV. In a still further aspect, the Coronavirus is SARS-CoV-2.

In a further aspect, the antiviral agent is selected from selected from acemannan, acyclovir, acyclovir sodium, adamantanamine, adefovir, adenine arabinoside, alovudine, alvircept sudotox, amantadine hydrochloride, aranotin, arildone, atevirdine mesylate, avridine, cidofovir, cipamfylline, cytarabine hydrochloride, BMS 806, C31G, carrageenan, cellulose sulfate, cyclodextrins, dapivirine, delavirdine mesylate, desciclovir, dextrin 2-sulfate, didanosine, disoxaril, dolutegravir, edoxudine, enviradene, envirozime, etravirine, famciclovir, famotine hydrochloride, fiacitabine, fialuridine, fosarilate, foscarnet sodium, fosfonet sodium, FTC, ganciclovir, ganciclovir sodium, GSK 1265744, 9-2-hydroxy-ethoxy methylguanine, ibalizumab, idoxuridine, interferon, 5-iodo-2'-deoxyuridine, IQP-0528, kethoxal, lamivudine, lobucavir, maraviroc, memotine pirodavir, penciclovir, raltegravir, ribavirin, rimantadine hydrochloride, rilpivirine (TMC-278), saquinavir mesylate, SCH-C, SCH-D, somantadine hydrochloride, sorivudine, statolon, stavudine, T20, tilorone hydrochloride, TMC120, TMC125, trifluridine, trifluorothymidine, tenofovir, tenofovir alefenamide, tenofovir disoproxyl fumarate, prodrugs of tenofovir, UC-781, UK-427, UK-857, valacyclovir, valacyclovir hydrochloride, vidarabine, vidarabine phosphate, vidarabine sodium phosphate, viroxime, zalcitabene, zidovudine, and zinviroxime.

In a further aspect, the immunity booster is selected from vitamin D, elderberry, *Echinacea*, a probiotic, vitamin C, vitamin B, green tea, turmeric, zinc, ashwagandha, a prebiotic, and a synbiotic.

In a further aspect, the compound and the antiviral agent are co-packaged. In a still further aspect, the compound and the antiviral agent are co-formulated.

In a further aspect, the compound and the immunity booster are co-packaged. In a still further aspect, the compound and the immunity booster are co-formulated.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

K. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. General Experimental Method

The reactions were performed under a dry argon atmosphere and reaction temperatures were measured externally. Anhydrous solvents over molecular sieves were purchased from Aldrich and used as such in reactions. Microwave (MW) reactions were performed in CEM Discover Labmate System with Intelligent Technology for Focused™ Microwave Synthesizer (Explorer 48) or Biotage Initiator+ equipped with Robot Eight microwave system. The reactions were monitored by thin-layer chromatography (TLC) on pre-coated silica gel (60F$_{254}$) aluminium plates (0.25 mm) from E. Merck and visualized using UV light (254 nm). Purification of compounds was performed on an Isco Teledyne Combiflash Rf200. Universal RediSep solid sample loading pre-packed cartridges (5.0 g silica) were used to absorb crude product and purified on 12 g silica RediSep Rf Gold Silica (20-40 μm spherical silica) columns using appropriate solvent gradients. Pure samples were dried overnight under high vacuum before analyses. The high resolution electrospray ionization mass spectral data (HR-ESIMS) were obtained on an Agilent LC-MSTOF. $^1$H NMR spectra were recorded at 400 MHz on Agilent/Varian MR-400 spectrometer in CDCl$_3$, CD$_3$OD, or DMSO-d$_6$ as solvents. The chemical shifts (δ) are in ppm downfield from standard tetramethylsilane (TMS). HPLC of final compounds were run on an Agilent 1100 LC equipped with a diode array UV detector and were monitored at 254 nm using the following using Sunfire C18 column (5 μm, 4.6×150 mm) using H$_2$O—CH$_3$CN (both containing 0.1% formic acid) 5-95% in 20 min with flow rate 1.0 mL/min.

b. Preparation of Compound Nos. 1-5, 10-13, 19, 29, 30-31, 34, and 40-45

General Scheme 1

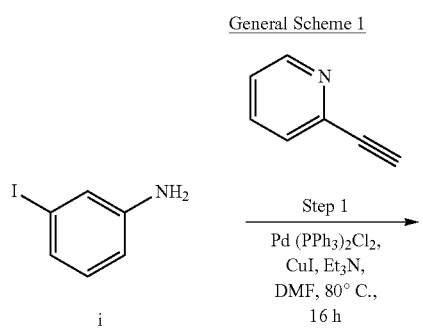

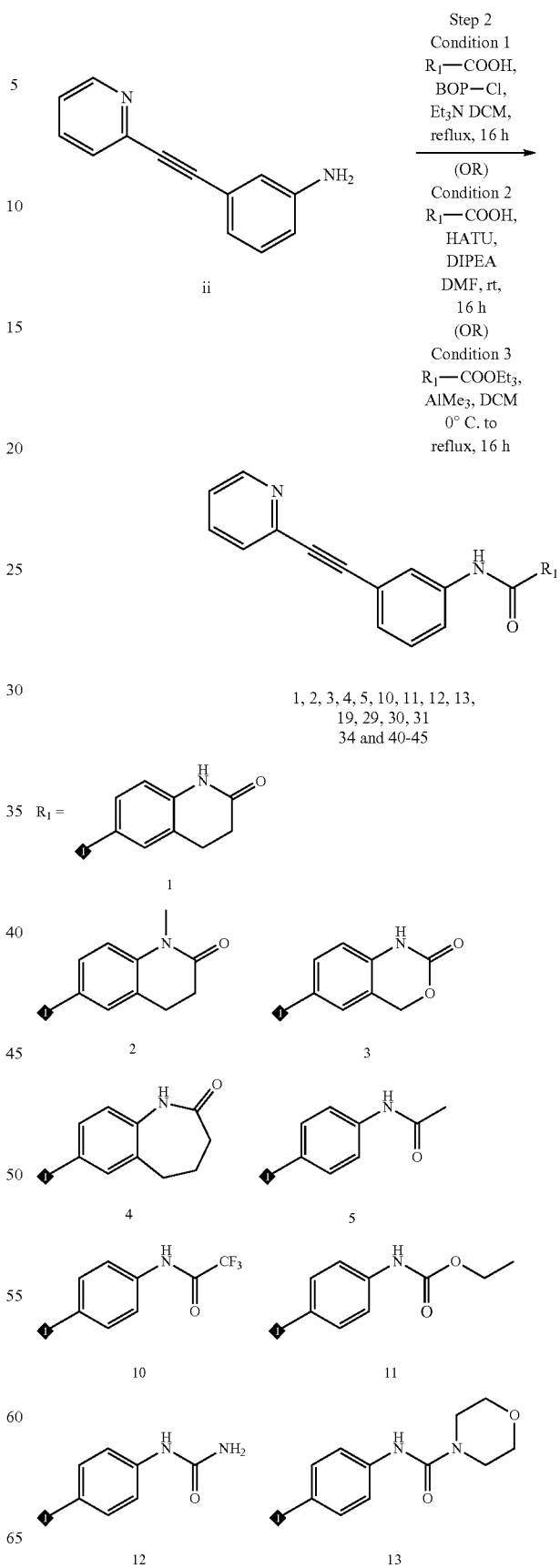

-continued

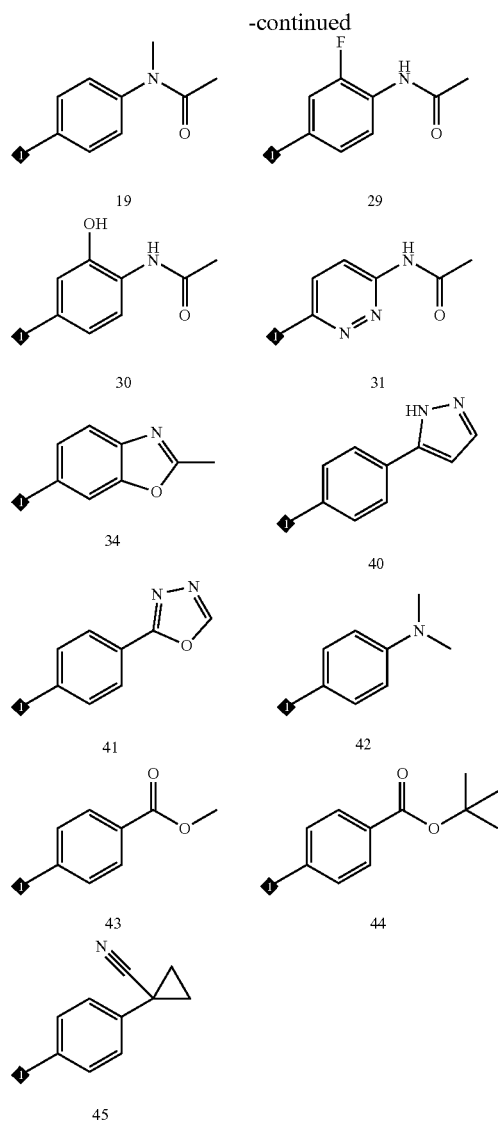

i. Step 1: Synthesis of 3-(pyridin-2-ylethynyl)aniline (II)

3-Iodoaniline (0.55 mL, 4.57 mmol) (i) and 2-ethynylpyridine (0.56 mL, 5.48 mmol) were dissolved in anhydrous DMF (6.5 mL) under nitrogen atmosphere in a microwave vial. To the reaction mixture, copper iodide (21.74 mg, 0.11 mmol), bis(triphenylphosphine)palladium(II) dichloride (32.05 mg, 0.05 mmol) and triethylamine (3.5 mL, 25.11 mmol) were added. The reaction mixture was stirred at 80° C. for 16 h. After cooling to room temperature, the reaction mixture was diluted with water (50 mL) and filtered over a short pad of celite, given washings with EtOAc. The filtrate was further extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-4% MeOH in DCM (30 min) gave the pure product (ii). Yield: 642 mg (72.4%). $^1$H NMR (DMSO-$d_6$) δ 8.60-8.56 (m, 1H), 7.83 (td, J=7.7, 1.8 Hz, 1H), 7.62-7.57 (m, 1H), 7.39 (ddd, J=7.6, 4.9, 1.2 Hz, 1H), 7.08 (t, J=7.8 Hz, 1H), 6.77 (t, J=1.9 Hz, 1H), 6.72 (dt, J=7.5, 1.3 Hz, 1H), 6.64 (ddd, J=8.1, 2.4, 1.0 Hz, 1H), 5.32 (s, 2H). ESIMS: m/z 195.1 [M+H]$^+$.

ii. Step 2: General Synthetic Procedure

Condition 1: To a solution of carboxylic acid (1 mmol) in anhydrous DCM (5 mL) under nitrogen atmosphere at room temperature, BOP-Cl (1.5 mmol) was added followed by the addition of triethylamine (3 mmol) and the reaction mixture was stirred at same temperature for 5 min. 3-(pyridin-2-ylethynyl)aniline (ii) (1 mmol) was added to the reaction mixture and refluxed for 16 h. After completion of the reaction. The reaction mixture was cooled to room temperature, diluted with water (50 mL) and extracted with DCM (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

Condition 2: To a solution of carboxylic acid (1 mmol) in anhydrous DMF (5 mL) under nitrogen atmosphere at room temperature, HATU (1.5 mmol) was added followed by DIPEA (3 mmol) and the reaction was stirred at same temperature for about 10 min. 3-(pyridin-2-ylethynyl)aniline (ii) (1 mmol) was added to the reaction mixture and allowed to stir at room temperature for 16 h. After completion of the reaction, the reaction mixture was diluted with water (50 mL) and extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

Condition 3: To a solution of 3-(pyridin-2-ylethynyl) aniline (ii) (1 mmol) in anhydrous DCM (5 mL) under nitrogen atmosphere at 0° C., was added a 2 M solution of $AlMe_3$ in toluene (3 mmol) dropwise. After complete addition, the reaction was stirred at room temperature for 30 min. Appropriate ester (1 mmol) was added to the reaction mixture and refluxed for 16 h. After completion of the reaction, the reaction was cooled to room temperature and quenched by dropwise addition of MeOH (3 mL), then it was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) 2-Oxo-N-(3-(pyridin-2-ylethynyl)phenyl)-1,2,3,4-tetrahydroquinoline-6-carboxamide (1)

This compound was synthesized by using condition 2. Purification on pre-packed Silica gel column on ISCO using 0-20% MeOH in DCM (35 min). Yield: 153 mg (39.5%). $^1$H NMR (DMSO-$d_6$) δ 10.35 (s, 1H), 10.20 (s, 1H), 8.60 (ddd, J=4.9, 1.8, 1.0 Hz, 1H), 8.07 (t, J=1.9 Hz, 1H), 7.88-7.73 (m, 4H), 7.67-7.61 (m, 1H), 7.49-7.36 (m, 2H), 7.31 (dt, J=7.7, 1.3 Hz, 1H), 6.94 (d, J=8.2 Hz, 1H), 2.96 (t, J=7.6 Hz, 2H), 2.54-2.49 (m, 2H). HR-ESIMS: m/z 368.1394 [M+H]$^+$ calcd. for $C_{23}H_{18}N_3O_2$, found 368.1393. HPLC purity: 99.1% (Retention Time=9.3 min).

(ii) 1-Methyl-2-oxo-N-(3-(pyridin-2-ylethynyl)phenyl)-1,2,3,4-tetrahydroquinoline-6-carboxamide (2)

This compound was synthesized by using condition 2. Purification on Biotage Isolera, Sfar using 0-35% acetone in DCM (30 min). Yield: 56.6 mg (36.7%). $^1$H NMR (DMSO-$d_6$) δ 10.29 (d, J=2.9 Hz, 1H), 8.62 (dq, J=5.2, 2.5, 1.9 Hz, 1H), 8.10 (p, J=1.9 Hz, 1H), 7.96-7.91 (m, 1H), 7.91-7.80 (m, 3H), 7.67 (dq, J=7.9, 1.5 Hz, 1H), 7.49-7.38 (m, 2H), 7.34 (dt, J=7.5, 1.8 Hz, 1H), 7.24 (dd, J=8.5, 2.8 Hz, 1H), 3.32 (s, 3H), 3.02-2.93 (m, 2H), 2.61 (td, J=7.7, 6.9, 2.9 Hz, 2H). HR-ESIMS: m/z 382.1550 [M+H]$^+$ calcd. for $C_{24}H_{20}N_3O_2$, found 382.1550. HPLC purity: 96% (Retention Time=10.2 min).

(iii) Oxo-N-(3-(pyridin-2-ylethynyl)phenyl)-1,4-dihydro-2H-benzo[d][1,3]oxazine-6-carboxamide (3)

This compound was synthesized by using condition 2. Purification on pre-packed Silica gel column on ISCO using 0-5% MeOH in DCM (35 min). Yield: 29 mg (29.4%). $^1$H NMR (DMSO-$d_6$) δ 10.50 (s, 1H), 10.30 (s, 1H), 8.63-8.60 (m, 1H), 8.07 (d, J=1.9 Hz, 1H), 7.92-7.78 (m, 4H), 7.67 (dd, J=7.8, 1.1 Hz, 1H), 7.47-7.40 (m, 2H), 7.34 (dt, J=7.7, 1.3 Hz, 1H), 6.99 (d, J=8.3 Hz, 1H), 5.39 (s, 2H). HR-ESIMS: m/z 370.1186 [M+H]$^+$ calcd. for $C_{22}H_{16}N_3O_3$, found 370.1195. HPLC purity: 97% (Retention Time=9.0 min).

(iv) 2-Oxo-N-(3-(pyridin-2-ylethynyl)phenyl)-2,3,4,5-tetrahydro-1H-benzo[b]azepine-7-carboxamide (4)

This compound was synthesized by using condition 2. Purification on Biotage Isolera, Sfar using 5-35% acetone in DCM (30 min). Yield: 45.4 mg (23.3%). $^1$H NMR (DMSO-$d_6$) δ 10.30 (s, 1H), 9.79 (s, 1H), 8.62 (ddd, J=4.9, 1.8, 1.0 Hz, 1H), 8.09 (t, J=1.9 Hz, 1H), 7.91-7.88 (m, 1H), 7.88-7.79 (m, 3H), 7.67 (dt, J=7.8, 1.1 Hz, 1H), 7.49-7.39 (m, 2H), 7.34 (dt, J=7.7, 1.3 Hz, 1H), 7.09 (d, J=8.2 Hz, 1H), 2.78 (t, J=6.8 Hz, 2H), 2.19 (dd, J=12.7, 6.0 Hz, 4H). HR-ESIMS: m/z 382.1550 [M+H]$^+$ calcd. for $C_{24}H_{20}N_3O_2$, found 382.1558. HPLC purity: 95.4% (Retention Time=9.5 min).

(v) 4-Acetamido-N-(3-(pyridin-2-ylethynyl)phenyl)benzamide (5)

This compound was synthesized using condition 2. Purified by recrystallization using EtOAc. Yield: 105.8 mg (52%). $^1$H NMR (DMSO-$d_6$) δ 10.24 (d, J=8.3 Hz, 2H), 8.62 (ddd, J=4.9, 1.8, 0.9 Hz, 1H), 8.10 (t, J=1.8 Hz, 1H), 7.98-7.91 (m, 2H), 7.86 (td, J=7.7, 1.8 Hz, 1H), 7.83 (ddd, J=8.2, 2.2, 1.1 Hz, 1H), 7.77-7.71 (m, 2H), 7.67 (dt, J=7.8, 1.1 Hz, 1H), 7.48-7.39 (m, 2H), 7.33 (dt, J=7.6, 1.3 Hz, 1H), 2.09 (s, 3H). HR-ESIMS: m/z 356.13935 [M+H]$^+$ calcd. for $C_{22}H_{18}N_3O_2$, found 356.14031. HPLC purity: 97.4% (Retention Time=9.2 min).

(vi) N-(3-(Pyridin-2-ylethynyl)phenyl)-4-(2,2,2-trifluoroacetamido)benzamide (10)

This compound was synthesized using condition 2. Purification on pre-packed Silica gel column on ISCO using 0-3.5% MeOH in DCM (25 min). Yield: 54 mg (59.2%). $^1$H NMR (DMSO-$d_6$) δ 11.42 (s, 1H), 10.38 (s, 1H), 8.62 (ddd, J=4.9, 1.8, 0.9 Hz, 1H), 8.10 (d, J=1.9 Hz, 1H), 8.05-8.00 (m, 2H), 7.89-7.81 (m, 4H), 7.67 (dt, J=7.8, 1.1 Hz, 1H), 7.47-7.40 (m, 2H), 7.35 (dt, J=7.7, 1.3 Hz, 1H). HR-ESIMS: m/z 410.1111 [M+H]$^+$ calcd. for $C_{22}H_{15}F_3N_3O_2$, found 410.1107. HPLC purity: 96.2% (Retention Time=11.6 min).

(vii) Ethyl (4-((3-(pyridin-2-ylethynyl)phenyl)carbamoyl)phenyl)carbamate (11)

This compound was synthesized using condition 2. Purification on pre-packed Silica gel column on ISCO using 0-4% MeOH in DCM (30 min). Yield: 32 mg (27.8%). $^1$H NMR (DMSO-$d_6$) δ 10.22 (s, 1H), 9.97 (s, 1H), 8.64-8.60 (m, 1H), 8.09 (t, J=1.9 Hz, 1H), 7.95-7.90 (m, 2H), 7.89-7.80 (m, 2H), 7.67 (dq, J=7.8, 1.0 Hz, 1H), 7.61 (d, J=8.7 Hz, 2H), 7.46-7.40 (m, 2H), 7.35-7.31 (m, 1H), 4.16 (q, J=7.1 Hz, 2H), 1.27 (t, 3H). HR-ESIMS: m/z 386.1499 [M+H]$^+$ calcd. for $C_{23}H_{20}N_3O_3$, found 386.1503. HPLC purity: 96.1% (Retention Time=11.1 min).

(viii) N-(3-(pyridin-2-ylethynyl)phenyl)-4-ureidobenzamide (12)

This compound was synthesized using condition 2. Purification on pre-packed Silica gel column on ISCO using 0-10% MeOH in DCM (40 min). Yield: 47 mg (50.3%). $^1$H NMR (DMSO-$d_6$) δ 10.18 (s, 1H), 8.89 (s, 1H), 8.62 (ddd, J=4.8, 1.8, 1.0 Hz, 1H), 8.09 (t, J=1.9 Hz, 1H), 7.90-7.86 (m, 3H), 7.85-7.80 (m, 1H), 7.67 (dt, J=7.8, 1.1 Hz, 1H), 7.57-7.51 (m, 2H), 7.45-7.40 (m, 2H), 7.32 (dt, J=7.7, 1.3 Hz, 1H), 6.02 (s, 2H). HR-ESIMS: m/z 357.1346 [M+H]$^+$ calcd. for $C_{21}H_{17}N_4O_2$, found 357.1350. HPLC purity: 98.7% (Retention Time=8.4 min).

(ix) N-(4-((3-(Pyridin-2-ylethynyl)phenyl)carbamoyl)phenyl)morpholine-4-carboxamide (13)

This compound was synthesized using condition 2. Purification on pre-packed Silica gel column on ISCO using 0-4% MeOH in DCM (35 min). Yield: 63 mg (59.8%). $^1$H NMR (DMSO-$d_6$) δ 10.19 (s, 1H), 8.86 (s, 1H), 8.62 (d, J=4.7 Hz, 1H), 8.10 (s, 1H), 7.93-7.80 (m, 4H), 7.69-7.60 (m, 3H), 7.46-7.39 (m, 2H), 7.34-7.29 (m, 1H), 3.62 (t, J=4.8 Hz, 4H), 3.46 (t, J=4.8 Hz, 4H). HR-ESIMS: m/z 427.1765 [M+H]$^+$ calcd. for $C_{25}H_{23}N_4O_3$, found 427.1767. HPLC purity: 97.1% (Retention Time=9.3 min).

(x) 4-(N-methylacetamido)-N-(3-(pyridin-2-ylethynyl)phenyl)benzamide (19)

This compound was synthesized using condition 2. Purified on preparative TLC plate using DCM-MeOH (19:1). Yield: 54 mg (55.5%). $^1$H NMR (DMSO-$d_6$) δ 10.43 (s, 1H), 8.62 (ddd, J=4.9, 1.8, 0.9 Hz, 1H), 8.10 (d, J=2.0 Hz, 1H), 8.02 (d, J=8.3 Hz, 2H), 7.89-7.81 (m, 2H), 7.67 (dq, J=7.8, 1.1 Hz, 1H), 7.52 (d, J=8.3 Hz, 2H), 7.48-7.40 (m, 2H), 7.38-7.33 (m, 1H), 3.23 (s, 3H), 1.90 (s, 3H). HR-ESIMS: m/z 370.1550 [M+H]$^+$ calcd. for $C_{23}H_{20}N_3O_2$, found 370.1546. HPLC purity: 98.3% (Retention Time=7.9 min).

(xi) 4-Acetamido-3-fluoro-N-(3-(pyridin-2-ylethynyl)phenyl)benzamide (29)

This compound was synthesized using condition 1. Purification on pre-packed Silica gel column on ISCO using 0-5% MeOH in DCM (30 min). Yield: 55 mg (38%). $^1$H NMR (DMSO-$d_6$) δ 10.35 (s, 1H), 10.00 (s, 1H), 8.62 (dt, J=5.0, 1.5 Hz, 1H), 8.19 (t, J=8.2 Hz, 1H), 8.09 (t, J=1.9 Hz, 1H), 7.89-7.78 (m, 4H), 7.69-7.65 (m, 1H), 7.48-7.41 (m, 2H), 7.35 (dt, J=7.6, 1.4 Hz, 1H), 2.15 (s, 3H). HR-ESIMS: m/z 374.1299 [M+H]$^+$ calcd. for $C_{22}H_{17}FN_3O_2$, found 374.1302. HPLC purity: 99.5% (Retention Time=9.5 min).

(xii) 4-Acetamido-3-hydroxy-N-(3-(pyridin-2-yl-ethynyl)phenyl)benzamide (30)

This compound was synthesized using condition 3. Purification on pre-packed Silica gel column on ISCO using 0-10% MeOH in DCM (39 min). Yield: 11 mg (9.45%). $^1$H NMR (DMSO-$d_6$) δ 10.24 (s, 1H), 9.41 (s, 1H), 8.62 (dd, J=4.8, 1.4 Hz, 1H), 8.11-8.08 (m, 1H), 8.02 (d, J=8.3 Hz, 1H), 7.89-7.79 (m, 2H), 7.67 (dt, J=7.8, 1.1 Hz, 1H), 7.47-7.40 (m, 4H), 7.34-7.30 (m, 1H), 2.14 (s, 3H). HR-ESIMS: m/z 372.1343 [M+H]$^+$ calcd. for $C_{22}H_{18}N_3O_3$, found 372.1353. HPLC purity: 98.4% (Retention Time=8.8 min).

(xiii) 6-Acetamido-N-(3-(pyridin-2-ylethynyl)phenyl)pyridazine-3-carboxamide (31)

This compound was synthesized using condition 3. Purification on pre-packed Silica gel column on ISCO using 0-3% MeOH in DCM (25 min). Yield: 10 mg (13.6%). $^1$H NMR (DMSO-$d_6$) δ 11.46 (s, 1H), 11.08 (s, 1H), 8.64-8.61 (m, 1H), 8.55 (d, J=9.3 Hz, 1H), 8.30 (d, J=9.3 Hz, 1H), 8.23 (t, J=1.8 Hz, 1H), 7.99 (dt, J=7.5, 1.3 Hz, 1H), 7.87 (td, J=7.7, 1.8 Hz, 1H), 7.68 (dt, J=7.7, 1.0 Hz, 1H), 7.50-7.36 (m, 3H), 2.22 (s, 3H). HR-ESIMS: m/z 358.1299 [M+H]$^+$ calcd. for $C_{20}H_{16}N_5O_2$, found 358.1299. HPLC purity: 100% (Retention Time=9.2 min).

(xiv) 2-Methyl-N-(3-(pyridin-2-ylethynyl)phenyl)benzo[d]oxazole-6-carboxamide (34)

This compound was synthesized using condition 2. Purification on pre-packed Silica gel column on ISCO using 0-4% MeOH in DCM (35 min). Yield: 52 mg (51%). $^1$H NMR (DMSO-$d_6$) δ 10.45 (s, 1H), 8.62 (ddd, J=4.9, 1.8, 1.0 Hz, 1H), 8.28 (dd, J=1.6, 0.7 Hz, 1H), 8.13-8.11 (m, 1H), 7.99 (dd, J=8.3, 1.6 Hz, 1H), 7.89-7.84 (m, 2H), 7.82-7.79 (m, 1H), 7.67 (dt, J=7.8, 1.1 Hz, 1H), 7.49-7.41 (m, 2H), 7.36 (ddd, J=7.6, 1.6, 1.0 Hz, 1H), 2.68 (s, 3H). HR-ESIMS: m/z 354.1237 [M+H]$^+$ calcd. for $C_{22}H_{16}N_3O_2$, found 354.1231. HPLC purity: 97.8% (Retention Time=10.2 min).

(xv) 4-(1H-Pyrazol-5-yl)-N-(3-(pyridin-2-ylethynyl)phenyl)benzamide (40)

This compound was synthesized using condition 1. Purification on pre-packed Silica gel column on ISCO using 0-20% MeOH in DCM (30 min). Yield: 22 mg (31.8%). $^1$H NMR (CDCl$_3$) δ 8.60-8.54 (m, 1H), 7.96-7.90 (m, 2H), 7.90-7.76 (m, 4H), 7.70 (td, J=7.7, 1.8 Hz, 1H), 7.61 (d, J=2.3 Hz, 1H), 7.52 (dt, J=7.9, 1.1 Hz, 1H), 7.38-7.31 (m, 2H), 7.24 (dd, J=4.9, 1.2 Hz, 1H), 6.66 (d, J=2.3 Hz, 1H). HR-ESIMS: m/z 365.1397 [M+H]$^+$ calcd. for $C_{22}H_{17}N_4O$, found 365.1396. HPLC purity: 95% (Retention Time=9.9 min).

(xvi) 4-(1,3,4-Oxadiazol-2-yl)-N-(3-(pyridin-2-yl-ethynyl)phenyl)benzamide (41)

This compound was synthesized using condition 1. Purification on ACCQ prep HP-125 reverse phase column using 0-100% CH$_3$CN in H$_2$O with 0.1% TFA (30 min). Yield: 45 mg (47.7%). $^1$H NMR (CDCl$_3$) δ 8.61 (ddd, J=5.0, 1.9, 1.0 Hz, 1H), 8.53 (s, 1H), 8.26-8.18 (m, 2H), 8.12-7.99 (m, 3H), 7.88 (d, J=1.9 Hz, 1H), 7.78-7.65 (m, 2H), 7.53 (dt, J=7.9, 1.1 Hz, 1H), 7.45-7.35 (m, 2H). HR-ESIMS: m/z 367.1189 [M+H]$^+$ calcd. for $C_{22}H_{15}N_4O_2$, found 367.1196. HPLC purity: 100% (Retention Time=9.6 min).

(xvii) 4-(Dimethylamino)-N-(3-(pyridin-2-ylethynyl)phenyl)benzamide, trifluoroacetate salt (42)

This compound was synthesized using condition 1. Purification on ACCQ prep HP-125 reverse phase column using 0-100% CH$_3$CN in H$_2$O with 0.1% TFA (30 min). Yield: 15 mg (28.4%). $^1$H NMR (CDCl$_3$) δ 8.59 (s, 1H), 7.85 (dt, J=7.6, 2.0 Hz, 1H), 7.83-7.71 (m, 4H), 7.57 (d, J=7.9 Hz, 1H), 7.37-7.27 (m, 3H), 6.74-6.60 (m, 2H), 3.01 (s, 6H). HR-ESIMS: m/z 342.1528 [M+H]$^+$ calcd. for $C_{22}H_{20}N_3O$, found 342.1601. HPLC purity: 100% (Retention Time=9.6 min).

(xviii) Methyl 4-((3-(pyridin-2-ylethynyl)phenyl)carbamoyl)benzoate (43)

This compound was synthesized using condition 1. Purification on pre-packed Silica gel column on ISCO using 0-60% EtOAc in hexanes (30 min). Yield: 390 mg (67.5%). $^1$H NMR (CDCl$_3$) δ 8.61 (ddd, J=5.0, 1.7, 1.0 Hz, 1H), 8.18-8.09 (m, 2H), 8.01 (s, 1H), 7.98-7.90 (m, 2H), 7.86 (d, J=1.9 Hz, 1H), 7.77-7.64 (m, 2H), 7.53 (dt, J=7.8, 1.1 Hz, 1H), 7.44-7.34 (m, 2H), 3.96 (s, 3H). HR-ESIMS: m/z 357.1234 [M+H]$^+$ calcd. for $C_{22}H_{17}N_2O_3$, found 357.1235. HPLC purity: 100% (Retention Time=11.3 min).

(xix) tert-Butyl 4-((3-(pyridin-2-ylethynyl)phenyl)carbamoyl)benzoate (44)

This compound was synthesized using condition 1. Purification on pre-packed Silica gel column on ISCO using 0-20% MeOH in DCM (30 min). Yield: 40 mg (39%). $^1$H NMR (CDCl$_3$) δ 8.61 (ddd, J=5.0, 2.0, 1.1 Hz, 1H), 8.11-8.05 (m, 2H), 8.04 (s, 1H), 7.95-7.88 (m, 2H), 7.86 (t, J=1.7 Hz, 1H), 7.76-7.66 (m, 2H), 7.52 (dq, J=7.8, 1.1 Hz, 1H), 7.43-7.33 (m, 2H), 1.61 (d, J=0.9 Hz, 9H). HR-ESIMS: m/z 399.1703 [M+H]$^+$ calcd. for $C_{25}H_{23}N_2O_3$, found 399.1699. HPLC purity: 92.7% (Retention Time=14.0 min; HPLC conditions: 0.1% TFA, 5-95% H$_2$O—CH$_3$CN).

(xx) 4-(1-Cyanocyclopropyl)-N-(3-(pyridin-2-yl-ethynyl)phenyl)benzamide (45)

This compound was synthesized using condition 1. Purification on pre-packed Silica gel column on ISCO using 0-20% MeOH in DCM (30 min). Yield: 35 mg (26.7%). $^1$H NMR (CDCl$_3$) δ 8.61 (ddd, J=4.9, 1.8, 1.0 Hz, 1H), 7.98 (s, 1H), 7.90-7.82 (m, 3H), 7.75-7.66 (m, 2H), 7.53 (dt, J=7.8, 1.1 Hz, 1H), 7.43-7.35 (m, 4H), 1.89-1.75 (m, 2H), 1.56-1.41 (m, 2H). HR-ESIMS: m/z 364.1444 [M+H]$^+$ calcd. for $C_{22}H_{17}N_3O$, found 364.1444. HPLC purity: 100% (Retention Time=11.4 min).

c. Preparation of Compound Nos. 6-9

General Scheme 2

Step 1

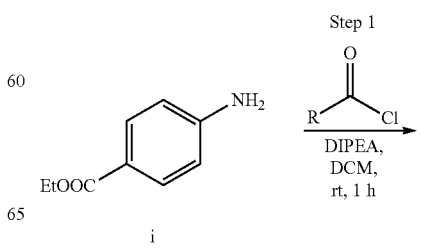

i

-continued

Step 2

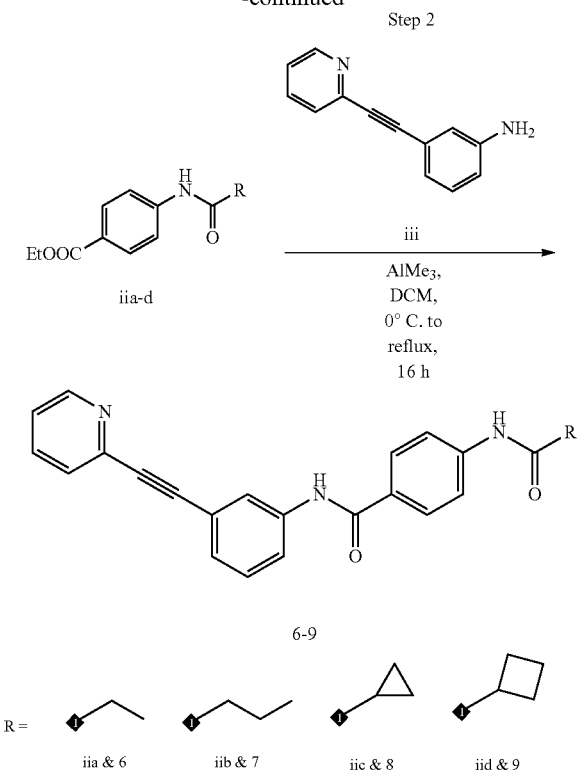

i. Step 1: General Synthetic Procedure

To a solution of ethyl 4-aminobenzoate (i) (1 mmol) in anhydrous DCM (15 mL) under nitrogen atmosphere at room temperature, N,N-Diisopropylethylamine (2 mmol) was added followed by appropriate acid chloride (1.2 mmol). The reaction mixture was allowed to stir at room temperature for 1 h. After completion of the reaction, the mixture was evaporated to dryness under reduced pressure to give a residue, followed by purification using pre-packed Silica gel column on ISCO gave the pure product.

(i) Ethyl 4-propionamidobenzoate (iia)

Purification on pre-packed Silica gel column on ISCO using 0-5% MeOH in DCM (30 min). Yield: 102 mg (30.5%). $^1$H NMR (DMSO-$d_6$) δ 10.20 (s, 1H), 7.92-7.86 (m, 2H), 7.75-7.69 (m, 2H), 4.27 (q, J=7.1 Hz, 2H), 2.36 (q, J=7.5 Hz, 2H), 1.30 (t, J=7.1 Hz, 3H), 1.08 (t, J=7.5 Hz, 3H). ESIMS: m/z 222.0 [M+H]$^+$.

(ii) Ethyl 4-butyramidobenzoate (iib)

Purification on pre-packed Silica gel column on ISCO using 0-2% MeOH in DCM (25 min). Yield: 297 mg (83.4%). $^1$H NMR (DMSO-$d_6$) δ 10.20 (s, 1H), 7.92-7.86 (m, 2H), 7.75-7.70 (m, 2H), 4.27 (q, J=7.1 Hz, 2H), 2.32 (t, J=7.3 Hz, 2H), 1.61 (h, J=7.4 Hz, 2H), 1.30 (t, J=7.1 Hz, 3H), 0.91 (t, J=7.4 Hz, 3H). ESIMS: m/z 236.1 [M+H]$^+$.

(iii) Ethyl 4-(cyclopropanecarboxamido)benzoate (iic)

Purification on pre-packed Silica gel column on ISCO using 0-10% MeOH in DCM (27 min). Yield: 185 mg (52.4%). $^1$H NMR (DMSO-$d_6$) δ 10.53 (s, 1H), 7.92-7.87 (m, 2H), 7.75-7.69 (m, 2H), 4.28 (q, J=7.1 Hz, 2H), 1.81 (p, J=6.2 Hz, 1H), 1.30 (t, J=7.1 Hz, 3H), 0.83 (d, J=5.8 Hz, 4H). ESIMS: m/z 234.0 [M+H]$^+$.

(iv) ethyl 4-(cyclobutanecarboxamido)benzoate (iid)

Purification on pre-packed Silica gel column on ISCO using 0-2% MeOH in DCM (26 min). Yield: 200 mg (53.4%). $^1$H NMR (DMSO-$d_6$) δ 10.06 (s, 1H), 7.91-7.85 (m, 2H), 7.76-7.71 (m, 2H), 4.27 (q, J=7.1 Hz, 2H), 3.29-3.19 (m, 1H), 2.28-2.17 (m, 2H), 2.16-2.06 (m, 2H), 2.00-1.88 (m, 1H), 1.86-1.76 (m, 1H), 1.30 (t, J=7.1 Hz, 3H). ESIMS: m/z 248.0 [M+H]$^+$.

ii. Step 2: General Synthetic Procedure

To a solution of 3-(pyridin-2-ylethynyl)aniline (iii) (1 mmol) in anhydrous DCM (5 mL) under nitrogen atmosphere at 0° C., was added a 2 M solution of AlMe$_3$ in toluene (3 mmol) dropwise. After complete addition, the reaction was stirred at room temperature for 30 min. Appropriate ester (1 mmol) was added to the reaction mixture and refluxed for 16 h. After completion of reaction, the reaction was cooled to room temperature and quenched by dropwise addition of MeOH (3 mL). Reaction mixture was concentrated under reduced pressure and diluted with water (50 mL), aqueous layer was extracted with EtOAc (3×50 mL). The combined organic layer was washed with brine (50 mL), dried over Na$_2$SO$_4$, filtered and evaporated to dryness under reduced pressure to give a residue, followed by purification using pre-packed Silica gel column on ISCO gave the pure product.

(i) 4-Propionamido-N-(3-(pyridin-2-ylethynyl)phenyl)benzamide (6)

Purification on pre-packed Silica gel column on ISCO using 0-4% MeOH in DCM (28 min). Yield: 45 mg (26.3%). $^1$H NMR (DMSO-$d_6$) δ 10.25 (s, 1H), 10.17 (s, 1H), 8.62 (dt, J=5.5, 1.2 Hz, 1H), 8.10 (t, J=1.9 Hz, 1H), 7.97-7.91 (m, 2H), 7.89-7.80 (m, 2H), 7.77-7.72 (m, 2H), 7.67 (dt, J=7.8, 1.1 Hz, 1H), 7.46-7.40 (m, 2H), 7.33 (dt, J=7.7, 1.3 Hz, 1H), 2.37 (q, J=7.5 Hz, 2H), 1.10 (t, J=7.5 Hz, 3H). HR-ESIMS: m/z 370.155 [M+H]$^+$ calcd. for $C_{22}H_{20}N_3O_2$, found 370.1555. HPLC purity: 99.6% (Retention Time=9.9 min).

(ii) 4-Butyramido-N-(3-(pyridin-2-ylethynyl)phenyl)benzamide (7)

Purification on pre-packed Silica gel column on ISCO using 0-3% MeOH in DCM (34 min). Yield: 73 mg (59.4%). $^1$H NMR (DMSO-$d_6$) δ 10.25 (s, 1H), 10.17 (s, 1H), 8.63-8.60 (m, 1H), 8.10 (t, J=1.8 Hz, 1H), 7.97-7.92 (m, 2H), 7.89-7.80 (m, 2H), 7.77-7.72 (m, 2H), 7.67 (dt, J=7.9, 1.2 Hz, 1H), 7.46-7.40 (m, 2H), 7.33 (dt, J=7.6, 1.3 Hz, 1H), 2.33 (t, J=7.3 Hz, 2H), 1.63 (h, J=7.4 Hz, 2H), 0.93 (t, J=7.4 Hz, 3H). HR-ESIMS: m/z 384.1707 [M+H]$^+$ calcd. for $C_{24}H_{22}N_3O_2$, found 384.1713. HPLC purity: 99.4% (Retention Time=9.9 min).

(iii) 4-(Cyclopropanecarboxamido)-N-(3-(pyridin-2-ylethynyl)phenyl)benzamide (8)

Purification on pre-packed Silica gel column on ISCO using 0-4% MeOH in DCM (30 min). Yield: 40 mg (13.3%). $^1$H NMR (DMSO-$d_6$) δ 10.50 (s, 1H), 10.25 (s, 1H), 8.62 (d, J=4.9 Hz, 1H), 8.11-8.08 (m, 1H), 7.94 (d, J=8.5 Hz, 2H), 7.89-7.80 (m, 2H), 7.74 (d, J=8.5 Hz, 2H), 7.67 (d, J=7.8 Hz, 1H), 7.46-7.40 (m, 2H), 7.33 (d, J=7.6 Hz, 1H), 1.86-1.78 (m, 1H), 0.87-0.79 (m, 4H). HR-ESIMS: m/z 382.155 [M+H]$^+$ calcd. for $C_{24}H_{20}N_3O_2$, found 382.1553. HPLC purity: 99.7% (Retention Time=10.3 min).

(iv) 4-(Cyclobutanecarboxamido)-N-(3-(pyridin-2-ylethynyl)phenyl)benzamide (9)

Purification on pre-packed Silica gel column on ISCO using 0-5% MeOH in DCM (25 min). Yield: 45 mg (13.9%). $^1$H NMR (DMSO-d$_6$) δ 10.25 (s, 1H), 10.02 (s, 1H), 8.62 (dt, J=4.9, 1.3 Hz, 1H), 8.10 (t, J=1.9 Hz, 1H), 7.96-7.92 (m, 2H), 7.89-7.81 (m, 2H), 7.78-7.74 (m, 2H), 7.67 (dt, J=7.8, 1.2 Hz, 1H), 7.46-7.40 (m, 2H), 7.33 (dt, J=7.7, 1.3 Hz, 1H), 3.29-3.22 (m, 1H), 2.30-2.19 (m, 2H), 2.17-2.08 (m, 2H), 2.01-1.90 (m, 1H), 1.86-1.77 (m, 1H). HR-ESIMS: m/z 396.1706 [M+H]$^+$ calcd. for $C_{25}H_{22}N_3O_2$, found 396.1707. HPLC purity: 98.7% (Retention Time=11.1 min).

d. Preparation of Compound Nos. 14-17

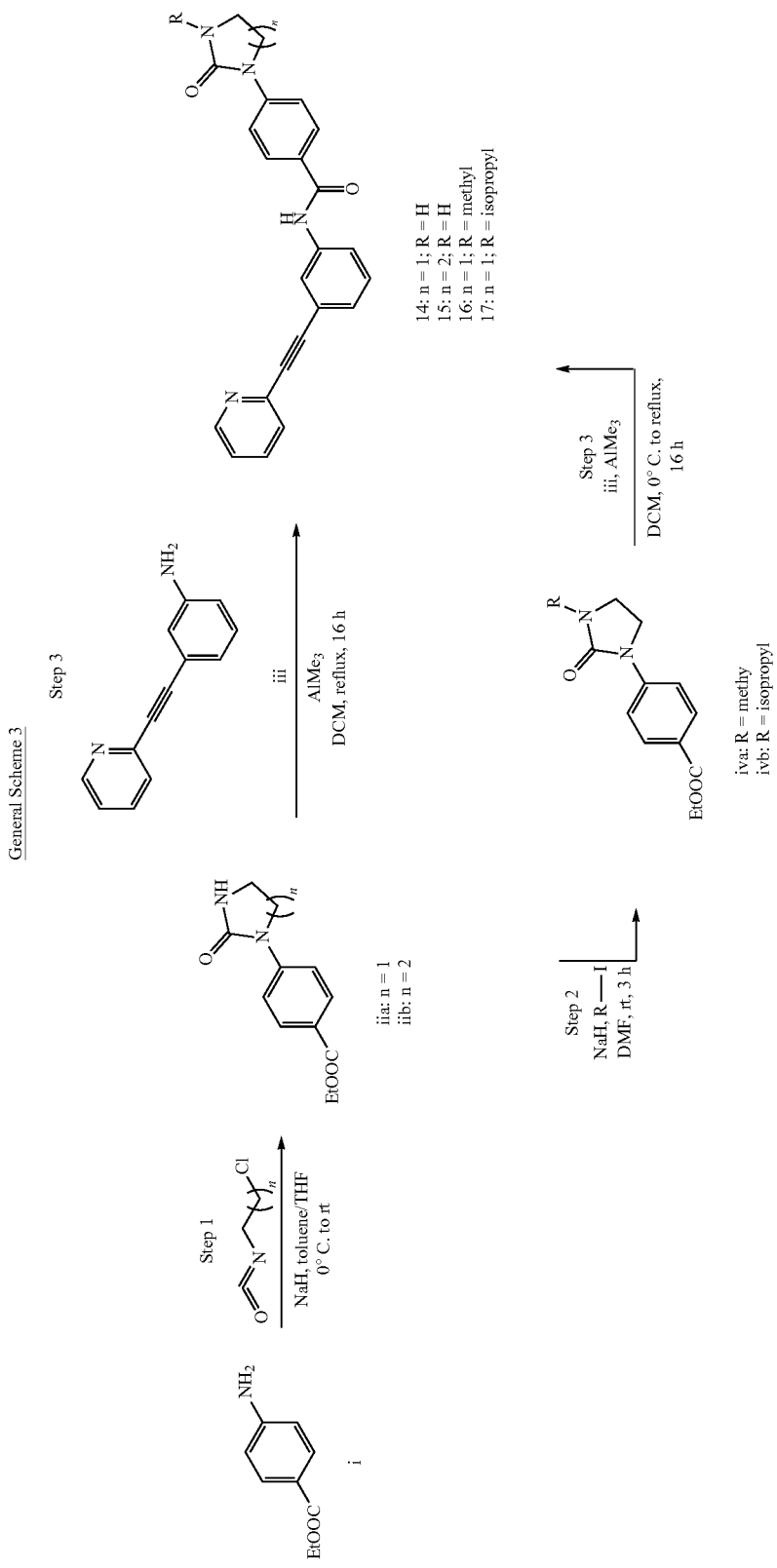

i. Step 1: General Synthetic Procedure

To a solution of ethyl 4-aminobenzoate (i) (1 mmol) in anhydrous toluene (7.6 mL) under nitrogen atmosphere at room temperature, appropriate isocyanate (1.1 mmol) was added and allowed to stir at 50° C. for 6 h. After completion of the reaction, the mixture was allowed to cool down to room temperature. The white precipitates were filtered off and washed with toluene and water and dried under vacuum. The precipitates were re-dissolved in anhydrous THF (15 mL) under nitrogen atmosphere and cooled to 0° C. Sodium hydride (3 mmol) was added under nitrogen atmosphere in small portions, and allowed the reaction to stir at same temperature for 30 min and later at room temperature for 10 h. After completion of the reaction, the reaction mixture was cooled in an ice bath and quenched by dropwise addition of water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by trituration with DCM and hexanes yielded pure product.

(i) Ethyl 4-(2-oxoimidazolidin-1-yl)benzoate (iia)

Purification by trituration with DCM and hexanes. Yield: 350 mg (83.4%). $^1$H NMR (DMSO-$d_6$) δ 7.91-7.87 (m, 2H), 7.71-7.66 (m, 2H), 7.22 (s, 1H), 4.28 (q, J=7.1 Hz, 2H), 3.92-3.87 (m, 2H), 3.43 (ddd, J=9.0, 6.7, 1.0 Hz, 2H), 1.31 (t, J=7.1 Hz, 3H). ESIMS: m/z 235.1 [M+H]$^+$.

(ii) Ethyl 4-(2-oxotetrahydropyrimidin-1(2H)-yl) benzoate (iib)

Purification by trituration with DCM and hexanes. Yield: 70 mg (15.5%). $^1$H NMR (DMSO-$d_6$) δ 7.87 (d, J=8.6 Hz, 2H), 7.49-7.44 (m, 2H), 6.81 (s, 1H), 4.29 (q, J=7.1 Hz, 2H), 3.68 (t, J=5.7 Hz, 2H), 3.23 (td, J=6.1, 2.4 Hz, 2H), 1.96 (p, J=5.9 Hz, 2H), 1.31 (t, J=7.0 Hz, 3H). ESIMS: m/z 249.0 [M+H]$^+$.

ii. Step 2: General Synthetic Procedure

To a solution of ethyl 4-(2-oxoimidazolidin-1-yl)benzoate (iia) (1 mmol) in anhydrous DMF (3.5 mL) under nitrogen atmosphere at 0° C., NaH (1.5 mmol) was added and the reaction mixture was allowed to stir at room temperature. After 30 min, appropriate iodoalkane (1.5 mmol) was added at room temperature and allowed the reaction to stir at same temperature for 3 h. After completion of reaction, the reaction was quenched by dropwise addition of water. Aqueous layer was extracted with EtOAc (3×50 mL). The combined organic layer was washed with brine (50 mL), dried over $Na_2SO_4$, filtered and evaporated to dryness under reduced pressure to give a residue, followed by trituration with DCM and hexanes yielded pure product.

(i) Ethyl 4-(3-methyl-2-oxoimidazolidin-1-yl)benzoate (iva)

Purification by trituration with DCM and hexanes. Yield: 50 mg (37.7%). $^1$H NMR (DMSO-$d_6$) δ 7.93-7.87 (m, 2H), 7.72-7.67 (m, 2H), 4.28 (q, J=7.1 Hz, 2H), 3.86-3.80 (m, 2H), 3.47 (dd, J=9.2, 6.6 Hz, 2H), 2.78 (s, 3H), 1.30 (t, J=7.1 Hz, 3H). ESIMS: m/z 249.1 [M+H]$^+$.

(ii) Ethyl 4-(3-isopropyl-2-oxoimidazolidin-1-yl) benzoate (ivb)

Purification by trituration with DCM and hexanes. Yield: 70 mg (59.3%). $^1$H NMR (DMSO-$d_6$) δ 7.92-7.86 (m, 2H), 7.71-7.66 (m, 2H), 4.27 (q, J=7.1 Hz, 2H), 4.05 (p, J=6.8 Hz, 1H), 3.83 (dd, J=9.3, 6.7 Hz, 2H), 3.44 (dd, J=9.3, 6.6 Hz, 2H), 1.30 (t, J=7.1 Hz, 3H), 1.13 (d, J=6.7 Hz, 6H). ESIMS: m/z 277.1 [M+H]$^+$.

iii. Step 3: General Synthetic Procedure

To a solution of 3-(pyridin-2-ylethynyl)aniline (iii) (1 mmol) in anhydrous DCM (5 mL) under nitrogen atmosphere at 0° C., was added a 2 M solution of $AlMe_3$ in toluene (3 mmol) dropwise. After complete addition, the reaction was stirred at room temperature for 30 min. Appropriate ester (1 mmol) was added to the reaction mixture and refluxed for 16 h. After completion of reaction, the reaction was cooled to room temperature and quenched by dropwise addition of MeOH. Reaction mixture was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) 4-(2-Oxoimidazolidin-1-yl)-N-(3-(pyridin-2-ylethynyl)phenyl)benzamide (14)

Purification on pre-packed Silica gel column on ISCO using 0-5% MeOH in DCM (37 min). Yield: 16 mg (13.4%). $^1$H NMR (DMSO-$d_6$) δ 10.23 (s, 1H), 8.62 (d, J=4.9 Hz, 1H), 8.12-8.08 (m, 1H), 7.96 (d, J=8.5 Hz, 2H), 7.89-7.81 (m, 2H), 7.69 (dd, J=18.3, 8.1 Hz, 3H), 7.46-7.40 (m, 2H), 7.33 (d, J=7.6 Hz, 1H), 7.18 (s, 1H), 3.92 (dd, J=9.2, 6.7 Hz, 2H), 3.45 (t, J=8.0 Hz, 2H). HR-ESIMS: m/z 383.1503 [M+H]+ calcd. for $C_{23}H_{19}N_4O_2$, found 383.1506. HPLC purity: 99.3% (Retention Time=9.3 min).

(ii) 4-(2-Oxotetrahydropyrimidin-1(2H)-yl)-N-(3-(pyridin-2-ylethynyl)phenyl)benzamide (15)

Purification on pre-packed Silica gel column on ISCO using 0-10% MeOH in DCM (38 min). Yield: 27 mg (24.8%). $^1$H NMR (DMSO-$d_6$) δ 10.30 (s, 1H), 8.62 (d, J=4.6 Hz, 1H), 8.10 (t, J=1.8 Hz, 1H), 7.94-7.81 (m, 4H), 7.67 (d, J=7.8 Hz, 1H), 7.51-7.40 (m, 4H), 7.33 (d, J=7.6 Hz, 1H), 6.78-6.74 (m, 1H), 3.71 (t, J=5.7 Hz, 2H), 3.25 (td, J=6.0, 2.4 Hz, 2H), 1.98 (p, J=5.9 Hz, 2H). HR-ESIMS: m/z 397.1659 [M+H]+ calcd. for $C_{24}H_{21}N_4O_2$, found 397.1664. HPLC purity: 99.7% (Retention Time=9.1 min).

(iii) 4-(3-Methyl-2-oxoimidazolidin-1-yl)-N-(3-(pyridin-2-ylethynyl)phenyl)benzamide (16)

Purification on pre-packed Silica gel column on ISCO using 0-5% MeOH in DCM (23 min). Yield: 20 mg (26.7%). $^1$H NMR (DMSO-$d_6$) δ 10.23 (s, 1H), 8.62 (ddt, J=4.9, 1.7, 0.7 Hz, 1H), 8.10 (t, J=1.9 Hz, 1H), 7.99-7.94 (m, 2H), 7.89-7.82 (m, 2H), 7.75-7.70 (m, 2H), 7.68-7.65 (m, 1H), 7.46-7.40 (m, 2H), 7.33 (dt, J=7.5, 1.5 Hz, 1H), 3.89-3.83 (m, 2H), 3.52-3.46 (m, 2H), 2.80 (s, 3H). HR-ESIMS: m/z 397.1659 [M+H]+ calcd. for $C_{24}H_{21}N_4O_2$, found 397.1664. HPLC purity: 100% (Retention Time=10.0 min).

(iv) 4-(3-Isopropyl-2-oxoimidazolidin-1-yl)-N-(3-(pyridin-2-ylethynyl)phenyl)benzamide (17)

Purification on pre-packed Silica gel column on ISCO using 0-3% MeOH in DCM (15 min). Yield: 56 mg (52.1%).

¹H NMR (DMSO-d₆) δ 10.23 (s, 1H), 8.62 (ddd, J=4.8, 1.8, 0.9 Hz, 1H), 8.10 (t, J=1.8 Hz, 1H), 7.99-7.94 (m, 2H), 7.89-7.82 (m, 2H), 7.75-7.70 (m, 2H), 7.67 (dt, J=7.9, 1.1 Hz, 1H), 7.46-7.41 (m, 2H), 7.33 (dt, J=7.6, 1.3 Hz, 1H), 4.07 (p, J=6.7 Hz, 1H), 3.86 (dd, J=9.3, 6.6 Hz, 2H), 3.48-3.42 (m, 2H), 1.14 (d, J=6.8 Hz, 6H). HR-ESIMS: m/z 425.1972 [M+H]+ calcd. for $C_{26}H_{25}N_4O_2$, found 425.1975. HPLC purity: 100% (Retention Time=11.3 min).

e. Preparation of Compound Nos. 18, 22, and 25

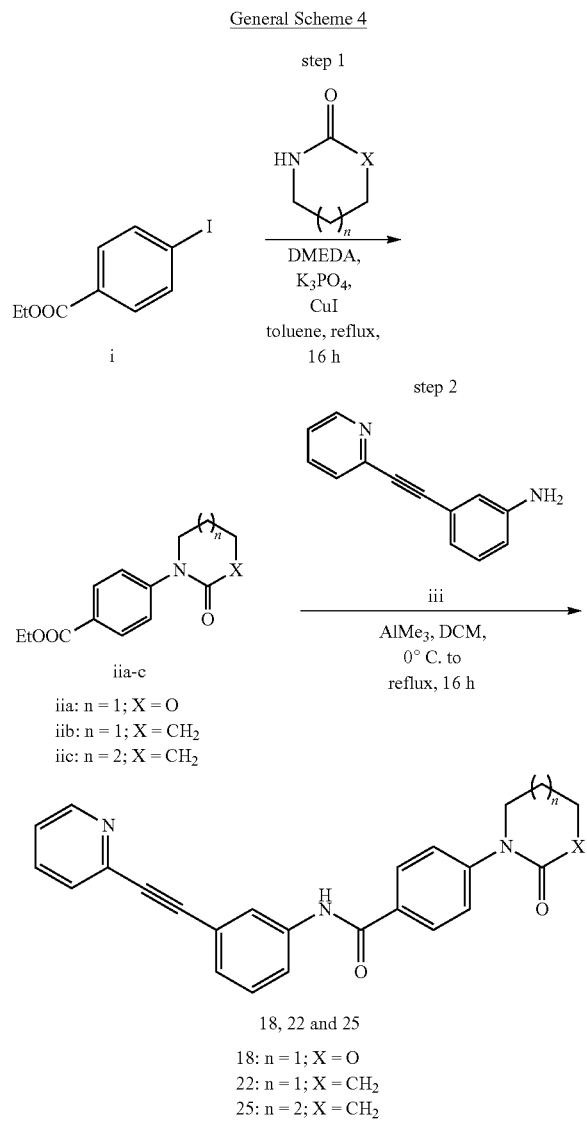

i. Step 1: General Synthetic Procedure

To a nitrogen atmosphere at room temperature, was added appropriate cyclic carbamate (OR) lactam (2 mmol) followed by anhydrous potassium phosphate tribasic (2 mmol), CuI (0.1 mmol) and N,N'-dimethylethylenediamine (0.2 mmol). The reaction mixture was allowed to reflux for 16 h. After completion of the reaction, it was cooled to room temperature and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) Ethyl 4-(2-oxo-1,3-oxazinan-3-yl)benzoate (iia)

Purification on pre-packed Silica gel column on ISCO using 0-3% MeOH in DCM (23 min). Yield: 75 mg (41.5%). ¹H NMR (CDCl₃) δ 8.06 (d, J=8.5 Hz, 2H), 7.44 (d, J=8.5 Hz, 2H), 4.44 (t, J=5.4 Hz, 2H), 4.37 (q, J=7.1 Hz, 2H), 3.78 (t, J=6.1 Hz, 2H), 2.24 (p, J=5.9 Hz, 2H), 1.39 (t, J=7.1 Hz, 3H). ESIMS: m/z 250.0 [M+H]+.

(ii) Ethyl 4-(2-oxopiperidin-1-yl)benzoate (iib)

Purification on pre-packed Silica gel column on ISCO using 0-3% MeOH in DCM (17 min). Yield: 400 mg (89.3%). ¹H NMR (DMSO-d₆) δ 7.99-7.89 (m, 2H), 7.51-7.40 (m, 2H), 4.31 (q, J=7.1, 1.6 Hz, 2H), 3.66 (t, J=5.7 Hz, 2H), 2.42 (t, J=6.4 Hz, 2H), 1.92-1.79 (m, 4H), 1.32 (t, J=7.1, 1.6 Hz, 3H). ESIMS: m/z 248.1 [M+H]+.

(iii) Ethyl 4-(2-oxoazepan-1-yl)benzoate (iic)

Purification on pre-packed Silica gel column on ISCO using 0-60% EtOAc in hexanes (29 min). Yield: 120 mg (84.5%). ¹H NMR (CDCl₃) δ 8.06-8.02 (m, 2H), 7.32-7.28 (m, 2H), 4.37 (q, J=7.1 Hz, 2H), 3.81-3.77 (m, 2H), 2.74-2.69 (m, 2H), 1.87-1.81 (m, 6H), 1.38 (t, J=7.1 Hz, 3H). ESIMS: m/z 261.9 [M+H]+.

ii. Step 2: General Synthetic Procedure

To a solution of 3-(pyridin-2-ylethynyl)aniline (iii) (1 mmol) in anhydrous DCM (5 mL) under nitrogen atmosphere at 0° C., was added a 2 M solution of AlMe₃ in toluene (3 mmol) dropwise. After complete addition, the reaction was stirred at room temperature for 30 min. Appropriate ester (1 mmol) was added to the reaction mixture and refluxed for 16 h. After completion of reaction, the reaction was cooled to room temperature and quenched by dropwise addition of MeOH (3 mL). Reaction mixture was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) 4-(2-Oxo-1,3-oxazinan-3-yl)-N-(3-(pyridin-2-ylethynyl)phenyl)benzamide (18)

Purification on pre-packed Silica gel column on ISCO using 0-5% MeOH in DCM (30 min). Yield: 11 mg (10.8%). ¹H NMR (DMSO-d₆) δ 10.39 (s, 1H), 8.64-8.61 (m, 1H), 8.10 (d, J=2.1 Hz, 1H), 7.98 (d, J=8.3 Hz, 2H), 7.90-7.82 (m, 2H), 7.67 (d, J=7.8 Hz, 1H), 7.55 (d, J=8.4 Hz, 2H), 7.48-7.41 (m, 2H), 7.35 (d, J=7.6 Hz, 1H), 4.37 (t, J=5.4 Hz, 2H), 3.75 (t, J=6.0 Hz, 2H), 2.14 (p, J=5.8 Hz, 2H). HR-ESIMS: m/z 398.1499 [M+H]+ calcd. for $C_{24}H_{20}N_3O_3$, found 398.1498. HPLC purity: 99.3% (Retention Time=9.1 min).

(ii) 4-(2-Oxopiperidin-1-yl)-N-(3-(pyridin-2-ylethynyl)phenyl)benzamide (22)

Purification on pre-packed Silica gel column on ISCO using 0-3% MeOH in DCM (42 min). Yield: 64 mg (50%). $^1$H NMR (DMSO-$d_6$) δ 10.38 (s, 1H), 8.62 (ddd, J=4.9, 1.8, 1.0 Hz, 1H), 8.11 (t, J=1.8 Hz, 1H), 7.99-7.94 (m, 2H), 7.89-7.81 (m, 2H), 7.67 (dt, J=7.9, 1.1 Hz, 1H), 7.50-7.41 (m, 4H), 7.35 (dt, J=7.7, 1.3 Hz, 1H), 3.68 (t, J=5.5 Hz, 2H), 2.43 (t, J=6.4 Hz, 2H), 1.93-1.81 (m, 4H). HR-ESIMS: m/z 396.1706 [M+H]+ calcd. for $C_{25}H_{22}N_3O_2$, found 396.1709. HPLC purity: 99.8% (Retention Time=9.7 min).

(iii) 4-(2-Oxoazepan-1-yl)-N-(3-(pyridin-2-ylethynyl)phenyl)benzamide (25)

Purification on pre-packed Silica gel column on ISCO using 0-5% MeOH in DCM (31 min). Yield: 75 mg (79%). $^1$H NMR (DMSO-$d_6$) δ 10.38 (s, 1H), 8.62 (d, J=4.8 Hz, 1H), 8.10 (s, 1H), 7.96 (d, J=8.3 Hz, 2H), 7.90-7.81 (m, 2H), 7.67 (d, J=7.8 Hz, 1H), 7.48-7.32 (m, 5H), 3.81 (d, J=5.3 Hz, 2H), 2.64 (d, J=8.7 Hz, 2H), 1.80-1.66 (m, 6H). HR-ESIMS: m/z 410.1863 [M+H]+ calcd. for $C_{26}H_{24}N_3O_3$, found 410.1860. HPLC purity: 95.4% (Retention Time=10.1 min).

f. Preparation of Compound No. 23

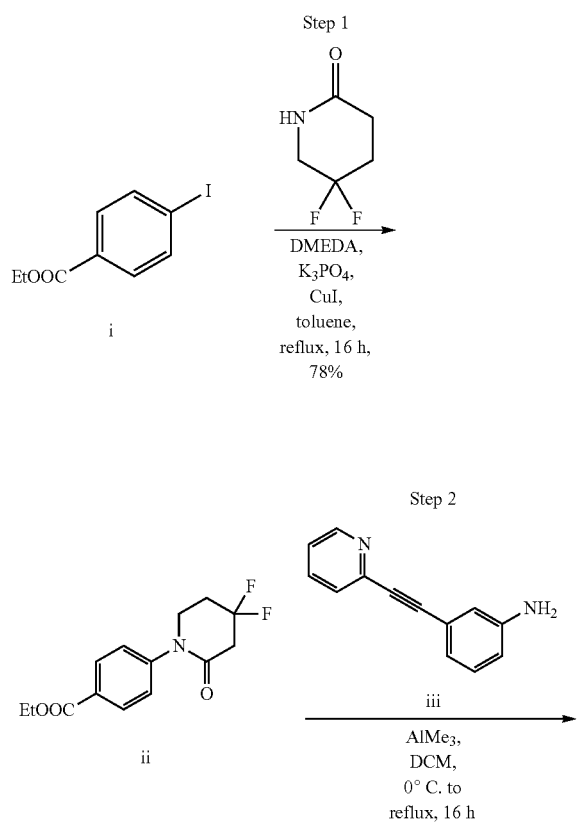

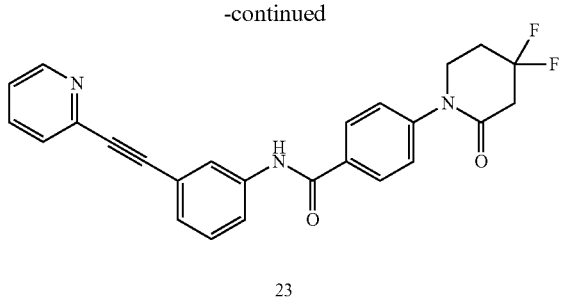

23 i. Step 1: Ethyl 4-(4,4-difluoro-2-oxopiperidin-1-yl)benzoate (ii)

To a solution of ethyl 4-iodobenzoate (i) (0.12 mL, 0.72 mmol) in anhydrous toluene (7 mL) under nitrogen atmosphere at room temperature, was added 5,5-difluoropiperidin-2-one (196 mg, 1.45 mmol) followed by anhydrous potassium phosphate tribasic (307 mg, 1.45 mmol), CuI (13.8 mg, 0.07 mmol) and N,N'-dimethylethylenediamine (0.016 mL. 0.14 mmol). The reaction mixture was allowed to reflux for 16 h. After completion of reaction, it was cooled to room temperature and diluted with water (50 mL). Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-3% MeOH in DCM (31 min) gave the pure product (ii). Yield: 160 mg (78%). $^1$H NMR (CDCl$_3$) δ 8.11-8.07 (m, 2H), 7.37-7.32 (m, 2H), 4.38 (q, J=7.1 Hz, 2H), 4.03-3.95 (m, 2H), 2.78 (t, J=7.2 Hz, 2H), 2.46 (tt, J=14.2, 7.2 Hz, 2H), 1.39 (t, J=7.1 Hz, 3H). ESIMS: m/z 284.1 [M+H]+.

ii. Step 2: 4-(4,4-Difluoro-2-oxopiperidin-1-yl)-N-(3-(pyridin-2-ylethynyl)phenyl)benzamide (23)

To a solution of 3-(pyridin-2-ylethynyl)aniline (iii) (50 mg, 0.26 mmol) in anhydrous DCM (2.5 mL) under nitrogen atmosphere at 0° C., was added a 2 M solution of AlMe$_3$ in toluene (0.39 mL, 0.77 mmol) dropwise. After complete addition, the reaction was stirred at room temperature for 30 min. Ethyl 4-(4,4-difluoro-2-oxopiperidin-1-yl)benzoate (ii) (73 mg, 0.26 mmol) was added to the reaction mixture and refluxed for 16 h. After completion of reaction, it was cooled to room temperature and quenched by dropwise addition of MeOH (3 mL). The reaction mixture was concentrated under reduced pressure and diluted with 30 mL of water. Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-5% MeOH in DCM (33 min) gave the pure product (23). Yield: 37 mg (32.4%). $^1$H NMR (DMSO-$d_6$) δ 10.40 (s, 1H), 8.62 (ddd, J=4.8, 1.8, 1.0 Hz, 1H), 8.10 (t, J=1.8 Hz, 1H), 8.02-7.98 (m, 2H), 7.89-7.82 (m, 2H), 7.67 (dt, J=7.8, 1.1 Hz, 1H), 7.50-7.46 (m, 2H), 7.46-7.41 (m, 2H), 7.35 (dt, J=7.6, 1.2 Hz, 1H), 4.17 (t, J=12.6 Hz, 2H), 2.67 (t, J=7.1 Hz, 2H), 2.49-2.42 (m, 2H). HR-ESIMS: m/z 432.1518 [M+H]+ calcd. for $C_{25}H_{20}F_2N_3O_2$, found 432.1522. HPLC purity: 97.4% (Retention Time=10.6 min).

g. Preparation of Compound No. 24

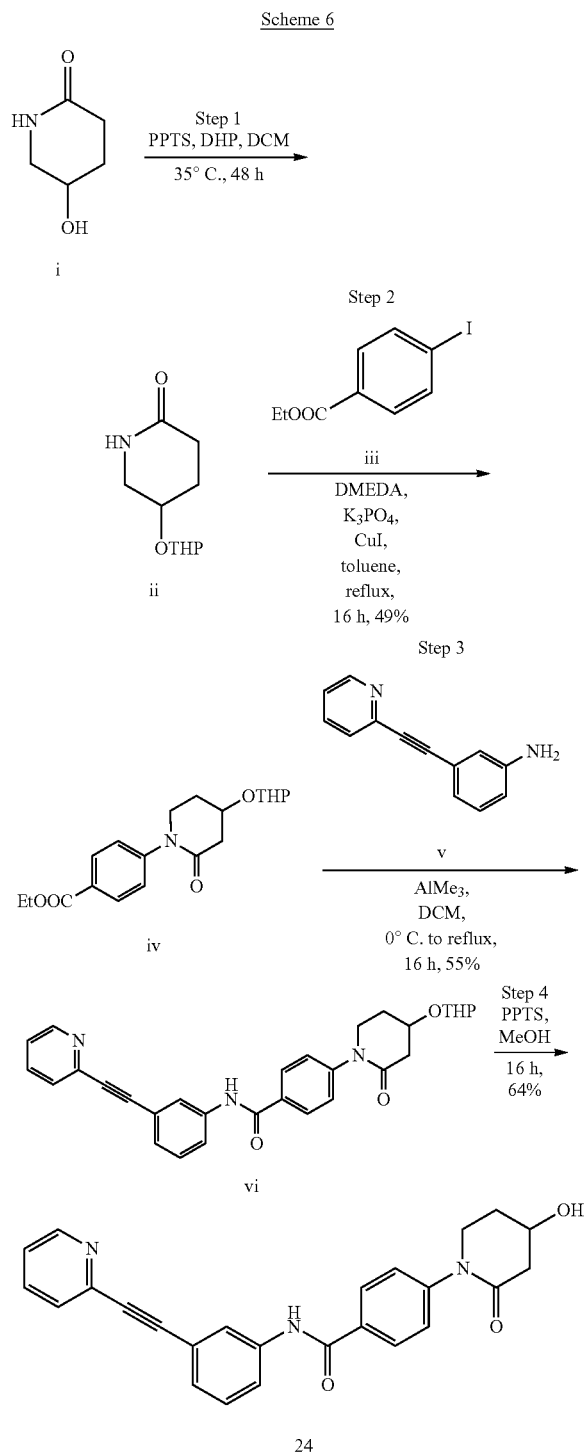

i. Step 1: 5-((Tetrahydro-2H-pyran-2-yl)oxy)piperidin-2-one (ii)

To a solution of 5-hydroxypiperidin-2-one (i) (100 mg, 0.87 mmol) and pyridinium p-toluenesulfonate (26.2 mg, 0.10 mmol) in anhydrous DCM (14 mL) under nitrogen atmosphere was added 3,4-dihydro-2H-pyran (0.32 mL, 3.47 mmol). The reaction mixture was allowed to stir at 35° C. for 48 h. After completion of the reaction, the reaction mixture was diluted with water (50 mL), followed by the extraction with DCM (3×30 mL). The combined organic layer was washed with brine (50 mL), dried over $Na_2SO_4$, filtered and evaporated to dryness under reduced pressure to give a residue, which was directly used into the next step. ESIMS: m/z 200.0 $[M+H]^+$.

ii. Step 2. Ethyl 4-(2-oxo-4-((tetrahydro-2H-pyran-2-yl)oxy)piperidin-1-yl)benzoate (iv)

To a solution of ethyl 4-iodobenzoate (iii) (0.07 mL, 0.43 mmol) in anhydrous toluene (5 mL) under nitrogen atmosphere at room temperature, was added 5-((tetrahydro-2H-pyran-2-yl)oxy)piperidin-2-one (ii) (173 mg, 0.87 mmol) followed by anhydrous potassium phosphate tribasic (184 mg, 0.87 mmol), CuI (8.28 mg, 0.04 mmol) and N,N'-dimethylethylenediamine (0.01 mL. 0.09 mmol). The reaction mixture was allowed to reflux for 16 h. After completion of reaction, it was cooled to room temperature and diluted with water (50 mL). Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-40% EtOAc in hexanes (18 min) gave the pure product (iv). Yield: 74 mg (49%). $^1$H NMR (400 MHz, $CDCl_3$) δ 8.09-8.03 (m, 2H), 7.41-7.32 (m, 2H), 4.76 (ddd, J=16.1, 4.4, 2.9 Hz, 1H), 4.37 (q, J=7.1 Hz, 2H), 4.28-4.19 (m, 1H), 3.94-3.75 (m, 2H), 3.57-3.45 (m, 1H), 2.87-2.69 (m, 1H), 2.61-2.50 (m, 1H), 2.22-2.12 (m, 1H), 2.12-2.05 (m, 1H), 1.92-1.68 (m, 2H), 1.65-1.47 (m, 5H), 1.38 (t, J=7.1 Hz, 3H). ESIMS: m/z 348.0 $[M+H]^+$.

iii. Step 3: 4-(2-Oxo-4-((tetrahydro-2H-pyran-2-yl)oxy)piperidin-1-yl)-N-(3-(pyridin-2-ylethynyl)phenyl)benzamide (vi)

To a solution of 3-(pyridin-2-ylethynyl)aniline (v) (41.4 mg, 0.21 mmol) in anhydrous DCM (2.13 mL) under nitrogen atmosphere at 0° C., was added a 2 M solution of $AlMe_3$ in toluene (0.32 mL, 0.64 mmol) dropwise. After complete addition, the reaction was stirred at room temperature for 30 min. Ethyl 4-(2-oxo-4-((tetrahydro-2H-pyran-2-yl)oxy)piperidin-1-yl)benzoate (iv) (74 mg, 0.21 mmol) was added to the reaction mixture and refluxed for 16 h. After completion of reaction, it was cooled to room temperature and quenched by dropwise addition of MeOH (3 mL). The reaction mixture was concentrated under reduced pressure and diluted with water (30 mL). Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-5% MeOH in DCM (37 min) gave the pure product (vi). Yield: 58 mg (55%). $^1$H NMR (400 MHz, $CDCl_3$) δ 8.62 (d, J=4.9 Hz, 1H), 8.31 (d, J=8.3 Hz, 1H), 7.87 (dd, J=8.7, 2.0 Hz, 3H), 7.77-7.67 (m, 2H), 7.54 (d, J=7.8 Hz, 1H), 7.39-7.29 (m, 4H), 7.28-7.23 (m, 2H), 4.76 (dt, J=17.3, 3.6 Hz, 1H), 4.27-4.18 (m, 1H), 3.93-3.74 (m, 2H), 3.56-3.45 (m, 1H), 2.90-2.70 (m, 1H), 2.63-2.51 (m, 1H), 2.20-2.04 (m, 2H), 1.89-1.67 (m, 2H), 1.64-1.47 (m, 4H). ESIMS: m/z 495.9 $[M+H]^+$.

iv. Step 4: 4-(4-hydroxy-2-oxopiperidin-1-yl)-N-(3-(pyridin-2-ylethynyl)phenyl)benzamide (24)

To the solution of 4-(2-oxo-4-((tetrahydro-2H-pyran-2-yl)oxy)piperidin-1-yl)-N-(3-(pyridin-2-ylethynyl)phenyl)benzamide (vi) (56 mg, 0.11 mmol) in anhydrous MeOH (1.17 mL) under nitrogen atmosphere at room temperature, was added pyridinium p-toluenesulfonate (28.4 mg, 0.11 mmol). Reaction mixture was allowed to stir at 40° C. for 4 h. After completion of the reaction, it was concentrated under reduced pressure and diluted with water (50 mL). Aqueous layer was extracted with EtOAc (3×50 mL). The combined organic layer was washed with brine (50 mL), dried over Na$_2$SO$_4$, filtered and evaporated to dryness under reduced pressure, followed by purification on pre-packed Silica gel column on ISCO using 0-7% MeOH in DCM (37 min) gave the pure product (24). Yield: 30 mg (64.5%). $^1$H NMR (DMSO-d$_6$) δ 10.38 (s, 1H), 8.64-8.61 (m, 1H), 8.10 (d, J=1.9 Hz, 1H), 7.99-7.95 (m, 2H), 7.89-7.82 (m, 2H), 7.67 (dt, J=7.8, 1.1 Hz, 1H), 7.49-7.41 (m, 4H), 7.35 (dd, J=7.6, 1.4 Hz, 1H), 5.18 (d, J=3.6 Hz, 1H), 4.13 (d, J=7.7 Hz, 1H), 3.81 (dd, J=12.0, 3.7 Hz, 1H), 3.52 (dd, J=12.0, 5.0 Hz, 1H), 2.57 (dd, J=17.0, 7.6 Hz, 1H), 2.40 (dt, J=17.4, 6.4 Hz, 1H), 2.07-1.98 (m, 1H), 1.89-1.80 (m, 1H). HR-ESIMS: m/z 412.1656 [M+H]$^+$ calcd. for C$_{25}$H$_{22}$N$_3$O$_3$, found 412.1660. HPLC purity: 100% (Retention Time=8.0 min).

h. Preparation of Compound Nos. 32-33

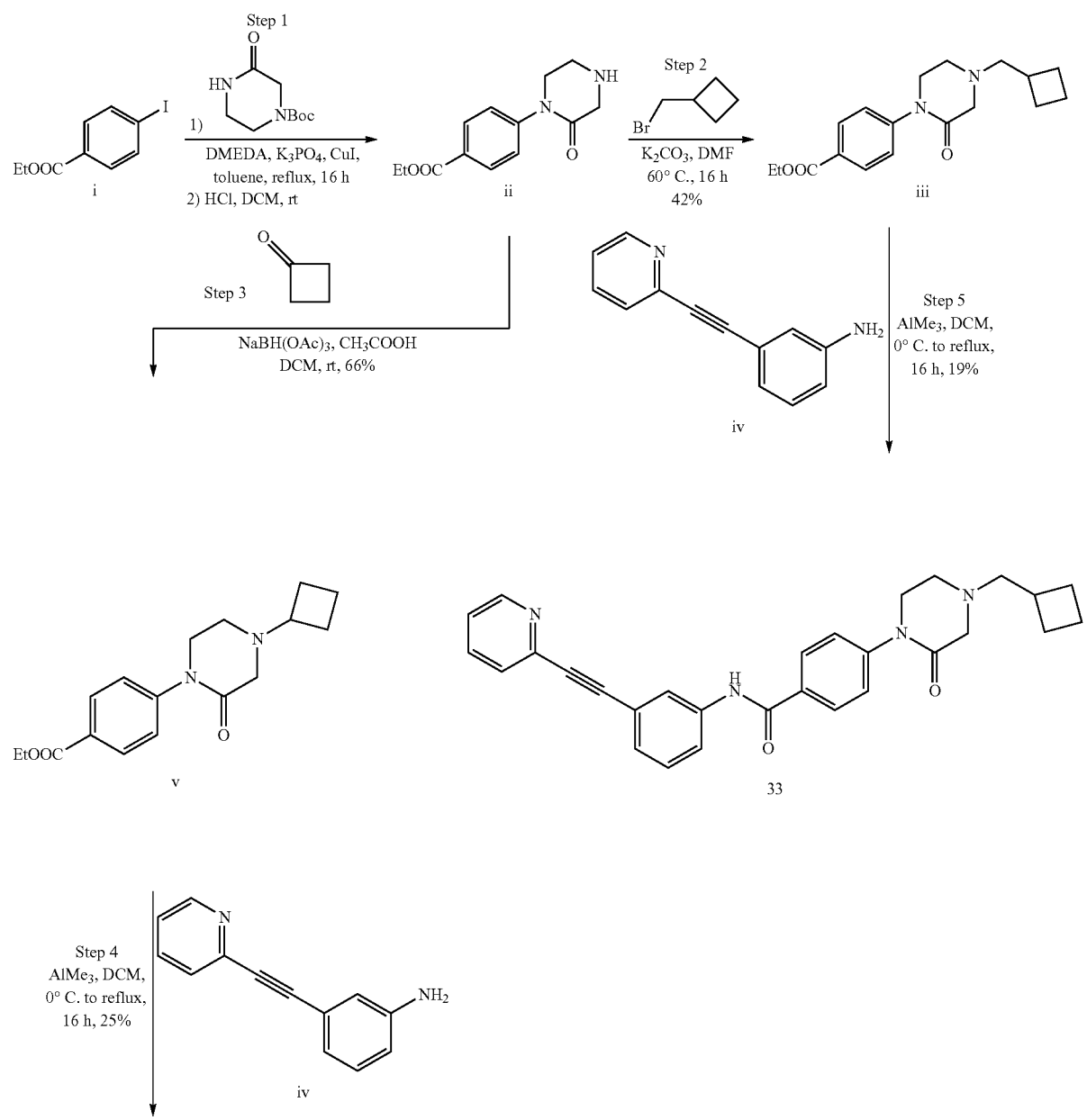

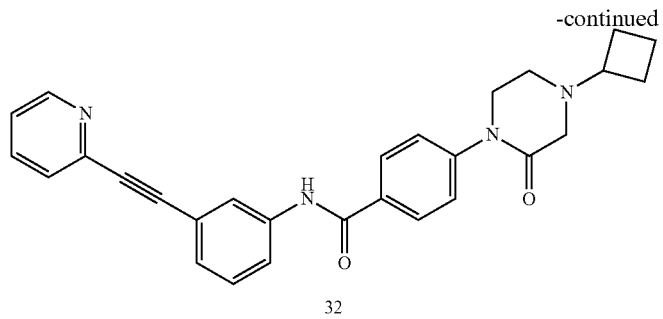

32 i. Step 1: Ethyl 4-(2-oxopiperazin-1-yl)benzoate (ii)

To a solution of ethyl 4-iodobenzoate (i) (0.14 mL, 0.91 mmol) in anhydrous toluene (7 mL) under nitrogen atmosphere at room temperature, was added tert-butyl 3-oxopiperazine-1-carboxylate (363 mg, 1.81 mmol) followed by anhydrous potassium phosphate tribasic (384 mg, 1.81 mmol), CuI (17.2 mg, 0.09 mmol) and N,N'-dimethylethylenediamine (0.02 mL. 0.18 mmol). The reaction mixture was allowed to reflux for 16 h. After completion of reaction, it was cooled to room temperature and diluted with water (50 mL). Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-5% MeOH in DCM (17 min) gave tert-butyl 4-(4-(ethoxycarbonyl)phenyl)-3-oxopiperazine-1-carboxylate as a white solid. Yield: 270 mg (85.6%). $^1$H NMR (DMSO-$d_6$) δ 7.99-7.95 (m, 2H), 7.55-7.51 (m, 2H), 4.31 (q, J=7.1 Hz, 2H), 4.10 (s, 2H), 3.79 (dd, J=6.9, 3.9 Hz, 2H), 3.68 (t, J=5.4 Hz, 2H), 1.44 (s, 9H), 1.32 (t, J=7.1 Hz, 3H). Tert-butyl 4-(4-(ethoxycarbonyl)phenyl)-3-oxopiperazine-1-carboxylate (270 mg, 0.77 mmol) was dissolved in anhydrous DCM (8 mL) under nitrogen atmosphere and cooled to 0° C. To the reaction mixture 4 M hydrochloric acid in dioxane (1 mL, 3.87 mmol) was added. After complete addition, reaction mixture was allowed to stir at room temperature for 16 h. After the completion of reaction (TLC analysis), reaction mixture was concentrated under reduced pressure and used directly into next step as a hydrochloride salt (ii). Yield: 210 mg (95.2%). $^1$H NMR (DMSO-$d_6$) δ 9.91 (s, 2H), 8.04-7.98 (m, 2H), 7.54-7.48 (m, 2H), 4.32 (q, J=7.1 Hz, 2H), 3.97-3.92 (m, 2H), 3.89 (s, 2H), 3.56-3.51 (m, 2H), 1.32 (t, J=7.1 Hz, 3H). ESIMS: m/z 249.0 [M+H]$^+$.

ii. Step 2: Ethyl 4-(4-(cyclobutylmethyl)-2-oxopiperazin-1-yl)benzoate (iii)

To a solution of ethyl 4-(2-oxopiperazin-1-yl)benzoate hydrochloride salt (ii) (101 mg, 0.35 mmol) in anhydrous DMF (3.5 mL) under nitrogen atmosphere at room temperature, (bromomethyl)cyclobutane (0.05 mL, 0.43 mmol) and potassium carbonate (147 mg, 1.06 mmol) were added and reaction was allowed to stir at 60° C. for 16 h. After completion of the reaction (TLC analysis), the reaction was cooled to room temperature and diluted with water (50 mL). Aqueous layer was extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-100% EtOAc in hexanes (35 min) gave the pure product (iii). Yield: 47 mg (42%). $^1$H NMR (DMSO-$d_6$) δ 7.98-7.93 (m, 2H), 7.55-7.51 (m, 2H), 4.31 (q, J=7.1 Hz, 2H), 3.69 (dd, J=6.3, 4.5 Hz, 2H), 3.16 (s, 2H), 2.75 (t, J=5.4 Hz, 2H), 2.59-2.52 (m, 1H), 2.47-2.44 (m, 2H), 2.08-1.98 (m, 2H), 1.92-1.76 (m, 2H), 1.73-1.62 (m, 2H), 1.32 (t, J=7.1 Hz, 3H). ESIMS: m/z 317.0 [M+H]$^+$.

iii. Step 3: Ethyl 4-(4-cyclobutyl-2-oxopiperazin-1-yl)benzoate (v)

To the solution of ethyl 4-(2-oxopiperazin-1-yl)benzoate (ii) (90 mg, 0.36 mmol) in anhydrous DCM (3.6 mL) under nitrogen atmosphere, acetic acid (0.03 mL, 0.54 mmol) was added at room temperature. After stirring for 5 min, cyclobutanone (0.04 mL, 0.54 mmol) was added and allowed to stir at same temperature. After 20 min, sodium triacetoxyborohydride (115 mg, 0.54 mmol) was added and allowed to stir for 3 h. After completion of reaction, the reaction mixture was quenched by addition of saturated solution of $NaHCO_3$ and extracted with DCM (3×30 mL). The combined organic layer was washed with brine (30 mL), dried over $Na_2SO_4$, filtered and evaporated to dryness under reduced pressure, followed by purification on pre-packed Silica gel column on ISCO using 0-70% EtOAc in hexanes (30 min) gave the pure product (v). Yield: 72 mg (65.7%). $^1$H NMR (CDCl$_3$) δ 8.09-8.05 (m, 2H), 7.43-7.38 (m, 2H), 4.37 (q, J=7.1 Hz, 2H), 3.76 (s, 2H), 3.26 (s, 2H), 2.92 (s, 1H), 2.75 (s, 2H), 2.17-2.07 (m, 2H), 2.05-1.89 (m, 2H), 1.85-1.70 (m, 2H), 1.38 (t, J=7.1 Hz, 3H). ESIMS: m/z 303.0 [M+H]$^+$.

iv. Step 4: 4-(4-Cyclobutyl-2-oxopiperazin-1-yl)-N-(3-(pyridin-2-ylethynyl)phenyl)benzamide (32)

To a solution of 3-(pyridin-2-ylethynyl)aniline (iv) (45 mg, 0.23 mmol) in anhydrous DCM (2.3 mL) under nitrogen atmosphere at 0° C., was added a 2 M solution of AlMe$_3$ in toluene (0.35 mL, 0.70 mmol) dropwise. After complete addition, the reaction was stirred at room temperature for 30 min. Ethyl 4-(4-cyclobutyl-2-oxopiperazin-1-yl)benzoate (v) (70 mg, 0.23 mmol) was added to the reaction mixture and refluxed for 16 h. After completion of reaction (TLC analysis), the reaction was cooled to room temperature and quenched by dropwise addition of MeOH. Reaction mixture was concentrated under reduced pressure and diluted with water (30 mL). Aqueous layer was extracted with EtOAc (3×30 mL). The combined organic layer was washed with brine (30 mL), dried over $Na_2SO_4$, filtered and evaporated to dryness under reduced pressure, followed by purification on pre-packed Silica gel column on ISCO using 0-4% MeOH in DCM (37 min) gave the pure product (32). Yield: 26 mg (25%). $^1$H NMR (DMSO-$d_6$) δ 10.39 (s, 1H), 8.64-8.61 (m, 1H), 8.12-8.08 (m, 1H), 7.99 (d, J=8.5 Hz, 2H), 7.85 (ddd, J=15.1, 7.6, 2.0 Hz, 2H), 7.69-7.65 (m, 1H), 7.54 (d, J=8.2 Hz, 2H), 7.48-7.41 (m, 2H), 7.35 (d, J=7.6 Hz, 1H), 3.72 (t, J=5.5 Hz, 2H), 3.09 (s, 2H), 2.88 (p, J=7.7 Hz, 1H), 2.69 (t, J=5.4 Hz, 2H), 2.07-1.97 (m, 2H), 1.86 (p, J=9.6 Hz, 2H), 1.73-1.62 (m, 2H). HR-ESIMS: m/z 451.2128 [M+H]+ calcd. for $C_{28}H_{27}N_4O_2$, found 451.2118. HPLC purity: 98.4% (Retention Time=8.0 min).

v. Step 5: 4-(4-(Cyclobutylmethyl)-2-oxopiperazin-1-yl)-N-(3-(pyridin-2-ylethynyl)phenyl)benzamide (33)

To a solution of 3-(pyridin-2-ylethynyl)aniline (iv) (28 mg, 0.15 mmol) in anhydrous DCM (1.45 mL) under nitrogen atmosphere at 0° C., was added a 2 M solution of AlMe₃ in toluene (0.22 mL, 0.44 mmol) dropwise. After complete addition, the reaction was stirred at room temperature for 30 min. Ethyl 4-(4-(cyclobutylmethyl)-2-oxopiperazin-1-yl)benzoate (iii) (46 mg, 0.15 mmol) was added to the reaction mixture and refluxed for 16 h. After completion of reaction, it was cooled to room temperature and quenched by dropwise addition of MeOH (3 mL). The reaction mixture was concentrated under reduced pressure and diluted with water (30 mL). Aqueous layer was extracted with EtOAc (3×30 mL). The combined organic layer was washed with brine (30 mL), dried over Na₂SO₄, filtered and evaporated to dryness under reduced pressure, followed by purification on pre-packed Silica gel column on ISCO using 0-5% MeOH in DCM (37 min) gave the pure product (33). Yield: 13 mg (19.2%). ¹H NMR (DMSO-d₆) δ 10.39 (s, 1H), 8.64-8.60 (m, 1H), 8.10 (d, J=2.2 Hz, 1H), 7.98 (d, J=8.5 Hz, 2H), 7.86 (qd, J=7.7, 1.8 Hz, 2H), 7.67 (d, J=7.9 Hz, 1H), 7.57-7.51 (m, 2H), 7.44 (q, J=7.2, 6.4 Hz, 2H), 7.35 (d, J=7.6 Hz, 1H), 3.71 (t, J=5.3 Hz, 2H), 3.16 (s, 2H), 2.77 (t, J=5.5 Hz, 2H), 2.60-2.52 (m, 1H), 2.47 (d, J=7.2 Hz, 2H), 2.09-1.99 (m, 2H), 1.94-1.76 (m, 2H), 1.69 (p, J=8.9 Hz, 2H). HR-ESIMS: m/z 465.2285 [M+H]+ calcd. for $C_{29}H_{29}N_4O_2$, found 465.2286. HPLC purity: 97.3% (Retention Time=8.5 min).

i. Preparation of Compound No. 35

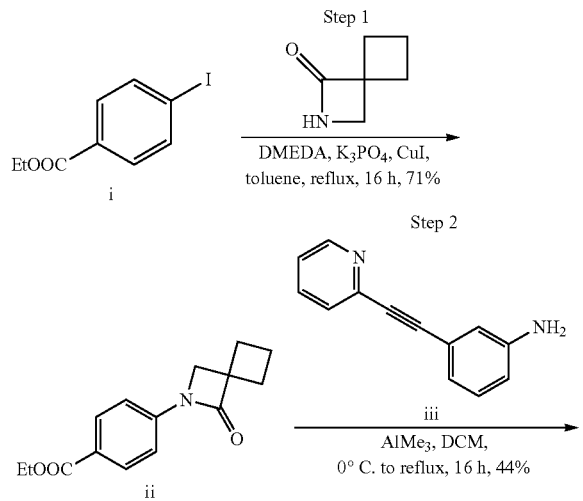

Scheme 8

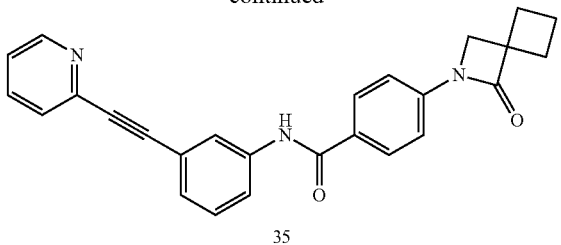

i. Step 1: Ethyl 4-(1-oxo-2-azaspiro[3.3]heptan-2-yl)benzoate (ii)

To a solution of ethyl 4-iodobenzoate (i) (0.05 mL, 0.27 mmol) in anhydrous toluene (2.7 mL) under nitrogen atmosphere at room temperature, was added 2-azaspiro[3.3]heptan-1-one (0.06 mL, 0.54 mmol) followed by anhydrous potassium phosphate tribasic (115 mg, 0.54 mmol), CuI (5.17 mg, 0.03 mmol) and N,N'-dimethylethylenediamine (0.01 mL, 0.05 mmol). The reaction mixture was allowed to reflux for 16 h. After completion of the reaction, it was cooled to room temperature and diluted with water (50 mL). Aqueous layer was extracted with EtOAc (3×50 mL). The combined organic layer was washed with brine (50 mL), dried over Na₂SO₄, filtered and evaporated to dryness under reduced pressure, followed by purification on pre-packed Silica gel column on ISCO using 0-15% EtOAc in hexanes (19 min) gave the pure product. Yield: 50 mg (71%). ¹H NMR (CDCl₃) δ 8.03-7.99 (m, 2H), 7.37-7.33 (m, 2H), 4.35 (q, J=7.1 Hz, 2H), 3.67 (s, 2H), 2.63-2.55 (m, 2H), 2.34 (ddd, J=12.5, 9.4, 6.7 Hz, 2H), 2.19-2.08 (m, 1H), 1.98 (dddd, J=15.4, 11.7, 9.4, 6.0 Hz, 1H), 1.39 (t, J=7.1 Hz, 3H). ESIMS: m/z 260.1 [M+H]+.

ii. Step 2: 4-(1-Oxo-2-azaspiro[3.3]heptan-2-yl)-N-(3-(pyridin-2-ylethynyl)phenyl)benzamide (35)

To a solution of 3-(pyridin-2-ylethynyl)aniline (iii) (35.9 mg, 0.19 mmol) in anhydrous DCM (1.9 mL) under nitrogen atmosphere at 0° C., was added a 2 M solution of AlMe₃ in toluene (0.28 mL, 0.56 mmol) dropwise. After complete addition, the reaction was stirred at room temperature for 30 min. Ethyl 4-(1-oxo-2-azaspiro[3.3]heptan-2-yl)benzoate (ii) (48 mg, 0.19 mmol) was added to the reaction mixture and refluxed for 16 h. After completion of reaction it was cooled to room temperature and quenched by dropwise addition of MeOH (3 mL). Reaction mixture was concentrated under reduced pressure and diluted with water (30 mL). Aqueous layer was extracted with EtOAc (3×30 mL). The combined organic layer was washed with brine (30 mL), dried over Na₂SO₄, filtered and evaporated to dryness under reduced pressure, followed by purification on pre-packed Silica gel column on ISCO using 0-5% MeOH in DCM (37 min) gave the pure product (35). Yield: 33 mg (43.7%). ¹H NMR (DMSO-d₆) δ 10.30 (s, 1H), 8.62 (d, J=4.9 Hz, 1H), 8.09 (d, J=1.9 Hz, 1H), 8.01 (d, J=8.2 Hz, 2H), 7.85 (ddd, J=10.8, 8.4, 6.6 Hz, 2H), 7.67 (d, J=7.8 Hz, 1H), 7.47-7.39 (m, 4H), 7.34 (dd, J=7.9, 1.4 Hz, 1H), 3.78 (s, 2H), 2.44-2.31 (m, 4H), 2.01-1.87 (m, 2H). HR-ESIMS: m/z 408.1706 [M+H]+ calcd. for $C_{26}H_{22}N_3O_2$, found 408.1709. HPLC purity: 100% (Retention Time=12.1 min).

j. Preparation of Compound No. 36

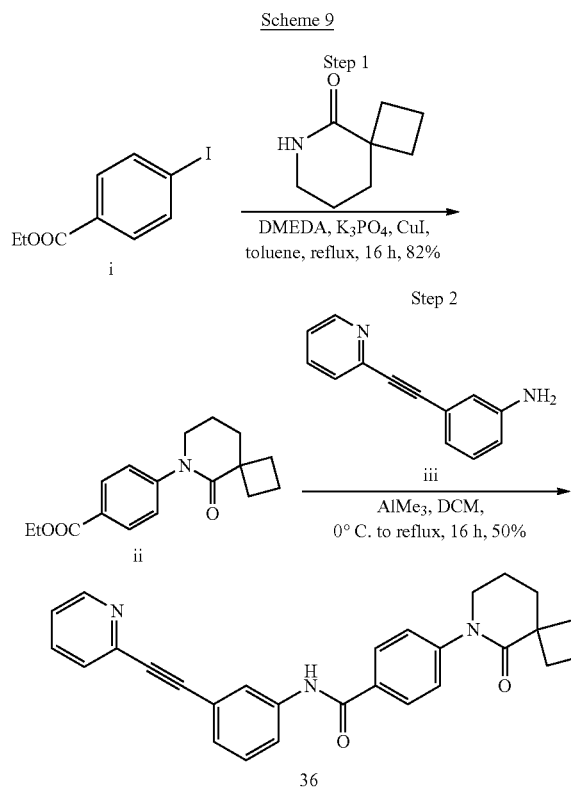

i. Step 1: Ethyl 4-(5-oxo-6-azaspiro[3.5]nonan-6-yl)benzoate (ii)

To a solution of ethyl 4-iodobenzoate (i) (0.06 mL, 0.36 mmol) in anhydrous toluene (3.6 mL) under nitrogen atmosphere at room temperature, was added 6-azaspiro[3.5]nonan-5-one (101 mg, 0.72 mmol) followed by anhydrous potassium phosphate tribasic (154 mg, 0.72 mmol), CuI (6.89 mg, 0.04 mmol) and N,N'-dimethylethylenediamine (0.01 mL. 0.07 mmol). The reaction mixture was allowed to reflux for 16 h. After completion of reaction, it was cooled to room temperature and diluted with water (50 mL). Aqueous layer was extracted with EtOAc (3×50 mL). The combined organic layer was washed with brine (50 mL), dried over Na$_2$SO$_4$, filtered and evaporated to dryness under reduced pressure, followed by purification on pre-packed Silica gel column on ISCO using 0-20% EtOAc in hexanes (19 min) gave the pure product (ii). Yield: 85 mg (81.7%). $^1$H NMR (CDCl$_3$) δ 8.05-8.01 (m, 2H), 7.35-7.31 (m, 2H), 4.37 (q, J=7.1 Hz, 2H), 3.64 (t, J=6.0 Hz, 2H), 2.68 (ddd, J=11.9, 10.0, 8.3 Hz, 2H), 2.12-1.90 (m, 6H), 1.86-1.78 (m, 2H), 1.39 (t, J=7.1 Hz, 3H). ESIMS: m/z 287.9 [M+H]$^+$.

ii. Step 2: 4-(5-Oxo-6-Azaspiro[3.5]nonan-6-yl)-N-(3-(pyridin-2-ylethynyl)phenyl)benzamide (36)

To a solution of 3-(pyridin-2-ylethynyl)aniline (iii) (40.5 mg, 0.21 mmol) in anhydrous DCM (2.1 mL) under nitrogen atmosphere at 0° C., was added a 2 M solution of AlMe$_3$ in toluene (0.31 mL, 0.63 mmol) dropwise. After complete addition, the reaction was stirred at room temperature for 30 min. Ethyl 4-(5-oxo-6-azaspiro[3.5]nonan-6-yl)benzoate (ii) (60 mg, 0.21 mmol) was added to the reaction mixture and refluxed for 16 h. After completion of the reaction, it was cooled to room temperature and quenched by dropwise addition of MeOH (3 mL). Reaction mixture was concentrated under reduced pressure and diluted with water (30 mL). Aqueous layer was extracted with EtOAc (3×30 mL). The combined organic layer was washed with brine (50 mL), dried over Na$_2$SO$_4$, filtered and evaporated to dryness under reduced pressure, followed by purification on pre-packed Silica gel column on ISCO using 0-5% MeOH in DCM (22 min) gave the pure product (36). Yield: 46 mg (50.4%). $^1$H NMR (CD$_3$OD) δ 8.55 (ddd, J=5.0, 1.8, 0.9 Hz, 1H), 8.03-7.96 (m, 3H), 7.88 (td, J=7.8, 1.8 Hz, 1H), 7.78 (dt, J=7.7, 1.9 Hz, 1H), 7.66 (dt, J=7.9, 1.1 Hz, 1H), 7.46-7.37 (m, 5H), 3.69 (t, J=6.0 Hz, 2H), 2.67-2.57 (m, 2H), 2.18-1.85 (m, 8H). HR-ESIMS: m/z 436.2019 [M+H]$^+$ calcd. for C$_{28}$H$_{26}$N$_3$O$_2$, found 436.2016. HPLC purity: 99.6% (Retention Time=11.9 min).

k. Preparation of Compound No. 20

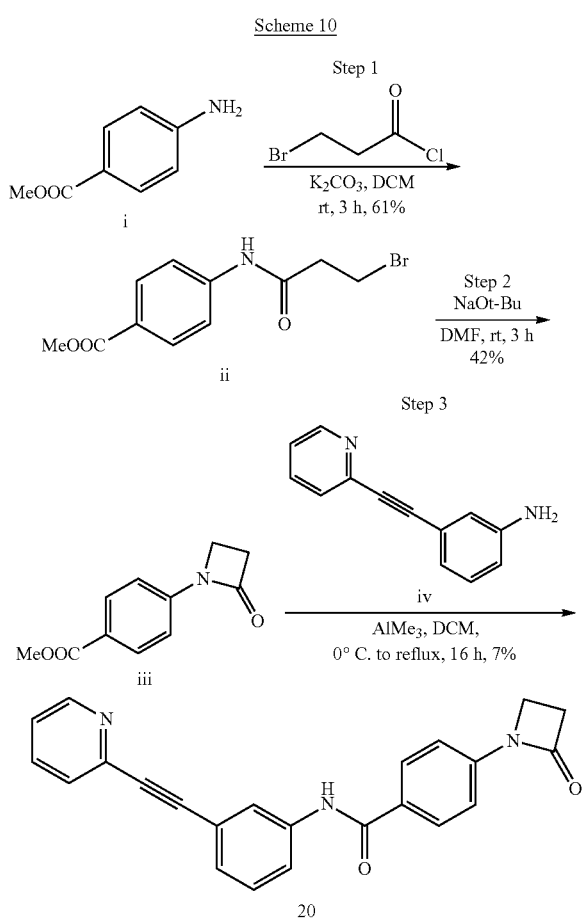

i. Step 1: Methyl 4-(3-bromopropanamido)benzoate

To a solution of methyl 4-aminobenzoate (i) (300 mg, 1.98 mmol) in anhydrous DCM (5 mL) under nitrogen atmosphere, potassium carbonate (329 mg, 2.38 mmol) was added at room temperature. To the reaction mixture, 3-bromopropionyl chloride (0.24 mL, 2.38 mmol) was added dropwise. After complete addition, the reaction was allowed to stir for 3 h at the same temperature. After completion of reaction, the reaction mixture was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, which was used into next step without further purification. Yield: 350 mg (61.6%). $^1$H NMR (CDCl$_3$) δ 9.78 (s, 1H), 8.08-7.89 (m, 2H), 7.75-7.61 (m, 2H), 3.94 (s, 3H), 3.70 (t, J=6.7 Hz, 2H), 2.99 (t, J=6.7 Hz, 2H). ESIMS: m/z 288.0 [M+2]$^+$.

ii. Step 2: Methyl 4-(2-oxoazetidin-1-yl)benzoate (iii)

To the solution of methyl 4-(3-bromopropanamido)benzoate (ii) (200 mg, 0.70 mmol) in anhydrous DMF (3 mL) under nitrogen atmosphere at 0° C., sodium tert-butoxide (74 mg, 0.77 mmol) was added. The reaction was allowed to stir at room temperature for 3 h. After completion of reaction, the reaction mixture was diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, which was used into next step without further purification. ESIMS: m/z 206.1 [M+H]$^+$.

iii. Step 3: 4-(2-oxoazetidin-1-yl)-N-(3-(pyridin-2-ylethynyl)phenyl)benzamide (20)

To a solution of 3-(pyridin-2-ylethynyl)aniline (iv) (31.2 mg, 0.16 mmol) in anhydrous DCM (5 mL) under nitrogen atmosphere at 0° C., was added a 2 M solution of AlMe$_3$ in toluene (0.24 mL, 0.48 mmol) dropwise. After complete addition, the reaction was stirred at room temperature for 30 min. Methyl 4-(2-oxoazetidin-1-yl)benzoate (iii) (33 mg, 0.16 mmol) was added to the reaction mixture and refluxed for 16 h. After completion of reaction, it was cooled to room temperature and quenched by dropwise addition of MeOH (7 mL). Reaction mixture was concentrated under reduced pressure and diluted with water (30 mL). Aqueous layer was extracted with EtOAc (3×30 mL). The combined organic layer was washed with brine, dried over $Na_2SO_4$, filtered and evaporated to dryness under reduced pressure, followed by purification on ACCQ prep HP-125 reverse phase column using 0-100% CH$_3$CN in H$_2$O with 0.1% TFA (30 min) gave the pure product (20). Yield: 14 mg (23.7%). $^1$H NMR (CDCl$_3$) δ 8.56 (d, J=4.2 Hz, 1H), 7.91 (dd, J=8.8, 2.0 Hz, 2H), 7.88-7.84 (m, 2H), 7.76 (ddd, J=7.7, 4.4, 2.0 Hz, 4H), 7.32 (ddd, J=7.8, 5.0, 1.3 Hz, 1H), 6.50-6.33 (m, 2H), 5.79 (dd, J=9.5, 2.3 Hz, 1H), 3.69 (s, 4H). HR-ESIMS: m/z 368.1393 [M+H]$^+$ calcd. for $C_{23}H_{18}N_3O_2$, found 368.1398. HPLC purity: 100% (Retention Time=10.0 min).

l. Preparation of Compound No. 21

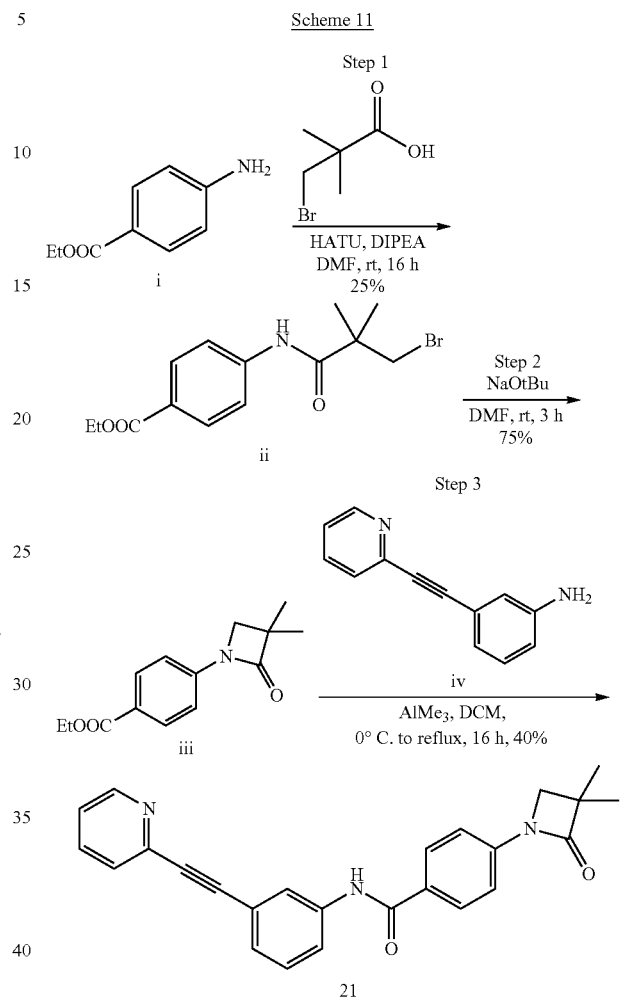

Scheme 11 i. Step 1: Ethyl 4-(3-bromo-2,2-dimethylpropanamido)benzoate (ii)

To a solution of 3-bromo-2,2-dimethylpropanoic acid (200 mg, 1.10 mmol) in anhydrous DMF (5.5 mL) under nitrogen atmosphere at room temperature, HATU (504 mg, 1.33 mmol) was added, followed by DIPEA (0.39 mL, 2.21 mmol) and the reaction was stirred at same temperature for about 10 min. Ethyl 4-aminobenzoate (i) (219 mg, 1.33 mmol) was added to the reaction mixture and allowed to stir at room temperature for 16 h. After completion of the reaction, the reaction mixture was diluted with water (50 mL) and extracted with EtOAc (3×50 mL). The combined organic layer was washed with brine, dried over $Na_2SO_4$, filtered and evaporated to dryness under reduced pressure, followed by purification on pre-packed Silica gel column on ISCO using 0-40% EtOAc in hexanes (35 min) gave the pure product (ii). Yield: 92 mg (25.4%). $^1$H NMR (CDCl$_3$) δ 8.02 (d, J=8.6 Hz, 2H), 7.62 (d, J=8.6 Hz, 2H), 7.56 (s, 1H), 4.36 (q, J=7.1 Hz, 2H), 3.60 (s, 2H), 1.47 (s, 6H), 1.39 (t, J=7.1 Hz, 3H). ESIMS: m/z 330.0 [M+2]$^+$.

ii. Step 2: Ethyl 4-(3,3-dimethyl-2-oxoazetidin-1-yl)benzoate (iii)

To a solution of ethyl 4-(3-bromo-2,2-dimethylpropanamido)benzoate (ii) (92 mg, 0.28 mmol) in anhydrous DMF (2.8 mL) under nitrogen atmosphere at 0° C., sodium tert-butoxide (30.3 mg, 0.31 mmol) was added. The reaction mixture was allowed to stir at room temperature for 3 h. After completion of the reaction, the mixture was diluted with water (50 mL) and extracted with EtOAc (3×50 mL). The combined organic layer was washed with brine (50 mL), dried over $Na_2SO_4$, filtered and evaporated to dryness under reduced pressure to give a residue, which was used directly into next step. Yield: 52 mg (75%). $^1$H NMR (CDCl$_3$) δ 8.05-7.99 (m, 2H), 7.39-7.34 (m, 2H), 4.36 (q, J=7.1 Hz, 2H), 3.48 (s, 2H), 1.41 (d, J=13.6 Hz, 9H). ESIMS: m/z 248.0 [M+H]$^+$.

iii. Step 3: 4-(3,3-Dimethyl-2-oxoazetidin-1-yl)-N-(3-(pyridin-2-ylethynyl)phenyl)benzamide (21)

To a solution of 3-(pyridin-2-ylethynyl)aniline (iv) (40.1 mg, 0.21 mmol) in anhydrous DCM (2.1 mL) under nitrogen atmosphere at 0° C., was added a 2 M solution of AlMe$_3$ in toluene (0.31 mL, 0.62 mmol) dropwise. After complete addition, the reaction was stirred at room temperature for 30 min. Ethyl 4-(3,3-dimethyl-2-oxoazetidin-1-yl)benzoate (iii) (51 mg, 0.21 mmol) was added to the reaction mixture and refluxed for 16 h. After completion of reaction, it was cooled to room temperature and quenched by dropwise addition of MeOH (3 mL). Reaction mixture was concentrated under reduced pressure and diluted with water (30 mL). Aqueous layer was extracted with EtOAc (3×30 mL). The combined organic layer was washed with brine (30 mL), dried over $Na_2SO_4$, filtered and evaporated to dryness under reduced pressure, followed by purification on pre-packed Silica gel column on ISCO using 0-5% MeOH in DCM (37 min) gave the pure product (21). Yield: 33 mg (40.5%). $^1$H NMR (DMSO-d$_6$) δ 10.31 (s, 1H), 8.62 (d, J=4.8 Hz, 1H), 8.11-8.08 (m, 1H), 8.05-8.00 (m, 2H), 7.89-7.81 (m, 2H), 7.69-7.65 (m, 1H), 7.49-7.39 (m, 4H), 7.34 (d, J=7.4 Hz, 1H), 3.58 (s, 2H), 1.33 (s, 6H). HR-ESIMS: m/z 396.1706 [M+H]$^+$ calcd. for $C_{25}H_{22}N_3O_2$, found 396.1704. HPLC purity: 100% (Retention Time=11.6 min).

m. Preparation of Compound Nos. 26-28

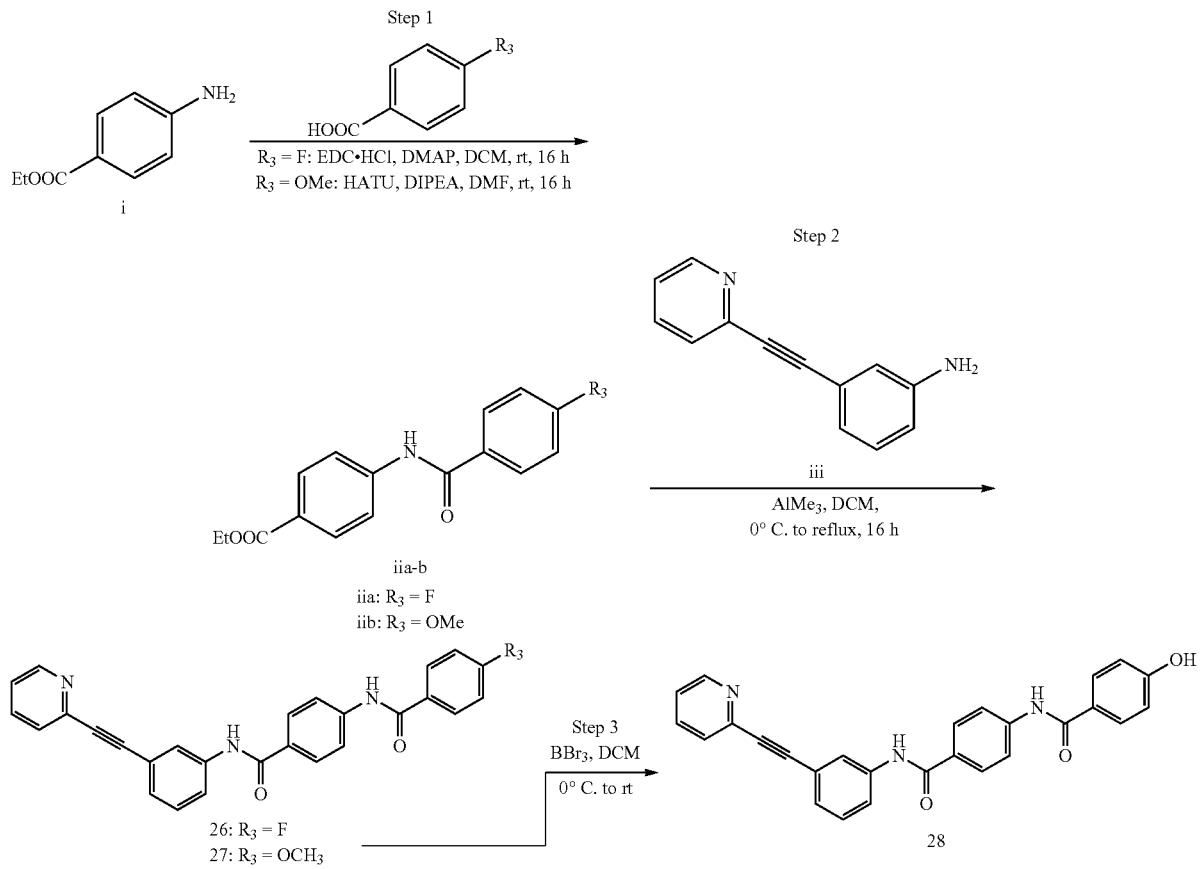

Scheme 12 i. Step 1: Ethyl 4-(4-fluorobenzamido)benzoate (iia)

To a solution of ethyl 4-aminobenzoate (i) (100 mg, 0.61 mmol) and 4-fluorobenzoic acid (84.82 mg, 0.61 mmol) in anhydrous DCM (6 mL) under nitrogen atmosphere, N-(3-

Dimethylaminopropyl)-N'-ethylcarbodiimide hydrochloride (232 mg, 1.21 mmol) and 4-(dimethylamino)pyridine (37 mg, 0.30 mmol) was added. The reaction mixture was allowed to stir at room temperature for 16 h. After completion of the reaction, the reaction mixture was concentrated under vacuum. The concentrated reaction mixture was diluted with water (50 mL) and extracted with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-5% MeOH in DCM (25 min) gave the pure product (iia). Yield: 110 mg (63.2%). $^1$H NMR (DMSO-$d_6$) δ 10.56 (s, 1H), 8.08-8.03 (m, 2H), 7.98-7.91 (m, 4H), 7.42-7.35 (m, 2H), 4.30 (q, J=7.1 Hz, 2H), 1.32 (t, J=7.1 Hz, 3H).

ii. Step 1: Ethyl 4-(4-methoxybenzamido)benzoate (iib)

To a solution of 4-methoxybenzoic acid (100 mg, 0.66 mmol) in anhydrous DMF (3.3 mL) under nitrogen atmosphere at room temperature, HATU (300 mg, 0.79 mmol) was added, followed by DIPEA (0.23 mL, 1.31 mmol) and the reaction was stirred at same temperature for about 10 min. Ethyl 4-aminobenzoate (i) (119 mg, 0.72 mmol) was added to the reaction mixture and allowed to stir at room temperature for 16 h. After completion of the reaction, the mixture was diluted with water (30 mL) and extracted with EtOAc (3×30 mL). The combined organic layer was washed with brine (30 mL), dried over $Na_2SO_4$, filtered and evaporated to dryness under reduced pressure, followed by purification on pre-packed Silica gel column on ISCO using 0-3% MeOH in DCM (30 min) gave the pure product (iib). Yield: 75 mg (38.1%). $^1$H NMR (DMSO-$d_6$) δ 10.40 (s, 1H), 8.00-7.92 (m, 6H), 7.08 (d, J=8.7 Hz, 2H), 4.30 (q, J=7.1 Hz, 2H), 3.85 (s, 3H), 1.32 (t, J=7.1 Hz, 3H). ESIMS: m/z 299.9 $[M+H]^+$.

iii. Step 2: General Synthetic Procedure

To a solution of 3-[2-(2-pyridyl)ethynyl]aniline (iii) (1 mmol) in anhydrous DCM (5 mL) under nitrogen atmosphere at 0° C., was added a 2 M solution of $AlMe_3$ in toluene (3 mmol) dropwise. After complete addition, the reaction was stirred at room temperature for 30 min. Appropriate ester (1 mmol) was added to the reaction mixture and refluxed for 16 h. After completion of reaction, the reaction was cooled to room temperature and quenched by dropwise addition of MeOH. Reaction mixture was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) 4-Fluoro-N-(4-((3-(pyridin-2-ylethynyl)phenyl)carbamoyl)phenyl)benzamide (26)

Purification on pre-packed Silica gel column on ISCO using 0-3% MeOH in DCM (30 min). Yield: 57 mg (62%). $^1$H NMR (DMSO-$d_6$) δ 10.54 (s, 1H), 10.31 (s, 1H), 8.64-8.60 (m, 1H), 8.14-8.04 (m, 3H), 8.03-7.92 (m, 4H), 7.90-7.82 (m, 2H), 7.67 (d, J=7.8 Hz, 1H), 7.47-7.32 (m, 5H). HR-ESIMS: m/z 436.1456 $[M+H]^+$ calcd. for $C_{27}H_{19}FN_3O_2$, found 436.1459. HPLC purity: 99% (Retention Time=12.2 min).

(ii) 4-Methoxy-N-(4-((3-(pyridin-2-ylethynyl)phenyl)carbamoyl)phenyl)benzamide (27)

Purification on pre-packed Silica gel column on ISCO using 0-5% MeOH in DCM (30 min). Yield: 45 mg (42.4%). $^1$H NMR (DMSO-$d_6$) δ 10.37 (s, 1H), 10.29 (s, 1H), 8.63 (d, J=4.9 Hz, 1H), 8.12 (s, 1H), 8.02-7.93 (m, 6H), 7.90-7.82 (m, 2H), 7.68 (d, J=7.8 Hz, 1H), 7.47-7.40 (m, 2H), 7.34 (d, J=7.6 Hz, 1H), 7.09 (d, J=8.7 Hz, 2H), 3.85 (s, 3H). HR-ESIMS: m/z 448.1656 $[M+H]^+$ calcd. for $C_{28}H_{22}N_3O_3$, found 448.1658. HPLC purity: 99.4% (Retention Time=12.1 min).

iv. Step 3: 4-Hydroxy-N-(4-((3-(pyridin-2-ylethynyl)phenyl)carbamoyl)phenyl)benzamide (28)

4-Methoxy-N-(4-((3-(pyridin-2-ylethynyl)phenyl)carbamoyl)phenyl)benzamide (27) (32 mg, 0.07 mmol) was dissolved in anhydrous DCM (5 mL) under nitrogen atmosphere and cooled to 0° C., followed by addition of 1 M solution of $BBr_3$ (0.36 mL, 0.36 mmol). After complete addition, reaction mixture was allowed to stir at room temperature for 16 h. After completion of the reaction, it was quenched by dropwise addition of MeOH. Reaction mixture was concentrated under reduced pressure and diluted with saturated solution of $NaHCO_3$ (50 mL) and allowed to stir for 30 min at room temperature. Aqueous layer was extracted with EtOAc (3×50 mL). The combined organic layer was washed with brine, dried over $Na_2SO_4$, filtered and evaporated to dryness under reduced pressure, followed by purification on pre-packed Silica gel column on ISCO using 0-5% MeOH in DCM (30 min) gave the pure product (28). Yield: 12 mg (38.5%). $^1$H NMR (DMSO-$d_6$) δ 10.28 (d, J=6.7 Hz, 2H), 10.17 (s, 1H), 8.64-8.60 (m, 1H), 8.12 (s, 1H), 7.96 (q, J=8.7 Hz, 4H), 7.91-7.81 (m, 4H), 7.68 (dd, J=7.8, 1.2 Hz, 1H), 7.47-7.40 (m, 2H), 7.35-7.31 (m, 1H), 6.88 (d, J=8.4 Hz, 2H). HR-ESIMS: m/z 434.1499 $[M+H]^+$ calcd. for $C_{27}H_{20}N_3O_3$, found 434.1501. HPLC purity: 99.5% (Retention Time=10.5 min).

n. Preparation of Compound Nos. 37-39

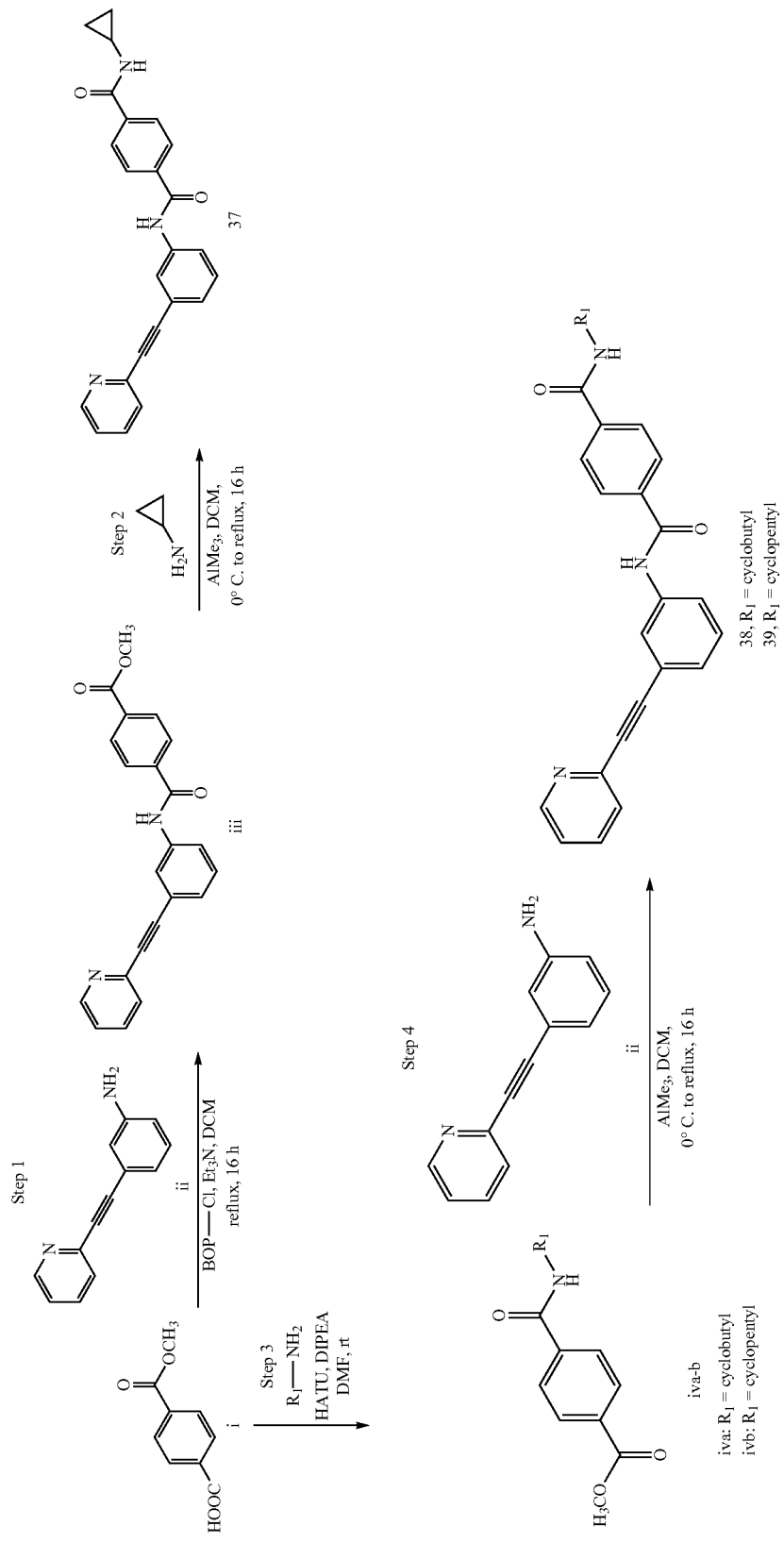
General Scheme 13 i. Step 1: Methyl 4-((3-(pyridin-2-ylethynyl)phenyl)carbamoyl)benzoate (iii)

To a solution of 4-(methoxycarbonyl)benzoic acid (i) (292 mg, 1.62 mmol) in anhydrous DCM (5 mL) under nitrogen atmosphere at room temperature, BOP-Cl (619 mg, 2.43 mmol) was added followed by the addition of triethylamine (492 mg, 4.87 mmol), and the reaction mixture was stirred at same temperature for 5 min. 3-(Pyridin-2-ylethynyl)aniline (ii) (315 mg, 1.62 mmol) was added to the reaction mixture and refluxed for 16 h. After completion of the reaction, it was cooled to room temperature, diluted with water (50 mL) and extracted with DCM (2×100 mL). The combined organic layer was washed with brine (50 mL), dried over $Na_2SO_4$, filtered and evaporated to dryness under reduced pressure, followed by purification on pre-packed Silica gel column on ISCO using 0-60% EtOAc in hexanes (30 min) gave the pure product (iii). Yield: 390 mg (67.5%). $^1$H NMR (CDCl$_3$) δ 8.61 (ddd, J=5.0, 1.7, 1.0 Hz, 1H), 8.18-8.09 (m, 2H), 8.01 (s, 1H), 7.98-7.90 (m, 2H), 7.86 (d, J=1.9 Hz, 1H), 7.77-7.64 (m, 2H), 7.53 (dt, J=7.8, 1.1 Hz, 1H), 7.44-7.34 (m, 2H), 3.96 (s, 3H). ESIMS: m/z 357.0 [M+H]$^+$.

ii. Step 2: N$^1$-cyclopropyl-N$^4$-(3-(pyridin-2-ylethynyl)phenyl)terephthalamide (37)

To a solution of cyclopropanamine (9.61 mg, 0.17 mmol) in anhydrous DCM (5 mL) under nitrogen atmosphere at 0° C., was added a 2 M solution of AlMe$_3$ in toluene (30 mg, 0.42 mmol) dropwise. After complete addition, the reaction was stirred at room temperature for 30 min. Methyl 4-((3-(pyridin-2-ylethynyl)phenyl)carbamoyl)benzoate (iii) (50 mg, 0.14 mmol) was added to the reaction mixture and refluxed for 16 h. After completion of reaction, it was cooled to room temperature and quenched by dropwise addition of MeOH (3 mL). Reaction mixture was concentrated under reduced pressure and diluted with saturated solution of NaHCO$_3$ (30 mL). Aqueous layer was extracted with EtOAc (3×50 mL). The combined organic layer was washed with brine (50 mL), dried over Na$_2$SO$_4$, filtered and evaporated to dryness under reduced pressure, followed by purification on pre-packed Silica gel column on ISCO using 0-10% MeOH in DCM (30 min) gave the pure product (37). Yield: 22 mg (40.3%). $^1$H NMR (CDCl$_3$+CD$_3$OD) δ 8.48-8.42 (m, 1H), 7.86 (d, J=8.4 Hz, 2H), 7.82-7.72 (m, 4H), 7.66 (td, J=7.7, 1.8 Hz, 1H), 7.50-7.43 (m, 1H), 7.32-7.27 (m, 2H), 7.21 (ddd, J=7.8, 4.9, 1.2 Hz, 1H), 2.79 (m, 1H) 0.85-0.71 (m, 2H), 0.65-0.44 (m, 2H). HR-ESIMS: m/z 382.155 [M+H]$^+$ calcd. for C$_{24}$H$_{20}$N$_3$O$_2$, found 382.1561. HPLC purity: 97.9% (Retention Time=9.5 min).

iii. Step 3: General Synthetic Procedure

To a solution of 4-(methoxycarbonyl)benzoic acid (i) (1 mmol) in anhydrous DMF (5 mL) under nitrogen atmosphere at room temperature, HATU (1.5 mmol) was added followed by DIPEA (3 mmol) and the reaction was stirred at same temperature for about 10 min. Appropriate alkyl amine (1 mmol) was added to the reaction mixture and allowed to stir at room temperature for 16 h. After completion of the reaction, it was diluted with water (50 mL) and extracted with EtOAc (2×50 mL). The combined organic layer was washed with brine (50 mL), dried over Na$_2$SO$_4$, filtered and evaporated to dryness under reduced pressure to give a residue, followed by purification using pre-packed Silica gel column on ISCO gave pure product.

(i) Methyl 4-(cyclobutylcarbamoyl)benzoate (iva)

Purification on pre-packed Silica gel column on ISCO using 0-70% EtOAc in hexanes (30 min). Yield: 433 mg (67%). $^1$H NMR (CDCl$_3$) δ 8.11-7.99 (m, 2H), 7.86-7.72 (m, 2H), 4.67-4.45 (m, 1H), 3.93 (d, J=0.7 Hz, 3H), 2.51-2.36 (m, 2H), 2.07-1.89 (m, 2H), 1.85-1.70 (m, 2H). ESIMS: m/z 234.1 [M+H]$^+$.

(ii) Methyl 4-(cyclopentylcarbamoyl)benzoate (ivb)

Purification on pre-packed Silica gel column on ISCO using 0-70% EtOAc in hexanes (30 min). Yield: 411 mg (60%). $^1$H NMR (CDCl$_3$) δ 8.12-8.01 (m, 2H), 7.88-7.76 (m, 2H), 4.36 (q, J=7.1 Hz, 1H), 3.95 (s, 3H), 2.16-2.01 (m, 2H), 1.82-1.70 (m, 2H), 1.70-1.61 (m, 2H), 1.62-1.44 (m, 2H). ESIMS: m/z 248.1 [M+H]$^+$.

iv. Step 4: General Synthetic Procedure

To a solution of 3-[2-(2-pyridyl)ethynyl]aniline (ii) (1 mmol) in anhydrous DCM (5 mL) under nitrogen atmosphere at 0° C., was added a 2 M solution of AlMe$_3$ in toluene (3 mmol) dropwise. After complete addition, the reaction was stirred at room temperature for 30 min. Appropriate ester (1 mmol) was added to the reaction mixture and refluxed for 16 h. After completion of reaction, it was cooled to room temperature and quenched by dropwise addition of MeOH (3 mL). Reaction mixture was concentrated under reduced pressure and diluted with water (50 mL). Aqueous layer was extracted with EtOAc (3×50 mL). The combined organic layer was washed with brine (50 mL), dried over Na$_2$SO$_4$, filtered and evaporated to dryness under reduced pressure to give a residue, followed by purification using pre-packed Silica gel column on ISCO gave pure product.

(i) N$^1$-cyclobutyl-N$^4$-(3-(pyridin-2-ylethynyl)phenyl)terephthalamide (38)

Purification on pre-packed Silica gel column on ISCO using 0-10% MeOH in DCM (30 min). Yield: 17 mg (16.5%). $^1$H NMR (DMSO-d$_6$) δ 10.46 (s, 1H), 8.74 (d, J=7.6 Hz, 1H), 8.59 (ddd, J=4.9, 1.8, 0.9 Hz, 1H), 8.07 (t, J=1.9 Hz, 1H), 8.03-7.98 (m, 2H), 7.98-7.94 (m, 2H), 7.85-7.79 (m, 2H), 7.64 (dt, J=7.8, 1.1 Hz, 1H), 7.48-7.36 (m, 2H), 7.33 (dt, J=7.7, 1.3 Hz, 1H), 4.41 (d, J=8.2 Hz, 1H), 2.19 (td, J=7.6, 7.1, 3.6 Hz, 2H), 2.13-2.00 (m, 2H), 1.72-1.61 (m, 2H). HR-ESIMS: m/z 396.1706 [M+H]$^+$ calcd. for C$_{25}$H$_{22}$N$_3$O$_2$, found 396.1716. HPLC purity: 99.1% (Retention Time=10.6 min).

(ii) N$^1$-cyclopentyl-N$^4$-(3-(pyridin-2-ylethynyl)phenyl)terephthalamide (39)

Purification on pre-packed Silica gel column on ISCO using 0-15% MeOH in DCM (35 min). Yield: 57 mg (51.4%). $^1$H NMR (CDCl$_3$) δ 8.47-8.41 (m, 1H), 7.86 (d, J=8.2 Hz, 2H), 7.75 (d, J=8.1 Hz, 4H), 7.70-7.62 (m, 1H), 7.50-7.44 (m, 1H), 7.33-7.26 (m, 2H), 7.23-7.19 (m, 1H), 4.26 (t, J=7.0 Hz, 1H), 2.06-1.90 (m, 2H), 1.65 (d, J=7.6 Hz, 2H), 1.60-1.51 (m, 2H), 1.45 (dd, J=12.8, 6.7 Hz, 2H). HR-ESIMS: m/z 410.1863 [M+H]$^+$ calcd. for C$_{26}$H$_{24}$N$_3$O$_2$, found 410.1862. HPLC purity: 94.6% (Retention Time=11.2 min).

o. Preparation of Compound Nos. 46, 48, and 51-53

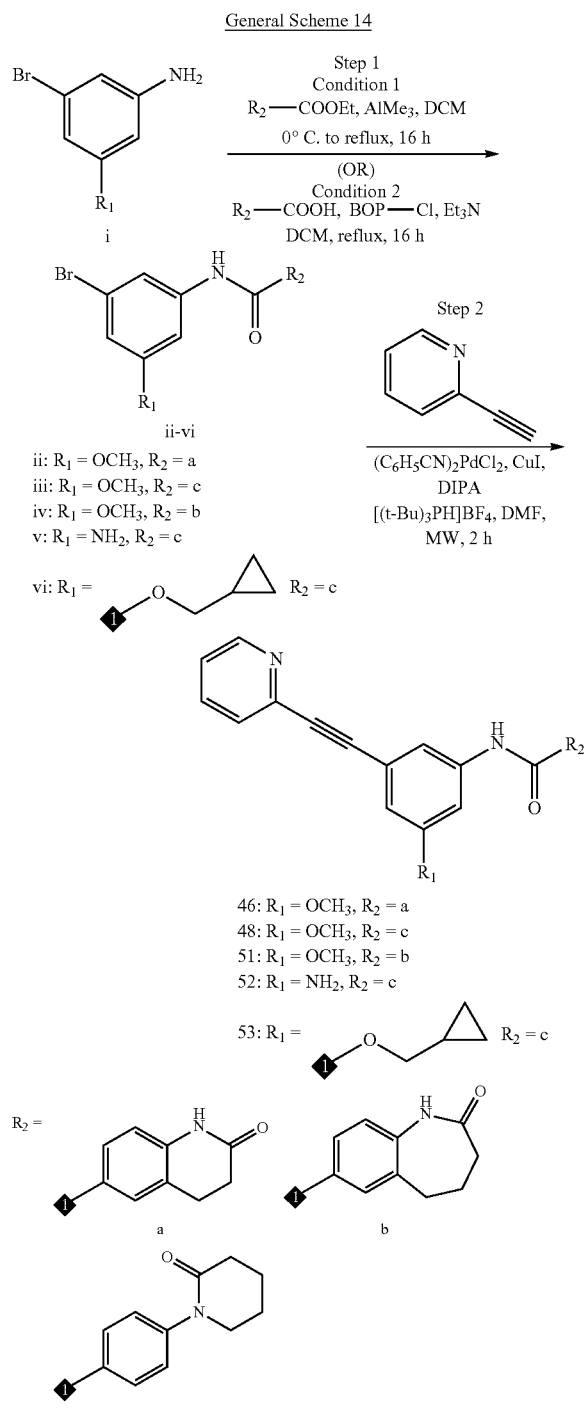

i. Step 1: General Synthetic Procedure

Condition 1: To a solution of substituted bromo aniline (1 mmol) in anhydrous DCM (5 mL) under nitrogen atmosphere at 0° C., was added a 2 M solution of AlMe$_3$ in toluene (3 mmol) dropwise. After complete addition, the reaction was stirred at room temperature for 30 min. Appropriate ester (1 mmol) was added to the reaction mixture and refluxed for 16 h. After completion of the reaction, the reaction mixture was cooled to room temperature and quenched by dropwise addition of MeOH (3 mL). Reaction mixture was concentrated under reduced pressure and diluted with water (50 mL). Aqueous layer was extracted with EtOAc (3×50 mL). The combined organic layer was washed with brine (50 mL), dried over Na$_2$SO$_4$, filtered and evaporated to dryness under reduced pressure to give a residue, followed by purification using pre-packed Silica gel column on ISCO gave the pure product.

Condition 2: To a solution of carboxylic acid (1 mmol) in anhydrous DCM (5 mL) under nitrogen atmosphere at room temperature, BOP-Cl (1.5 mmol) was added followed by the addition of triethylamine (3 mmol) and the reaction mixture was stirred at the same temperature for 5 min. Substituted bromo aniline (1 mmol) was added to the reaction mixture and refluxed for 16 h. After completion of the reaction (TLC analysis), the reaction mixture was cooled to room temperature, diluted with water (50 mL) and extracted with DCM (3×50 mL). The combined organic layer was washed with brine (50 mL), dried over Na$_2$SO$_4$, filtered and evaporated to dryness under reduced pressure to give a residue, followed by purification using pre-packed Silica gel column on ISCO gave the pure product.

(i) N-(3-Bromo-5-methoxyphenyl)-2-oxo-1,2,3,4-tetrahydroquinoline-6-carboxamide (ii)

This compound was synthesized by using condition 2. Purification on pre-packed Silica gel column on ISCO using 0-5% MeOH in DCM (45 min). Yield: 245 mg (44%). $^1$H NMR (DMSO-d$_6$) δ 10.37 (s, 1H), 10.15 (s, 1H), 7.82-7.74 (m, 2H), 7.68 (t, J=1.8 Hz, 1H), 7.43 (t, J=2.1 Hz, 1H), 6.95 (d, J=8.2 Hz, 1H), 6.87 (t, J=2.0 Hz, 1H), 3.77 (s, 3H), 2.97 (t, J=7.6 Hz, 2H), 2.54-2.51 (m, 2H). ESIMS: m/z 374.9 [M]$^+$, 376.8 [M+2]$^+$.

(ii) N-(3-Bromo-5-methoxyphenyl)-4-(2-oxopiperidin-1-yl)benzamide (iii)

This compound was synthesized by using condition 1. Purification on pre-packed Silica gel column on ISCO using 0-3% MeOH in DCM (23 min). Yield: 70 mg (40.1%). $^1$H NMR (DMSO-d$_6$) δ 10.31 (s, 1H), 7.96-7.92 (m, 2H), 7.69 (t, J=1.8 Hz, 1H), 7.48-7.43 (m, 3H), 6.90 (t, J=2.0 Hz, 1H), 3.77 (s, 3H), 3.67 (t, J=5.7 Hz, 2H), 2.43 (t, J=6.4 Hz, 2H), 1.94-1.81 (m, 4H). ESIMS: m/z 405.0 [M+2]$^+$.

(iii) N-(3-Bromo-5-methoxyphenyl)-2-oxo-2,3,4,5-tetrahydro-1H-benzo[b]azepine-7-carboxamide (iv)

This compound was synthesized by using condition 2. Purification on pre-packed Silica gel column on ISCO using 0-3% MeOH in DCM (37 min). Yield: 150 mg (62.3%). $^1$H NMR (DMSO-d$_6$) δ 10.24 (s, 1H), 9.79 (s, 1H), 7.86 (d, J=2.0 Hz, 1H), 7.81 (dd, J=8.2, 2.1 Hz, 1H), 7.68 (dt, J=2.3, 1.2 Hz, 1H), 7.43 (t, J=2.0 Hz, 1H), 7.08 (d, J=8.2 Hz, 1H), 6.89 (t, J=2.0 Hz, 1H), 3.77 (s, 3H), 2.77 (t, J=6.7 Hz, 2H), 2.24-2.11 (m, 4H). ESIMS: m/z 388.8 [M]$^+$, 391.0 [M+2]$^+$.

(iv) N-(3-Amino-5-bromophenyl)-4-(2-oxopiperidin-1-yl)benzamide (v)

This compound was synthesized by using condition 2. Purification on pre-packed Silica gel column on ISCO using 0-4.5% MeOH in DCM (38 min). Yield: 79 mg (62.8%). $^1$H NMR (DMSO-d$_6$) δ 10.05 (s, 1H), 7.90 (d, J=8.2 Hz, 2H), 7.42 (dd, J=12.7, 8.3 Hz, 2H), 7.10 (dt, J=23.5, 1.9 Hz, 2H), 6.48 (d, J=1.8 Hz, 1H), 5.44 (s, 2H), 3.65 (q, J=5.5 Hz, 2H), 2.42 (t, J=6.3 Hz, 2H), 1.92-1.80 (m, J=7.0, 5.8 Hz, 4H). ESIMS: m/z 389.8 [M+2]$^+$.

(v) N-(3-Bromo-5-(cyclopropylmethoxy)phenyl)-4-(2-oxopiperidin-1-yl)benzamide (vi)

This compound was synthesized by using condition 1. Purification on pre-packed Silica gel column on ISCO using 0-3% MeOH in DCM (28 min). Yield: 82 mg (38.1%). $^1$H NMR (DMSO-d$_6$) δ 10.29 (s, 1H), 7.95-7.90 (m, 2H), 7.66 (t, J=1.8 Hz, 1H), 7.48-7.41 (m, 3H), 6.87 (t, J=2.0 Hz, 1H), 3.83 (d, J=7.0 Hz, 2H), 3.67 (t, J=5.5 Hz, 2H), 2.43 (t, J=6.3 Hz, 2H), 1.93-1.81 (m, 4H), 1.27-1.17 (m, 1H), 0.60-0.54 (m, 2H), 0.36-0.30 (m, 2H). ESIMS: m/z 444.7 [M+2]$^+$.

ii. Step 2: General Synthetic Procedure

CuI (0.02 mmol), Bis(benzonitrile)palladium(II) chloride (0.06 mmol) and tri-tert-butylphosphonium tetrafluoroborate (0.03 mmol) were dissolved in anhydrous DMF (5 mL) in a microwave vial at room temperature, the reaction mixture was degassed and purged with nitrogen. To the reaction was added substituted bromo amide (1 mmol), 2-ethynylpyridine (1.2 mmol) and diisopropylamine (2 mmol). Reaction mixture was irradiated in a microwave for 2 h at 100° C. After completion of the reaction, the reaction mixture was filtered over a short pad of celite, given washings with EtOAc. Filtrate was further diluted with EtOAc (100 mL) and washed with water (3×50 mL), brine (50 mL), dried over Na$_2$SO$_4$, filtered and evaporated to dryness under reduced pressure to give a residue, followed by purification using pre-packed Silica gel column on ISCO gave the pure product.

(i) N-(3-Methoxy-5-(pyridin-2-ylethynyl)phenyl)-2-oxo-1,2,3,4-tetrahydroquinoline-6-carboxamide (46)

Purification on pre-packed Silica gel column on ISCO using 0-10% MeOH in DCM (35 min). Yield: 10 mg (7.4%). $^1$H NMR (DMSO-d$_6$) δ 10.37 (s, 1H), 10.17 (s, 1H), 8.62 (d, J=5.1 Hz, 1H), 7.89-7.76 (m, 3H), 7.71-7.64 (m, 2H), 7.52 (t, J=2.2 Hz, 1H), 7.45-7.40 (m, 1H), 6.96 (d, J=8.2 Hz, 1H), 6.90 (dd, J=2.4, 1.3 Hz, 1H), 3.81 (s, 3H), 2.97 (t, J=7.6 Hz, 2H), 2.55-2.51 (m, 2H). HR-ESIMS: m/z 398.1499 [M+H]$^+$ calcd. for C$_{24}$H$_{20}$N$_3$O$_3$, found 398.1502. HPLC purity: 95% (Retention Time=9.7 min).

(ii) N-(3-Methoxy-5-(pyridin-2-ylethynyl)phenyl)-4-(2-oxopiperidin-1-yl)benzamide (48)

Purification on pre-packed Silica gel column on ISCO using 0-3% MeOH in DCM (35 min). Yield: 26 mg (33.6%). $^1$H NMR (DMSO-d$_6$) δ 10.33 (s, 1H), 8.62 (d, J=4.8 Hz, 1H), 7.96 (d, J=8.3 Hz, 2H), 7.87 (td, J=7.8, 1.8 Hz, 1H), 7.72-7.65 (m, 2H), 7.54-7.52 (m, 1H), 7.49-7.40 (m, 3H), 6.92 (dd, J=2.6, 1.3 Hz, 1H), 3.81 (s, 3H), 3.68 (t, J=5.6 Hz, 2H), 2.43 (t, J=6.3 Hz, 2H), 1.93-1.81 (m, 4H). HR-ESIMS: m/z 426.1812 [M+H]$^+$ calcd. for C$_{26}$H$_{24}$N$_3$O$_3$, found 426.1811. HPLC purity: 95.5% (Retention Time=10.3 min).

iii. N-(3-Methoxy-5-(pyridin-2-ylethynyl)phenyl)-2-oxo-2,3,4,5-tetrahydro-1H-benzo[b]azepine-7-carboxamide (51)

Purification on pre-packed Silica gel column on ISCO using 0-5% MeOH in DCM (38 min). Yield: 23 mg (14.8%). $^1$H NMR (DMSO-d$_6$) δ 10.26 (s, 1H), 9.80 (s, 1H), 8.62 (ddd, J=5.0, 1.9, 1.0 Hz, 1H), 7.89-7.81 (m, 3H), 7.72-7.65 (m, 2H), 7.52 (t, J=2.1 Hz, 1H), 7.43 (ddd, J=7.4, 4.8, 1.1 Hz, 1H), 7.09 (d, J=8.2 Hz, 1H), 6.91 (dd, J=2.4, 1.3 Hz, 1H), 3.81 (s, 3H), 2.78 (t, J=6.8 Hz, 2H), 2.24-2.12 (m, 4H). HR-ESIMS: m/z 412.1656 [M+H]$^+$ calcd. for C$_{25}$H$_{22}$N$_3$O$_3$, found 412.1653. HPLC purity: 98.3% (Retention Time=10.2 min).

iv. N-(3-Amino-5-(pyridin-2-ylethynyl)phenyl)-4-(2-oxopiperidin-1-yl)benzamide (52)

Purification on pre-packed Silica gel column on ISCO using 0-20% MeOH in DCM (51 min). Yield: 9 mg (10.7%). $^1$H NMR (DMSO-d$_6$) δ 10.08 (s, 1H), 8.60 (d, J=4.6 Hz, 1H), 7.93 (d, J=8.3 Hz, 2H), 7.84 (td, J=7.7, 1.8 Hz, 1H), 7.64-7.60 (m, 1H), 7.46-7.37 (m, 3H), 7.18 (s, 2H), 6.53 (t, J=1.7 Hz, 1H), 5.39 (s, 2H), 3.67 (t, J=5.7 Hz, 2H), 2.43 (t, J=6.3 Hz, 2H), 1.93-1.80 (m, 4H). HR-ESIMS: m/z 411.1815 [M+H]$^+$ calcd. for C$_{25}$H$_{23}$N$_4$O$_2$, found 411.1816. HPLC purity: 99.3% (Retention Time=7.9 min).

v. N-(3-(Cyclopropylmethoxy)-5-(pyridin-2-ylethynyl)phenyl)-4-(2-oxopiperidin-1-yl)benzamide (53)

Purification on pre-packed Silica gel column on ISCO using 0-3% MeOH in DCM (35 min). Yield: 22 mg (24.7%). $^1$H NMR (DMSO-d$_6$) δ 10.30 (s, 1H), 8.62 (ddd, J=4.8, 1.8, 0.9 Hz, 1H), 7.97-7.93 (m, 2H), 7.86 (td, J=7.8, 1.8 Hz, 1H), 7.69-7.64 (m, 2H), 7.53 (t, J=2.1 Hz, 1H), 7.50-7.45 (m, 2H), 7.43 (ddd, J=7.7, 4.8, 1.2 Hz, 1H), 6.89 (dd, J=2.4, 1.3 Hz, 1H), 3.87 (d, J=7.0 Hz, 2H), 3.68 (t, J=5.6 Hz, 2H), 2.43 (t, J=6.3 Hz, 2H), 1.93-1.81 (m, 4H), 1.31-1.19 (m, 1H), 0.62-0.55 (m, 2H), 0.38-0.32 (m, 2H). HR-ESIMS: m/z 466.2125 [M+H]$^+$ calcd. for C$_{29}$H$_{28}$N$_3$O$_3$, found 466.2131. HPLC purity: 94.4% (Retention Time=12.1 min).

p. Preparation of Compound Nos. 47 and 50

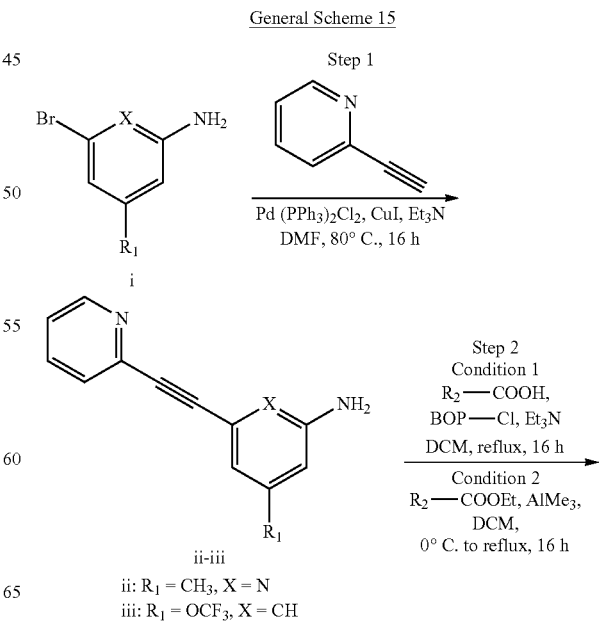

General Scheme 15

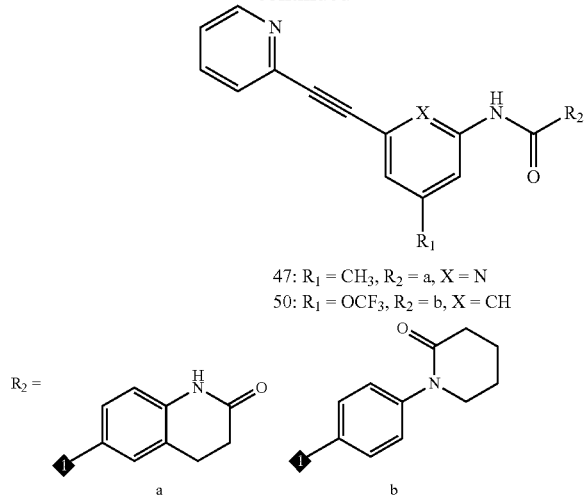

47: R₁ = CH₃, R₂ = a, X = N
50: R₁ = OCF₃, R₂ = b, X = CH i. Step 1: General Synthetic Procedure

To the solution of substituted bromoaniline (1 mmol) and 2-ethynylpyridine (1.2 mmol) in anhydrous DMF (5 mL), under nitrogen atmosphere at room temperature, was added bis(triphenylphosphine)palladium(II) dichloride (0.01 mmol), followed by CuI (0.025 mmol) and triethylamine (5.5 mmol). The reaction mixture was stirred at 80° C. for 16 h. After completion of reaction, the reaction mixture was filtered over a short pad of celite and washed with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) 4-Methyl-6-(pyridin-2-ylethynyl)pyridin-2-amine (ii)

Purification on pre-packed Silica gel column on ISCO using 0-15% MeOH in DCM (30 min). Yield: 172 mg (51.2%). ¹H NMR (CDCl₃) δ 8.62 (ddd, J=4.8, 1.8, 0.9 Hz, 1H), 7.67 (td, J=7.7, 1.8 Hz, 1H), 7.58 (dt, J=7.8, 1.1 Hz, 1H), 7.25-7.20 (m, 1H), 6.92-6.82 (m, 1H), 6.37-6.29 (m, 1H), 2.23 (t, J=0.7 Hz, 3H). ESIMS: m/z 210.0 [M+H]⁺.

(ii) 3-(Pyridin-2-ylethynyl)-5-(trifluoromethoxy)aniline (iii)

Purification on pre-packed Silica gel column on ISCO using 0-3% MeOH in DCM (40 min). Yield: 14 mg (8.6%). ¹H NMR (CDCl₃) δ 8.63 (ddd, J=4.9, 1.8, 1.0 Hz, 1H), 7.70 (ddd, J=9.5, 7.1, 1.8 Hz, 1H), 7.52 (dt, J=7.8, 1.1 Hz, 1H), 7.31-7.26 (m, 1H), 6.86-6.80 (m, 2H), 6.54-6.50 (m, 1H). ESIMS: m/z 279.0 [M+H]⁺.

ii. Step 2: General Synthetic Procedure

Condition 1: To a solution of carboxylic acid (1 mmol) in anhydrous DCM (5 mL) under nitrogen atmosphere at room temperature, BOP-Cl (1.5 mmol) was added followed by the addition of triethylamine (3 mmol) and the reaction mixture was stirred at the same temperature for appropriate aniline (1 mmol) was added to the reaction mixture and refluxed for 16 h. After completion of the reaction (TLC analysis), the reaction mixture was cooled to room temperature, diluted with water (50 mL) and extracted with DCM (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

Condition 2: To a solution of appropriate aniline (1 mmol) in anhydrous DCM (5 mL) under nitrogen atmosphere at 0° C., was added a 2 M solution of AlMe₃ in toluene (3 mmol) dropwise. After complete addition, the reaction was stirred at room temperature for 30 min. Appropriate ester (1 mmol) was added to the reaction mixture and refluxed for 16 h. After completion of the reaction (TLC analysis), the reaction was cooled to room temperature and quenched by dropwise addition of MeOH (3 mL). Reaction mixture was concentrated under reduced pressure and diluted with water (50 mL). Aqueous layer was extracted with EtOAc (3×50 mL). The combined organic layer was washed with brine (50 mL), dried over $Na_2SO_4$, filtered and evaporated to dryness under reduced pressure to give a residue, followed by purification using pre-packed Silica gel column on ISCO gave the pure product.

(i) N-(4-Methyl-6-(pyridin-2-ylethynyl)pyridin-2-yl)-2-oxo-1,2,3,4-tetrahydroquinoline-6-carboxamide (47)

This compound was synthesized by using condition 1. Purification on pre-packed Silica gel column on ISCO using 0-15% MeOH in DCM (30 min). Yield: 28 mg (38.5%). ¹H NMR (CDCl₃) δ 8.68-8.63 (m, 1H), 8.61 (s, 1H), 8.53 (s, 1H), 8.25 (dd, J=1.5, 0.8 Hz, 1H), 7.82-7.72 (m, 2H), 7.72-7.66 (m, 1H), 7.61-7.55 (m, 1H), 7.29 (ddd, J=7.6, 4.9, 1.3 Hz, 1H), 6.89 (d, J=8.1 Hz, 1H), 3.06 (t, J=7.6 Hz, 2H), 2.70 (dd, J=8.5, 6.6 Hz, 2H), 2.42 (t, J=0.7 Hz, 3H). HR-ESIMS: m/z 383.1502 [M+H]⁺ calcd. for $C_{23}H_{19}N_4O_2$, found 383.1497. HPLC purity: 95.6% (Retention Time=10.3 min).

(ii) 4-(2-Oxopiperidin-1-yl)-N-(3-(pyridin-2-ylethynyl)-5-(trifluoromethoxy)phenyl)benzamide (50)

This compound was synthesized by using condition 2. Purification on pre-packed Silica gel column on ISCO using 0-4% MeOH in DCM (30 min). Yield: 9 mg (37.2%). ¹H NMR (DMSO-d₆) δ 10.61 (s, 1H), 8.66-8.62 (m, 1H), 8.09 (d, J=1.8 Hz, 1H), 8.01-7.95 (m, 3H), 7.89 (td, J=7.8, 1.8 Hz, 1H), 7.72 (d, J=7.8 Hz, 1H), 7.52-7.43 (m, 3H), 7.36 (s, 1H), 3.68 (t, J=5.6 Hz, 2H), 2.44 (t, J=6.4 Hz, 2H), 1.93-1.80 (m, 4H). HR-ESIMS: m/z 480.1529 [M+H]⁺ calcd. for $C_{26}H_{21}F_3N_3O_3$, found 480.1531. HPLC purity: 99.6 (Retention Time=12.9 min).

q. Preparation of Compound No. 49

Scheme 16

Step 1

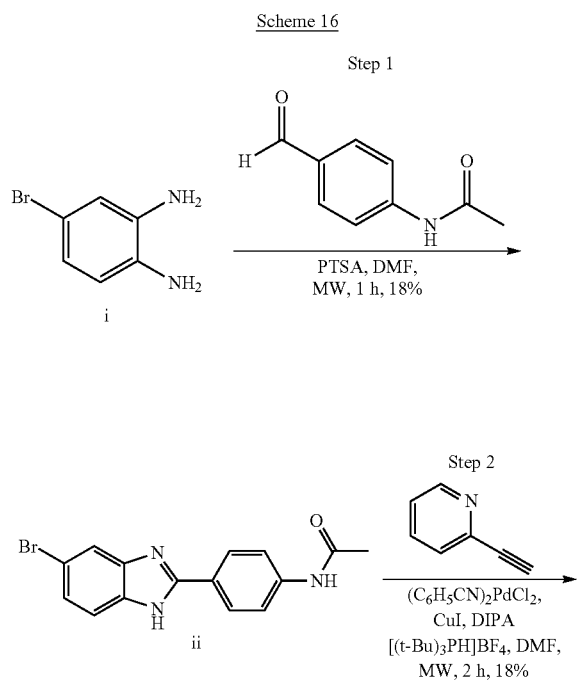

Step 2 i. Step 1: N-(4-(5-Bromo-1H-benzo[d]imidazol-2-yl)phenyl)acetamide (ii)

In a microwave vial 4-acetamidobenzaldehyde (109 mg, 0.67 mmol), 4-bromobenzene-1,2-diamine (i) (125 mg, 0.67 mmol) and p-toluenesulfonic acid (12.7 mg, 0.07 mmol) were dissolved in anhydrous DMF (2.5 mL), and purged with nitrogen. The reaction mixture was irradiated in a microwave at 100° C. for 1 h. After completion of reaction, reaction mixture was diluted with water (50 mL) and washed with EtOAc (3×50 mL). The combined organic layer was washed with brine (50 mL), dried over $Na_2SO_4$, filtered and evaporated to dryness under reduced pressure, followed by purification on pre-packed Silica gel column on ISCO using 0-7% MeOH in DCM (40 min) gave the pure product. Yield: 40 mg (18%). $^1$H NMR (DMSO-$d_6$) δ 10.18 (s, 1H), 8.08 (d, J=8.6 Hz, 2H), 7.75 (d, J=8.5 Hz, 3H), 7.51 (d, J=8.5 Hz, 1H), 7.31 (dd, J=8.5, 1.9 Hz, 1H), 2.09 (s, 3H). ESIMS: m/z 331.8 [M+H]$^+$.

ii. Step 2: N-(4-(5-(Pyridin-2-ylethynyl)-1H-benzo[d]imidazol-2-yl)phenyl)acetamide (49)

CuI (0.93 mg, 0.005 mmol), bis(benzonitrile)palladium (II) chloride (2.82 mg, 0.007 mmol) and tri-tert-butylphosphonium tetrafluoroborate (4.25 mg, 0.01 mmol) were dissolved in anhydrous DMF (2.4 mL) in a microwave vial at room temperature, the reaction mixture was degassed and purged with nitrogen. To the reaction was added N-(4-(5-bromo-1H-benzo[d]imidazol-2-yl)phenyl)acetamide (ii) (81 mg, 0.24 mmol), 2-ethynylpyridine (0.03 mL, 0.29 mmol) and diisopropylamine (0.07 mL, 0.49 mmol). Reaction mixture was irradiated in a microwave for 2 h at 80° C. After completion of the reaction, reaction mixture was filtered over a short pad of celite, given washings with EtOAc. EtOAc layer was washed with water (3×50 mL), brine, dried over $Na_2SO_4$, filtered and evaporated to dryness under reduced pressure, followed by purification using pre-packed Silica gel column on ISCO using 0-15% MeOH in DCM (55 min) gave the pure product (49). Yield: 16 mg (18.4%). $^1$H NMR (DMSO-$d_6$) δ 10.20 (s, 1H), 8.61 (d, J=4.9 Hz, 1H), 8.12 (d, J=8.4 Hz, 2H), 7.89-7.72 (m, 4H), 7.68-7.59 (m, 2H), 7.43-7.37 (m, 2H), 2.09 (s, 3H). HR-ESIMS: m/z 353.1397 [M+H]$^+$ calcd. for $C_{22}H_{17}N_4O$, found 353.1395. HPLC purity: 99.6 (Retention Time=7.7 min).

r. Preparation of Compound Nos. 54-59, 61, 67-71, and 74

General Scheme 17

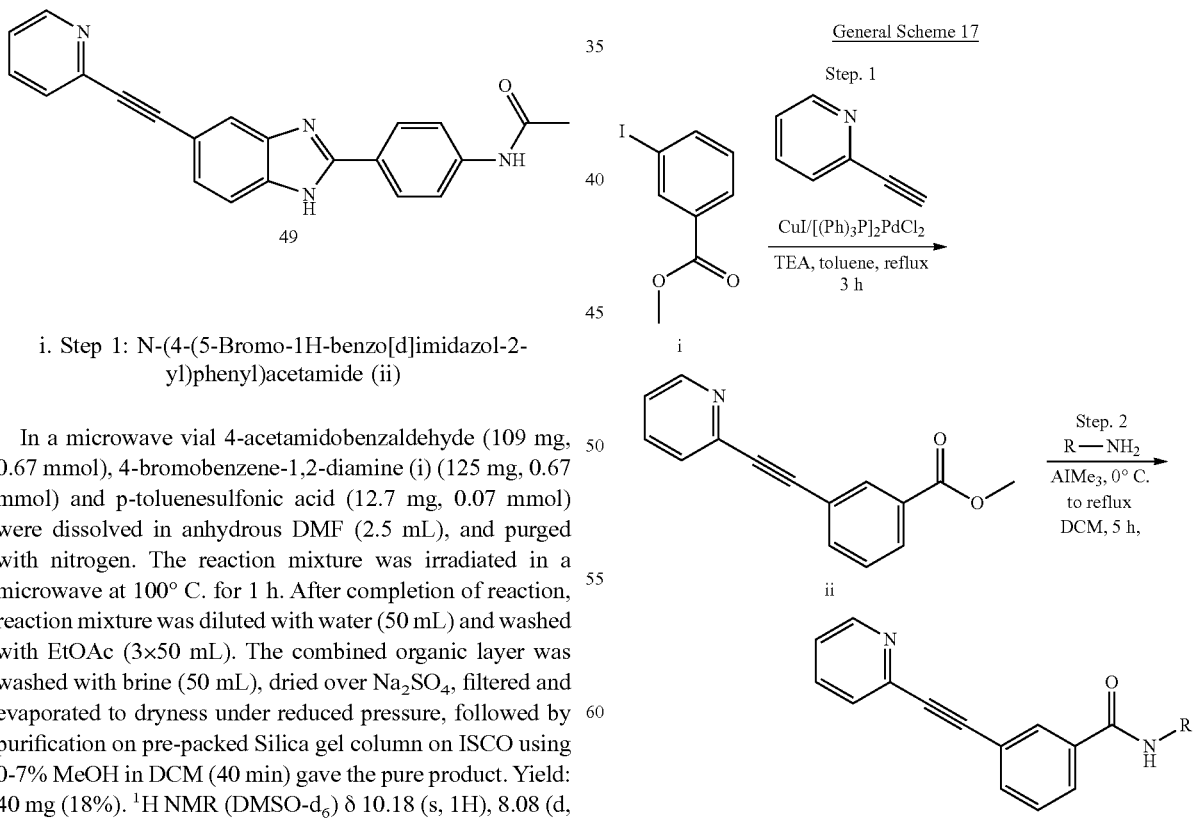

54, 55, 56, 57, 58, 59, 61, 67, 68, 69, 70, 71 and 74

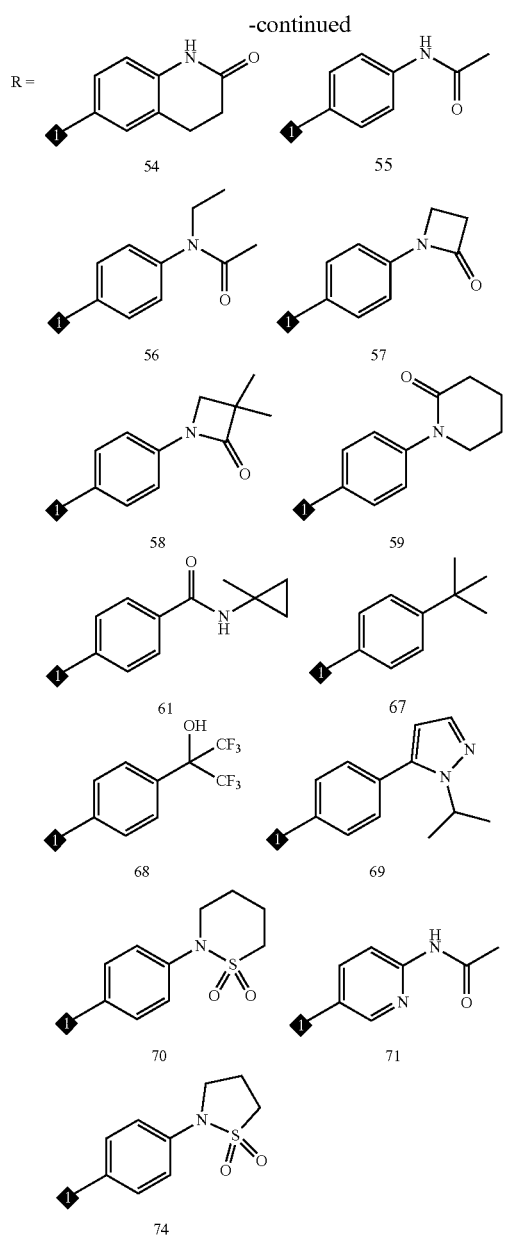

i. Step 1: methyl 3-(pyridin-2-ylethynyl)benzoate (ii)

Methyl 3-iodobenzoate (i) (2 g, 7.60 mmol), 2-Ethynylpyridine (1.247 mL, 12.2 mmol), and triethylamine (2.34 mL, 16.8 mmol) were dissolved in anhydrous toluene and purged with nitrogen, then Copper(I) iodide (0.29 g, 1.50 mmol), and [(Ph)$_3$P]$_2$PdCl$_2$ (0.955 g, 1.50 mmol) were added and resulting suspension was stirred at 100° C. for 3 hours, reaction was cooled to room temperature, filtered through a short pad of celite, then the filtrate was diluted with deionized water and extracted with EtOAc (2×500 mL). The combined organic layer was dried over anhydrous Na$_2$SO$_4$, concentrated under reduced pressure followed by purification on ISCO system gave the pure product (ii). Purification on pre-packed Silica gel column on ISCO using 0-10% MeOH in DCM (30 min). Yield: 1.35 g (74.5%). $^1$H NMR (400 MHz, CDCl$_3$) δ 8.63 (ddd, J=4.9, 1.8, 1.0 Hz, 1H), 8.31-8.23 (m, 1H), 8.03 (dt, J=7.9, 1.5 Hz, 1H), 7.77 (dt, J=7.7, 1.5 Hz, 1H), 7.70 (td, J=7.7, 1.8 Hz, 1H), 7.54 (dt, J=7.9, 1.1 Hz, 1H), 7.45 (td, J=7.7, 0.6 Hz, 1H), 7.29-7.26 (m, 1H), 3.93 (d, J=0.6 Hz, 3H). ESIMS: m/z 238.0 [M+1].$^+$ ii. Step 2: General Synthetic Procedure for Trimethylaluminum Mediated Amidation To a solution of amine (1 mmol) in anhydrous DCM (5 mL) under nitrogen at 0° C., trimethylaluminum (3 mmol) was added dropwise, after that ice bath was removed and the reaction mass was allowed to stir at room temperature for 30 min, then corresponding ester (3 mmol) was added and the reaction was refluxed for 5 h. The mixture was allowed to cool to room temperature, quenched with the addition of 3 mL of methanol, concentrated under reduced pressure, crude mass was diluted with water (100 mL) and extracted with EtOAc (2×150 mL). The organic layer was washed with brine, dried over anhydrous Na$_2$SO$_4$ and solvent was removed under reduced pressure. The crude was purified using pre-packed Silica gel column on ISCO purification system to yield product.

(i) N-(2-oxo-1,2,3,4-tetrahydroquinolin-6-yl)-3-(pyridin-2-ylethynyl)benzamide (54)

Purification on pre-packed Silica gel column on ISCO using 0-50% EtOAc in Hexanes (35 min). Yield: 24 mg (30%). $^1$H NMR (CDCl$_3$) δ 8.48 (ddd, J=4.9, 1.8, 0.9 Hz, 1H), 8.08 (d, J=1.9 Hz, 1H), 7.89 (d, J=7.9 Hz, 1H), 7.73-7.60 (m, 2H), 7.55 (d, J=2.4 Hz, 1H), 7.49 (dt, J=7.8, 1.1 Hz, 1H), 7.42 (t, J=7.8 Hz, 1H), 7.37 (dd, J=8.4, 2.4 Hz, 1H), 7.25-7.22 (m, 1H), 6.72 (d, J=8.5 Hz, 1H), 2.89 (t, J=7.6 Hz, 2H), 2.52 (dd, J=8.6, 6.7 Hz, 2H). HR-ESIMS: m/z 368.1321 [M+H]$^+$ calcd. for C$_{23}$H$_{18}$N$_3$O$_2$, found 368.13878. HPLC purity: 96.9% (Retention Time=9.3 min).

(ii) N-(4-acetamidophenyl)-3-(pyridin-2-ylethynyl)benzamide (55)

Purification on pre-packed Silica gel column on ISCO using 0-15% MeOH in CH$_2$Cl$_2$ (35 min). Yield: 33 mg (42.5%). $^1$H NMR (CDCl$_3$) δ 8.65 (d, J=4.9 Hz, 1H), 8.01 (d, J=11.1 Hz, 2H), 7.91 (d, J=8.0 Hz, 1H), 7.78-7.68 (m, 2H), 7.61 (d, J=8.6 Hz, 2H), 7.58-7.53 (m, 1H), 7.54-7.47 (m, 3H), 7.43 (s, 1H), 7.33-7.26 (m, 1H), 2.19 (s, 3H). HR-ESIMS: m/z 356.1321 [M+H]$^+$ calcd. for C$_{22}$H$_{18}$N$_3$O$_2$, found 356.1395. HPLC purity: 96.6% (Retention Time=8.7 min).

iii. N-(4-(N-ethylacetamido)phenyl)-3-(pyridin-2-ylethynyl)benzamide, trifluoroacetate salt (56)

Purification on C-18 column (Accq prep Hp-125) using 0-100% CH$_3$CN in H$_2$O each solvent containing 0.1% TFA (35 min). Yield: 21 mg (20%). $^1$H NMR (CDCl$_3$) δ 8.65 (ddd, J=4.9, 1.9, 1.0 Hz, 1H), 8.56 (s, 1H), 8.04 (t, J=1.7 Hz, 1H), 7.93 (dt, J=8.1, 1.4 Hz, 1H), 7.82-7.75 (m, 2H), 7.71 (td, J=7.8, 1.8 Hz, 2H), 7.56-7.45 (m, 2H), 7.29 (ddd, J=7.7, 4.9, 1.2 Hz, 1H), 7.18-7.12 (m, 2H), 3.73 (q, J=7.2 Hz, 2H), 1.82 (s, 3H), 1.10 (t, J=7.1 Hz, 3H). HR-ESIMS: m/z 384.1634 [M+H]$^+$ calcd. for C$_{24}$H$_{22}$N$_3$O$_2$, found 384.1708 [M+H]$^+$. HPLC purity: 97.7% (Retention Time=10.4 min).

iv. N-(4-(2-oxoazetidin-1-yl)phenyl)-3-(pyridin-2-ylethynyl)benzamide, trifluoroacetate salt (57)

Purification on C-18 column (Accq prep Hp-125) using 0-100% CH$_3$CN in H$_2$O each solvent containing 0.1% TFA (35 min). Yield: 9 mg (7%). $^1$H NMR (CDCl$_3$) δ 8.54 (s, 1H), 8.12 (s, 1H), 7.93 (d, J=7.9 Hz, 1H), 7.78-7.70 (m, 1H), 7.67 (d, J=8.8 Hz, 3H), 7.54 (d, J=8.0 Hz, 1H), 7.45 (t, J=7.8 Hz, 1H), 7.30 (d, J=8.7 Hz, 3H), 3.60 (t, J=4.4 Hz, 2H), 3.06 (t, J=4.4 Hz, 2H). HR-ESIMS: m/z 368.1321 [M+H]$^+$ calcd. for C$_{25}$H$_{18}$N$_3$O$_2$, found 368.1398 [M+H]$^+$. HPLC purity: 95.5% (Retention Time=10.1 min).

(iii) N-(4-(3,3-dimethyl-2-oxoazetidin-1-yl)phenyl)-3-(pyridin-2-ylethynyl)benzamide (58)

Purification on pre-packed Silica gel column on ISCO using 0-20% MeOH in CH$_2$Cl$_2$ (35 min). Yield: 45 mg (53%). $^1$H NMR (CDCl$_3$) δ 8.63-8.56 (m, 1H), 8.07 (d, J=1.8 Hz, 1H), 7.92 (dd, J=7.9, 1.5 Hz, 1H), 7.74-7.63 (m, 4H), 7.52 (dd, J=7.8, 1.1 Hz, 1H), 7.45 (t, J=7.8 Hz, 1H), 7.36-7.30 (m, 2H), 7.31-7.26 (m, 1H), 3.43 (s, 2H), 1.39 (s, 6H). HR-ESIMS: m/z 396.1634 [M+H]$^+$ calcd. for C$_{25}$H$_{22}$N$_3$O$_2$, found 396.1710. HPLC purity: 97.2% (Retention Time=11.5 min).

(iv) N-(4-(2-oxopiperidin-1-yl)phenyl)-3-(pyridin-2-ylethynyl)benzamide (59)

Purification on pre-packed Silica gel column on ISCO using 0-20% MeOH in CH$_2$Cl$_2$ (35 min). Yield: 67 mg (78%). $^1$H NMR (CDCl$_3$) δ 10.35 (s, 1H), 8.59 (ddd, J=4.9, 1.8, 1.0 Hz, 1H), 8.20 (d, J=1.8 Hz, 1H), 8.00 (dt, J=7.9, 1.4 Hz, 1H), 7.81 (dd, J=7.7, 1.8 Hz, 1H), 7.79-7.73 (m, 3H), 7.63 (dt, J=7.9, 1.1 Hz, 1H), 7.57 (t, J=7.8 Hz, 1H), 7.38 (ddd, J=7.6, 4.9, 1.1 Hz, 1H), 7.23-7.17 (m, 2H), 3.58 (t, J=5.6 Hz, 2H), 2.37 (t, J=6.2 Hz, 2H), 1.86 (dd, J=7.6, 4.7 Hz, 4H). HR-ESIMS: m/z 396.1634 [M+H]$^+$ calcd. for C$_{25}$H$_{22}$N$_3$O$_2$, found 396.1702. HPLC purity: 96.9% (Retention Time=9.7 min).

(v) N-(4-((1-methylcyclopropyl)carbamoyl)phenyl)-3-(pyridin-2-ylethynyl)benzamide (61)

Purification on pre-packed Silica gel column on ISCO using 0-20% MeOH in CH$_2$Cl$_2$ (35 min). Yield: 26 mg (15%). $^1$H NMR (CDCl$_3$) δ 8.57 (ddd, J=4.9, 1.8, 0.9 Hz, 1H), 8.15-8.08 (m, 1H), 7.95 (ddd, J=7.9, 1.9, 1.2 Hz, 1H), 7.81-7.75 (m, 2H), 7.74-7.67 (m, 4H), 7.53 (dt, J=7.9, 1.1 Hz, 1H), 7.46 (td, J=7.8, 0.6 Hz, 1H), 7.29 (ddd, J=7.7, 4.9, 1.2 Hz, 1H), 6.82 (s, 1H), 1.45 (s, 3H), 0.86-0.81 (m, 2H), 0.72-0.67 (m, 2H). HR-ESIMS: m/z 396.1634 [M+H]$^+$ calcd. for C$_{25}$H$_{22}$N$_3$O$_2$, found 396.1702. HPLC purity: 95.8% (Retention Time=9.5 min).

(vi) N-(4-(tert-butyl)phenyl)-3-(pyridin-2-ylethynyl)benzamide (67)

Purification on pre-packed Silica gel column on ISCO using 0-55% EtOAc in Hex (35 min). Yield: 61 mg (81%). $^1$H NMR (CDCl$_3$) δ 8.64 (ddq, J=4.8, 1.8, 1.0 Hz, 1H), 8.24 (s, 1H), 8.06-8.00 (m, 1H), 7.90 (dp, J=7.8, 1.7 Hz, 1H), 7.70 (tdd, J=6.8, 2.8, 1.3 Hz, 2H), 7.63-7.56 (m, 2H), 7.53 (dddd, J=6.8, 4.8, 2.1, 1.1 Hz, 1H), 7.50-7.42 (m, 2H), 7.38 (ddd, J=8.7, 4.3, 1.9 Hz, 2H), 7.28 (ddt, J=4.8, 2.1, 1.0 Hz, 1H), 1.34-1.30 (m, 9H). HR-ESIMS: m/z 355.1732 [M+H]$^+$ calcd. for C$_{24}$H$_{23}$N$_2$O, found 355.1812. HPLC purity: 98.4% (Retention Time=14.5 min).

(vii) N-(4-(1,1,1,3,3,3-hexafluoro-2-hydroxypropan-2-yl)phenyl)-3-(pyridin-2-ylethynyl)benzamide (68)

Purification on pre-packed Silica gel column on ISCO using 0-20% MeOH in CH$_2$Cl$_2$ (30 min). Yield: 14 mg (17%). $^1$H NMR (CDCl$_3$) δ 8.59 (ddd, J=5.0, 1.8, 0.9 Hz, 1H), 7.99 (d, J=1.7 Hz, 1H), 7.94 (dt, J=7.8, 1.5 Hz, 1H), 7.85 (s, 1H), 7.81-7.68 (m, 4H), 7.57 (dt, J=7.8, 1.1 Hz, 1H), 7.54-7.43 (m, 3H), 7.33 (ddd, J=7.7, 5.0, 1.2 Hz, 1H). HR-ESIMS: m/z 465.0959 [M+H]$^+$ calcd. for C$_{23}$H$_{15}$F$_6$N$_2$O$_2$, found 465.1039. HPLC purity: 95.0% (Retention Time=13.2 min).

(viii) N-(4-(1-isopropyl-1H-pyrazol-5-yl)phenyl)-3-(pyridin-2-ylethynyl)benzamide (69)

Purification on pre-packed Silica gel column on ISCO using 0-20% MeOH in CH$_2$Cl$_2$ (30 min). Yield: 35 mg (29%). $^1$H NMR (CDCl$_3$) δ 8.69-8.63 (m, 1H), 8.09 (d, J=2.1 Hz, 2H), 7.95 (dt, J=7.8, 1.5 Hz, 1H), 7.81-7.75 (m, 3H), 7.72 (td, J=7.7, 1.8 Hz, 1H), 7.61-7.49 (m, 3H), 7.39 (d, J=8.4 Hz, 2H), 7.29 (ddd, J=7.7, 4.9, 1.2 Hz, 1H), 6.24 (d, J=1.8 Hz, 1H), 4.64-4.50 (m, 1H), 1.48 (d, J=6.6 Hz, 6H). HR-ESIMS: m/z 407.1794 [M+H]$^+$ calcd. for C$_{26}$H$_{23}$N$_4$O, found 407.1864. HPLC purity: 100% (Retention Time=2.2 min).

(ix) N-(4-(1,1-dioxido-1,2-thiazinan-2-yl)phenyl)-3-(pyridin-2-ylethynyl)benzamide (70)

Purification on pre-packed Silica gel column on ISCO using 0-10% MeOH in CH$_2$Cl$_2$ (30 min). Yield: 43 mg (46%). $^1$H NMR (CDCl$_3$) δ 8.57 (s, 1H), 8.18 (s, 1H), 8.11-7.89 (m, 2H), 7.79-7.58 (m, 4H), 7.45 (q, J=9.6, 7.8 Hz, 2H), 7.35-7.24 (m, 3H), 3.78-3.56 (m, 2H), 3.29-3.12 (m, 2H), 2.32 (p, J=6.5 Hz, 2H), 1.90 (p, J=5.7 Hz, 2H). HR-ESIMS: m/z 432.1304 [M+H]$^+$ calcd. for C$_{24}$H$_{22}$N$_3$O$_3$S, found 432.1373. HPLC purity: 97.5% (Retention Time=10.9 min).

(x) N-(6-acetamidopyridin-3-yl)-3-(pyridin-2-ylethynyl)benzamide (71)

Purification on pre-packed Silica gel column on ISCO using 0-15% MeOH in CH$_2$Cl$_2$ (30 min). Yield: 120 mg (79%). $^1$H NMR (CDCl$_3$) δ 9.74 (s, 1H), 8.66 (t, J=2.7 Hz, 1H), 8.57-8.49 (m, 1H), 8.22-8.11 (m, 2H), 8.11-8.03 (m, 1H), 7.98 (d, J=7.9 Hz, 1H), 7.77-7.65 (m, 2H), 7.53 (d, J=7.9 Hz, 1H), 7.47 (t, J=7.8 Hz, 1H), 7.29 (dd, J=7.8, 5.1 Hz, 1H), 2.16 (s, 3H). HR-ESIMS: m/z 357.1273 [M+H]$^+$ calcd. for C$_{21}$H$_{17}$N$_4$O$_2$, found 357.1344. HPLC purity: 99.4% (Retention Time=7.4 min).

(xi) N-(4-(1,1-dioxidoisothiazolidin-2-yl)phenyl)-3-(pyridin-2-ylethynyl)benzamide (74)

Purification on pre-packed Silica gel column on ISCO using 0-10% MeOH in CH$_2$Cl$_2$ (30 min). Yield: 35 mg (43%). $^1$H NMR (CDCl$_3$) δ 8.57 (ddd, J=4.9, 1.8, 1.0 Hz, 1H), 8.14 (t, J=1.7 Hz, 1H), 7.96 (dt, J=8.2, 1.4 Hz, 1H), 7.71 (tdd, J=7.9, 4.2, 2.4 Hz, 4H), 7.59-7.42 (m, 2H), 7.31-7.26 (m, 2H), 7.25 (d, J=2.2 Hz, 1H), 3.76 (t, J=6.5 Hz, 2H), 3.37 (t, J=7.6 Hz, 2H), 2.51 (dd, J=7.8, 6.5 Hz, 2H). HR-ESIMS: m/z 418.1147 [M+H]$^+$ calcd. for C$_{23}$H$_{20}$N$_3$O$_3$S, found 418.1212. HPLC purity: 100% (Retention Time=12.5 min).

s. Preparation of Compound Nos. 63-66

General Scheme 18

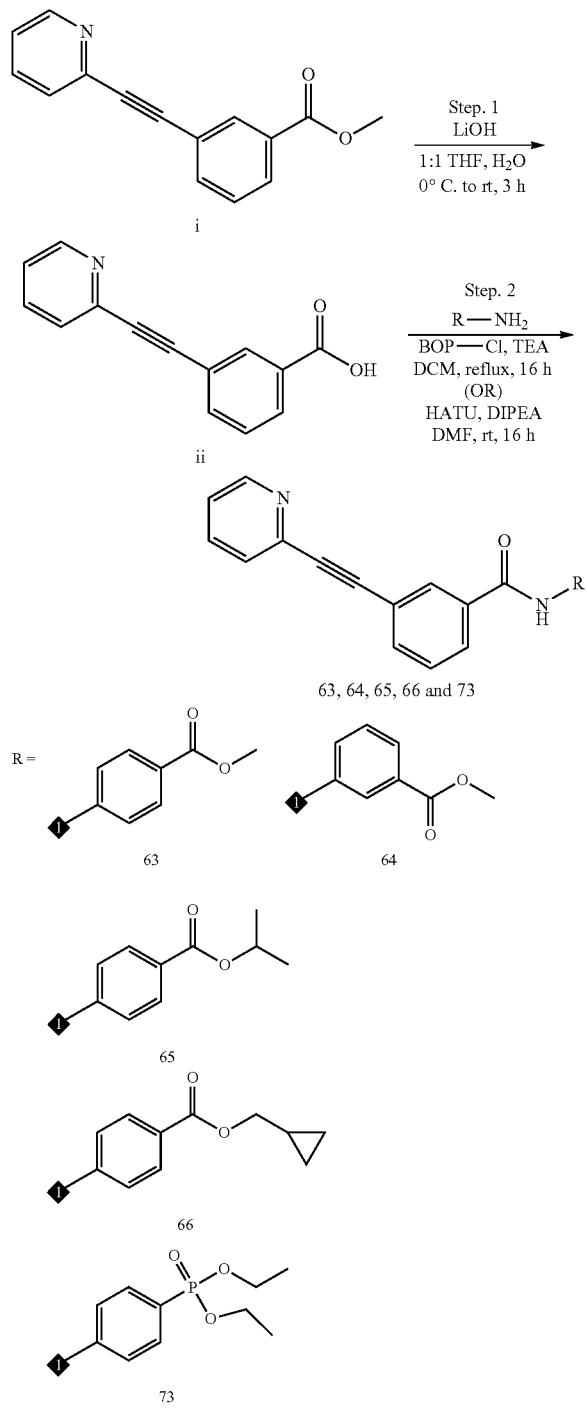

i. Step 1: 3-(pyridin-2-ylethynyl)benzoic acid (ii)

Lithium hydroxide monohydrate (18.9 mmol) was added to a solution of methyl 3-(pyridin-2-ylethynyl)benzoate (i) (6.3 mmol) in THF (5 mL) and $H_2O$ (5 mL). The reaction mixture was then stirred at rt for 3 h. The solution was concentrated to dryness under reduced pressure, and the residue was neutralized with 1N HCl. A precipitate was formed immediately which was collected by filtration, and washed with $H_2O$ to yield the product (ii). Yield: 670 mg (47%). $^1$H NMR (DMSO-$d_6$) δ 8.52 (ddd, J=4.9, 1.8, 1.0 Hz, 1H), 8.15 (s, 1H), 7.97 (d, J=7.7 Hz, 1H), 7.73 (td, J=7.7, 1.8 Hz, 1H), 7.50 (ddt, J=7.6, 4.0, 1.2 Hz, 2H), 7.38-7.21 (m, 2H).

ii. Step 2: General Synthetic Procedure for BOP-Cl Mediated Amidation

To an anhydrous DCM (5 mL) solution of 3-(pyridin-2-ylethynyl)benzoic acid (ii) (1 mmol) under nitrogen at room temperature, BOP-Cl (1.5 mmol) was added followed by the addition of triethylamine (3 mmol) and the reaction mixture was stirred at same temperature for about 10 min. Then corresponding amine was added to the reaction mixture and refluxed for 16 h. The reaction was allowed to cool to room temperature, diluted with water (50 mL) and extracted with DCM (2×100 mL). The organic layer was washed with brine, dried over anhydrous $Na_2SO_4$, and solvent was removed under reduced pressure, followed by purification.

iii. Step 2: General Synthetic Procedure for HATU Mediated Amidation

To a solution of carboxylic acid (1 mmol) in anhydrous DMF (5 mL) under nitrogen at room temperature, HATU (1.5 mmol) was added followed by the addition of DIPEA (3 mmol) and the reaction was stirred at same temperature for about 10 min. Appropriate amine was added to the reaction mixture and stirring continued at rt for 16 hrs. After completion of the reaction, the reaction mixture was diluted with water (50 mL) and extracted with EtOAc (2×100 mL). The combined organic layer was washed with brine, dried over anhydrous $Na_2SO_4$ and solvent was removed under reduced pressure followed by purification using pre-packed Silica gel column on ISCO gave pure product.

(i) Methyl 4-(3-(pyridin-2-ylethynyl)benzamido)benzoate (63)

This compound synthesized by BOP-Cl method. Purification on pre-packed Silica gel column on ISCO using 0-100% EtOAc in Hex (30 min). Yield: 25 mg (38%). $^1$H NMR (CDCl$_3$) δ 8.65 (s, 1H), 8.19 (s, 1H), 8.11-8.02 (m, 3H), 7.92 (dt, J=7.9, 1.6 Hz, 1H), 7.82-7.68 (m, 4H), 7.58-7.47 (m, 2H), 7.33-7.26 (m, 1H), 3.92 (s, 3H). HR-ESIMS: m/z 357.1161 [M+H]$^+$ calcd. for $C_{22}H_{17}N_2O_3$, found 357.1234. HPLC purity: 96% (Retention Time=11.5 min).

(ii) Methyl 3-(3-(pyridin-2-ylethynyl)benzamido)benzoate (64)

This compound synthesized by HATU method. Purification on pre-packed Silica gel column on ISCO using 0-20% MeOH in $CH_2Cl_2$ (30 min). Yield: 23 mg (46%). $^1$H NMR (CDCl$_3$) δ 8.61 (dd, J=5.1, 1.7 Hz, 1H), 8.32 (t, J=1.9 Hz, 1H), 8.22 (d, J=1.8 Hz, 1H), 8.07 (ddd, J=8.1, 2.2, 1.1 Hz, 1H), 8.01 (s, 1H), 7.83 (dt, J=7.7, 1.3 Hz, 2H), 7.77 (d, J=7.8 Hz, 1H), 7.65-7.61 (m, 1H), 7.54 (s, 1H), 7.47 (s, 1H), 7.42-7.38 (m, 1H), 3.94 (d, J=0.8 Hz, 3H). HR-ESIMS: m/z 357.1161 [M+H]$^+$ calcd. for $C_{22}H_{17}N_2O_3$, found 357.1243. HPLC purity: 99.3% (Retention Time=11.7 min).

(iii) Isopropyl 4-(3-(pyridin-2-ylethynyl)benzamido)benzoate (65)

This compound synthesized by BOP-Cl method. Purification on pre-packed Silica gel column on ISCO using 0-20% MeOH in CH$_2$Cl$_2$ (30 min). Yield: 44 mg (50%). $^1$H NMR (CDCl$_3$) δ 8.65 (ddd, J=4.9, 1.8, 1.0 Hz, 1H), 8.55 (s, 1H), 8.08-8.00 (m, 3H), 7.92 (ddd, J=7.8, 1.9, 1.2 Hz, 1H), 7.83-7.76 (m, 2H), 7.74-7.67 (m, 2H), 7.55-7.43 (m, 2H), 7.28 (ddd, J=7.7, 4.9, 1.2 Hz, 1H), 5.33-5.11 (m, 1H), 1.37 (d, J=6.3 Hz, 6H). HR-ESIMS: m/z 385.1474 [M+H]$^+$ calcd. for C$_{24}$H$_{21}$N$_2$O$_3$, found 385.1546. HPLC purity: 98.7% (Retention Time=13.1 min).

(iv) Cyclopropylmethyl 4-(3-(pyridin-2-ylethynyl)benzamido)benzoate (66)

This compound was synthesized by using HATU method. Purification on pre-packed Silica gel column on ISCO using 0-90% EtOAc in Hex (30 min). Yield: 20 mg (31%). $^1$H NMR (CDCl$_3$) δ 8.65 (ddd, J=4.9, 1.8, 0.9 Hz, 1H), 8.52 (s, 1H), 8.11-8.05 (m, 2H), 8.04 (d, J=1.8 Hz, 1H), 7.92 (ddd, J=7.9, 1.9, 1.1 Hz, 1H), 7.83-7.78 (m, 2H), 7.71 (td, J=7.8, 1.7 Hz, 2H), 7.55-7.44 (m, 2H), 7.29 (ddd, J=7.7, 4.9, 1.2 Hz, 1H), 4.14 (d, J=7.2 Hz, 2H), 1.31-1.21 (m, 1H), 0.70-0.56 (m, 2H), 0.36 (dt, J=6.2, 4.6 Hz, 2H). HR-ESIMS: m/z 397.1474 [M+H]$^+$ calcd. for C$_{25}$H$_{21}$N$_2$O$_3$, found 397.1543. HPLC purity: 97.4% (Retention Time=13.9 min).

(v) Diethyl (4-(3-(pyridin-2-ylethynyl)benzamido)phenyl)phosphonate, trifluoroacetate salt (73)

This compound was synthesized by using BOP-Cl method. Purification on C-18 column (Accq prep Hp-125) using 0-100% CH$_3$CN in H$_2$O each solvent containing 0.1% TFA (35 min). Yield: 40 mg (54%). $^1$H NMR (CDCl$_3$) δ 8.98 (s, 1H), 8.63 (d, J=4.9 Hz, 1H), 8.07 (t, J=1.7 Hz, 1H), 7.94 (dt, J=8.0, 1.4 Hz, 1H), 7.86 (dd, J=8.5, 3.6 Hz, 2H), 7.81-7.67 (m, 4H), 7.53 (dt, J=7.9, 1.1 Hz, 1H), 7.45 (t, J=7.8 Hz, 1H), 7.30 (ddd, J=7.6, 4.9, 1.2 Hz, 1H), 4.22-3.94 (m, 4H), 1.30 (t, J=7.1 Hz, 6H). HR-ESIMS: m/z 435.1395 [M+H]$^+$ calcd. for C$_{24}$H$_{24}$N$_2$O$_4$P, found 435.1463 [M+H]$^+$. HPLC purity: 100% (Retention Time=1.99 min).

t. Preparation of Compound No. 60

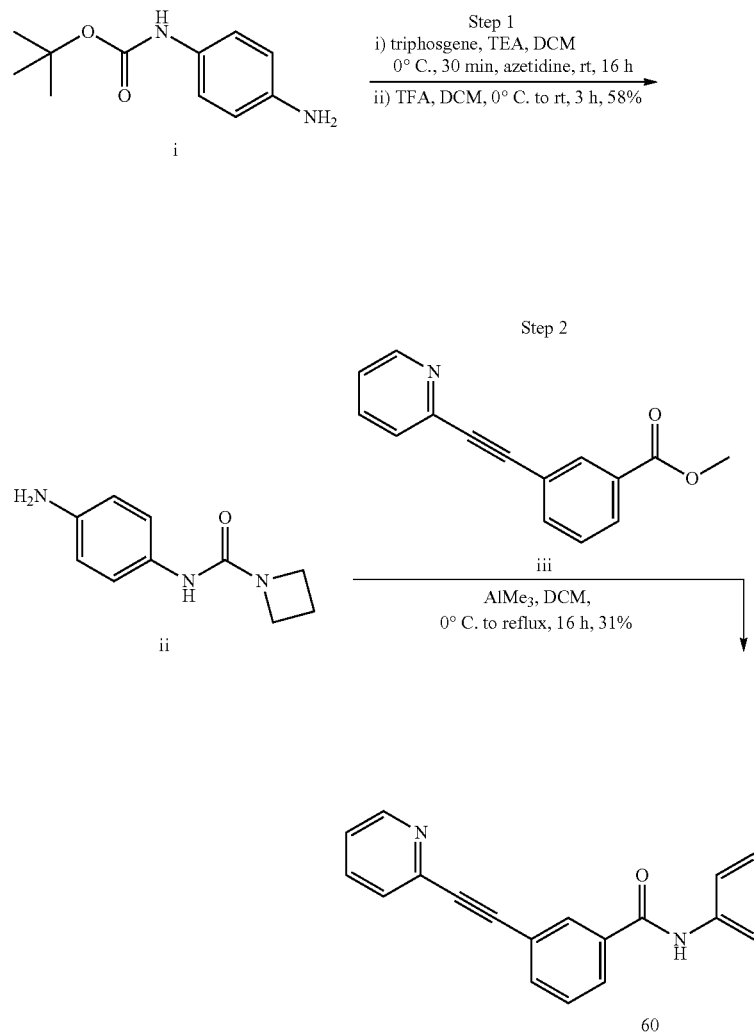

i. Step 1: Synthesis of N-(4-aminophenyl)azetidine-1-carboxamide (ii)

tert-butyl (4-aminophenyl)carbamate (i) (250 mg, 1.2 mmol) was dissolved in anhydrous DCM (5 mL) to this solution at 0° C. under inert atmosphere triphosgene (356.2 mg, 1.2 mmol) was added followed by the addition of triethylamine (0.50 mL, 3.6 mmol) and the reaction stirred at room temperature for 30 min then azetidine (68.5 mg, 1.2 mmol) was added to the reaction and stirring continued for 16 h. After completion of reaction diluted with aq Sat NaHCO$_3$ solution and extracted with DCM (2×100 mL), the combined organic layer was dried over anhydrous Na$_2$SO$_4$, filtered and concentrated under reduced pressure. Then dissolved in 3 mL of DCM, at 0° C. trifluoroacetic acid (0.91 mL, 12 mmol) was added and stirred at rt for 3 h. After completion of reaction concentrated under reduced pressure diluted with aq sat NaHCO$_3$ and then extracted with EtOAc (2×100 mL). The combined organic layer was dried over anhydrous Na$_2$SO$_4$, filtered, concentrated under reduced pressure, followed by purification on ISCO using 0-20% MeOH in DCM. Yield: 133 mg (58%). $^1$H NMR (CDCl$_3$) δ H NMR (400 MHz, cdcl$_3$) δ 7.17-7.08 (m, 2H), 6.66-6.57 (m, 2H), 4.01 (t, J=7.5 Hz, 4H), 3.54 (s, 2H), 2.47-2.11 (m, 2H). ESIMS: m/z 192.1[M+1].$^+$ ii. Step 2: Synthesis of N-(4-(3-(pyridin-2-ylethynyl)benzamido)phenyl)azetidine-1-carboxamide (60)

N-(4-aminophenyl)azetidine-1-carboxamide (ii) (28.mg, 0.1500 mmol) was dissolved in anhydrous DCM, to this solution under nitrogen at 0° C., trimethylaluminium (31.5 mg, 0.45 mmol) was added dropwise, after which ice bath was removed and the reaction mass was allowed to stir at room temperature for 30 min, then methyl 3-[2-(2-pyridyl)ethynyl]benzoate (iii) (34.7 mg, 0.15 mmol) was added to the reaction and refluxed for 16 h, The mixture was allowed to cool to room temperature, quenched with the addition of 3 mL of methanol, concentrated under reduced pressure, crude mass was diluted with water (100 mL) and extracted with EtOAc (2×150 mL). The organic layer was washed with brine, dried over anhydrous Na$_2$SO$_4$ and solvent was removed under reduced pressure. The crude was purified using pre-packed Silica gel column on ISCO using 0-20% MeOH in DCM (30 min). Yield: 19 mg (31%). $^1$H NMR (CDCl$_3$) δ 8.54 (ddd, J=5.0, 1.8, 1.0 Hz, 1H), 8.09 (t, J=1.8 Hz, 1H), 7.92 (dt, J=7.9, 1.5 Hz, 1H), 7.74-7.64 (m, 2H), 7.59-7.49 (m, 3H), 7.44 (td, J=7.8, 0.6 Hz, 1H), 7.35-7.29 (m, 2H), 7.29-7.26 (m, 1H), 4.16-3.81 (m, 4H), 2.36-2.15 (m, 2H). HR-ESIMS: m/z 397.1586 [M+H]$^+$ calcd. for C$_{24}$H$_{21}$N$_4$O$_2$, found 397.1663. HPLC purity: 95% (Retention Time=9.0 min).

u. Preparation of Compound No. 62

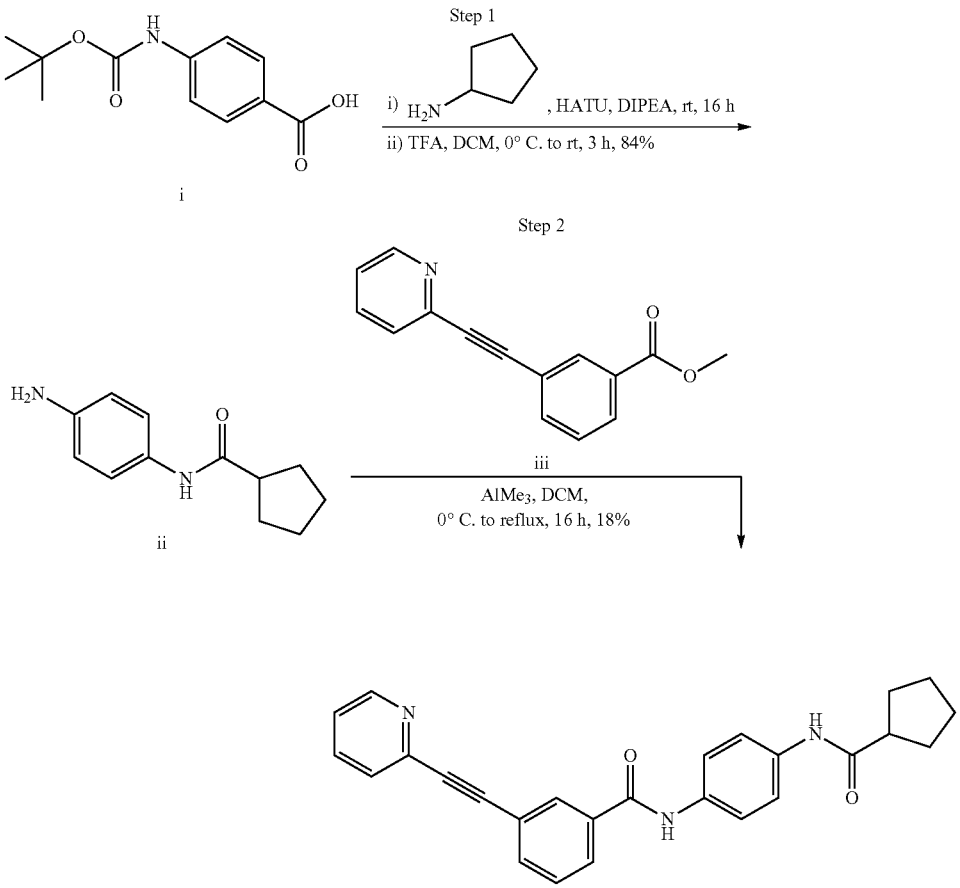

Scheme 20 i. Step 1: Synthesis of 4-amino-N-cyclopentylbenzamide 4-((tert-butoxycarbonyl)amino)benzoic acid (i) (200 mg, 0.84 mmol) was dissolved in anhydrous DMF, to this solution under nitrogen at room temperature HATU (480.8 mg, 1.26 mmol) was added followed by the addition of N,N-Diisopropylethylamine (0.44 mL, 2.53 mmol) and the reaction stirred at rt for 5 min, then Cyclopentylamine (0.083 mL, 0.84 mmol) was added to the reaction and stirring continued at rt for 16 h. After completion of reaction diluted with water (50 mL), extracted with EtOAc (2×100 mL). The combined organic layer was dried over anhydrous $Na_2SO_4$, filtered, concentrated under reduced pressure. This crude material was dissolved in 5 mL of DCM, at 0° C. to this solution trifluoroacetic acid (0.64 mL, 8.43 mmol) was added, stirred at rt for 3 h. After completion of reaction concentrated under reduced pressure, diluted with 100 mL aq $NaHCO_3$ solution, extracted with EtOAc (2×100 mL), the combined organic layer was dried over anhydrous $Na_2SO_4$, filtered, concentrated under reduced pressure. Purification was not needed for this material. Yield: 145 mg (84%). $^1$H NMR (CDCl$_3$) δ 7.62-7.51 (m, 2H), 6.63 (dd, J=8.0, 1.3 Hz, 2H), 4.36 (q, J=7.0 Hz, 1H), 2.14-1.97 (m, 2H), 1.78-1.55 (m, 4H), 1.53-1.38 (m, 2H). ESIMS: m/z 205.1[M+1].$^+$ ii. Step 2: Synthesis of N-(4-(cyclopentylcarbamoyl)phenyl)-3-(pyridin-2-ylethynyl)benzamide (62)

4-amino-N-cyclopentylbenzamide (ii) (50 mg, 0.24 mmol) was dissolved in anhydrous DCM to this solution under nitrogen at 0° C., trimethylaluminium (53.0 mg, 0.73 mmol) was added dropwise, after which, ice bath was removed and the reaction mass was allowed to stir at room temperature for 30 min, then methyl 3-(pyridin-2-ylethynyl)benzoate (iii) (58.0 mg, 0.24 mmol) was added to the reaction and refluxed for 16 h, The mixture was allowed to cool to room temperature, quenched with the addition of 3 mL of methanol, concentrated under reduced pressure, crude mass was diluted with water (50 mL) and extracted with EtOAc (2×100 mL). The combined organic layer was washed with brine, dried over anhydrous $Na_2SO_4$ and solvent was removed under reduced pressure. The crude was purified using pre-packed Silica gel column on ISCO using 0-20% MeOH in DCM (30 min). Yield: 18 mg (18%). $^1$H NMR (CDCl$_3$) δ 10.53 (s, 1H), 8.63 (ddd, J=4.9, 1.8, 1.0 Hz, 1H), 8.22 (td, J=1.7, 0.6 Hz, 1H), 8.17 (d, J=7.3 Hz, 1H), 8.02 (ddd, J=7.8, 1.9, 1.2 Hz, 1H), 7.91-7.78 (m, 6H), 7.69 (dt, J=7.8, 1.1 Hz, 1H), 7.63 (td, J=7.8, 0.6 Hz, 1H), 7.44 (ddd, J=7.7, 4.8, 1.2 Hz, 1H), 4.32-4.10 (m, 1H), 1.87 (dt, J=8.6, 5.1 Hz, 2H), 1.79-1.60 (m, 2H), 1.60-1.32 (m, 4H). HR-ESIMS: m/z 410.1790 [M+H]$^+$ calcd. for $C_{26}H_{24}N_3O_2$, found 410.1867. HPLC purity: 100% (Retention Time=11.4 min).

v. Preparation of Compound Nos. 72 and 75

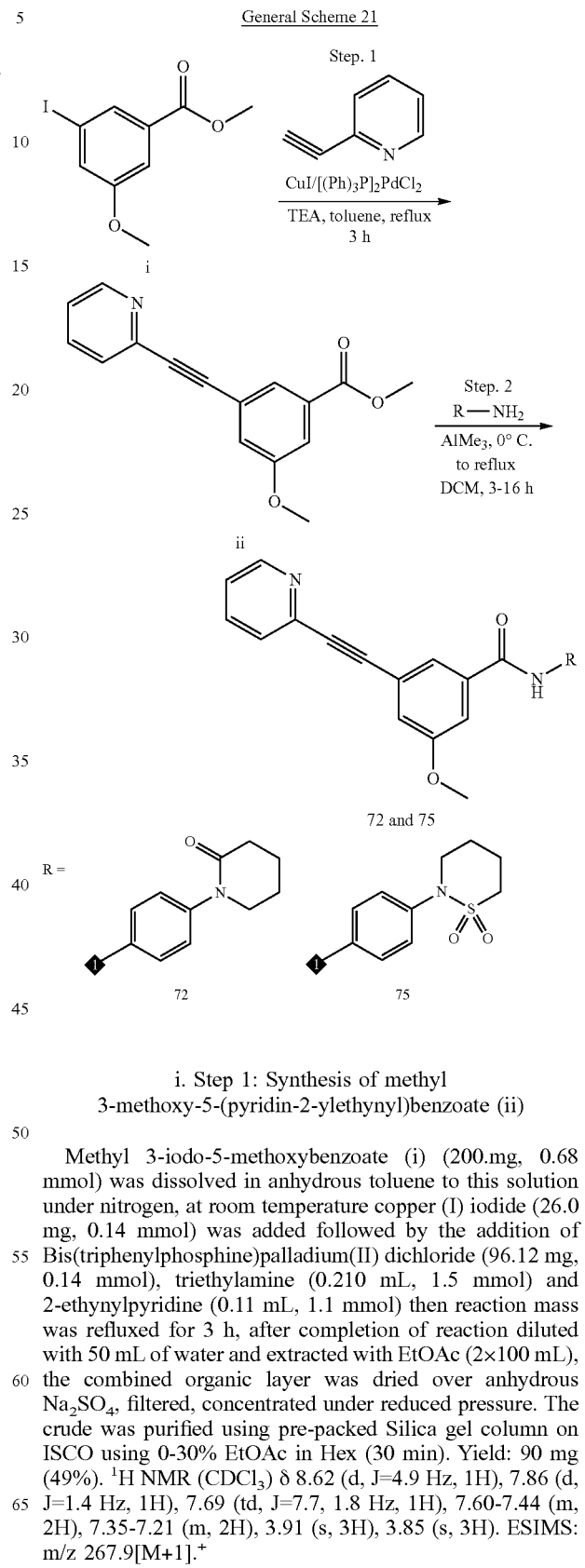

i. Step 1: Synthesis of methyl 3-methoxy-5-(pyridin-2-ylethynyl)benzoate (ii)

Methyl 3-iodo-5-methoxybenzoate (i) (200.mg, 0.68 mmol) was dissolved in anhydrous toluene to this solution under nitrogen, at room temperature copper (I) iodide (26.0 mg, 0.14 mmol) was added followed by the addition of Bis(triphenylphosphine)palladium(II) dichloride (96.12 mg, 0.14 mmol), triethylamine (0.210 mL, 1.5 mmol) and 2-ethynylpyridine (0.11 mL, 1.1 mmol) then reaction mass was refluxed for 3 h, after completion of reaction diluted with 50 mL of water and extracted with EtOAc (2×100 mL), the combined organic layer was dried over anhydrous $Na_2SO_4$, filtered, concentrated under reduced pressure. The crude was purified using pre-packed Silica gel column on ISCO using 0-30% EtOAc in Hex (30 min). Yield: 90 mg (49%). $^1$H NMR (CDCl$_3$) δ 8.62 (d, J=4.9 Hz, 1H), 7.86 (d, J=1.4 Hz, 1H), 7.69 (td, J=7.7, 1.8 Hz, 1H), 7.60-7.44 (m, 2H), 7.35-7.21 (m, 2H), 3.91 (s, 3H), 3.85 (s, 3H). ESIMS: m/z 267.9[M+1].$^+$ ii. Step 2: Synthesis of 3-methoxy-N-(4-(2-oxopiperidin-1-yl)phenyl)-5-(pyridin-2-ylethynyl)benzamide (72)

1-(4-Aminophenyl)piperidin-2-one (35.6 mg, 0.19 mmol) was dissolved in anhydrous DCM, to this solution under nitrogen at 0° C., trimethylaluminium (40.5 mg, 0.56 mmol) was added dropwise, after which, ice bath was removed and the reaction mass was allowed to stir at room temperature for 30 min, then methyl 3-methoxy-5-[12-(2-pyridyl)ethynyl] benzoate (ii) (50.0 mg, 0.19 mmol) was added to the reaction and refluxed for 3 h, The mixture was allowed to cool to room temperature, quenched with the addition of 3 mL of methanol, concentrated under reduced pressure, crude mass was diluted with water (50 mL) and extracted with EtOAc (2×100 mL). The combined organic layer was washed with brine, dried over anhydrous $Na_2SO_4$ and solvent was removed under reduced pressure. The crude was purified using pre-packed Silica gel column on ISCO using 0-20% MeOH in DCM (30 min). Yield: 52 mg (65%). $^1$H NMR ($CDCl_3$) δ 8.59 (d, J=4.6 Hz, 1H), 7.76-7.67 (m, 2H), 7.66-7.59 (m, 2H), 7.54 (d, J=7.8 Hz, 1H), 7.50 (dd, J=2.7, 1.4 Hz, 1H), 7.28 (dd, J=7.6, 4.7 Hz, 1H), 7.23 (dd, J=2.6, 1.2 Hz, 1H), 7.12 (d, J=8.5 Hz, 2H), 3.85 (s, 3H), 3.57 (d, J=6.0 Hz, 2H), 2.53 (t, J=6.0 Hz, 2H), 1.94-1.83 (m, 4H). HR-ESIMS: m/z 426.1739 $[M+H]^+$ calcd. for $C_{26}H_{24}N_3O_3$, found 426.8167. HPLC purity: 100% (Retention Time=1.9 min).

iii. Synthesis of N-(4-(1,1-dioxido-1,2-thiazinan-2-yl)phenyl)-3-methoxy-5-(pyridin-2-ylethynyl)benzamide (75)

4-(1,1-dioxothiazinan-2-yl)aniline (59.3 mg, 0.26 mmol) was dissolved in anhydrous DCM to this solution under nitrogen at 0° C., trimethylaluminium (56.6 mg, 0.79 mmol) was added dropwise, after which, ice bath was removed and the reaction mass was allowed to stir at room temperature for 30 min, then methyl 3-methoxy-5-[2-(2-pyridyl)ethynyl] benzoate (ii) (70.0 mg, 0.26 mmol) was added to the reaction and refluxed for 16 h, The mixture was allowed to cool to room temperature, quenched with the addition of 3 mL of methanol, concentrated under reduced pressure, crude mass was diluted with water (50 mL) and extracted with EtOAc (2×100 mL). The combined organic layer was washed with brine, dried over anhydrous $Na_2SO_4$ and solvent was removed under reduced pressure. The crude was purified using pre-packed Silica gel column on ISCO using 0-5% MeOH in DCM (30 min). Yield: 87 mg (72%). $^1$H NMR ($CDCl_3$) δ 8.63 (ddd, J=4.9, 1.8, 1.0 Hz, 1H), 8.50 (s, 1H), 7.74-7.64 (m, 3H), 7.60 (t, J=1.4 Hz, 1H), 7.52 (dt, J=7.8, 1.1 Hz, 1H), 7.47 (dd, J=2.5, 1.5 Hz, 1H), 7.28 (dd, J=8.2, 3.5 Hz, 3H), 7.23 (dd, J=2.6, 1.2 Hz, 1H), 3.84 (s, 3H), 3.71-3.64 (m, 2H), 3.25-3.17 (m, 2H), 2.29 (t, J=6.3 Hz, 2H), 1.93-1.83 (m, 2H). HR-ESIMS: m/z 462.1409 $[M+H]^+$ calcd. for $C_{25}H_{24}N_3O_4S$, found 462.1483. HPLC purity: 100% (Retention Time=11.6 min).

2. Biology Experimentals a. Method for Coronavirus CPE Reduction Assay

Screening Strategy: A cell based assay measuring the cytopathic effect (CPE) of the virus infecting Vero E6 host cells was used. The CPE reduction assay is a popular and widely used assay format to screen for antiviral agents because of its ease of use in high throughput screening (HTS). In this assay, host cells infected with virus die as a consequence of the virus hijacking the cellular mechanisms for genome replication. The CPE reduction assay indirectly monitors the effect of antiviral agents acting through various molecular mechanisms by measuring the viability of host cells three days after inoculation with virus. Anti-viral compounds are identified as those that protect the host cells from the cytopathic effect of the virus, thereby increasing viability.

b. Method for Measuring Antiviral Effect of Compounds

Vero E6 cells were selected for expression of the SARS CoV receptor (ACE2; angiotensin-converting enzyme 2) was used for the CPE assay. Cells were grown in MEM/10% HI FBS supplemented and harvested in MEM/1% PSG/ supplemented with 2% HI FBS. Cells were batch inoculated with appropriate coronavirus (Toronto 2 SARS CoV-1 or USA_WA1/2020 SARS CoV-2) at M.O.I.~0.002, which results in 5% cell viability 72 (for SARS) hours post infection. Assay Ready Plates (ARPs; Corning 3712BC) pre-drugged with test compounds (30-90 nL sample in 100% DMSO per well dispensed using a Labcyte ECHO 550) were prepared in the BSL-2 lab by adding 5 μL assay media to each well. The plates were passed into the BSL-3 facility where a 25 μL aliquot of virus inoculated cells (4000 Vero E6 cells/well) was added to each well in columns 3-22. The wells in columns 23-24 contained virus infected cells only (no compound treatment). Prior to virus infection, a 25 μL aliquot of cells was added to columns 1-2 of each plate for the cell only (no virus) controls. After incubating plates at 37° C./5% $CO_2$ and 90% humidity for 72 hours, 30 μL of Cell Titer-Glo (Promega) was added to each well. Luminescence was read using a Perkin Elmer Envision or BMG CLARIOstar plate reader following incubation at room temperature for 10 minutes to measure cell viability. Raw data from each test well was normalized to the average signal of non-infected cells (Avg Cells; 100% inhibition) and virus infected cells only (Avg Virus; 0% inhibition) to calculate % inhibition of CPE using the following formula: % inhibition=100*(Test Cmpd−Avg Virus)/(Avg Cells−Avg Virus). The SARS CPE assay was conducted in BSL-3 containment with plates being sealed with a clear cover and surface decontaminated prior to luminescence reading.

c. Method for Measuring Cytotoxic Effect of Compounds

Compound cytotoxicity was assessed in a BSL-2 counter screen as follows: Host cells in media were added in 25 μl aliquots (4000 cells/well) to each well of assay ready plates prepared with test compounds as above. Cells only (100% viability) and cells treated with hyamine at 100 μM final concentration (0% viability) serve as the high and low signal controls, respectively, for cytotoxic effect in the assay. DMSO was maintained at a constant concentration for all wells (0.3%) as dictated by the dilution factor of stock test compound concentrations. After incubating plates at 37° C./5% $CO_2$ and 90% humidity for 72 hours, 30 μl Cell Titer-Glo (Promega) was added to each well. Luminescence was read using a BMG PHERAstar plate reader following incubation at room temperature for 10 minutes to measure cell viability.

3. Evaluation of Antiviral Activity

A list of compounds evaluated for antiviral activity is shown in Tables 1 and 2 below.

TABLE 1
| No. | Structure |
|---|---|
| 1–16 | 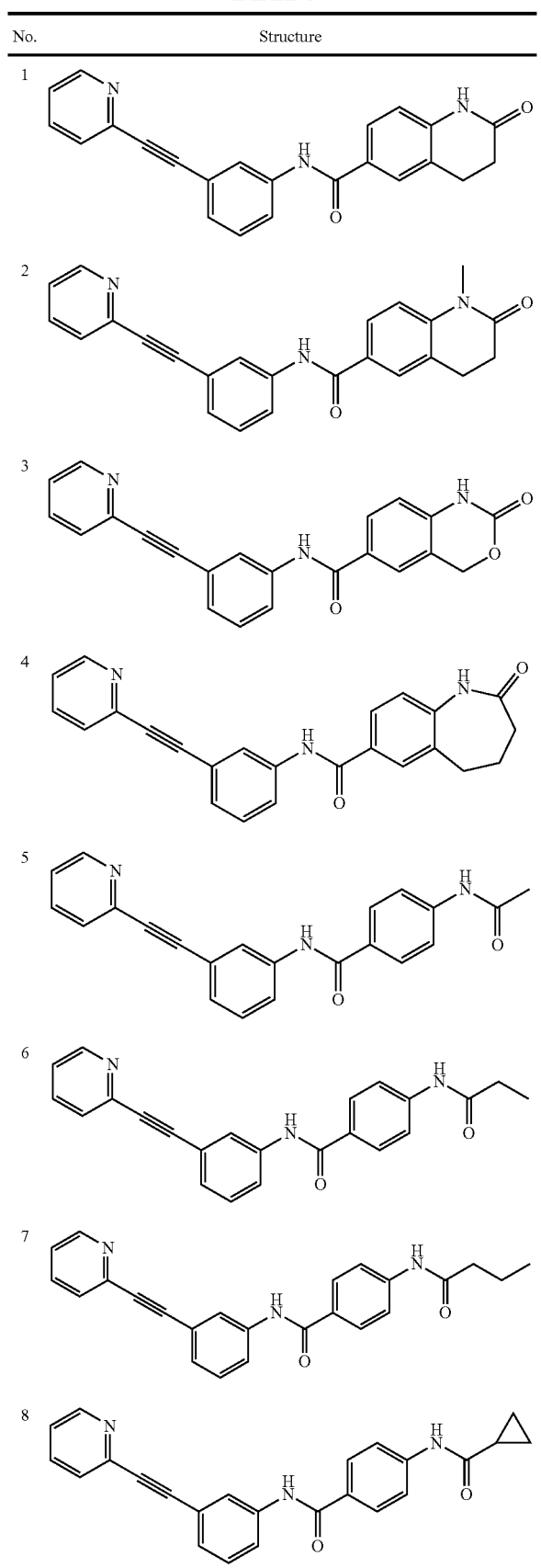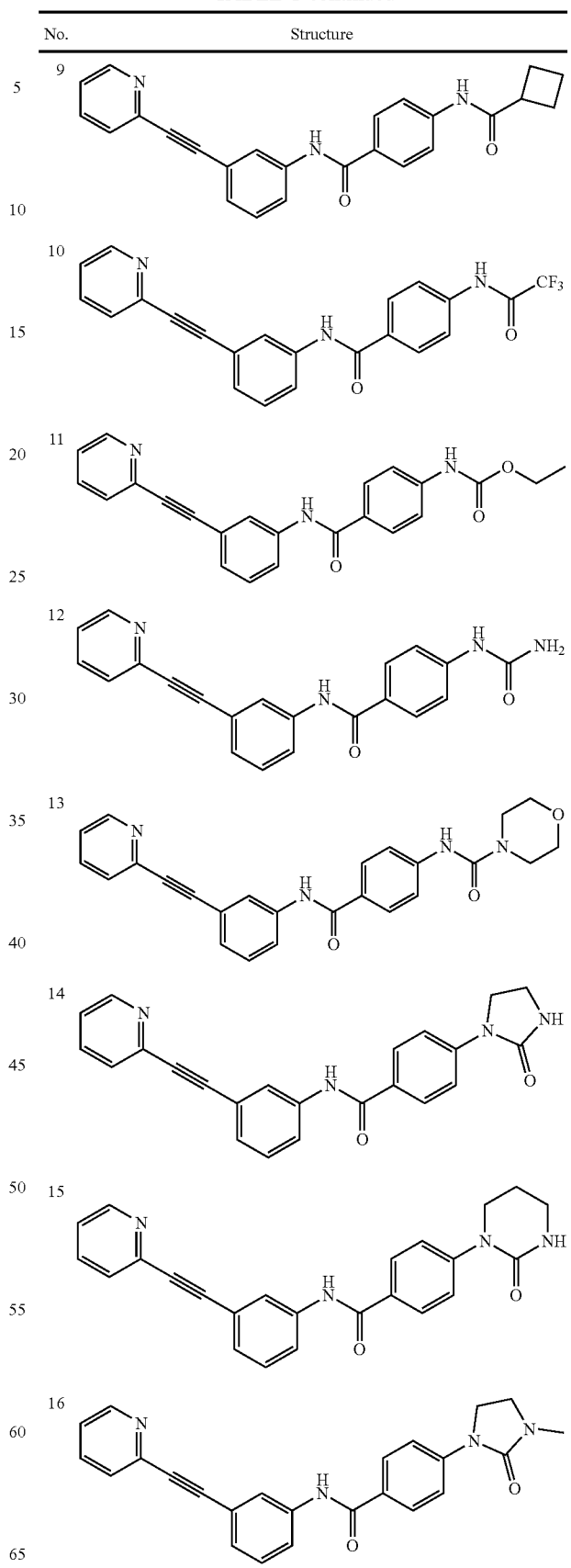 |

TABLE 1-continued
| No. | Structure |
|---|---|
| 17 | 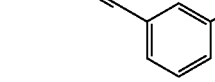 |
| 18 | 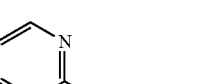 |
| 19 | 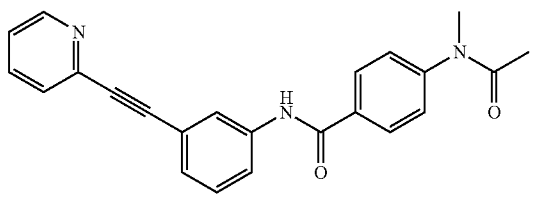 [SMILES: CC(=O)N(C)c1ccc(C(=O)Nc2cccc(C#Cc3ccccn3)c2)cc1] |
| 20 | 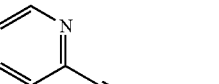 |
| 21 | 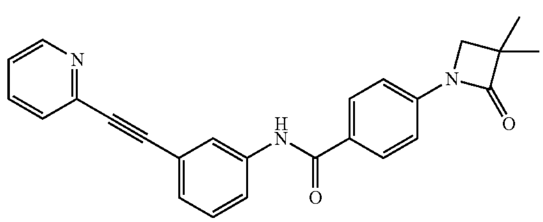 [SMILES: CC1(C)CN(c2ccc(C(=O)Nc3cccc(C#Cc4ccccn4)c3)cc2)C1=O] |
| 22 | 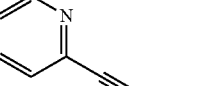 |
| 23 | 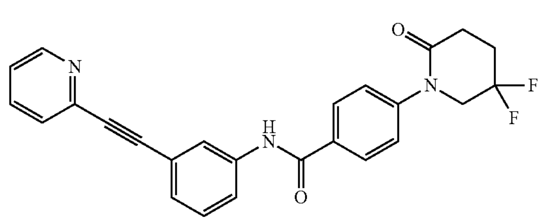 [SMILES: O=C(Nc1cccc(C#Cc2ccccn2)c1)c1ccc(N2CC(F)(F)CCC2=O)cc1] |
| 24 | 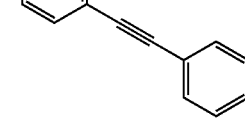 |
| 25 | 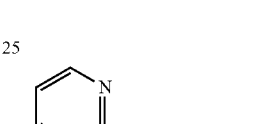 |
| 26 | 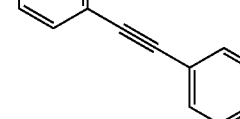 |
| 27 | 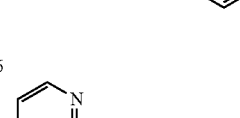 |
| 28 | 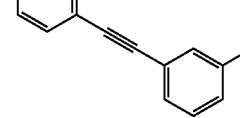 |
| 29 |  |
| 30 | 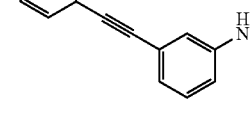 |

TABLE 1-continued
| No. | Structure |
|---|---|
| 31 | 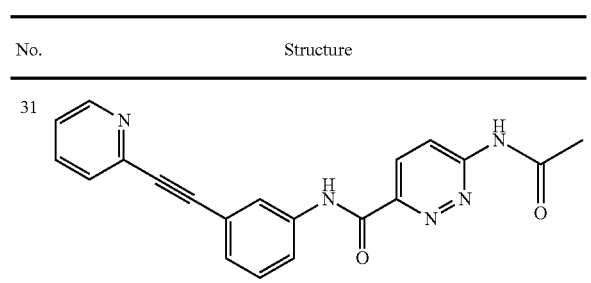 |
| 32 | 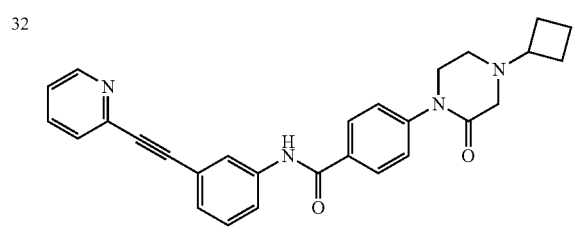 |
| 33 | 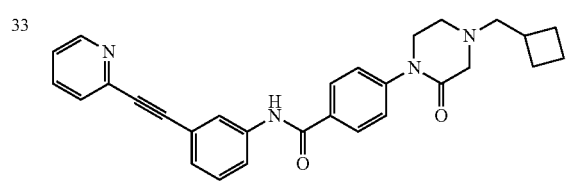 |
| 34 | 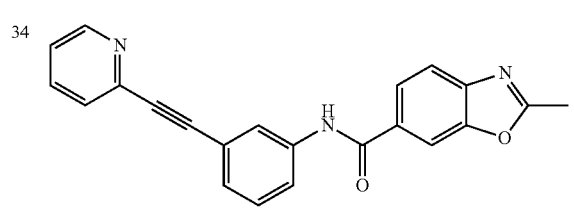 |
| 35 | 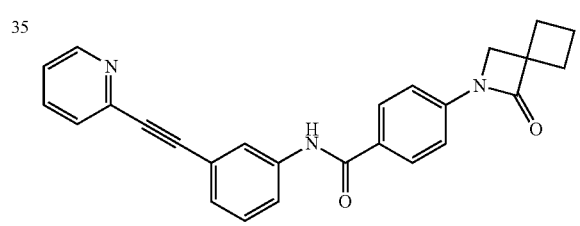 |
| 36 | 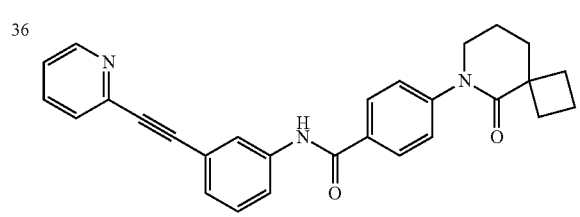 |
| 37 | 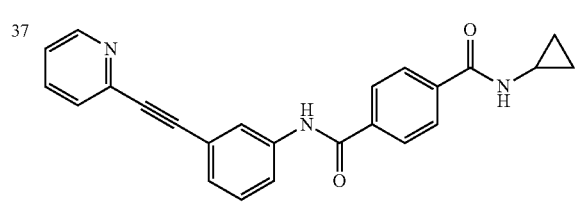 |
TABLE 1-continued
| No. | Structure |
|---|---|
| 38 | 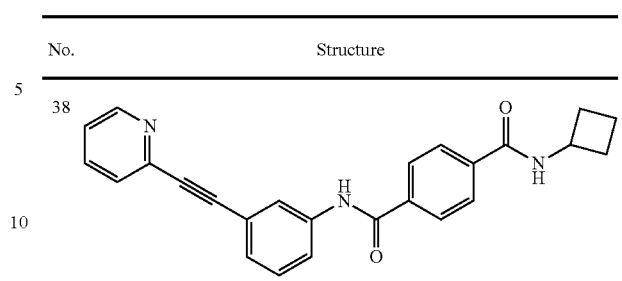 |
| 39 | 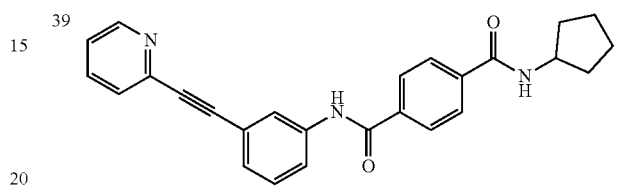 |
| 40 | 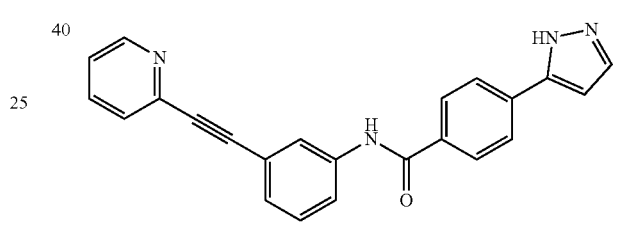 |
| 41 | 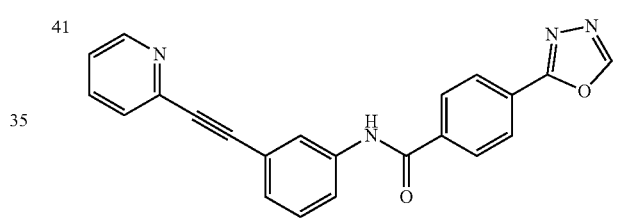 |
| 42 | 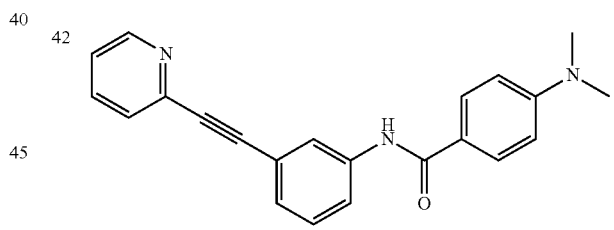 |
| 43 | 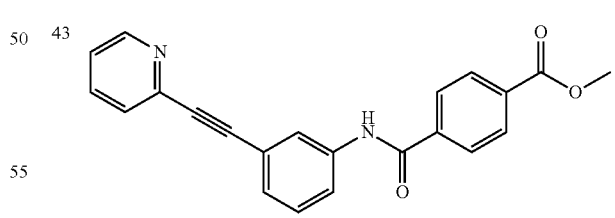 |
| 44 | 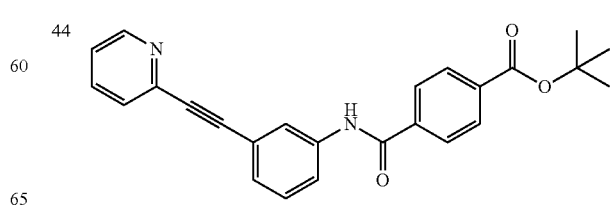 |

TABLE 1-continued

| No. | Structure |
|---|---|
| 45 | 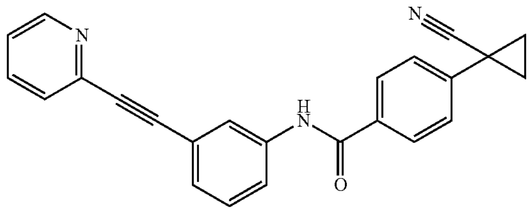 [SMILES: N#CC1(c2ccc(C(=O)Nc3cccc(C#Cc4ccccn4)c3)cc2)CC1] |
| 46 | 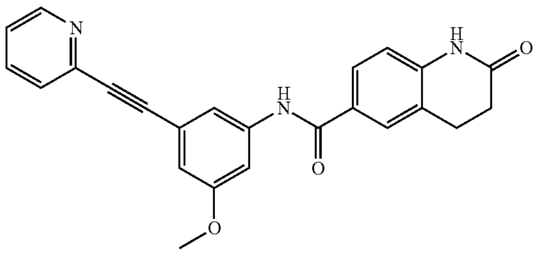 [SMILES: COc1cc(C#Cc2ccccn2)cc(NC(=O)c2ccc3c(c2)CCC(=O)N3)c1] |
| 47 | 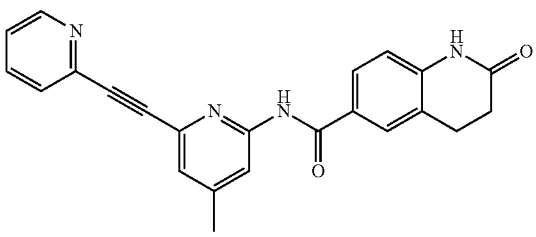 [SMILES: Cc1cc(C#Cc2ccccn2)nc(NC(=O)c2ccc3c(c2)CCC(=O)N3)c1] |
| 48 | 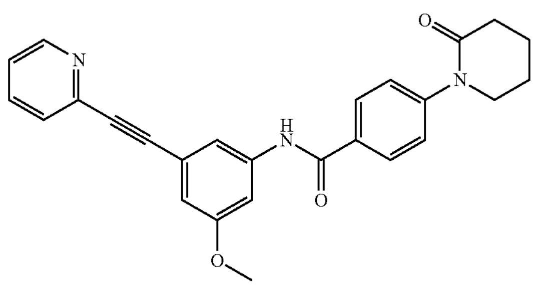 [SMILES: COc1cc(C#Cc2ccccn2)cc(NC(=O)c2ccc(N3CCCCC3=O)cc2)c1] |
| 49 | 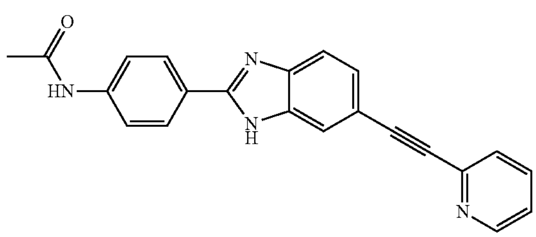 [SMILES: CC(=O)Nc1ccc(-c2nc3ccc(C#Cc4ccccn4)cc3[nH]2)cc1] |
| 50 | 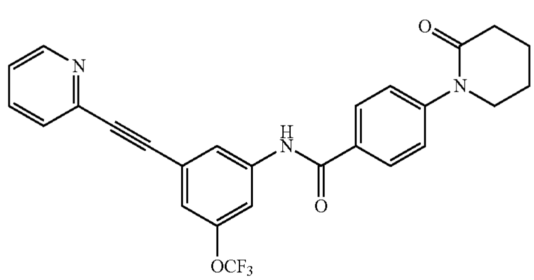 [SMILES: Nc1cc(C#Cc2ccccn2)cc(NC(=O)c2ccc(N3CCCCC3=O)cc2)c1] |
| 51 | |
| 52 | |
| 53 | |
| 54 | |
| 55 | |
| 56 | |

TABLE 1-continued
| No. | Structure |
|---|---|
| 57 | 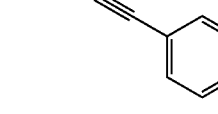 |
| 58 | 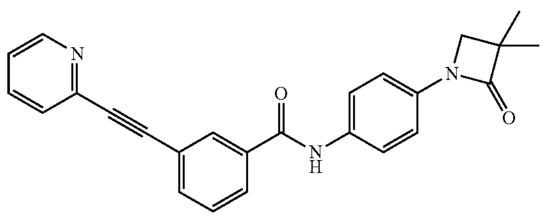 [SMILES: CC1(C)CN(c2ccc(NC(=O)c3cccc(C#Cc4ccccn4)c3)cc2)C1=O] |
| 59 | 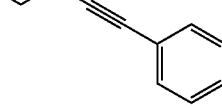 |
| 60 | 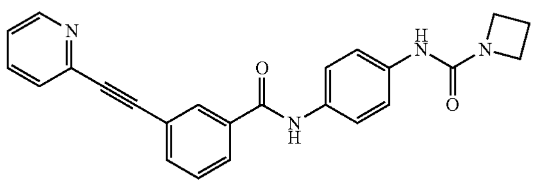 [SMILES: O=C(Nc1ccc(NC(=O)N2CCC2)cc1)c1cccc(C#Cc2ccccn2)c1] |
| 61 | 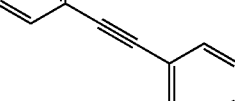 |
| 62 | 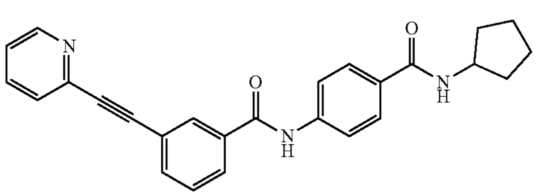 [SMILES: O=C(Nc1ccc(C(=O)NC2CCCC2)cc1)c1cccc(C#Cc2ccccn2)c1] |
| 63 | 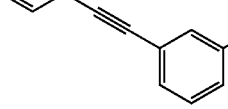 |
| 64 |  |
| 65 | 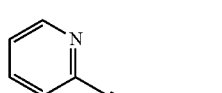 |
| 66 |  |
| 67 | 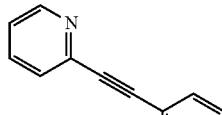 |
| 68 | 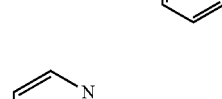 |
| 69 | 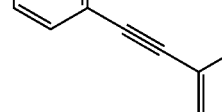 |
| 70 | 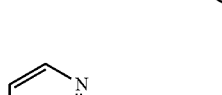 |

TABLE 1-continued

| No. | Structure |
|---|---|
| 71 | (structure) |
| 72 | (structure) |
| 73 | (structure) |
| 74 | (structure) |
| 75 | (structure) |
| 76 | (structure) |
| 77 | (structure) |
| 78 | (structure) |
| 79 | (structure) |
| 80 | (structure) |

TABLE 2

| No. | SARS-1 EC$_{50}$ (µM) VeroE6 | SARS-2 EC$_{50}$ (µM) VeroE6 | CC$_{50}$ (µM) VeroE6 | MW | SARS-2 VU-VTR @ 20 µM (A549-hACE2) (logs) | SARS-2 VU-EC$_{50}$ (µM) (A549-hACE2) |
|---|---|---|---|---|---|---|
| 1 | 5.07 ± 2.89 | 5.81 ± 2.51 | >30 | 367.4 | 1.95 | 7.32 |
| 2 | 1.46 | 2.55 | >30 | 381.4 | 3.32 | 3.59 |
| 3 | >30 | 11.59 | 15.81 | 369.37 | ND | ND |
| 4 | 1.39 | 1.5 | 22.9 | 381.4 | 2.55 | 1.5 |
| 5 | 2.14 | 3.89 | >30 | 355.4 | 2.05 | 3.58 |
| 6 | 0.92 | 1.01 | >30 | 369.42 | ND | ND |
| 7 | 0.16 | 0.26 | >30 | 383.44 | ND | ND |
| 8 | 0.47 | 0.94 | >30 | 381.43 | 1.53 | 1.07 |
| 9 | 0.21 | 0.26 | >30 | 395.45 | 1.88 | 0.69 |
| 10 | 4.89 | 6.52 | >30 | 409.36 | ND | ND |
| 11 | 0.84 | 1.07 | >30 | 385.42 | ND | ND |
| 12 | >30 | >30 | >30 | 356.38 | ND | ND |
| 13 | 7.94 | 8.25 | >40 | 426.47 | ND | ND |
| 14 | 1.05 | 1.06 | >30 | 382.41 | 1.84 | 2.31 |
| 15 | 9.71 | 7.81 | >30 | 396.44 | ND | ND |
| 16 | 0.75 | 1.28 | >30 | 396.44 | ND | ND |
| 17 | 2.37 | 0.61 | >30 | 424.49 | 2.12 | 0.43 |
| 18 | >30 | >30 | >30 | 397.43 | ND | ND |
| 19 | 2.19 | 3.92 | >30 | 369.42 | ND | ND |
| 20 | 2.12 | 11.7 | >30 | 367.4 | ND | ND |

TABLE 2-continued

| No. | SARS-1 EC$_{50}$ (μM) VeroE6 | SARS-2 EC$_{50}$ (μM) VeroE6 | CC$_{50}$ (μM) VeroE6 | MW | SARS-2 VU-VTR @ 20 μM (A549-hACE2) (logs) | SARS-2 VU-EC$_{50}$ (μM) (A549-hACE2) |
|---|---|---|---|---|---|---|
| 21 | 0.52 | 0.32 | >30 | 395.45 | ND | ND |
| 22 | 1.3 | 1.87 | >30 | 395.45 | 2.4 | 1.05 |
| 23 | 1.737 | 2.44 | >30 | 431.43 | ND | ND |
| 24 | >30 | >30 | >30 | 411.45 | ND | ND |
| 25 | 0.52 | 1.09 | >30 | 409.48 | ND | ND |
| 26 | 0.35 | 0.49 | >30 | 435.45 | 1.16 | 0.69 |
| 27 | >30 | >30 | >30 | 447.48 | ND | ND |
| 28 | 17.05 | >30 | >30 | 433.46 | ND | ND |
| 29 | 0.76 | 1.07 | >30 | 373.38 | 2.6 | 1.86 |
| 30 | 6.18 | 4.37 | >30 | 371.39 | ND | ND |
| 31 | >30 | >30 | >30 | 357.37 | ND | ND |
| 32 | 6.08 | 5.02 | 23.09 | 450.53 | ND | ND |
| 33 | 4.62 | >30 | >30 | 464.56 | ND | ND |
| 34 | 2.01 | 2.11 | 26.14 | 353.37 | ND | ND |
| 35 | 0.43 | 1.64 | >30 | 407.46 | ND | ND |
| 36 | 0.35 | 0.49 | 15.34 | 435.52 | ND | ND |
| 37 | 2.12 | 4 | >30 | 381.43 | ND | ND |
| 38 | 0.75 | 1.64 | >30 | 395.16 | ND | ND |
| 39 | 0.53 | 1 | >40 | 409.18 | ND | ND |
| 40 | 0.53 | 1 | 38.6 | 364.41 | 3.2 | 0.81 |
| 41 | 0.93 | 1.54 | >30 | 366.11 | ND | ND |
| 42 | 1.57 | 6.52 | >30 | 341.41 | ND | ND |
| 43 | 0.26 | 0.52 | >30 | 356.12 | 2.36 | 0.58 |
| 44 | 0.07 | 0.16 | 24.2 | 398.45 | 2.41 | 0.22 |
| 45 | 3.12 | 3.72 | 20.76 | 363.42 | ND | ND |
| 46 | 0.83 | 0.78 | >30 | 397.43 | 2.66 | 0.53 |
| 47 | 5.51 | 6.29 | >30 | 382.41 | ND | ND |
| 48 | 0.21 | 0.45 | >30 | 425.48 | 3.08 | 0.10 |
| 49 | >30 | >30 | >30 | 352.39 | ND | ND |
| 50 | 0.13 | 0.18 | >30 | 479.45 | 2.59 | 0.09 |
| 51 | 0.51 | 0.52 | 12.23 | 411.45 | ND | ND |
| 52 | 26.01 | 25.99 | >30 | 410.47 | ND | ND |
| 53 | 0.062 | 0.18 | >30 | 465.54 | ND | ND |
| 54 | >30 | 3 | >30 | 367.41 | 2.24 | 1.42 |
| 55 | 2.82 | 4.18 | >30 | 355.40 | ND | ND |
| 56 | 1.11 | 1.58 | >30 | 383.45 | ND | ND |
| 57 | 1.74 | 4.01 | >30 | 367.40 | ND | ND |
| 58 | 0.30 | 0.5 | >40 | 395.45 | 1.93 | 0.38 |
| 59 | 1.05 | 2.0 | >30 | 395.45 | 2.98 | 0.66 |
| 60 | 3.93 | 7.75 | >30 | 396.45 | ND | ND |
| 61 | >30 | 0.71 | >30 | 395.45 | ND | ND |
| 62 | >30 | 0.48 | >30 | 409.48 | ND | ND |
| 63 | 0.43 | 0.55 | >30 | 356.37 | ND | ND |
| 64 | 4.19 | >30 | 21.74 | 356.11 | ND | ND |
| 65 | 0.16 | 0.46 | >30 | 384.43 | 2.78 | 0.29 |
| 66 | 0.49 | 0.83 | >30 | 396.14 | 1.73 | 0.46 |
| 67 | 3.51 | 4.25 | >30 | 354.17 | ND | ND |
| 68 | 0.52 | 27.7 | 9.72 | 464.36 | ND | ND |
| 69 | 0.24 | 0.45 | >30 | 406.17 | 3.3 | 0.22 |
| 70 | 1.29 | 1.08 | >30 | 431.51 | 2.47 | 0.82 |
| 71 | 3.98 | 4.13 | >30 | 356.13 | ND | ND |
| 72 | 0.24 | 0.51 | 26.58 | 425.48 | ND | ND |
| 73 | 0.18 | 0.45 | >30 | 434.43 | 2.93 | 0.003 |
| 74 | 0.91 | >30 | >30 | 417.11 | ND | ND |
| 75 | 0.065 | 0.128 | >30 | 461.14 | ND | ND |
| 76 | 0.172 | 0.189 | >30 | 461.53 | ND | ND |
| 77 | 0.791 | 0.957 | >30 | 431.51 | ND | ND |
| 78 | 1.545 | 1.973 | >30 | 420.46 | ND | ND |
| 79 | 4.452 | 8.187 | >30 | 439.46 | ND | ND |
| 80 | 14.33 | >30 | >30 | 393.42 | ND | ND |

It will be apparent to those skilled in the art that various modifications and variations can be made in the present invention without departing from the scope or spirit of the inv hydroxyalkyl, C1-C4 haloalkoxy, C1-C4 alkoxy, C1-C4 alkylamino, (C1-C4)(C1-C4) dialkylamino, and C1-C4 aminoalkyl;
- wherein $Cy^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- wherein each of $R^{16a}$ and $R^{16b}$, when present, is independently selected from hydrogen, C1-C4 alkyl, and $Cy^3$;
  - wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- wherein $R^{17}$, when present, is selected from hydrogen and C1-C4 alkyl;
- wherein $R^{18}$, when present is a C1-C4 alkyl;
- or wherein $R^{17}$ and $R^{18}$, when present, are covalently bonded, and together with the intermediate atoms, comprise a 5- to 7-membered heterocycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- wherein each occurrence of $R^{19}$, when present, is independently selected from hydrogen and C1-C4 alkyl;
- wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and
- wherein $Cy^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl,
- and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
- wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and
  - wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl,
- provided that when A is —NR$^{10}$C(O)—, then $R^3$ is —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$, and
- provided that when A is —NR$^{10}$C(O)— and $R^3$ is —NR$^{14}$C(O)R$^{15}$, then $R^{15}$ is selected from C1-C4 alkyl, C1-C4 haloalkyl, C1-C4 alkoxy, C1-C4 haloalkoxy, C1-C4 aminoalkyl, —NR$^{21a}$R$^{21b}$, and —CH$_2$NR$^{21a}$R$^{21b}$, or a pharmaceutically acceptable salt thereof.

2. The compound of claim 1, wherein A is —NR$^{10}$C(O)—.

3. The compound of claim 1, wherein A is —C(O)NR$^{11}$.

4. The compound of claim 1, wherein one of $Z^1$ and $Z^2$ is —N=.

5. The compound of claim 1, wherein each of $Z^1$ and $Z^2$ is —C(R$^{13}$)=.

6. The compound of claim 1, wherein each of $R^{1a}$, $R^{1b}$, $R^{1c}$, and $R^{1d}$ is hydrogen.

7. The compound of claim 1, wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

8. The compound of claim 1, wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a heteroaryl having a structure represented by a formula:

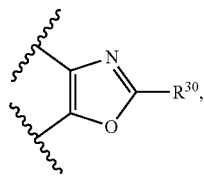

wherein $R^{30}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

9. The compound of claim 1, wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, and Cy$^1$.

10. The compound of claim 1, wherein $R^4$ is hydrogen.

11. The compound of claim 1, wherein the compound has a structure represented by a formula:

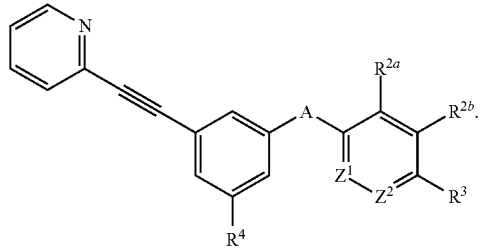

12. The compound of claim 1, wherein the compound has a structure represented by a formula:

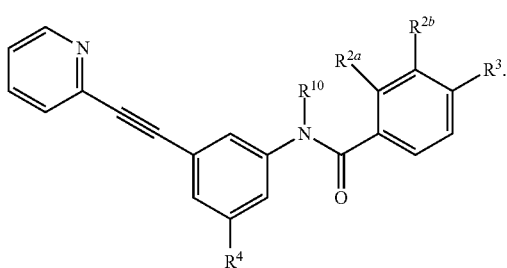

13. The compound of claim 1, wherein the compound has a structure represented by a formula:

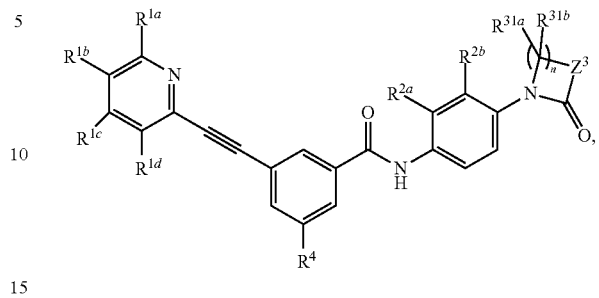

wherein n is selected from 1, 2, 3, 4, 5, and 6;
wherein $Z^3$ is selected from —O—, —NR$^{40}$—, and —CR$^{41a}$R$^{41b}$;
  wherein $R^{40}$, when present, is selected from hydrogen and C1-C4 alkyl;
  wherein each of $R^{41a}$ and $R^{41b}$, when present, is independently selected from hydrogen and C1-C4 alkyl; and
wherein each occurrence of $R^{31a}$ and $R^{31b}$, when present, is independently selected from hydrogen, halogen, and C1-C4 alkyl.

14. The compound of claim 1, wherein the compound has a structure represented by a formula:

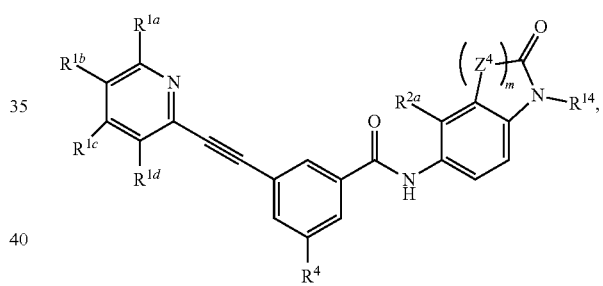

wherein m is selected from 1, 2, and 3;
wherein each occurrence of $Z^4$ is independently selected from —O—, —NR$^{42}$—, and —CR$^{43a}$R$^{43b}$;
  wherein each occurrence of $R^{42}$, when present, is independently selected from hydrogen and C1-C4 alkyl; and
  wherein each occurrence of $R^{43a}$ and $R^{43b}$, when present, is independently selected from hydrogen and C1-C4 alkyl,
provided that no more than one occurrence of $Z^4$ is —O— or —NR$^{42}$—.

15. The compound of claim 1, wherein the compound is selected from:

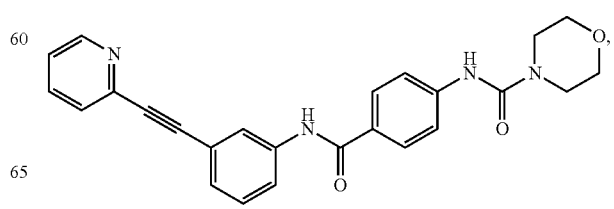

271
-continued
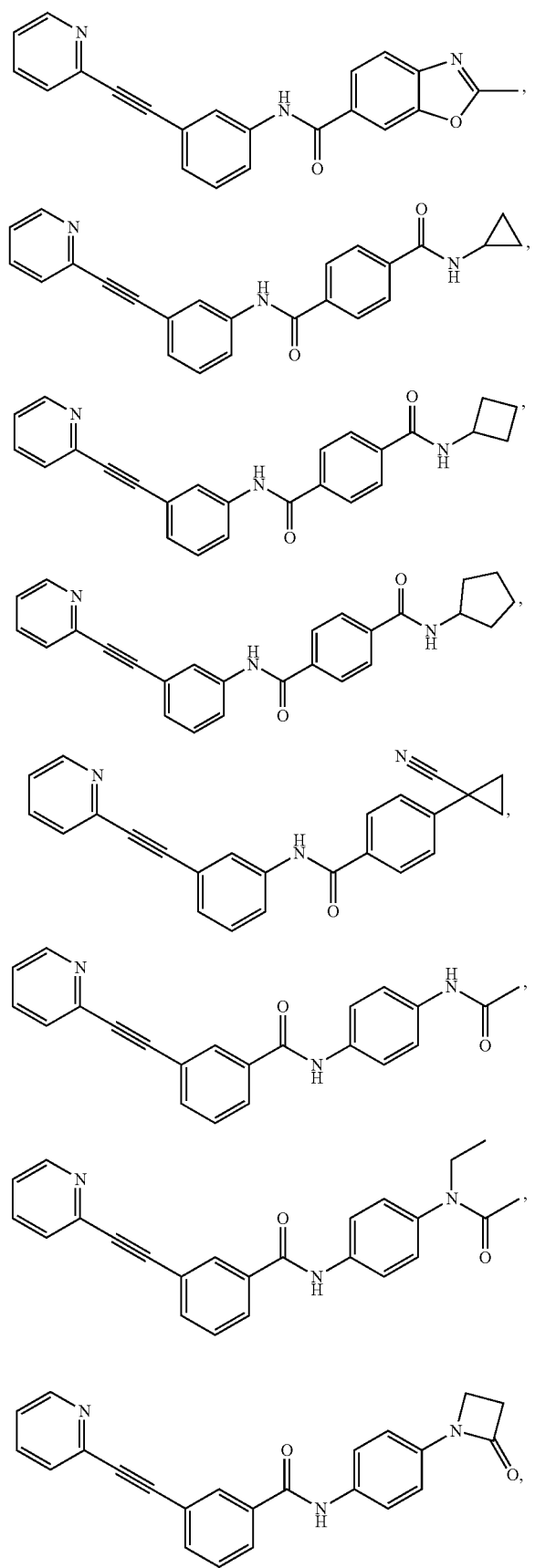
272
-continued
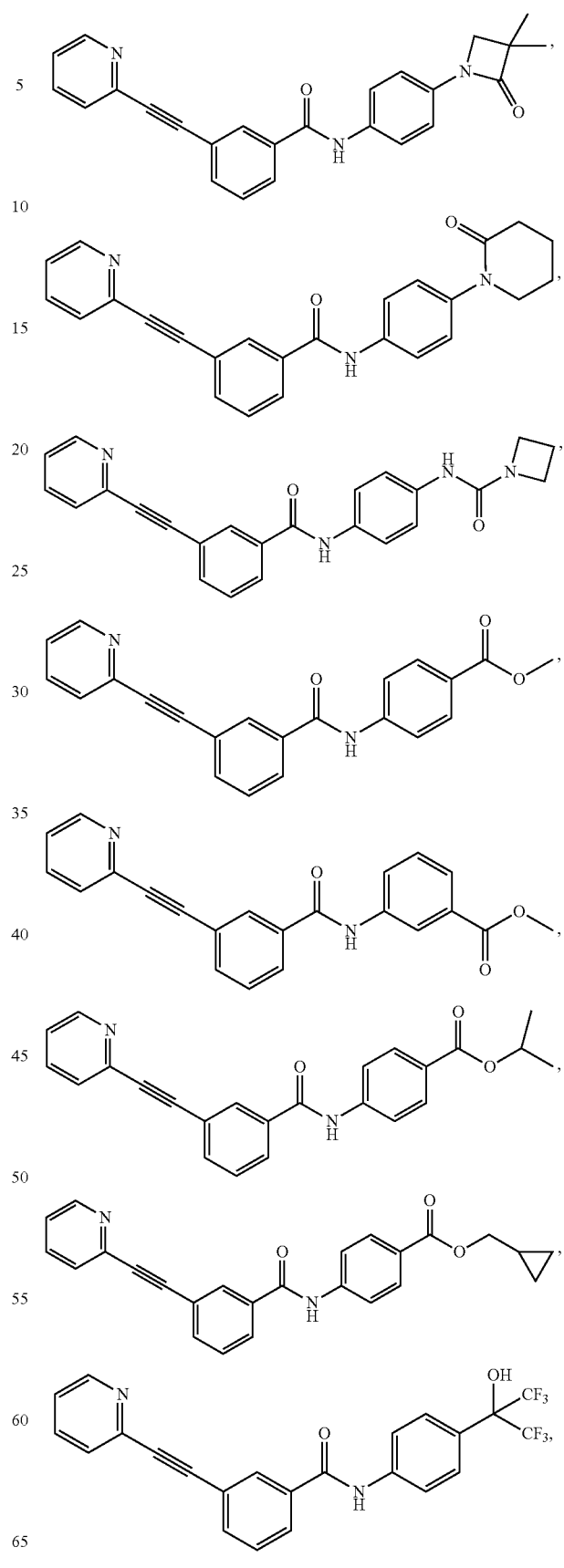

273
-continued

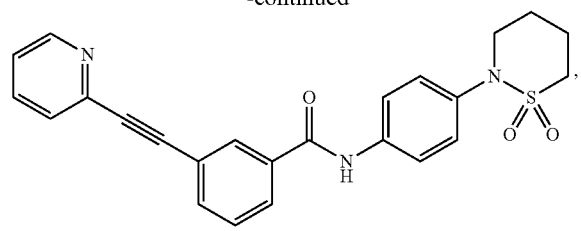

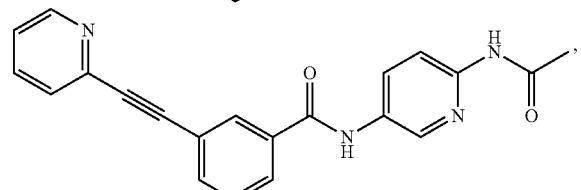

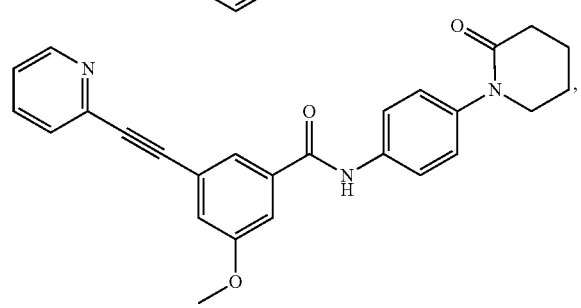

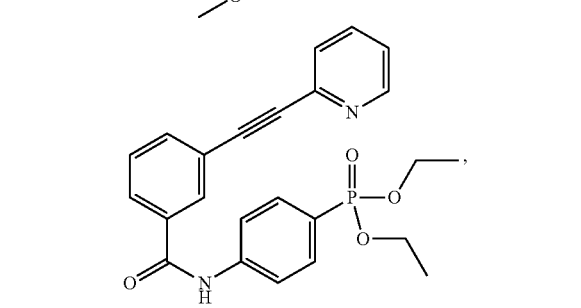

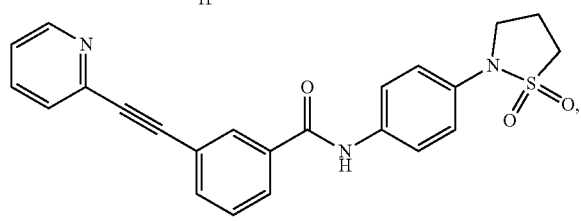

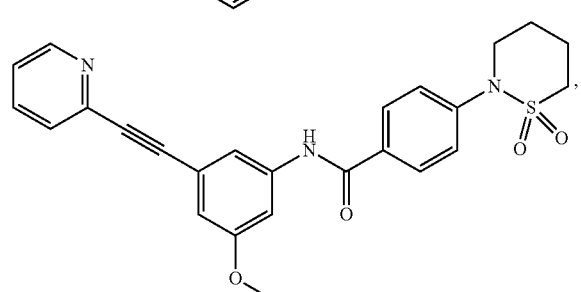

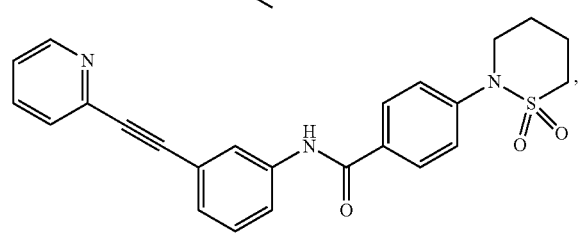

274
-continued

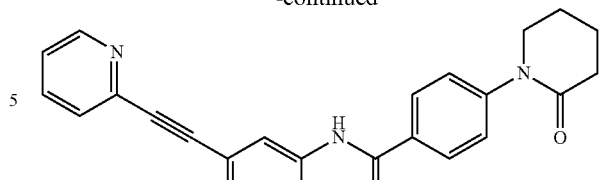

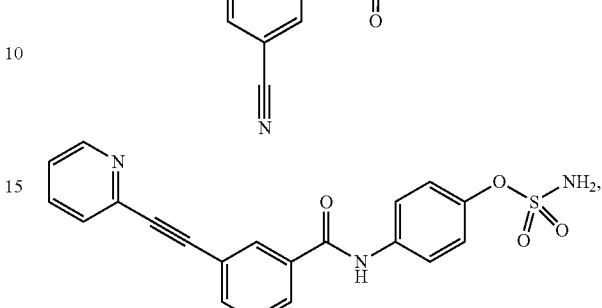

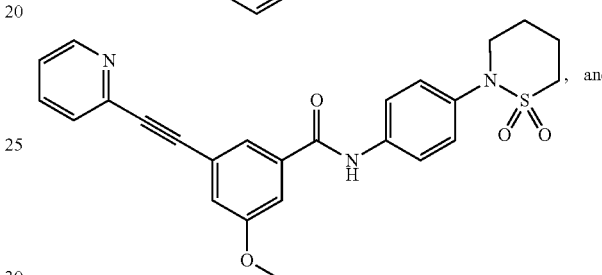

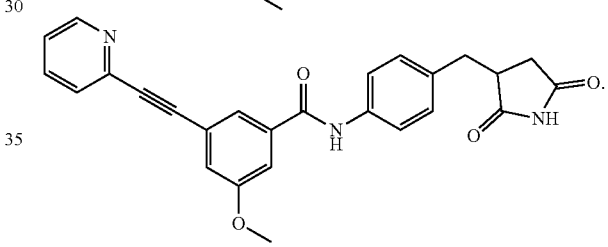

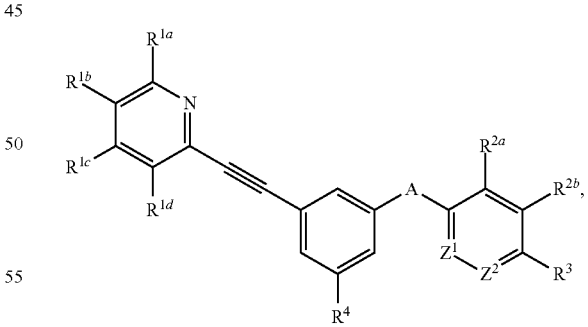

16. A pharmaceutical composition comprising a therapeutically effective amount of a compound having a structure represented by a formula:

wherein A is selected from —NR$^{10}$C(O)— and —C(O)NR$^{11}$;
wherein each of R$^{10}$, when present, and R$^{11}$, when present, is selected from hydrogen and C1-C4 alkyl;
wherein each of Z$^1$ and Z$^2$ is independently selected from —N= and —C(R$^{13}$)=;
wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{1a}$, $R^{1b}$, $R^{1c}$, and $R^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $R^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)$_N$R$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$;

wherein $R^{14}$, when present, is selected from hydrogen and C1-C4 alkyl;

wherein $R^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$;

wherein $R^{20}$, when present, is selected from hydrogen and C1-C4 alkyl;

wherein each of $R^{21a}$ and $R^{21b}$, when present, is independently selected from hydrogen and C1-C4 alkyl;

or wherein $R^{21a}$ and $R^{21b}$, when present, are covalently bonded, and, together with the intermediate atoms, comprise an unsubstituted 4- to 6-membered heterocycloalkyl;

wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{16a}$ and $R^{16b}$, when present, is independently selected from hydrogen, C1-C4 alkyl, and Cy$^3$;

wherein Cy$^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $R^{17}$, when present, is selected from hydrogen and C1-C4 alkyl;

wherein $R^{18}$, when present is a C1-C4 alkyl;

or wherein $R^{17}$ and $R^{18}$, when present, are covalently bonded, and together with the intermediate atoms, comprise an unsubstituted 5- to 7-membered heterocycloalkyl;

wherein each occurrence of $R^{19}$, when present, is independently selected from hydrogen and C1-C4 alkyl;

wherein Cy$^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein Cy$^5$, when present, is a C3-C6 heterocycloalkyl substituted with at least one =O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, Cy$^4$, and —O(C1-C4 alkyl)Cy$^4$; and wherein Cy$^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and a pharmaceutically acceptable carrier.

17. The composition of claim 16, wherein the compound is:

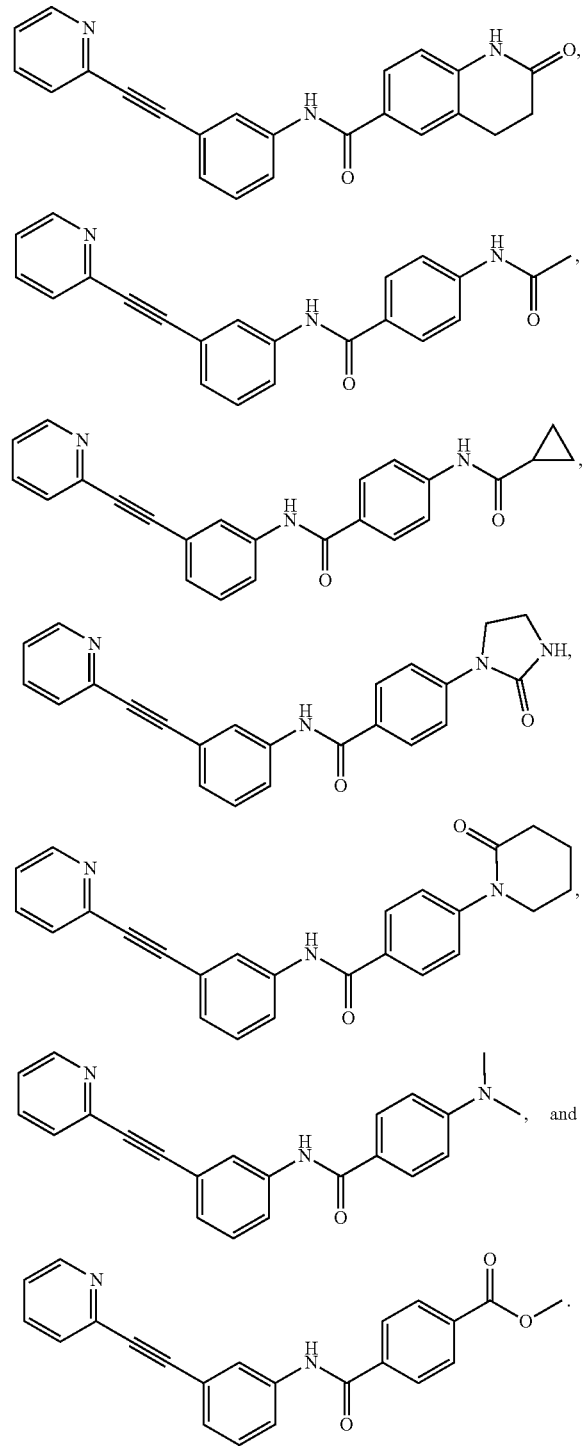

18. A method for treating a viral infection in a subject in need thereof, the method comprising administering to the subject a compound having a structure represented by a formula:

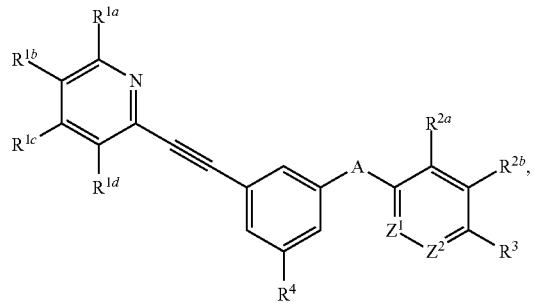

wherein A is selected from —NR$^{10}$C(O)— and —C(O)NR$^{11}$;

wherein each of R$^{10}$, when present, and R$^{11}$, when present, is selected from hydrogen and C1-C4 alkyl;

wherein each of Z$^1$ and Z$^2$ is independently selected from —N= and —C(R$^{13}$)=;

wherein each occurrence of R$^{13}$, when present, is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of R$^{1a}$, R$^{1b}$, R$^{1c}$, and R$^{1d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxy alkyl, C1-C4 haloalkoxy, C1-C4 alkoxy, C1-C4 alkylamino, (C1-C4)(C1-C4) dialkylamino, and C1-C4 aminoalkyl;

wherein each of R$^{2a}$ and R$^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein R$^3$ is selected from C1-C4 alkyl, C1-C4 haloalkyl, C1-C4 haloalkoxy, C1-C4 hydroxyhaloalkyl, —NR$^{14}$C(O)R$^{15}$, —C(O)NR$^{16a}$R$^{16b}$, —OSO$_2$NR$^{16a}$R$^{16b}$, —NR$^{17}$SO$_2$R$^{18}$, —P(O)(OR$^{19}$)$_2$, —CO$_2$(C1-C4 alkyl), —CO$_2$Cy$^1$, —CO$_2$(C1-C4 alkyl)Cy$^1$, Cy$^1$, and —CH$_2$Cy$^5$;

wherein R$^{14}$, when present, is selected from hydrogen and C1-C4 alkyl;

wherein R$^{15}$, when present, is selected from C1-C4 alkyl, C1-C4 haloalkyl, C1-C4 alkoxy, C1-C4 haloalkoxy, C1-C4 aminoalkyl, —OR$^{20}$, —NR$^{21a}$R$^{21b}$, —CH$_2$NR$^{21a}$R$^{21b}$, and Cy$^2$;

wherein R$^{20}$, when present, is selected from hydrogen and C1-C4 alkyl;

wherein each of R$^{21a}$ and R$^{21b}$, when present, is independently selected from hydrogen and C1-C4 alkyl;

or wherein R$^{21a}$ and R$^{21b}$, when present, are covalently bonded, and, together with the intermediate atoms, comprise an unsubstituted 4- to 6-membered heterocycloalkyl;

wherein Cy$^2$, when present, is selected from C3-C6 cycloalkyl, C3-C6 heterocycloalkyl, C6-C14 aryl, and C2-C10 heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{14}$ and $R^{15}$, when present, are covalently bonded, and, together with the intermediate atoms, comprise a 4- to 9-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{15}$, when present, and $R^{2b}$ are covalently bonded, and, together with the intermediate atoms, comprise a 5- to 7-membered heterocycloalkyl ring substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein each of $R^{16a}$ and $R^{16b}$, when present, is independently selected from hydrogen, C1-C4 alkyl, and $Cy^3$;

wherein $Cy^3$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $R^{17}$, when present, is selected from hydrogen and C1-C4 alkyl;

wherein $R^{18}$, when present is a C1-C4 alkyl;

or wherein $R^{17}$ and $R^{18}$, when present, are covalently bonded, and together with the intermediate atoms, comprise an unsubstituted 5- to 7-membered heterocycloalkyl;

wherein each occurrence of $R^{19}$, when present, is independently selected from hydrogen and C1-C4 alkyl;

wherein $Cy^1$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Cy^5$, when present, is a C3-C6 heterocycloalkyl substituted with at least one ═O group, and substituted with 0, 1, or 2 additional groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

or wherein $R^{2a}$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, and wherein $R^{2b}$ and $R^3$ are covalently bonded, and, together with the intermediate atoms, comprise a 5- or 6-membered heteroaryl, and are substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;

wherein $R^4$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, $Cy^4$, and —O(C1-C4 alkyl)$Cy^4$; and wherein $Cy^4$, when present, is a C3-C6 cycloalkyl substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, wherein the viral infection is due to a Coronavirus.

19. The method of claim 18, wherein the Coronavirus is selected from Middle East Respiratory Syndromes coronavirus (MERS-CoV), Severe Acute Respiratory Syndrome coronavirus (SARS-CoV), and SARS-CoV-2.

20. The method of claim 18, wherein the Coronavirus is SARS-CoV or SARS-CoV-2.

* * * * *

UNITED STATES PATENT AND TRADEMARK OFFICE
CERTIFICATE OF CORRECTION

| | | |
|---|---|---|
| PATENT NO. | : 11,905,306 B2 | Page 1 of 1 |
| APPLICATION NO. | : 18/086445 | |
| DATED | : February 20, 2024 | |
| INVENTOR(S) | : Syed Kaleem Ahmed et al. | |

It is certified that error appears in the above-identified patent and that said Letters Patent is hereby corrected as shown below:

In the Specification

Column 1, please replace Lines 16-22 after the heading "FEDERALLY SPONSORED RESEARCH AND DEVELOPMENT" with the following:

--"This invention was made with government support under AI142759 and AI109680 awarded by the National Institutes of Health. The government has certain rights in the invention."--

Signed and Sealed this
Fifteenth Day of July, 2025

Coke Morgan Stewart
*Acting Director of the United States Patent and Trademark Office*